United States Patent
Härter et al.

(10) Patent No.: US 7,498,460 B2
(45) Date of Patent: Mar. 3, 2009

(54) ISOPHTHALIC ACID DERIVATIVES

(75) Inventors: Michael Härter, Leverkusen (DE); Jens Ergüden, Wülfrath (DE); Frank Wunder, Wuppertal (DE); Hanna Tinel, Wuppertal (DE); Johannes Köbberling, Grevenbroich (DE); Eva-Maria Becker, Wuppertal (DE); Klaus Münter, Wülfrath (DE); Karl-Heinz Schlemmer, Wuppertal (DE); Raimund Kast, Wuppertal (DE); Peter Kolkhof, Wuppertal (DE); Gunter Karig, Köln (DE); Lars Bärfacker, Oberhausen (DE); Walter Hübsch, Wuppertal (DE); Joachim Schuhmacher, Wuppertal (DE); Susanne Zuleger, Köln (DE); Arnel Concepcion, Kyoto-fu (JP); Haruka Shimizu, Tokyo (JP)

(73) Assignee: Bayer Healthcare AG, Leverkusen (DE)

( * ) Notice: Subject to any disclaimer, the term of this patent is extended or adjusted under 35 U.S.C. 154(b) by 436 days.

(21) Appl. No.: 10/537,623

(22) PCT Filed: Nov. 28, 2003

(86) PCT No.: PCT/EP03/13433

§ 371 (c)(1),
(2), (4) Date: Dec. 14, 2005

(87) PCT Pub. No.: WO2004/052839

PCT Pub. Date: Jun. 24, 2004

(65) Prior Publication Data

US 2006/0154912 A1    Jul. 13, 2006

(30) Foreign Application Priority Data

Dec. 11, 2002 (DE) .............................. 102 57 785

(51) Int. Cl.
*C07C 229/10* (2006.01)
(52) U.S. Cl. ...................................... 562/450; 514/183
(58) Field of Classification Search ................ 562/450; 514/183

See application file for complete search history.

(56) References Cited

U.S. PATENT DOCUMENTS

2002/0045751 A1    4/2002    Kukkola ..................... 540/607

FOREIGN PATENT DOCUMENTS

| EP | 516069 A1 * | 12/1992 |
| EP | 0791576 | 8/1997 |
| EP | 791576 A2 * | 8/1997 |
| WO | 9840364 | 9/1998 |
| WO | 9840370 | 9/1998 |

* cited by examiner

*Primary Examiner*—Daniel M Sullivan
*Assistant Examiner*—Sudhakar Katakam
(74) *Attorney, Agent, or Firm*—Edwards Angell Palmer & Dodge LLP; Barry Kramer; Ralph Loren

(57) ABSTRACT

The present invention relates to isophthalic acid derivatives, to a process for their preparation and to their use for producing medicaments for the treatment and/or prophylaxis of diseases in humans and animals, in particular of cardiovascular disorders.

9 Claims, No Drawings

ISOPHTHALIC ACID DERIVATIVES

The present invention relates to isophthalic acid derivatives, to a process for their preparation and to their use for producing medicaments for the treatment and/or prophylaxis of diseases in humans and animals, in particular of cardiovascular disorders.

Cysteinyl-leukotrienes are important mediators for a large number of pathological disease states. They are formed from arachidonic acid on activation of inflammatory cells such as, for example, polymorphonuclear leukocytes, macrophages and mast cells, with the aid of 5-lipoxygenase. This involves initial production of leukotriene A4 (LTA4) which is then converted in further reaction steps by addition of glutathione into leukotriene C4 (LTC4). Further metabolism then results in leukotriene D4 (LTD4) and leukotriene E4 (LTE4). LTC4, LTD4 and LTE4 are referred to collectively as cysteinyl-leukotrienes.

The physiological effect of cysteinyl-leukotrienes are mediated via G protein-coupled receptors. Two cysteinyl-leukotriene receptors have been pharmacologically and molecular-biologically characterized:

Cysteinyl-leukotriene receptor 1 (CysLT1) is activated chiefly by LTD4, but also, more weakly, by LTC4 and LTE4. It is therefore also referred to as the LTD4 receptor. Cloning and characterization of the receptor were possible in 1999 (Lynch et. al. (1999) Nature 399; 789-793). The CysLT1 receptor shows strong expression in the spleen, peripheral leukocytes and lungs. Expression of the CysLT1 receptor in the human heart has not to date been detectable. CysLT1-specific receptor antagonists such as, for example, pranlukast, zafirlukast and montelukast lead to relaxation of the smooth muscles of the bronchi and have been developed for the treatment of bronchial asthma.

Cysteinyl-leukotriene receptor 2 (CysLT2) is activated chiefly by LTC4, but also, more weakly, by LTD4 and LTE4. It is therefore also referred to as LTC4 receptor. Identification and characterization of the receptor was possible in 2000 (Heise et. al. (2000) Journal of Biological Chemistry 275; 30531-30536; Takasaki et. al. (2000) Biochem. Biophys. Res. Commun. 274; 316-322; Nothacker et. al. (2000) Mol. Pharmacol 58; 1601-1608). The human CysLT2 receptor shows very strong expression in the heart, placenta, spleen and peripheral blood leukocytes (PBL). It was possible to show with the aid of PCR investigations and in-situ hybridzations that this receptor is expressed in the heart in smooth muscle cells of coronary arteries, in myocytes and very strongly also in Purkinje fibres (Kamohara et. al. (2001) Biochem. Biophys. Res. Commun. 287; 1088-1092; Hui et. al. (2001) Journal of Biological Chemistry 276; 47489-47495). On activation of the CysLT2 receptor there is, as with the CysLT1 receptor, an increase in the intracellular calcium concentration.

Cysteinyl-leukotrienes are vasoactive substances, i.e. they lead to a strong constriction of coronary arteries. In addition, they reduce the contractility of the heart, induce changes in the electrocardiogram, influence the blood pressure, increase the microvascular permeability, promote oedema formation and induce strong bronchoconstriction (Letts et. al. (1987) Cardiovasc. Clin. 18; 101-113; Fauler and Frölich (1989) Cardiovasc. Drugs and Therapy 3; 499-505; Piper et. al. (1990) Adv. Prostaglandin Thromboxane Leukotr. Res. 20; 146-152). Antagonists of cysteinyl-leukotriene receptors therefore form one therapeutic approach to the treatment of cardiovascular disorders.

EP-A 516 069 describes leukotriene B4 antagonists for the treatment of allergic and inflammatory disorders. EP-A 791 576 and EP-A 341 551 disclose leukotriene antagonists for the treatment of asthma.

The present invention relates to compounds of the formula (I)

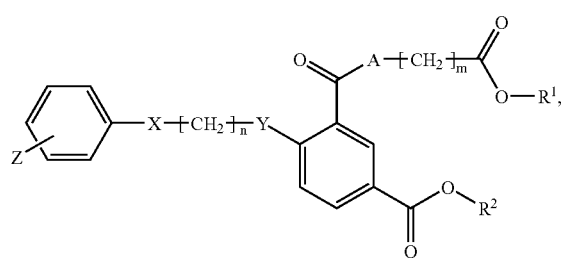

in which

A is a 4- to 7-membered nitrogen-containing saturated heterocycle which is bonded via the nitrogen atom to the keto group and which optionally has a carbonyl group adjacent to a nitrogen atom, or
a radical

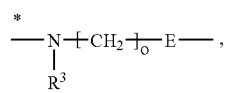

in which
E is $(C_3-C_7)$-cycloalkanediyl, $(C_5-C_7)$-cycloalkenediyl or is 5- to 10-membered heterocyclyl which is bonded via a carbon atom to the $[CH_2]_o$ group,
o is 0, 1 or 2,
$R^3$ is hydrogen or $(C_1-C_6)$-alkyl, and
* is the point of linkage to the keto group,
m 0, 1 or 2,
n is 1, 2, 3 or 4,
$R^1$ is hydrogen or $(C_1-C_6)$-alkyl,
$R^2$ is hydrogen or $(C_1-C_6)$-alkyl,
X is a bond, —CH=CH—, —C≡C— or O,
Y is O, *—NH—C(=O)— or NH,
in which
* is the point of linkage to the phenyl ring, and
Z is located in the position meta or para to the substituent X and is either $(C_6-C_{10})$-alkoxy which may comprise 1 or 2 further oxygen atoms in the chain, or
a radical

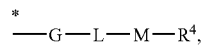

in which
G is a bond, O or S,
L is $(C_1-C_6)$-alkanediyl, $(C_3-C_6)$-alkenediyl or $(C_3-C_6)$-alkynediyl,
M is a bond, O or S,
$R^4$ is $(C_6-C_{10})$-aryl, biphenylyl, phenoxyphenyl, benzyloxyphenyl, (E)-phenylvinylphenyl, 2-phenylethylphenyl, tetrahydronaphthyl, benzyl, heteroaryl, 5- to 10-membered heterocyclyl, $(C_3-C_7)$-cycloalkyl or $(C_3-C_7)$-cycloalkylmethyl, where aryl, biphenylyl, phenoxyphenyl, benzyloxyphenyl, (E)-phenylvinylphenyl, 2-phenylethylphenyl, tetrahydronaphthyl, benzyl, heteroaryl, heterocyclyl, cycloalkyl and cycloalkylmethyl in turn may be substituted up to three times independently of one another by halogen, cyano, nitro, trifluoromethyl, trifluoromethoxy, ($C_1$-$C_6$)-alkyl, ($C_1$-$C_6$)-alkoxy, ($C_2$-$C_6$)-alkenyl, ($C_3$-$C_7$)-cycloalkyl, ($C_3$-$C_7$)-cycloalkylmethoxy, ($C_5$-$C_7$)-cycloalkenyl, ($C_3$-$C_7$)-cycloalkoxy or ($C_5$-$C_7$)-cycloalkenyloxy, and \* is the point of linkage to the phenyl ring, and the salts, hydrates, hydrates of the salts and solvates thereof.

Compounds according to the invention are the compounds of the formula (I) and the salts, solvates and solvates of the salts thereof, the compounds of the formulae mentioned below which are encompassed by formula (I), and the salts, solvates and solvates of the salts thereof, and the compounds encompassed by formula (I) and mentioned below as exemplary embodiments, and the salts, solvates and solvates of the salts thereof, insofar as the compounds encompassed by formula (I) and mentioned below are not already salts, solvates and solvates of the salts.

The compounds of the invention may, depending on their stricture, exist in stereoisomeric forms (enantiomers, diastereomers). The invention therefore relates to the enantiomers or diastereomers and respective mixtures thereof. The stereoisomerically pure substituents can be isolated in a known manner from such mixtures of enantiomers- and/or diastereomers.

Where the compounds of the invention can occur in tautomeric forms, the present invention encompasses all tautomeric forms.

Salts preferred for the purposes of the present invention are physiologically acceptable salts of the compounds of the invention. However, salts which are themselves unsuitable for pharmaceutical applications but can be used for example for isolating or purifying the compounds of the invention are also encompassed.

Physiologically acceptable salts of the compounds of the invention include acid addition salts of mineral acids, carboxylic acids and sulphonic acids, e.g. salts of hydrochloric acid, hydrobromic acid, sulphuric acid, phosphoric acid, methanesulphonic acid, ethanesulphonic acid, toluenesulphonic acid, benzenesulphonic acid, naphthalenedisulphonic acid, acetic acid, trifluoroacetic acid, propionic acid, lactic acid, tartaric acid, malic acid, citric acid, fumaric acid, maleic acid and benzoic acid.

Physiologically acceptable salts of the compounds of the invention also include salts of conventional bases such as, for example and preferably, alkali metal salts (e.g. sodium and potassium salts), alkaline earth metal salts (e.g. calcium and magnesium salts) and ammonium salts derived from ammonia or organic amines having 1 to 16 C atoms, such as, for example and preferably, ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylenediamine and N-methylpiperidine.

Solvates refer for the purposes of the invention to those forms of the compounds of the invention which form a complex in the solid or liquid state through coordination with solvent molecules. Hydrates are a specific form of solvates in which the coordination takes place with water.

For the purposes of the present invention, the substituents have, unless specified otherwise, the following meaning:

Alkyl per se and "alk" in alkoxy stand for a linear or branched alkyl radical having usually 1 to 6, preferably 1 to 4, particularly preferably 1 to 3, carbon atoms, by way of example and preferably methyl, ethyl, n-propyl, isopropyl, tert-butyl, n-pentyl and n-hexyl.

Alkoxy stands by way of example and preferably for methoxy, ethoxy, n-propoxy, isopropoxy, tert-butoxy, n-pentoxy and n-hexoxy.

Alkanediyl stands for a straight-chain or branched saturated alkanediyl radical having 1 to 6 carbon atoms. A straight-chain or branched alkanediyl having 1 to 4 carbon atoms is preferred. Preferred examples which may be mentioned are methylene, ethane-1,2-diyl, ethane-1,1-diyl, propane-1,3-diyl, propane-1,2-diyl, propane-2,2-diyl, butane-1,4-diyl, butane-1,3-diyl, butane-2,4-diyl, pentane-1,5-diyl, pentane-2,4-diyl, 2-methyl-pentane-2,4-diyl.

Alkenyl stands for a straight-chain or branched alkenyl radical having 2 to 6 carbon atoms. A straight-chain or branched alkenyl radical having 2 to 4 carbon atoms is preferred. Preferred examples which may be mentioned are: vinyl, allyl, n-prop-1-en-1-yl, n-but-2-en-1-yl and 2-methyl-2-buten-1-yl.

Alkenediyl stands for a straight-chain or branched alkenediyl radical having 2 to 6 carbon atoms. Preference is given to a straight-chain or branched alkenediyl radical having 3 to 6, particularly preferably having 4 or 5 carbon atoms. Preferred examples which may be mentioned are: propene-1,3-diyl, 2-butene-1,4-diyl and 1-pentene-1,5-diyl.

Alkynediyl stands for a straight-chain or branched alkynediyl radical having 2 to 6 carbon atoms. Preference is given: to a straight-chain or branched alkynediyl radical having 2 to 4, particularly preferably having 3 or 4, carbon atoms. Preferred examples to be mentioned are: propyne-1,3-diyl and 2-butyne-1,4-diyl.

Cycloalkyl per se and "cycloalk" in cycloalkoxy and cycloalkanediyl stands for a cycloalkyl group having usually 3 to 8, preferably 5 to 7, carbon atoms, by way of example and preferably cyclopropyl, cyclobutyl, cyclopentyl, cyclohexyl and cycloheptyl.

Cycloalkoxy stands by way of example and preferably for cyclopropyloxy, cyclobutyloxy, cyclopentyloxy, cyclohexyloxy and cycloheptyloxy.

Cycloalkanediyl stands by way of example and preferably for cyclopropane-1,2-diyl, cyclobutane-1,2-diyl, cyclobutane-1,3-diyl, cyclopentane-1,2-diyl, cyclopentane-1,3-diyl, cyclohexane-1,2-diyl, cyclohexane-1,3-diyl, cyclohexane-1,4-diyl, cycloheptane-1,2-diyl, cycloheptane-1,3-diyl and cycloheptane-1,4-diyl.

Cycloalkenyl per se and "cycloalken" in cycloalkenediyl and in cycloalkenyloxy stands for a cycloalkenyl group having usually 5 to 7 carbon atoms, by way of example and preferably cyclopent-2-en-1-yl, cyclopent-3-en-1-yl, cyclohex-2-en-1-yl, cyclohex-3-en-1-yl, cyclohept-2-en-1-yl, cyclohept-3-en-1-yl and cyclohept-4-en-1-yl.

Cycloalkenediyl stands by way of example and preferably for cyclopent-4-ene-1,3-diyl, cyclohex-2-ene-1,4-diyl, cyclohex-4-ene-1,3-diyl and cyclohept-5-ene-1,3-diyl.

Cycloalkenyloxy stands by way of example and preferably for cyclopent-2-en-1-yloxy, cyclopent-3-en-1-yloxy, cyclohex-2-en-1-yloxy, cyclohex-3-en-1-yloxy, cyclohept-2-en-1-yloxy, cyclohept-3-en-1-yloxy and cyclohept-4-en-1-yloxy.

Aryl stands for a mono- to tricyclic aromatic, carbocyclic radical having usually 6 to 10 carbon atoms; by way of example and preferably phenyl and naphthyl.

Heteroaryl stands for an aromatic, mono- or bicyclic, optionally benzo-fused, radical having usually 5 to 10, preferably 5 to 6, ring atoms and up to 5, preferably up to 4, heteroatoms from the series S, O and N, by way of example and preferably thienyl, furyl, pyrrolyl, thiazolyl, oxazolyl, imidazolyl, pyridyl, pyrimidyl, pyridazinyl, indolyl, indazolyl, benzofuranyl, benzothiophenyl, quinolinyl, isoquinolinyl, benzimidazolyl and benzoxazolyl.

Heterocyclyl stands for a mono- or polycyclic, preferably mono- or bicyclic, optionally benzo-fused, nonaromatic heterocyclic radical having usually 5 to 10, preferably 5 to 8, in particular 5 or 6, ring atoms and up to 3, preferably up to 2, heteroatoms and/or hetero groups from the series N, O, S, SO, $SO_2$. The heterocyclyl radicals may be saturated or partially unsaturated. 5- or 6-membered, monocyclic saturated heterocylyl radicals, having up to two heteroatoms from the series O, N and S, which may optionally be benzo-fused, are preferred, such as by way of example and preferably tetrahydrofuran-2-yl, pyrrolidin-2-yl, pyrrolidin-3-yl, pyrrolinyl, piperidinyl, morpholinyl, perhydroazepinyl, 1,3-benzodioxolyl, tetrahydro-2H-pyranyl, 1,3-dioxanyl, 1,4-dioxanyl, 2,3-dihydro-1,4-dioxinyl, 2,3-dihydro-1,4-benzodioxinyl and 4H-1,3-benzodioxinyl.

Halogen stands for fluorine, chlorine, bromine and iodine.

If radicals in the compounds of the invention are substituted, the radicals may, unless specified otherwise, have one or more identical or different substituents. Substitution by up to three identical or different substituents is preferred. Substitution by one substituent is very particularly preferred.

Preference is given to compounds of the formula (I)

in which

A is a 4- to 6-membered nitrogen-containing saturated heterocycle which is bonded via the nitrogen atom to the keto group, or a radical

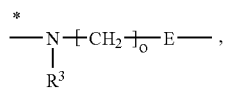

in which

E is $(C_5-C_6)$-cycloalkanediyl, o is 0 or 1, $R^3$ is hydrogen, and

* is the point of linkage to the keto group, m is 0 or 1, n is 1, 2 or 3, $R^1$ is hydrogen, $R^2$ is hydrogen, X is a bond or O, Y is O or *—NH—C(=O)—, in which

* is the point of linkage to the phenyl ring, and

Z is located in the position meta or para to the substituent X and is either $(C_7-C_9)$-alkoxy, which may comprise 1 further oxygen atom in the chain, or a radical

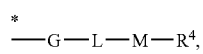

in which

G is a bond or O.

L is $(C_1-C_6)$-alkanediyl or $(C_3-C_6)$-alkenediyl,

M is a bond, O or S, $R^4$ is phenyl, naphthyl, biphenylyl, phenoxyphenyl, benzyloxyphenyl, (E)-phenylvinylphenyl, 2-phenylethylphenyl, tetrahydronaphthyl, benzyl, 1,3-dioxanyl, 1,4-dioxanyl, dimethyl-1,3-dioxanyl, tetrahydro-2H-pyranyl, $(C_3-C_7)$-cycloalkyl or $(C_3-C_7)$-cycloalkylmethyl, where phenyl, naphthyl, biphenylyl, phenoxyphenyl, benzyloxyphenyl, (E)-phenylvinylphenyl, 2-phenylethylphenyl, tetrahydronaphthyl, benzyl, cycloalkyl and cycloalkylmethyl in turn may be substituted up to three times independently of one another by halogen, cyano, nitro, tri-fluoromethyl, trifluoromethoxy, $(C_1-C_6)$-alkyl, $(C_1-C_6)$-alkoxy, $(C_3-C_7)$-cycloalkyl, $(C_3-C_7)$-cycloalkylmethoxy or $(C_3-C_7)$-cycloalkoxy, and

* is the point of linkage to the phenyl ring, and the salts, hydrates, hydrates of the salts and solvates thereof.

Particular preference is given compounds of the formula (I) in which n is 3.

Particular preference is likewise given to compounds of the formula (I) in which X is a bond.

Particular preference is likewise given to compounds of the formula (I) in which Y is O.

Particular preference is likewise given to compounds of the formula (I) in which Z is located in the position para to the substituent X.

Particular preference is likewise given to compounds of the formula (I)

in which

A-$[CH_2]_m$—$CO_2R^1$ is a radical

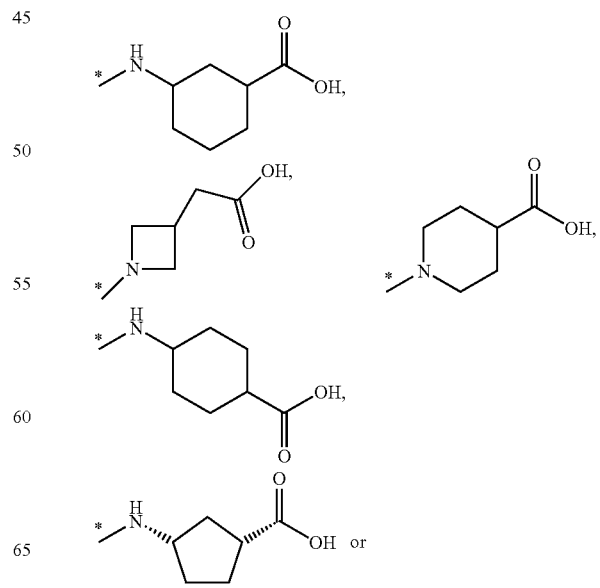

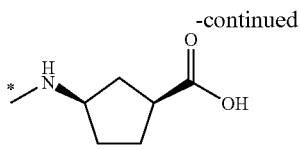

in which
* is the point of linkage to the keto group,
n is 3,
$R^2$ is hydrogen,
X is a bond,
Y is O, and
Z is located in the position para to the substituent X and is either n-octyloxy, n-heptyloxy, or
a radical

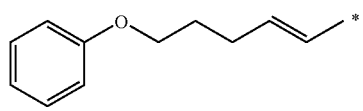

in which
* is the point of linkage to the phenyl ring, or
a radical

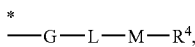

in which
G is O,
L is methanediyl, n-propanediyl or n-butanediyl,
M is a bond or O,
$R^4$ is phenyl, 4-biphenylyl, 4-phenoxyphenyl, 4-benzyloxyphenyl, 1,2,3,4-tetrahydronaphth-6-yl, 5,5-dimethyl-1,3-dioxan-2-yl or cyclohexyl, where phenyl in turn may be substituted once by halogen, trifluoromethoxy, $(C_3-C_4)$-alkyl, $(C_3-C_4)$-alkoxy, cyclopentyl, cyclo-hexyl or $(C_3-C_6)$-cycloalkylmethoxy, and
* is the point of linkage to the phenyl ring, and the salts, hydrates, hydrates of the salts and solvates thereof.

Very particular preference is given to compounds of the formula (I)
in which
$A\text{-}[CH_2]_m\text{—}CO_2R^1$ is a radical

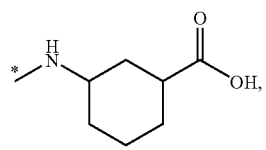

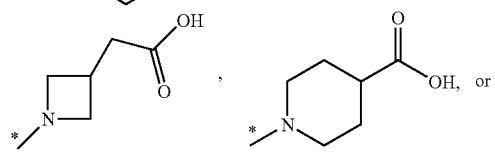

in which
* is the point of linkage to the keto group,
n is 3,
$R^2$ is hydrogen,
X is a bond,
Y is O, and
Z is located in the position para to the substituent X, and is either
n-octyloxy, n-heptyloxy, or
a radical

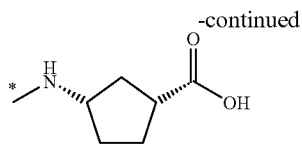

in which
* is the point of linkage to the phenyl ring, or
a radical *—O—$CH_2$—$R^4$,
in which
$R^4$ is phenyl, 4-biphenylyl, 4-phenoxyphenyl, 4-benzyloxyphenyl or 1,2,3,4-tetrahydronaphth-6-yl, where phenyl in turn may be substituted once by trifluoromethoxy, n-propyl, n-butyl, tert-butyl, n-propyloxy, isopropyloxy, isobutyloxy, cyclohexyl or cyclopropylmethoxy, and
* is the point of linkage to the phenyl ring, or
a radical *—$CH_2$—$CH_2$—$CH_2$—$R^4$,
in which
$R^4$ is 4-chlorophenyl, 5,5-dimethyl-1,3-dioxan-2-yl or cyclohexyl, and
* is the point of linkage to the phenyl ring, or
a radical *—O—$CH_2$—$CH_2$—$CH_2$—$CH_2$—O—$R^4$,
in which
$R^4$ is phenyl or cyclohexyl, and
* is the point of linkage to the phenyl ring, and the salts, hydrates, hydrates of the salts and solvates thereof.

Especial preference is given to compounds of the formula (I)
in which
$A\text{-}[CH_2]_m\text{—}CO_2R^1$ is a radical

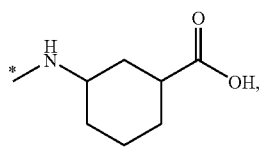

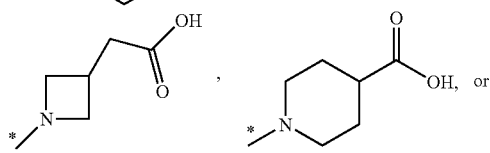

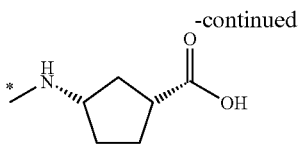

in which
* is the point of linkage to the keto group,
n is 3,
R² is hydrogen,
X is a bond,
Y is O, and
Z is located in the position para to the substituent X and is a radical

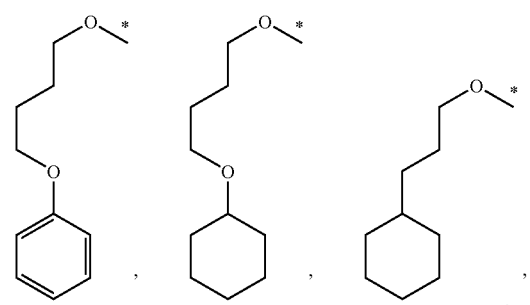

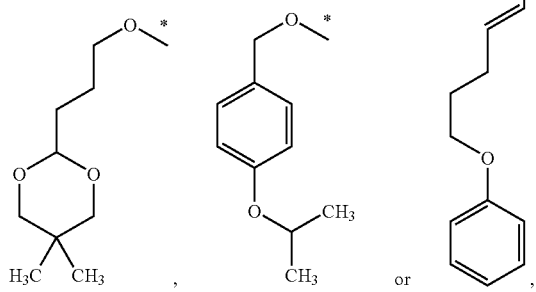

in which
* is the point of linkage to the phenyl ring, and the salts, hydrates, hydrates of the salts and solvates thereof.

Very particular preference is given in particular to the following compounds of formula (I):

3-{[(3-carboxycyclohexyl)amino]carbonyl}-4-{3-[4-(4-phenoxybutoxy)phenyl]-propoxy}benzoic acid, 3-{[(3-carboxycyclohexyl)amino]carbonyl}-4-{3-[4-(3-cyclohexylpropoxy)phenyl]-propoxy}benzoic acid, 3-{[(3-carboxycyclohexyl)amino]carbonyl}-4-(3-{4-[4-(cyclohexyloxy)butoxy]-phenyl}propoxy)benzoic acid, 1-(5-carboxy-2-{3-[4-(3-cyclohexylpropoxy)phenyl]propoxy}benzoyl)piperidine-4-carboxylic acid, 3-{[(3-carboxycyclohexyl)amino]carbonyl}-4-(3-{4-[(4-isopropoxybenzyl)oxy]-phenyl}propoxy)benzoic acid, 3-{[3-(carboxymethyl)azetidin-1-yl]carbonyl}-4-{3-[4-(3-cyclohexylpropoxy)-phenyl]propoxy}benzoic acid, 3-{[(3-carboxycyclohexyl)amino]carbonyl}-4-(3-{4-[(1E)-5-phenoxypent-1-en-1-yl]-phenyl}propoxy)benzoic acid.

Preference is likewise given to compounds of the formula (I) in which
A is a 4- to 7-membered nitrogen-containing saturated heterocycle which is bonded via the nitrogen atom to the keto group, which may comprise a further nitrogen atom in the ring and which optionally has a carbonyl group adjacent to a nitrogen atom, or
a radical

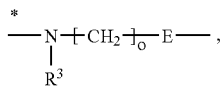

in which
E is $(C_3-C_7)$-cycloalkanediyl, $(C_5-C_7)$-cycloalkenediyl or is 5- to 10-membered heterocyclyl which is bonded via a carbon atom to the $[CH_2]_o$ group,
o is 0, 1 or 2,
R³ is hydrogen or $(C_1-C_6)$-alkyl, and
* is the point of linkage to the keto group,
m is 0, 1 or 2,
n is 1, 2, 3 or 4,
R¹ is hydrogen or $(C_1-C_6)$-alkyl,
R² is hydrogen or $(C_1-C_6)$-alkyl,
X is a bond, O, NH, N-methyl or N-acetyl,
Y is O, *—NH—C(=O)— or NH,
in which
* is the point of linkage to the phenyl ring, and
Z a radical

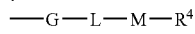

which is located in the position meta or para to the substituent X,
in which
G is a bond, O or S,
L is $(C_1-C_6)$-alkanediyl, $(C_3-C_6)$-alkenediyl or $(C_3-C_6)$-alkynediyl,
M is a bond, O or S,
R⁴ is $(C_6-C_{10})$-aryl, biphenylyl, heteroaryl, 5- to 10-membered hetero-cyclyl or $(C_3-C_7)$-cycloalkyl, where aryl, biphenylyl, heteroaryl, heterocyclyl and cycloalkyl in turn may be substituted up to three times independently of one another by halogen, cyano, nitro, trifluoromethyl, trifluoromethoxy, $(C_1-C_6)$-alkyl, $(C_1-C_6)$-alkoxy, $(C_2-C_6)$-alkenyl, $(C_3-C_7)$-cycloalkyl, $(C_5-C_7)$-cycloalkenyl, $(C_3-C_7)$-cycloalkoxy or $(C_5-C_7)$-cycloalkenyloxy,
* is the point of linkage to the phenyl ring, and the salts, hydrates, hydrates of the salts and solvates thereof.

Preference is likewise given to compounds of the formula (I),
in which
A a radical

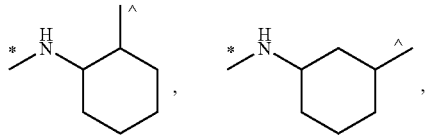

in which
* is the point of linkage to the keto group, and
^ is the point of linkage to the $$-\!\!\left[\mathrm{CH}_2\right]_m\!\!-$$

group,
m is 0 or 1,
n is 2 or 3,
$R^1$ is hydrogen,
$R^2$ is hydrogen,
X is a bond,
Y is O or *—NH—C(=O)—,
  in which
  * is the point of linkage to the phenyl ring, and
Z is a radical which is located in the position meta or para to the substituent X,
in which
$R^4$ and $R^4$ are, independently of one another, fluorine, chlorine, bromine, trifluoromethyl, trifluoromethoxy, $(C_1$-$C_6)$-alkyl or $(C_1$-$C_6)$-alkoxy, and
* is the point of linkage to the phenyl ring, and the salts, hydrates, hydrates of the salts and solvates thereof.

Combinations of two or more of the abovementioned preferred ranges are very particularly preferred.

The present invention also relates to a process for preparing the compounds of the formula (I), which is characterized in that either

[A] compounds of the formula (II)

(II)

in which
$R^2$ is $(C_1$-$C_6)$-alkyl and
n, X, Y and Z have the meaning indicated above, are reacted with compounds of the formula (III)

(III)

in which
$R^1$ is $(C_1$-$C_6)$-alkyl, and
m and A have the meaning indicated above, or

[B1] compounds of the formula (IVa)

(IVa)

in which
$Q^1$ is a suitable leaving group such as, for example, halogen, mesylate or tosylate, and
n, X and Z have the meaning indicated-above, are reacted with compounds of the formula (Va)

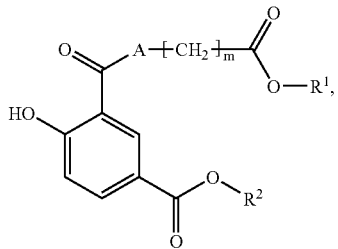

in which
R$^1$ and R$^2$ are (C$_1$-C$_6$)-alkyl, and
A and m have the meaning indicated above, or

[B2] compounds of the formula (IVb)

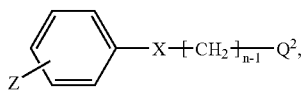
(IVb)

in which
Q$^2$ is an acid chloride group, and
n, X and Z have the meaning indicated above, are reacted with compounds of the formula (Vb)

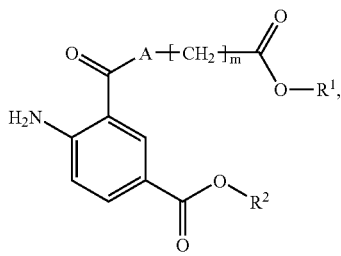
(Vb)

in which
R$^1$ and R$^2$ are (C$_1$-C$_6$)-alkyl, and
A and m have the meaning indicated above, or

[B3] compounds of the formula (IVa)

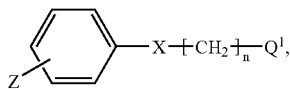
(IVa)

in which
Q$^1$ is a suitable leaving group such as, for example, halogen, mesylate or tosylate, and
n, X and Z have the meaning indicated above, are reacted with compounds of the formula (Vb)

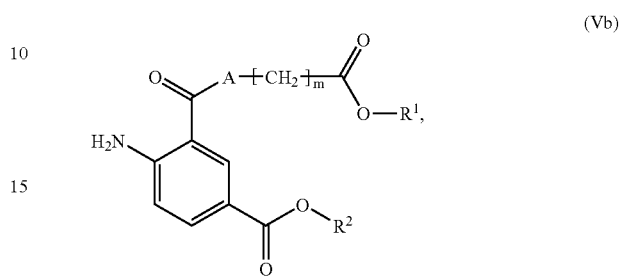
(Vb)

in which
R$^1$ and R$^2$ are (C$_1$-C$_6$)-alkyl and
A and m have the meaning indicated above, or

[C] compounds of the formula (XII)

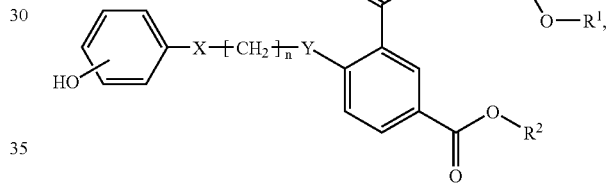
(XII)

in which
R$^1$ and R$^2$ are (C$_1$-C$_6$)-alkyl, and
n, m, X, Y and A have the meaning indicated above, are reacted with compounds of the formula (XIII)

$$R^4\text{-}M\text{-}L\text{-}Q^3 \quad (XIII),$$

in which
Q$^3$ is a suitable leaving group such as, for example, halogen, preferably bromine, chlorine or iodine, or mesylate or tosylate, and
R$^4$, M and L have the meaning indicated above, or

[D] the two ester groups in compounds prepared by process step [A], [B 1], [B2], [B3] or [C] are hydrolysed.

The process of the invention can be illustrated by way of example by the following formula scheme:

[A]

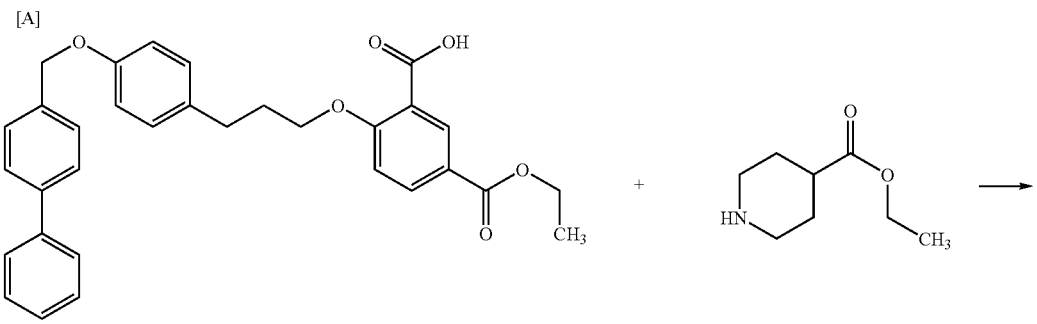

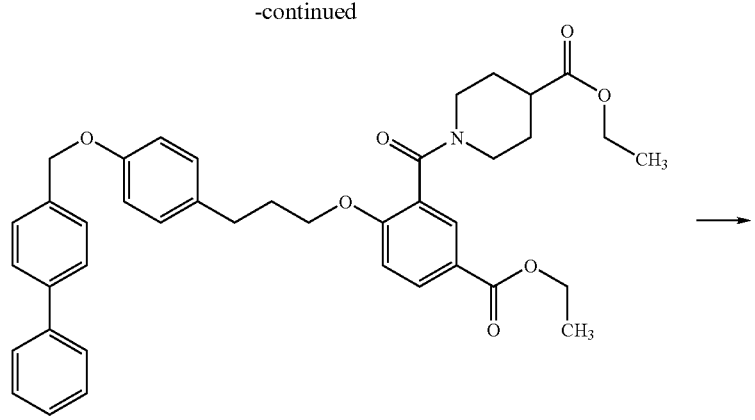
[D]
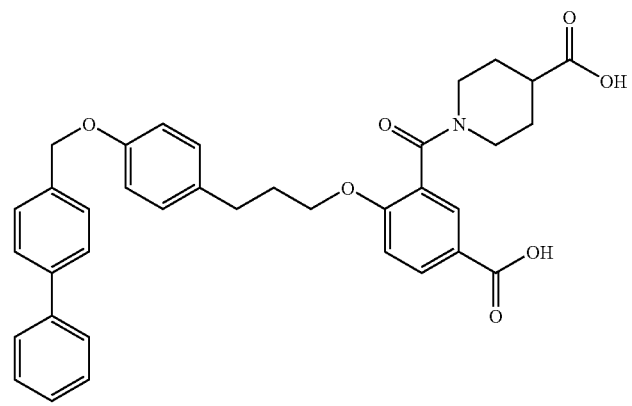
[B1]
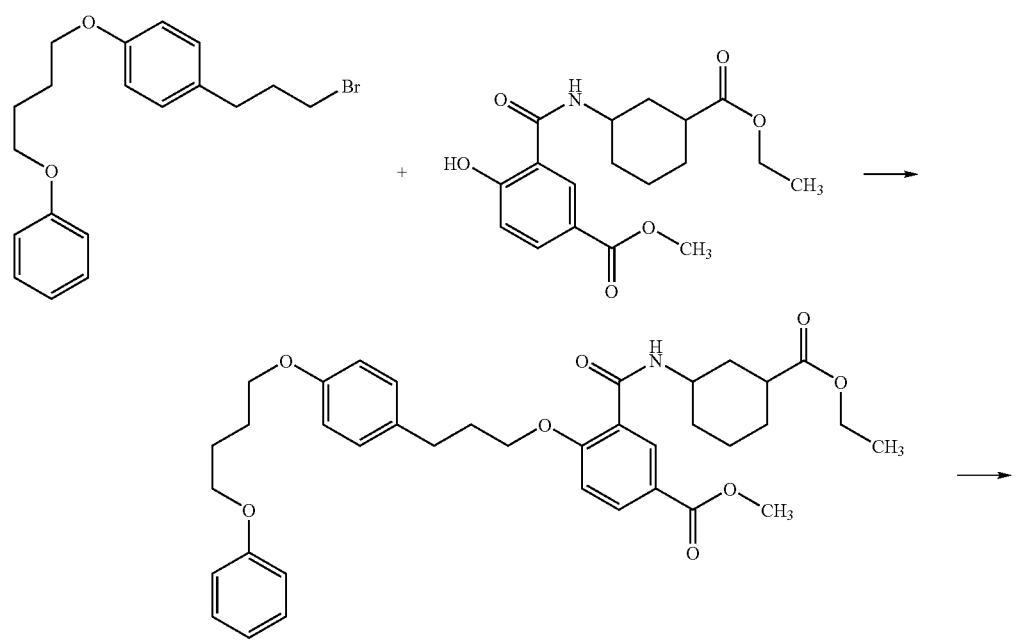

[D]
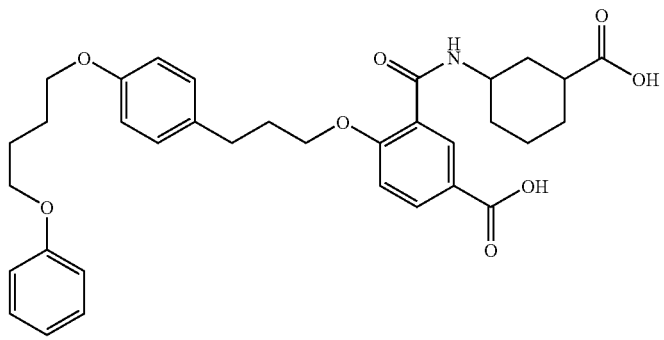
[C]
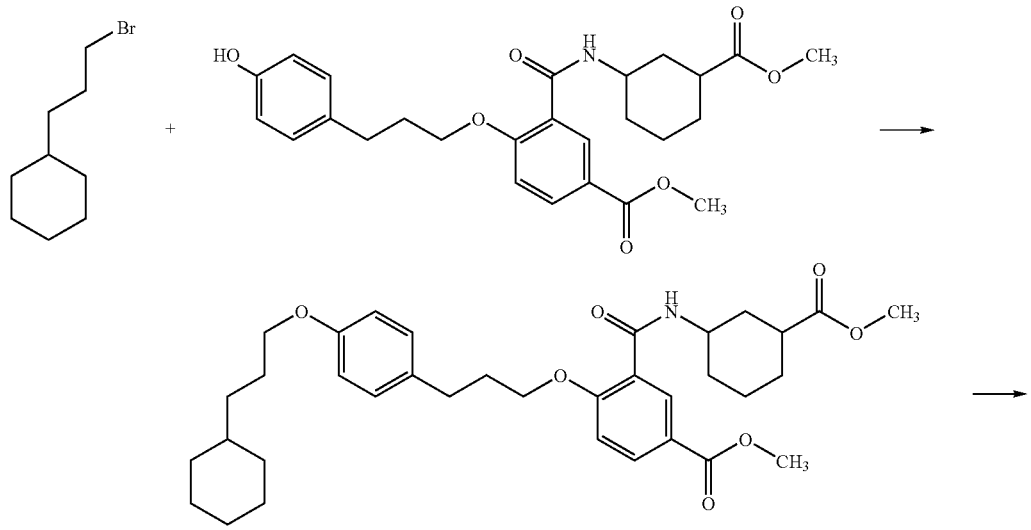
[D]
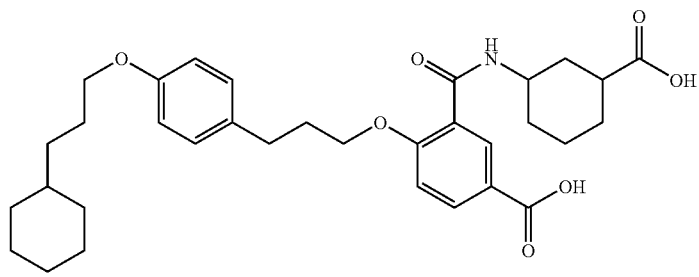
Compounds of the formula (II) can be prepared for example by reacting compounds of the formula (IVa) with compounds of the formula (VI)
in which
R² is (C₁-C₆)-alkyl,
to give compounds of the formula (VII)
(VI)
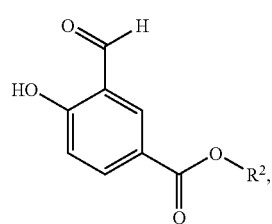
(VII)
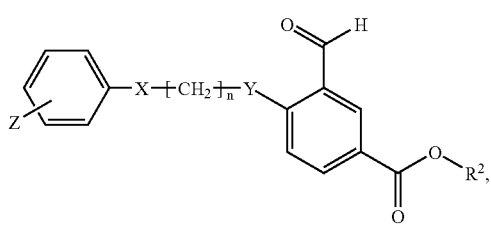

in which
R² is (C₁-C₆)-alkyl,
Y is O, and
n, X and Z have the meaning indicated above, and subsequently oxidizing the aldehyde group.

Compounds of the formula (IVa) can be prepared for example by converting compounds of the formula (VIII)

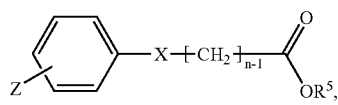
(VIII)

in which
R⁵ is hydrogen or an alkyl radical, and
n, X and Z have the meaning indicated above, by reduction of the carboxylic acid or ester group into the corresponding alcohols of the formula (IX)

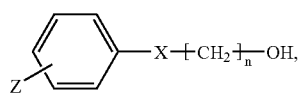
(IX)

in which
n, X and Z have the meaning indicated above, and finally converting the hydroxyl group into a leaving group such as, for example, halogen, mesylate or tosylate.

Compounds of the formula (IVb) can be prepared for example from compounds of the formula (VIII) by, in the case where R⁵ in compounds of the formula (VIII) is hydrogen, converting the carboxylic acid group into the corresponding acid chloride or, in the case of compounds of the formula (VIII) in which R⁵ is an alkyl group, in a preceding step hydrolysing the corresponding ester group initially to the carboxylic acid group.

Compounds of the formula (Va) can be prepared for example by reacting compounds of the formula (III) with compounds of the formula (X)

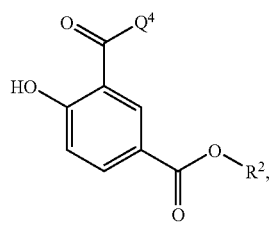
(X)

in which,
Q⁴ is hydroxyl or chlorine, and
R¹ is (C₁-C₆)-alkyl.

Compounds of the formula (Vb) can be prepared for example by, in a first amide coupling reaction, reacting compounds of the formula (III) with compounds of the formula (XI)

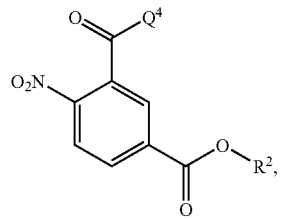
(XI)

in which
Q⁴ is hydroxyl or chlorine, and
R² is (C₁-C₆)-alkyl, and finally reducing the nitro group to the corresponding amino group.

Compounds of the formula (VIIIa), corresponding to compounds of the formula (VIII), in which X is an oxygen atom and R⁵ is an alkyl radical, can be prepared for example by reacting compounds of the formula (XIV)

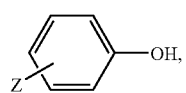
(XIV)

in which
Z has the meaning indicated above, with compounds of the formula (XV)

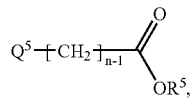
(XV)

in which
Q⁵ is a suitable leaving group such as, for example, halogen, mesylate or tosylate, and
R⁵ is an alkyl radical.

Compounds of the formula (VIIIb), corresponding to compounds of the formula (VIII), in which X is a bond or —CH=CH—, Z is *—O-L-M-R⁴ and R⁵ is an alkyl radical, can be prepared for example by reacting compounds of the formula (XIII) with compounds of the formula (XVI)

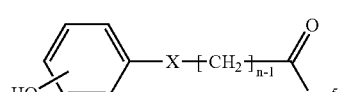
(XVI)

in which
R⁵ is an alkyl radical,
X is a bond or —CH=CH—, and
n has the meaning indicated above.

Compounds of the formula (VIIIc), corresponding to compounds of the formula (VIII), in which X is a bond, Z is

*-L-M-R⁴ and R⁵ is an alkyl radical, can be prepared for example by reacting compounds of the formula (XVII)

—R⁴-M-L-PPh₃⁺Br⁻ (XVII), in which
R⁴, M and L have the meaning indicated above, with compounds of the formula (XVIII)

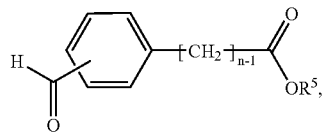

in which
R⁵ is an alkyl radical, and
n has the meaning indicated above.

Compounds of the formula (IXa), corresponding to compounds of the formula (IX), in which X is —C≡C— and n is 1, can be prepared for example by reacting compounds of the formula (XIX)

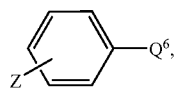

in which
Q⁶ is a suitable leaving leaving group such as, for example, bromine, iodine or trifluoromethanesulphonate, and
Z has the meaning indicated above, with propargyl alcohol.

Compounds of the formula (XII) can be prepared for example by reacting compounds of the formula (Va) with compounds of the formula (XX)

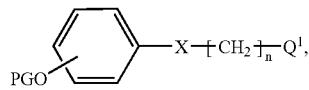

in which
Q¹ is a suitable leaving group such as, for example, halogen, mesylate or tosylate,
PG is a suitable protective group such as, for example, a silyl protective group, and
n and X have the meaning indicated above, and subsequently eliminating the protective group by conventional methods known to the skilled person.

Compounds of the formula (XX) can be prepared for example by reacting compounds of the formula (XVI) with conventional protective group reagents known to the skilled person, such as, for example, triisopropylsilyl chloride, and subsequently converting the carboxylic acid or ester group into the leaving group Q¹ as described for compounds of the formula (IVa).

Compounds of the formula (I) in which R¹ is hydrogen can also be prepared from the corresponding benzyl esters (R¹=benzyl) instead of from the corresponding alkyl esters of the compounds of the formulae (III), (Va) or (Vb) R¹=alkyl).

In the amide couplings of process steps (II)+(III)->(I); (III)+(X)->(Va) (for Q⁴=hydroxyl) and of the first constituent step (III)+(XI)->(Vb) (for Q⁴=hydroxyl), the amines are preferably employed in the form of their hydrochlorides. The reactions preferably take place under standard conditions in the presence of generally customary reagents for amide or peptide coupling such as, for example, N-[(3-dimethylamino)propyl]-N'-ethylcarbodiimide hydrochloride (EDC) and 1-hydroxy-1H-benzotriazole hydrate (HOBT) in the presence of auxiliary bases such as triethylamine or diisopropylethylamine, in solvents such as dichloromethane or dimethylformamide at room temperature.

In the amide couplings of process steps (III)+(X)->(Va) (for Q⁴=chlorine) and of the first constituent step (III)+(XI)->(Vb) (for Q⁴ equal to chlorine), the amines are preferably employed in the form of their hydrochlorides. The reactions preferably take place under standard conditions in the presence of auxiliary bases such as triethylamine or diisopropylethylamine, in solvents such as diethyl ether, tetrahydro-furan or methylene chloride at temperatures between 0° C. and room temperature.

The ester hydrolysis in the preparation of compounds (I) by process [D], in which R¹ and R² are hydrogen, and in the first constituent step of the reaction (VIII)->(IVb) preferably takes place in the presence of aqueous alkali metal hydroxide solution such as, for example, 2-molar sodium hydroxide solution, at temperatures between room temperature and 70° C. with addition of water-miscible organic solvents such as, for example, methanol or tetrahydrofuran or mixtures thereof.

Process steps (IVa)+(Va)->(I); (IVa)+(Vb)->(I); (IVa)+(VI)->(VII); (XII)+(XIII)->(I); (XIV)+(XV)->(VIIIa); (XIII)+(XVI)->(VIIIb) and (Va)+(XX)->(XII) preferably take place in inert solvents such as, for example, tetrahydrofuran, dioxane, dimethylformamide, N-methylpyrrolidone, acetonitrile, acetone or butyronitrile, in the presence of auxiliary bases such as, for example, potassium carbonate, sodium carbonate, caesium carbonate, triethylamine, ethyldiisopropyl-amine or pyridine in a temperature range between room temperature and the boiling point of the particular solvent.

An alternative possibility for the preparation of compound (VII) is also by reacting the alcohol (IX) with compound (VI) under Mitsunobu reaction conditions. Solvents suitable for this purpose are, in particular, ethers such as, for example, tetrahydrofuran or chlorohydrocarbons such as, for example, dichloromethane. The reaction takes place in the presence of triphenylphosphine and azo compounds such as, for example, diethyl azodicarboxylate (DEAD) or diisopropyl azodicarboxylate (DIAD). The preferred temperature range for carrying out the reaction is between –10° C. and room temperature.

Process step (IVb)+(Vb)->(I) preferably takes place in an inert solvent such as, for example, in ether, tetrahydrofuran, dichloromethane or chloroform in the presence of an auxiliary base such as, for example, triethylamine, diisopropylethylamine or pyridine at temperatures between 0° C. and room temperature.

Process step (VII)->(II) takes place under conventional conditions known to the skilled person for oxidizing aldehyde groups to carboxylic acid groups. Oxidation with sodium chlorite in the presence of hydrogen peroxide and sodium dihydrogen phosphate or in the presence of sulphamic acid in a solvent mixture composed of water with acetonitrile or tetrahydrofuran or dioxane in the temperature range between 0° C. and room temperature is very suitable for example in this connection.

Process step (VIII)->(IX) takes place under conventional conditions known to the skilled person for reducing carboxylic acid or ester groups to the corresponding alcohol groups such as, for example, with complex metal hydrides such as lithium aluminium hydride in inert solvents such as, for example, tetrahydrofuran in the temperature range between 0° C. and the boiling point of the particular solvent.

Conversion of the alcohol function into a leaving group $Q^1$ in process step (IX)->(IVa) can take place in various ways known to the skilled person. The reaction to give the corresponding bromide preferably takes place in tetrahydrofuran as solvent at room temperature with a mixture of triphenylphosphine and tetrabromomethane or in dichloromethane as solvent in the temperature range between 0° C. and room temperature with phosphorus tribromide, where appropriate in the presence of pyridine. The reaction to give the corresponding mesylate or tosylate preferably takes place in dichloromethane as solvent in the temperature range between 0° C. and room temperature with methanesulphonyl chloride or para-toluenesulphonyl chloride in the presence of tertiary amines such as, for example, triethylamine or diisopropylethylamine.

The carboxylic acid group obtained in the first constituent step of the reaction (VIII)->(IVb) is converted by chlorination into the corresponding acid chloride. Preferred chlorination reagents are thionyl chloride or oxalyl chloride. The reaction takes place where appropriate in the presence of catalytic amounts of dimethylformamide, it being possible to add halogenated hydrocarbons such as, for example, dichloromethane or chloroform as solvents. The reaction temperature in this case is between 0° C. and the boiling point of the particular solvent or chlorination reagent.

Reduction of the nitro group in the second constituent step of the reaction (III)+(XI)->(Vb) can take place for example with tin(II) chloride. Reduction with hydrogen on noble metal catalysts such as, for example, palladium on charcoal as support material, under a hydrogen pressure of from one to four bar and at room temperature in methanol, ethanol or ethyl acetate as solvent is preferred.

Process step (XVII)+(XVII)->(VIIIc) takes place under conventional conditions known to the skilled person for the Wittig reaction. The reaction preferably takes place in an inert solvent such as, for example, in hexane, diethyl ether, toluene or tetrahydrofuran, particularly preferably in tetrahydrofuran, in the presence of a strong base such as, for example n-butyllithium or sodium bis(trimethylsilyl)amide at temperatures between −50° C. and room temperature.

Process step (XIX)->(IXa) preferably takes place in triethylamine as solvent in the presence of copper(I) iodide, a palladium(II) salt such as, for example, dichlorobis(triphenylphosphine)palladium ([Pd(PPh$_3$)$_2$]Cl$_2$) and triphenylphosphine at temperatures between 50° C. and 70° C.

The compounds of the formula (III), (VI), (VIII), (X), (XI), (XIII), (XIV), (XV), (XVI), (XVII), (XVIII), (XIX) and (XX) are known per se to the skilled person or can be prepared by conventional processes known from the literature.

It is additionally possible to prepare compounds of the formula (I)

in which

A is

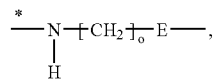

$R^1$ is hydrogen,
$R^2$ is hydrogen,
n is 3,
X is a bond,
Y is O,
Z is located in the position para to the substituent X,
G is O, and
E, L, M, $R^4$, m and o have the meaning indicated above also with the aid of solid-phase synthesis:

onto a solid phase from the group of micro- or macroporous polystyrene (PS) crosslinked with between 1 and 30% divinylbenzene (DVB), poly-styrene/polyethylene glycol (PS/PEG) graft or block copolymers and functionalized glass surfaces (controlled pore glass, CPG), primary amines are attached as imine via a benzaldehyde functionality present on the solid phase and are then reduced to the secondary amine. For this purpose preferably 4-(4-formyl-3-methoxyphenoxy) butyrylaminomethyl resin based on PS crosslinked with 2% DVB ("Pol-CHO", Nova Biochem) is reacted with a two- to five-fold excess of a cyclic or acyclic β-, γ- or δ-amino acid which is t-butyl- or t-hexyl-protected on the acid functionality, preferably as hydrochlorides thereof, in dimethylformamide, N-methylpyrrolidone, dichloromethane, dioxane, tetrahydrofuran, toluene or other suitable solvents with or without dehydrating agents such as trimethyl orthoformate, sodium sulphate or magnesium sulphate, where appropriate in the presence of auxiliary bases such as potassium carbonate, sodium carbonate, triethylamine, ethyldiisopropylamine and pyridine at temperatures between room temperature and 50° C. for 2 to 24 hours (reaction a):

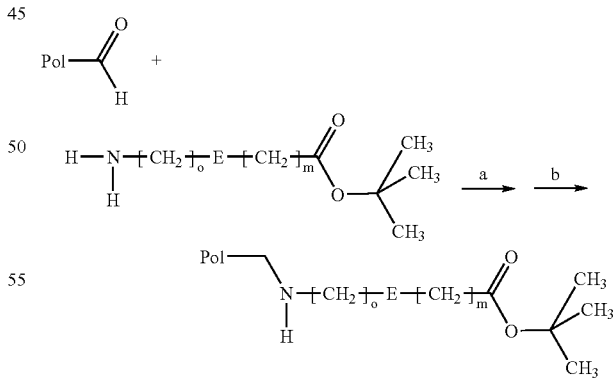

The solid phase is then either washed one or more times with various solvents such as dimethylformamide, N-methylpyrrolidone, dichloromethane, dioxane, tetrahydrofuran, toluene, acetonitrile or methanol or directly reacted further in the subsequent reduction. For this purpose, the solid phase is reacted with a two- to ten-fold excess of reducing agents such as sodium borohydride, sodium cyanoborohydride, sodium triacetoxyborohydride or tetrabutylammonium borohydride in solvents such as dichloromethane, dimethylformamide, tetrahydrofuran or methanol or else mixtures of these at temperatures between −78° C. and room temperture, where appropriate with addition of up to 100 equivalents of acetic acid for 0.5 to 18 hours (reaction b).

After the solid phase has been washed and dried by conventional processes known to the skilled person, it is then reacted with 2-hydroxy-5-methoxycarbonylbenzoic acid.

The reagents known to the skilled person for amide or peptide coupling are employed for this purpose. Examples thereof are N-[(3-dimethylamino)propyl]-N'-ethylcarbodiimide hydrochloride (EDC) and 1-hydroxy-1H-benzotriazole hydrate (HOBT), which are employed in the presence of auxiliary bases such as triethylamine or diisopropylethylamine in solvents such as dichloromethane or dimethylformamide at room temperature (reaction c).

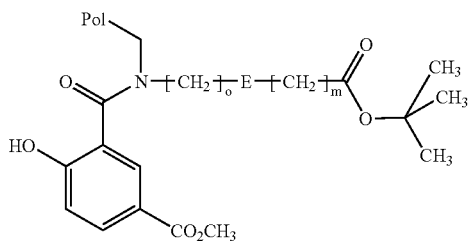

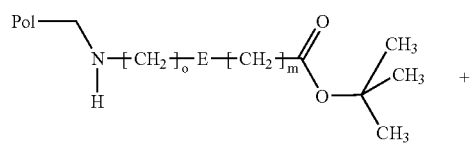

+

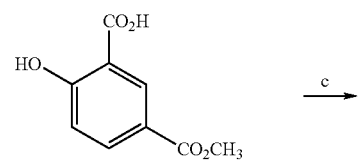

c →

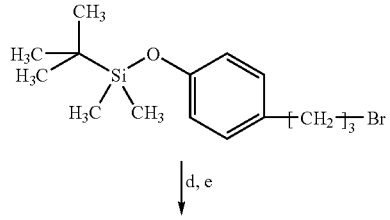

d, e ↓

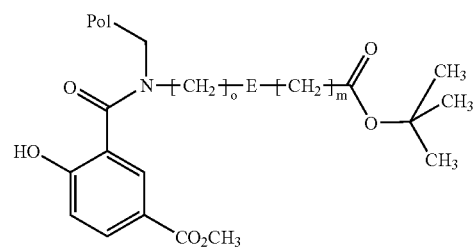

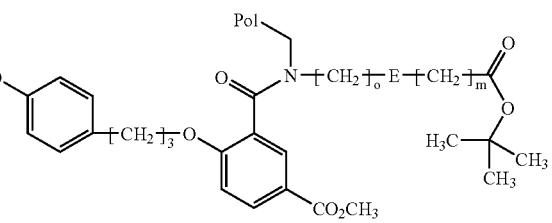

After the solid phase has been washed and dried by conventional processes known to the skilled person, it is then reacted with 1 to 5 equivalents of 3-bromo-1-(4-tert-butyldimethylsilyloxyphenyl)propane or 3-bromo-1-(4-tri-isopropylsilyloxy-phenyl)propane and a base from the group of sodium carbonate, sodium hydride, potassium carbonate and caesium carbonate in polar aprotic solvents such as tetrahydrofuran, dioxane, dimethylformamide, N-methylpyrrolidone, where appropriate with addition of 18-crown-6 or tetrabutylammonium iodide at temperatures between room temperature and the boiling point of the appropriate solvent for 1-24 hours (reaction d). After the solid phase has been washed and dried by conventional processes known to the skilled person it is then reacted with 2 to 10 equivalents of tetrabutylammonium fluoride in tetrahydrofuran at room temperature for 2-24 hours, and the silyl protective group is thus eliminated (reaction e).

After the solid phase has been washed and dried by conventional processes known to the skilled person, it is then reacted with compounds of the formula $R^4$-M-L-$Q^3$ where $Q^3$ is chlorine, bromine, iodine, mesylate, tosylate or another leaving group known to the skilled person in nucleophilic substitution reactions. The reactions are carried out using a base from the group of sodium carbonate, sodium hydride, potassium carbonate and caesium carbonate in polar aprotic solvents such as tetrahydrofuran, dioxane, dimethylformamide, N-methylpyrrolidone, where appropriate with addition of 18-crown-6 or tetrabutylammonium iodide, at temperatures between room temperature and the boiling point of the particular solvent for 1-24 hours (reaction f). After the solid phase has been washed and dried by conventional processes known to the skilled person, the methyl ester on it is then hydrolyzed with bases such as sodium carbonate, potassium carbonate, caesium carbonate, sodium hydroxide or potassium hydroxide in mixtures of polar solvents such as tetrahydrofuran, dioxane or N-methylpyrrolidone with water or methanol at temperatures between 0° C. and 60° C. (reaction g).

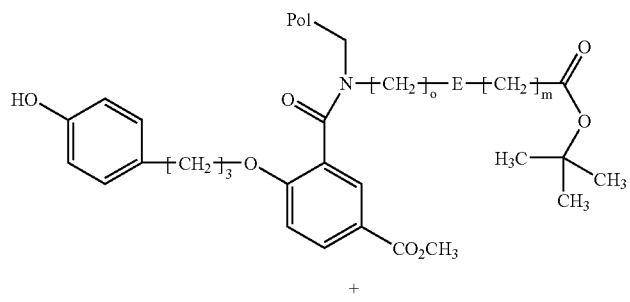

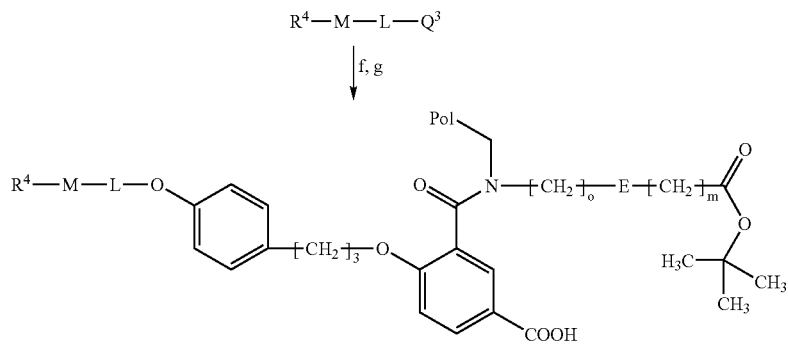

The solid phase is thoroughly washed with conventional solvents such as methanol, dichloromethane, water, dimethylformamide, N-methylpyrrolidone, dioxane, tetrahydrofuran, acetonitrile or toluene and then dried. The product is subsequently eliminated from the solid phase with a mixture of 20-70% trifluoroacetic acid in dichloromethane, with spontaneous removal of the t-butyl protective group (reaction h). After filtration to remove the solid phase and concentration in vacuo at temperatures between 0° C. and 100° C., the products have purities between 75% and 100%.

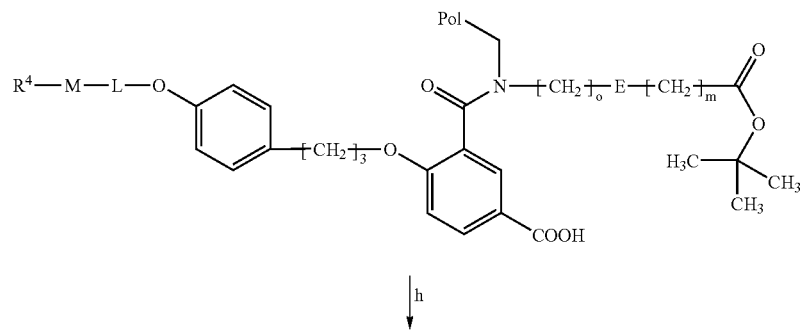

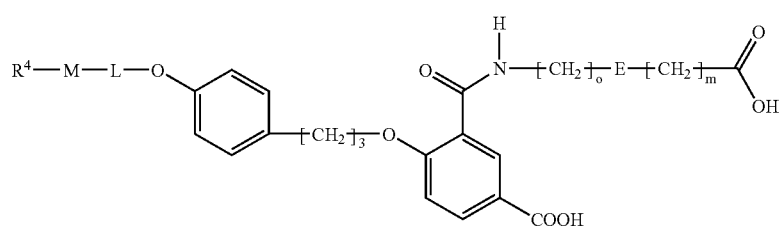

The compounds of the invention show a valuable pharmacological and pharmacokinetic spectrum of effects which could not have been predicted. They are therefore suitable for use as medicaments for the treatment and/or prophylaxis of diseases in humans and animals.

The pharmaceutical activity of the compounds of the invnetion of the formula (I) can be explained by their effect as selective antagonists of the cysteinyl-leukotriene receptor 2.

Cysteinyl-leukotriene receptor antagonists referred to as "selective" for the purposes of the present invention are those which inhibit the activity of the cysteinyl-leukotriene receptor 2 at a concentration which is lower by a factor of more than 10, preferably by a factor or more than 100, in particular by a factor of more than 1000, than an equivalent activity of the cysteinyl-leukotriene receptor 1. Concerning the test methods for determining the selectivity, reference may be made to the test methods described in section B 1. and B 2.

Modulators of the cysteinyl-leukotriene receptors referred to as "antagonists" for the purposes of the present invention are those having antagonistic activity and comprising merely a partial, preferably no measurable, agonistic component.

The compounds of the formula (I) are suitable for the prophylaxis and/or treatment of various disorders, in particular of cardiovascular disorders.

Preferred examples which may be mentioned are: atrial and ventricular arrhythmias, myocardial infarction, arteriosclerosis, heart failure, stable and unstable angina pectoris, myocardial ischaemia, transient ischaemic attacks, stroke, inflammatory cardiovascular disorders, coronary heart disease, peripheral and cardiac vascular disorders, peripheral blood flow disturbances, restenoses such as following thrombolysis therapies, percutaneous transluminal angioplasties (PTA) and transluminal coronary angioplasties (PTCA), pulmonary hypertension, coronary spasms, thromboses, thromboembolic disorders, bypass operations, heart transplants, oedema formation, shock, high blood pressure, acute renal failure, inflammatory disorders, asthmatic disorders, chronic obstructive airways disease (COPD), states of pain, prostate hypertrophy, inflammatory skin disorders, placental insufficiency, placentation disturbances, incontinence, cystitis, hyperactive bladder, disorders of the adrenal such as, for example, phaeochromocytoma and Waterhouse-Friderichsen syndrome, intestinal disorders such as, for example, Crohn's disease or diarrhoea.

The present invention further relates to the use of the compounds of the invention for the treatment and/or prophylaxis of disorders, in particular of the aforementioned disorders.

The present invention further relates to the use of the compounds of the invention for producing a medicament for the treatment and/or prophylaxis of disorders, in particular of the aforementioned disorders.

The present invention further relates to a method for the treatment and/or prophylaxis of disorders, in particular of the aforementioned disorders, using an effective amount of the compounds of the invention.

The present invention further relates to medicaments comprising at least one compound of the invention and one or more other active ingredients, in particular for the treatment and/or prophylaxis of the aforementioned disorders. Examples of suitable and preferred active ingredients in the combination which may be mentioned are: cysteinyl-leukotriene receptor 1 antagonist, cysteinyl-leukotriene-biosynthesis inhibitor, thrombolytics, a platelet aggregation inhibitor, β-blockers, nitrates, Ca channel blockers and/or an anti-inflammatory active ingredient such as, for example, a cyclooxygenase inhibitor.

The compounds of the invention may have systemic and/or local effects. They can for this purpose be administered in a suitable way, such as, for example, by the oral, parenteral, pulmonary, nasal, sublingual, lingual, buccal, rectal, dermal, transdermal, conjunctival or otic route or as implant or stent.

The compounds of the invention can be administered in suitable administration forms for these administration routes.

Administration forms suitable for oral administration are those which function according to the state of the art and deliver the compounds of the invention in a rapid and/or modified way, and which contain the compounds of the invention in crystalline and/or amorphized and/or dissolved form, such as, for example, tablets (uncoated or coated tablets, for example with coatings which are resistant to gastric juice or dissolve slowly or are insoluble and which control the release of the compound of the invention), tablets which rapidly disintegrate in the mouth, or films/wafers, films/lyophilisates, capsules (for example hard or soft gelatin capsules), sugar-coated tablets, granules, pellets, powders, emulsions, suspensions, aerosols or solutions.

Parenteral administration can take place with avoidance of an absorption step (e.g. intravenous, intraarterial, intracardiac, intraspinal or intralumbar) or with inclusion of an absorption (e.g. intramuscular, subcutaneous, intracutaneous, percutaneous or intraperitoneal). Administration forms suitable for parenteral administration are, inter alia, injection and infusion preparations in the form of solutions, suspensions, emulsions, lyophilisates or sterile powders.

Examples suitable for other administration routes are medicinal forms for inhalation (inter alia powder inhalators, nebulizers), nasal drops, solutions, sprays; tablets for lingual, sublingual or buccal administration, films/wafers or capsules, suppositories, preparations for the ears or eyes, vaginal capsules, aqueous suspensions (lotions, shaking mixtures), lipophilic suspensions, ointments, creams, transdermal therapeutic systems (such as, for example, plasters), milk, pastes, foams, dusting powders, implants or stents.

Parenteral, in particular intravenous administration is preferred, e.g. as iv bolus injection (i.e. as single dose, e.g. by syringe), short infusion (i.e. infusion over a period of up to one hour) or long infusion (i.e. infusion over a period of more than one hour). The administered volume may in these cases be, depending on the specific conditions, between 0.5 to 3.0, in particular 1 to 20, ml on iv bolus injection, between 25 to 500, in particular 50 to 250, ml on short infusion and between 50 to 1000, in particular 100 to 500, ml on long infusion. It may for this purpose be advantageous for the active ingredient to be provided in the solid form (e.g. as lyophilisate or as salt) and to be dissolved in the dissolving medium only directly before administration.

It is necessary in these cases that the administration forms be sterile and pyrogen-free. They may be based on aqueous or mixtures of aqueous and organic solvents. These include, for example, aqueous solutions, mixtures of aqueous and organic solvents (especially ethanol, polyethylene glycol (PEG) 300 or 400), aqueous solutions containing cyclodextrins or aqueous solutions containing emulsifiers (surface-active solubilizers, e.g. lecithin or Pluronic F 68, Solutol HS15, Cremophor). Aqueous solutions are preferred.

Formulations suitable for parenteral administration are those which are substantially isotonic and euhydric, e.g. those with a pH between 3 and 11, preferably between 6 and 8, in particular around 7.4.

Injection solutions are packaged in suitable containers made of glass or plastic, e.g. in vials. The solution can be removed directly therefrom and administered. In the case of a lyophilisate, it is dissolved in the vial by injecting a suitable solvent and is then removed. Infusion solutions are packaged in suitable containers made of glass or plastic, e.g. in bottles or collapsible plastic bags.

The compounds of the invention can be converted into the stated administration forms. This can take place in a manner known per se by mixing with inert, non-toxic, pharmaceutically suitable excipients. These excipients include, inter alia, carriers (for example microcrystalline cellulose, lactose, mannitol), solvents (e.g. liquid polyethylene glycols), emulsifiers and dispersants or wetting agents (for example sodium dodecylsulphate, polyoxysorbitan oleate), binders (for example polyvinylpyrrolidone), synthetic and natural polymers (for example albumin), stabilizers (e.g. antioxidants such as, for example, ascorbic acid), colours (e.g. inorganic pigments such as, for example, iron oxides) and masking tastes and/or odours.

The present invention further relates to medicaments which comprise at least one compound of the invention, normally together with one or more inert, non-toxic, pharmaceutically suitable excipients, and to the use thereof for the aforementioned purposes.

It has generally proved advantageous both in human and in veterinary medicine to administer the active ingredient of the invention in total amounts of about 0.01 to about 700, preferably 0.01 to 100 mg/kg of body weight every 24 hours, where appropriate in the form of a plurality of single doses, to achieve the desired results. A single dose preferably contains the active ingredient of the invention in amounts of about 0.1 to about 80, in particular 0.1 to 30, mg/kg of body weight.

It may nevertheless be necessary to deviate from the stated-amounts, in particular as a function of body weight, administration route, individual behaviour towards the active ingredient, type of preparation and time or interval over which administration takes place. Thus, it may in some cases be sufficient to make do with less than the aforementioned minimum amount, whereas in other cases the stated upper limit must be exceeded. Where larger amounts are administered, it may be advisable to divide them into a plurality of single doses over the day.

The percentage data in the following tests and examples are, unless indicated otherwise, percentages by weight; parts are parts by weight. Solvent ratios, dilution ratios and concentration data for liquid/liquid solutions are in each case based on volume.

A. EXAMPLES

Abbreviations:

| | |
|---|---|
| b.p. | boiling point |
| conc. | concentrated |
| DCI | direct chemical ionization (in MS) |
| TLCM | dichloromethane |
| DIEA | N,N-diisopropylethylamine |
| DMSO | dimethyl sulphoxide |
| DMF | N,N-dimethylformamide |
| EA | ethyl acetate (acetic acid ethyl ester) |
| EI | electron impact ionization (in MS) |
| ESI | electrospray ionization (in MS) |
| h | Hour |
| HPLC | high pressure, high performance liquid chromatography |
| LC-MS | coupled liquid chromatography/mass spectroscopy |
| LDA | lithium diisopropylamide |
| m.p. | melting point |
| MPLC | medium pressure, medium performance liquid chromatography |
| MS | mass spectroscopy |
| NMR | nuclear magnetic resonance spectroscopy |
| RP-HPLC | reverse phase HPLC |
| RT | room temperature |
| $R_f$ | retention index (in TLC) |
| $R_t$ | retention time (in HPLC) |
| sat. | Saturated |
| TFA | trifluoroacetic acid |
| THF | Tetrahydrofuran |
| TLC | thin-layer chromatography |

HPLC and LC-MS methods:

Method 1 (HPLC)

Instrument: HP 1100 with DAD; column: Kromasil RP-18, 60 mm×2 mm, 3.5 µm; eluent A: 5 ml $HClO_4$/l of water, eluent B: acetonitrile; gradient: 0 min 2% B, 0.5 min 2% B, 4.5 min 90% B, 6.5 min 90% B; flow rate: 0.75 ml/min; oven: 30° C.; UV detection: 210 nm.

Method 2 (HPLC)

Instrument: HP 1100 with DAD; column: Kromasil RP-18, 60 mm×2 mm, 3.5 µm; eluent A: 5 ml $HClO_4$/l of water, eluent B: acetonitrile; gradient: 0 min 2% B, 0.5 min 2% B, 4.5 min 90% B, 9 min 90% B; flow rate: 0.75 ml/min; oven: 30° C.; UV detection: 210 nm.

Method 3 (LC-MS)

MS apparatus type: Micromass ZQ; HPLC apparatus type: Waters Alliance 2790; column: Grom-Sil 120 ODS-4 HE 50 mm×2 mm, 3.0 µm; eluent B: acetonitrile+0.05% formic acid, eluent A: water+0.05% formic acid; gradient: 0.0 min 5% B→2.0 min 40% B→4.5 min 90% B→5.5 min 90% B; oven: 45° C.; flow rate: 0.0 min 0.75 ml/min→4.5 min 0.75 ml/min→5.5 min 1.25 ml/min; UV detection: 210 nm.

Method 4 (HPLC)

Instrument: HP 1100 with DAD; column: Kromasil RP-18, 60 mm×2 mm, 3.5 µm; eluent A: 5 ml of $HClO_4$/l of water, eluent B: acetonitrile; gradient: 0 min 2% B, 0.5 min 2% B, 4.5 min 90% B, 15 min 90% B; flow rate: 0.75 ml/min; oven: 30° C.; UV detection: 210 nm.

Method 5 (HPLC)

Instrument: Symmetry TM C18 3.9*150 mm; flow 1,5 ml/min; eluent water (A)/acetonitrile (B); gradient −0.6 min 10% of B, −3.8 min 100% B, −5.0 min 100% B, −5.5 min 10% B; stop time 6.0 min; injection volume 10 µl ; diode array detector signal 214 nM and 254 nm.

Method 6 (LC-MS)

MS apparatus type: Micromass ZQ; HPLC apparatus type: Waters Alliance 2795; column: Phenomenex Synergi 2µ Hydro-RP Mercury 20 mm×4 mm; eluent A: 1 l of water+0.5 ml of 50% strength formic acid, eluent B: 1 l of acetonitrile+ 0.5 ml of 50% strength formic acid; gradient: 0.0 min 90% A→2.5 min 30% A→3.0 min 5%/A→4.5 min 5%/A; flow rate: 0.0 min 1 ml/min, 2.5 min/3.0 min/4.5 min 2 ml/min; oven: 50° C.; UV detection: 210 nm.

Method 7 (LC-MS)

MS apparatus type: Micromass ZQ; HPLC apparatus type: HP 1100 series; UV DAD; column: Phenomenex Synergi 2µ Hydro-RP Mercury 20 mm×4 mm; eluent A: 1 l of water+0.5 ml of 50% strength formic acid, eluent B: 1 l of acetonitrile+ 0.5 ml of 50% strength formic acid; gradient: 0.0 min 90% A 2.5 min 30% A→3.0 min 5% A→4.5 min 5% A; flow rate: 0.0 min 1 ml/min, 2.5 min/3.0 min/4.5 min. 2 ml/min; oven: 50° C.; UV detection: 210 nm.

Method 8 (LC-MS)

MS apparatus type: Micromass ZQ; HPLC apparatus type: BP 11100 series; UV DAD; column: Grom-Sil 120 ODS-4 HE 50 mm×2 mm, 3.0 μm; eluent A: water+500 μl of 50% strength formic acid/1, eluent B: acetonitrile+500 μl of 50% strength formic acid/1; gradient: 0.0 min 0% B→2.9 min 70% B→3.1 min 90%/B→4.5 min 90% B; oven: 50° C.; flow rate: 0.8 ml/min; UV detection: 210 nm.

Method 9 (LC-MS)

MS apparatus type: Micromass ZQ; HPLC apparatus type: Waters Alliance 2795; column: Merck Chromolith Speed-ROD RP-18e 50 mm×4.6 mm; eluent A: water+500 μl of 50% strength formic acid/1; eluent B: acetonitrile+500 μl of 50% strength formic acid/1; gradient: 0.0 min 10% B→3.0 min 95% B→4.0 min 95% B; oven: 35° C.; flow rate: 0.0 min 1.0 ml/min→3.0 min 3.0 ml/min→4.0 min 3.0 ml/min; UV detection: 210 nm.

Method 10 (LC-MS)

Instrument: Micromass Platform LCZ with HPLC Agilent series 1100; column: Grom-SIL120 ODS-4 HE, 50 mm×2.0 mm, 3 μm; eluent A: 1 l of water+1 ml of 50% strength formic acid, eluent B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 210 nm.

Method 11 (LC-MS)

MS apparatus type: Micromass ZQ; HPLC apparatus type: Waters Alliance 2790; column: Grom-Sil 120 ODS-4 HE, 50 mm×2 mm, 3.0 μm; eluent A: 1 l of water+500 μl of 50% strength formic acid; eluent B: 1 l of acetonitrile+500 μl of 50% strength formic acid; gradient: 0.0 mm 0% B→0.2 min 0% B→2.9 min 70% B→3.1 min 90% B→4.5 min 90% B; oven: 45° C.; flow rate: 0.8 ml/min; UV detection: 210 nm.

Method 12 (HPLC)

Instrument: HP 1100 with DAD; column: Kromasil 100 RP-18, 125 mm×4 mm, 5 μm; eluent A: 1 l of water+4 vials PIC B7, eluent B: acetonitrile; gradient: 0.0 min 2% B, 1.0 min 2% B, 9.0 min 90% B, 13 min 90% B, 13.5 min 2% B, 15.5 min 2% B; flow rate: 2 ml/min; oven: 30° C.; UV detection: 210 nm. (PIC B7: heptanesulphonic acid from Millipore/Waters Corp.)

Method 13 (LC-MS)

Instrument: Micromass Platform LCZ with HPLC Agilent series 1100; column: Grom-SIL120 ODS-4 HE, 50 mm×2.0 mm, 3 μm; eluent A: 1 l of water+1 ml of 50% strength formic acid, eluent B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Method 14 (LC-MS)

Instrument: Micromass Quattro LCZ, with HPLC Agilent series 1100; column: Grom-SIL120 ODS-4 HE, 50 mm×2.0 mm, 3 μm; eluent A: 1 l of water+1 ml of 50% strength formic acid, eluent B: 1 l of acetonitrile+1 ml of 50% strength formic acid; gradient: 0.0 min 100% A→0.2 min 100% A→2.9 min 30% A→3.1 min 10% A→4.5 min 10% A; oven: 55° C.; flow rate: 0.8 ml/min; UV detection: 208-400 nm.

Starting Compounds

Example I

Methyl 3-[4-(4-phenoxybutoxy)phenyl]propanoate

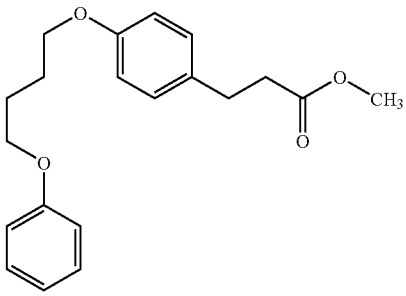

A solution of 10.0 g of methyl 3-(4-hydroxyphenyl)propanoate and 12.7 g of 4-phenoxy-1-butyl bromide in 100 ml of acetonitrile is mixed with 11.5 g of potassium carbonate and heated to reflux for 15 hours. The solvent is then removed in a rotary evaporator, and the residue is taken up in ethyl acetate and water. After phase separation, the aqueous phase is extracted with ethyl acetate. The combined organic phases are washed with saturated sodium chloride solution and dried over anhydrous sodium sulphate. The crude product after evaporation is purified by suction filtration through silica gel with cyclohexane/ethyl acetate 19:1. 12.6 g of product are obtained.

TLC: $R_f$: 0.36 (cyclohexane/ethyl acetate 1:1).

HPLC (method 1): $R_t$: 5.41 min.

$^1$H-NMR (200 MHz, DMSO-$d_6$, δ/ppm): 7.32-7.23 (m, 2H), 7.11 (d, 2H), 6.96-6.82 (m, 5H), 3.98 (m, 4H), 3.57 (s, 3H), 2.77 (t, 3H), 2.57 (t, 2H), 1.85 (m, 4H).

MS (ESI+): m/z=329 (M+H$^+$), 351 (M+Na$^+$).

Example II

3-[4-(4-phenoxybutoxy)phenyl]-1-propanol

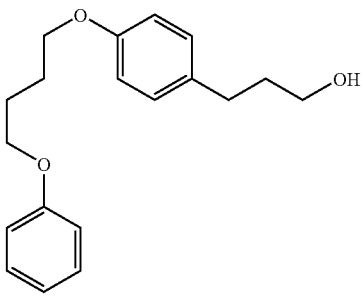

20.1 ml of a 1 molar solution of lithium aluminium hydride in tetrahydrofuran is introduced. While stirring, a solution of 12.0 g of methyl 3-[4-(4-phenoxybutoxy)-phenyl]propanoate in 40 ml of THF is added dropwise in such a way that the mixture just starts to boil. The mixture is stirred at room temperature for 30 minutes. 1 ml of methanol is cautiously added to the suspension in order to hydrolyze excess lithium aluminium hydride. The mixture is then added to 1 molar hydrochloric acid and extracted with ethyl acetate. The organic phase is separated off, washed with saturated sodium chloride solution and dried over anhydrous sodium sulphate. Filtration and evaporation result in 10.9 g of product.

HPLC (method 1): $R_t$: 4.94 min.

$^1$H-NMR (300 MHz, DMSO-$d_6$, δ/ppm): 7.30-7.24 (m, 2H), 7.08 (d, 2H), 6.95-6.88 (m, 3H), 6.83 (d, 2H), 4.39 (t, 1H), 4.01 (m, 4H), 3.38 (quart, 2H), 2.53 (t, 2H), 1.83 (m, 4H), 1.67 (m, 2H).

MS (ESI+): m/z=301 (M+H$^+$), 323 (M+Na$^+$).

Example III

3-[4-(1,1'-Biphenyl-4-ylmethoxy)phenyl]-1-propanol

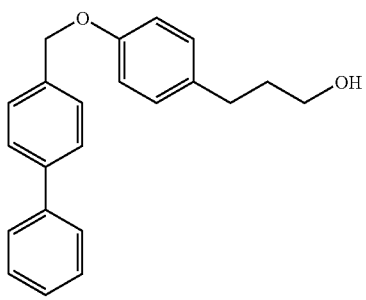

12.8 g (41.4 mmol) of 4-phenylbenzyl bromide, 6.94 g (45.6 mmol) of 4-hydroxy-phenylpropanol and 6.87 g (49.7 mmol) of potassium carbonate are stirred in 50 ml of butyronitrile at 120° C. for 6 hours. Cooling to room temperature is followed by removal of the inorganic salts by filtration with suction and concentration in vacuo. The crude product is purified by chromatography on silica gel 60 (mobile phase gradient cyclohexane-->cyclohexane/ethyl acetate 60:40). 4.90 g (37% of theory) of product are obtained.

m.p.: 128° C.

HPLC (method 1): $R_t$: 5.12 min.

$^1$H-NMR (300 MHz, DMSO-$d_6$, δ/ppm): 7.70-7.64 (m, 4H), 7.55-7.42 (m, 4H), 7.40-7.33 (m, 1H), 7.11 (d, 2H), 6.93 (d, 2H), 5.11 (s, 2H), 4.39 (t, 1H), 3.39 (m, 2H), 2.53 (m, 21, 1.67 (quint, 2H).

MS (DCI): m/z=336 (M+NH$_4^+$).

Example IV 1-(3-Bromopropyl)-4-(4-phenoxybutoxy)benzene

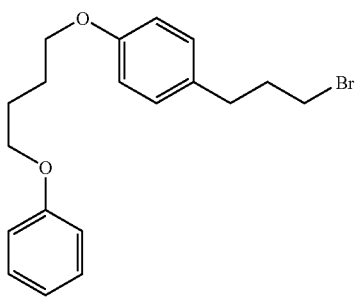

10.0 g of 3-[4-(4-phenoxybutoxy)phenyl]-1-propanol are dissolved in 50 ml of tetrahydrofuran, and 10.5 g of solid triphenylphosphine are added. 13.2 g of solid tetrabromomethane are added to the solution. After about 5 minutes, the mixture starts to become cloudy. The reaction is complete after one hour. The precipitate is filtered off, and the filtrate is concentrated. The crude product is purified by suction filtration on silica gel with cyclohexane/ethyl acetate 15:1 as mobile phase. 8.5 g of product are obtained.

HPLC (method 1): $R_t$: 6.01 min.

$^1$H-NMR (400 MHz, DMSO-$d_6$, δ/ppm) 7.29-7.24 (m, 2H), 7.12 (d, 2H), 6.94-6.89 (m, 3H), 6.86 (d, 2H), 4.00 (m, 4H), 3.48 (t, 2H), 2.63 (t, 2H), 2.05 (m, 2H), 1.84 (m, 4H).

MS (DCI, NH$_3$): m/z=380/382 (M+NH$_4^+$).

Example V

4-{[4-(3-Bromopropyl)phenoxy]methyl}-1,1'-biphenyl

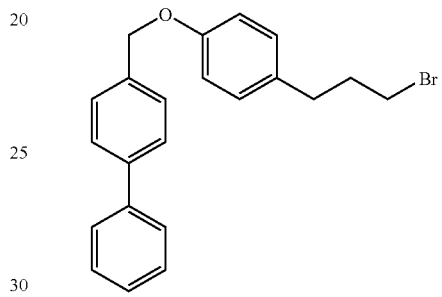

4-{[4-(3-Bromopropyl)phenoxy]methyl}-1,1'-biphenyl is obtained in analogy to the process described in Example IV by bromination of 3-[4-(1,1'-biphenyl-4-yl-methoxy)phenyl]-1-propanol.

HPLC (method 1): $R_t$: 6.10 min $^1$H-NMR (300 MHz, DMSO-$d_6$, δ/ppm): 7.70-7.64 (m, 4H), 7.55-7.43 (m, 4H), 7.40-7.33 (m, 1H), 7.14 (d, 2H), 6.96 (d, 2H), 5.12 (s, 2H), 3.48 (t, 2H), 2.64 (t, 2H), 2.05 (quint, 2H).

MS (DCI): m/z=400 (M+NH$_4^+$).

Example VI

3-[4-(4-phenoxybutoxy)phenyl]propanoic acid

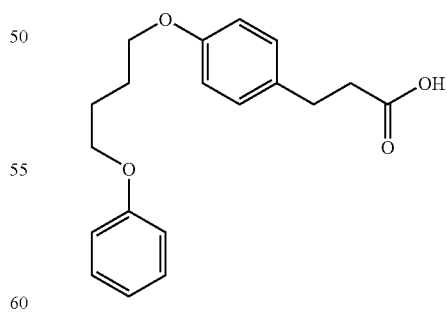

100 ml of methanol and 100 ml of 2 molar sodium hydroxide solution are added to a solution of 10 g of methyl 3-[4-(4-phenoxybutoxy)phenyl]propanoate in 100 ml of tetrahydrofuran. The mixture is heated at 60° C. for two hours. It is then acidified with 2 molar hydrochloric acid, and most of the organic solvent is removed in a rotary evaporator. A precipitate separates out and is filtered off with suction and washed with water at room temperature. 7.7 g of product are obtained.

HPLC (method 1): $R_t$: 4.77 min.

$^1$H-NMR (200 MHz, DMSO-$d_6$, δ/ppm): 12.10 (s, broad, 1H), 7.32-7.23 (m, 2H), 7.12 (d, 2H), 6.95-6.81 (m, 5H), 4.00 (m, 4H), 2.73 (t, 2H), 2.48 (t, 2H), 1.85 (m, 4H).

MS (DCI, NH$_3$): m/z=332.2 (M+NH$_4^+$).

Example VII

3-[4-(4-phenoxybutoxy)phenyl]propanoyl chloride

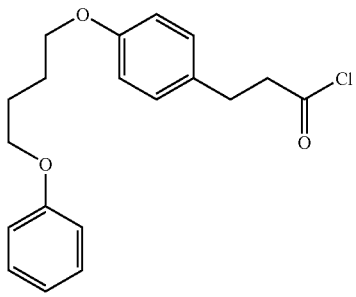

A suspension of 250 mg of 3-[4-(4-phenoxybutoxy)phenyl]propanoic acid in 10 ml of chloroform is heated to about 40° C. A solution is formed thereby. 1.4 ml of oxalyl chloride are added (evolution of gas). The mixture is heated to reflux. After two hours, the mixture is evaporated to dryness and the product is dried under high vacuum. 264 mg of product are obtained.

MS (DCI, NH$_3$): m/z=350/352 (M+NH$_4^+$).

Example VIII 5-(Methoxycarbonyl)-2-nitrobenzoic acid

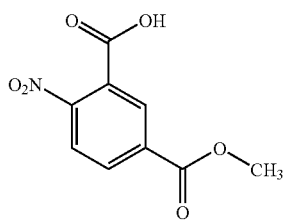

A solution of 320 mg of sodium dihydrogen phosphate in 10 ml of water and 1 ml of hydrogen peroxide (35% strength) is added to a solution 2.0 g of methyl 3-formyl-4-nitrobenzoate [M. G. Vetelino et al., *tetrahedron Lett.* 35, 219-222 (1994).] in 20 ml of acetonitrile at 10° C. A solution of 1.5 g of sodium chlorite in 10 ml of water is then added dropwise over the course of 15 minutes. The mixture is then stirred at 10° C. for a further 2 hours. The reaction is stopped by adding 400 mg of sodium sulphite. The mixture is diluted with 2 molar hydrochloric acid and extracted with ethyl acetate. The organic extract is washed with saturated sodium chloride solution and dried over anhydrous sodium sulphate. Filtration and evaporation result in 225 mg of product.

HPLC (method 1): $R_t$: 3.68 min.

$^1$H-NMR (300 MHz, DMSO-$d_6$, δ/ppm): 14.22 (s broad, 1H), 8.34 (d, 1H); 8.29 (dd, 1H), 8.09 (d, 1H), 3.92 (s, 3H).

MS (DCI, NH$_3$): m/z=243 (M+NH$_4^+$), 260 (M+N$_2$H$_7^+$).

Example IX

Methyl 4-hydroxy-3-({[3-(methoxycarbonyl)cyclohexyl]amino}carbonyl)benzoate

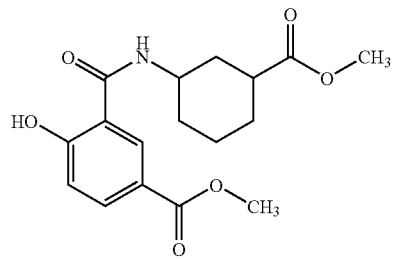

Method 1:

10 g of 3-aminocyclohexane-1-carboxylic acid hydrochloride are stirred together with 15.5 ml of trimethylsilyl chloride in 55 ml of methanol at room temperature overnight. Subsequent removal of the solvent and all other volatile components in the rotary evaporator results in 8 g of methyl 3-aminocyclohexane-1-carboxylate hydrochloride. 8.0 g of methyl 3-aminocyclohexane-1-carboxylate hydrochloride, 14.4 g of N-[(3-dimethylamino)propyl]-N'-ethylcarbodiimide hydrochloride (ETLC), 5.1 g of 1-hydroxy-1H-benzotriazole hydrate (HOBT) and 11 ml of triethylamine are added successively to a solution of 7.37 g of 2-hydroxy-5-carbomethoxybenzoic acid [CAS No. 79128-78-2] in 1000 ml of dichloromethane. After 15 hours at room temperture, 250 ml of water are added to the reaction mixture. After phase separation, the aqueous phase is extracted with ethyl acetate. The combined dichloromethane and ethyl acetate phases are washed with saturated sodium chloride solution and dried over anhydrous sodium sulphate. Filtration and concentration result in an oil which is initially prepurified by suction filtration through silica gel with cyclohexane/ethyl acetate 4:1 as mobile phase. The product obtained in this way contains a mixture of all four possible stereoisomers: cis racemate and trans racemate. Most of one of the two racemates is removed by crystallization from cyclohexane and mixed with about 5% ethyl acetate. This results in 4.18 g of product (racemate A). The product remaining after evaporation of the mother liquor is separated by preparative HPLC on an achiral RP column. This results in a further 0.2 g of the material of fraction 1, which is combined with the latter. In addition, 1.55 g of the other racemate are obtained (racemate B).

Racemate A:

HPLC (method 1): $R_t$: 4.50 min.

$^1$H-NMR (300 MHz, DMSO-$d_6$, δ/ppm): 13.34 (s broad, 1H), 8.92 (d broad, 1H), 8.57 (d, 1H), 7.97 (dd, 1H), 6.99 (d, 1H), 3.88 (m, 1H), 3.83 (s, 3H), 3.60 (s, 3H), 2.49 (m, 1H), 2.07 (m, 1H), 1.92-1.78 (m, 3H), 1.56-1.15 (m, 4H).

MS (DCI, NH$_3$): m/z=336.1 (M+H$^+$), 353 (M+NH$_4^+$).

Racemate B:

HPLC (method 1): $R_t$: 4.42 min.

$^1$H-NMR (300 MHz, DMSO-$d_6$, δ/ppm): 13.13 (s broad, 1H), 8.76 (d broad, 1H), 8.53 (d, 1H), 7.97 (dd, 1H), 7.00 (d, 1H), 4.12 (m, 1H), 3.83 (s, 3H), 3.62 (s, 3H), 2.82 (m, 1H), 1.93 (m, 1H), 1.83-1.45 (m, 7H).

MS (DCI, NH$_3$): m/z 336.1 (M+H+), 353 (M+NH$_4^+$).

Method 2:

Racemate B can be resolved into its optical antipodes by chromatography on a preparative scale.

Method: Chiral silica gel selector KBD 8361 (particle size 10 μm) based on the selector poly(N-methacryloyl-L-leucine 1-menthylamide); column: 420 mm×100 mm; 9:1 (vol/vol) tert-butyl methyl ether/ethyl acetate mixture as eluent; flow rate: 100 ml/min; UV detection: 254 nm; sample: 10 g dissolved in 1000 ml of eluent; sample loaded: 80 ml; temperature: 24° C.

(+) Enantiomer of racemate B [(+) Benantiomer]:

HPLC (KBD 8361 column as above, 250 mm×20 mm, isohexane/ethyl acetate 4:1, flow rate: 25 ml/min, WV detection: 280 nm, 24° C.): $R_t$: 15.8 min.

Specific rotation (methanol, 589 nm, 20° C.): +36.8°.

(−) Enantiomer of racemate B [(−) Benantiomer]:

HPLC (KBD 8361 column as above, 250 mm×20 mm, isohexane/ethyl acetate 4:1, flow rate: 25 ml/min, UV detection: 280 nm, 24° C.): $R_t$: 9.6 min.

Specific rotation (methanol, 589 nm, 20° C.): −37.60.

Method 3:

Racemate B can also be obtained specifically in the following way:

21.8 ml of thionyl chloride are added dropwise to a solution of 5.85 g of 2-hydroxy-5-(methoxycarbonyl)benzoic acid in 128 ml of anhydrous THF at 0° C. The reaction mixture is left to stir at room temperature overnight. The solvent and excess thionyl chloride are then completely removed in a rotary evaporator. The remaining residue is taken up 120 ml of anhydrous dichloromethane, and 5.5 g of methyl trans-3-aminocyclohexanecarboxylate hydrochloride and, at −20° C., 10.4 ml of triethylamine are added. The reaction mixture is then allowed to reach room temperature and is stirred at this temperature for a further 1.5 hours. Then about 50 ml of 0.01 molar hydrochloric acid are added. After phase separation, the aqueous phase is extracted twice more with ethyl acetate. The combined organic extracts are dried over anhydrous sodium sulphate. Filtration and evaporation are carried out. The product is purified by suction filtration through silica gel with cyclohexane/ethyl acetate 4:1 as mobile phase. 4.06 g of product are obtained. The product consists of 87% racemate B and 13% racemate A. Further purification can take place as described in Example IX, method 1.

Example X

Methyl 1-[2-hydroxy-5-(methoxycarbonyl)benzoyl]-4-piperidinecarboxylate

Method 1:

Methyl 1-[2-hydroxy-5-(methoxycarbonyl)benzoyl]-4-piperidinecarboxylate is prepared in analogy to the process described in Example IX, method 1, from 2-hydroxy-5-carbomethoxybenzoic acid [CAS No. 79128-78-2] and methyl piperidine-4-carboxylate hydrochloride.

HPLC (method 1): $R_t$: 3.64 min.

$^1$H-NMR (400 MHz, DMSO-$d_6$, δ/ppm): 10.78 (s, 1H), 7.83 (dd, 1H), 7.69 (d, 1H), 7.96 (d, 1H), 4.37 (broad, 1H), 3.79 (s, 3H), 3.61 (s, 3H), 3.36 (broad, 1H), 2.98 (m broad, 21), 2.63 (m, 1H), 1.83 (m, 2H), 1.50 (m, 2H).

MS (DCI, $NH_3$): m/z=322 (M+H$^+$), 339 (M+NH$_4^+$).

Method 2:

37 ml of thionyl chloride are added dropwise to a solution of 10.0 g of 2-hydroxy-5-carbomethoxybenzoic acid in 600 ml of THF at a temperature of about 0° C. The mixture is allowed to reach room temperature and is stirred for 15 hours. The mixture is then completely evaporated in a rotary evaporator. The remaining oil is dissolved in 400 ml of anhydrous dichloromethane. Then, at about −20° C., 11 ml of triethylamine and 8.76 g of methyl isonipecotate are added. The reaction mixture is allowed to reach room temperature. After two hours it is acidified with 0.1 molar hydrochloric acid (pH about 3) and extracted with ethyl acetate. The organic extract is washed successively with water and saturated sodium chloride solution. Drying over anhydrous sodium sulphate, filtration, evaporation. The crude product is initially prepurified by suction filtration through silica gel with cyclohexane/ethyl acetate 1:1 as mobile phase. The product-containg fractions are combined and evaporated, and the resulting residue is triturated with a little ethyl acetate. 13.4 g of a solid are obtained.

Example XI

Methyl 1-[5-(methoxycarbonyl)-2-nitrobenzoyl]-4-piperidinecarboxylate

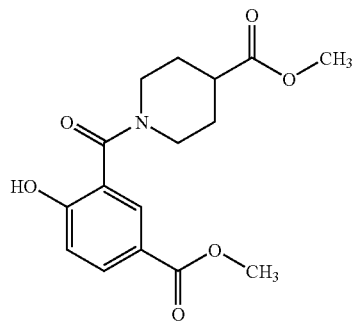

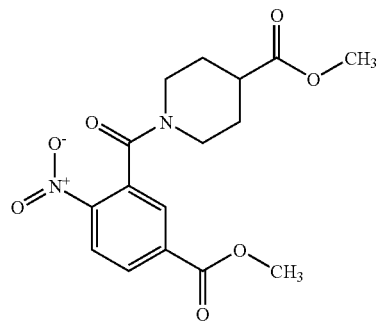

Methyl 1-[5-(methoxycarbonyl)-2-nitrobenzoyl]-4-piperidinecarboxylate is prepared in analogy to the process described in Example IX from 5-(methoxycarbonyl)-2-nitrobenzoic acid and methyl piperidine-4-carboxylate hydrochloride.

TLC: $R_f$: 0.21 (cyclohexane/ethyl acetate 1:1).

HPLC (method 1): $R_t$: 3.96 min.

$^1$H-NMR (200 MHz, DMSO-$d_6$, δ/ppm): 8.32 (d, 1H), 8.19 (dd, 1H), 8.00 (d, 1H), 4.34 (m, 1H), 3.92 (s; 3H), 3.62 (s, 3H), 3.18-2.94 (m, 2H), 2.77-2.63 (m, 1H), 1.97 (m, 1H), 1.80-1.48 (m, 4H).

Example XII

Methyl 1-[2-amino-5-(methoxycarbonyl)benzoyl]-4-piperidinecarboxylate

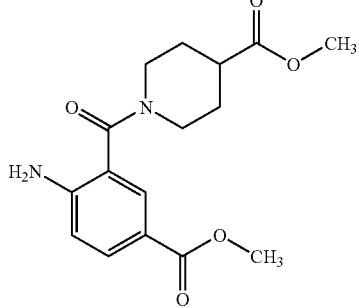

A solution of 600 mg of methyl 1-[5-(methoxycarbonyl)-2-nitrobenzoyl]-4-piperidinecarboxylate in 200 ml of methanol is mixed with a spatula tip of palladium (10% on activated carbon) and hydrogenated in a Parr apparatus under a pressure of 3.5 bar of hydrogen at room temperature. After three hours, the reaction mixture is filtered through a little silica gel and evaporated. 474 mg of product are obtained.

HPLC (method 1): $R_t$: 3.68 min.

$^1$H-NMR (300 MHz, DMSO-$d_6$, δ/ppm): 7.67 (dd, 1H), 7.57 (d, 1H), 6.72 (d, 1H), 5.98 (s broad, 2H), 3.82 (m, 1H), 3.76 (s, 3H), 3.62 (s, 3H), 3.02 (m, 2H), 2.63 (m, 1H), 1.85 (m, 2H), 1.63-1.48 (m, 3H).

MS (DCI, $NH_3$): m/z=321.2 (M+H$^+$), 338 (M+NH$_4^+$).

Example XIII

Ethyl 3-formyl-4-{3-[4-(4-phenoxybutoxy)phenyl]propoxy}benzoate

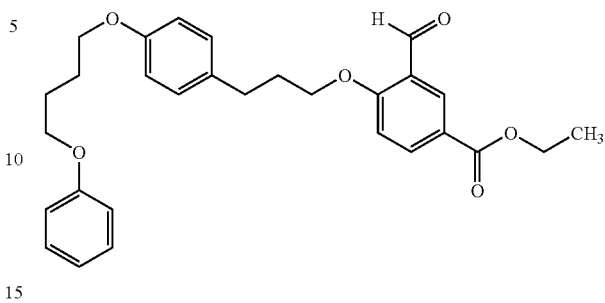

1.37 g (3.76 mmol) of 1-(3-bromopropyl)-4-(4-phenoxybutoxy)benzene, 0.79 g (3.76 mmol) of ethyl 3-formyl-4-hydroxybenzoate [CAS No. 82304-99-2] and 0.78 g (5.64 mmol) of potassium carbonate are dissolved in 20 ml of DMF, and the mixture is stirred at 40° C. for 16 hours. It is then concentrated, and the residue is taken up in 200 ml of water and extracted with dichloromethane (three times 100 ml). The combined organic phases are dried (sodium sulphate) and concentrated, and the crude product is purified by chromatography on silica gel (mobile phase gradient cyclohexane-->cyclohexane/ethyl acetate 5:1). 1.45 g of product are obtained.

HPLC (method 2): $R_t$: 5.62 min.

$^1$H-NMR (300 MHz, CDCl$_3$, δ/ppm): 10.48 (s, 1H), 8.49 (s, 1H), 8.20 (dd, 1H), 7.29-7.23 (m, 2H), 7.12-7.06 (d, 2H), 6.98-6.80 (m, 6H), 4.36 (q, 2H), 4.13 (t, 2H), 4.07-3.96 (m, 4H), 2.78 (t, 2H), 2.17 (quint, 2H), 1.97 (m, 4H), 1.38 (t, 3H).

MS (ESI+): m/z=477 (M+H$^+$).

Example XIV

Ethyl 4-{3-[4-(1,1'-biphenyl-4-ylmethoxy)phenyl]propoxy}-3-formylbenzoate

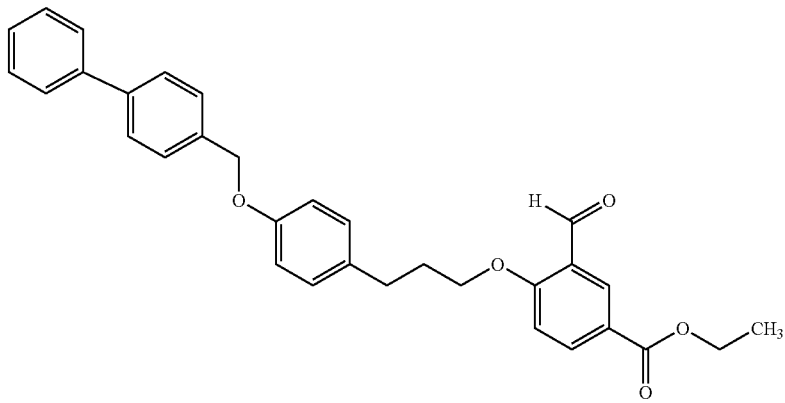

Preparation takes place in analogy to Example XIII from 1,1'-biphenyl-4-ylmethyl 4-(3-bromopropyl)phenyl ether and ethyl 3-formyl-4-hydroxybenzoate.

HPLC (method 2): $R_t$: 6.04 min.

$^1$H-NMR (200 MHz, DMSO-$d_6$, δ/ppm): 10.33 (s, 1H), 8.86 (d, 1H), 8.22 (dd, 1H), 7.65-7.55 (m, 4H), 7.53-7.34 (m, 5H), 7.16-6.90 (m, 5H), 5.08 (s, 2H), 4.38 (q, 2H), 4.29 (t, 2H), 2.80 (t, 2H), 2.24 (quint, 2H), 1.39 (t, 3H).

MS (DCI): m/z 512 (M+NH$_4^+$).

Example XV

2-{3-[4-(1,1'-Biphenyl-4-ylmethoxy)phenyl]propoxy}-5-(ethoxycarbonyl)benzoic acid

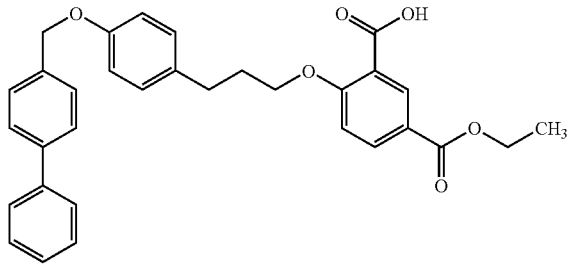

3.10 g (6.28 mmol) of ethyl 4-{3-[4-(1,1'-biphenyl-4-ylmethoxy)phenyl]propoxy}-3-formylbenzoate are introduced into 50 ml of THF. At about 0° C. (internal temperature), solutions of 2.13 g (18.8 nmol) of sodium chlorite in 2.5 ml of water and 1.83 g (18.8 mmol) of sulphamic acid in 9 ml of water are simultaneously added dropwise. The mixture is then stirred at 0° C. for 15 minutes. The reaction mixture is added to 120 ml of water and extracted with ethyl acetate (four times 60 ml). The combined organic phases are washed with saturated sodium chloride solution (twice 50 ml). A finely dispersed precipitate is evident in the organic phase. 300 ml of dichloromethane are added, and the solution is dried over sodium sulphate and concentrated. The resulting product (2.96 g) is reacted without further purification.

HPLC (method 2): $R_t$: 6.13 min.

$^1$H-NMR (200 MHz, CDCl$_3$, δ/ppm): 8.86 (d, 1H), 8.22 (dd, 1H), 7.64-7.55 (m, 4H), 7.53-7.33 (m, 5H), 7.15-6.92 (m, 5), 5.08 (s, 2H), 4.38 (q, 2H), 4.29 (t, 2H), 2.80 (t, 2H), 2.24 (quint., 2H), 1.39 (t, 3H).

LC-MS (method 3): $R_t$: 4.99 min.
MS (ESI+): m/z=511 (M+H$^+$).

Example XVI 5-(Ethoxycarbonyl)-2-{3-[4-(4-phenoxybutoxy)phenyl]propoxy}benzoic acid Preparation takes place in analogy to Example XV from ethyl 3-formyl-4-{3-[4-(4-phenoxybutoxy)phenyl]propoxy}benzoate.

$^1$H-NMR (300 MHz, CDCl$_3$, δ/ppm): 10.46 (s, broad, 1H), 8.85 (d, 1H), 8.22 (dd, 1H), 7.32-7.21 (m, 3H), 7.12-6.80 (m, 7H), 4.38 (q, 2H), 4.28 (t, 2H), 4.08-3.97 (m, 4H), 2.78 (t, 2H), 2.24 (quint, 2H), 1.97 (m, 4H), 1.39 (t, 3H).

LC-MS (method 3): $R_t$: 4.20 min.
MS (ESI+): m/z=493 (M+H$^+$).

Example XVII

Methyl 3-[4-(3-cyclohexylpropoxy)phenyl]propanoate

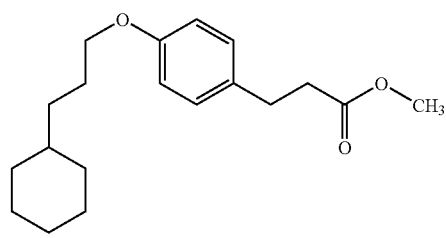

69.9 g of caesium carbonate are added to a solution of 32.21 g of methyl 3-(4-hydroxyphenyl)propanoate and 44.0 g 1-bromo-3-cyclohexylpropane in 100 ml of anhydrous DMF, and the mixture is stirred at a temperature of 50° C. for 6 hours. The reaction mixture is then poured into about 800 ml of water and, after addition of 12.3 ml of glacial acetic acid, extracted three times with ethyl acetate. The combined organic extracts are washed successively with water and saturated sodium chloride solution. After drying over anhydrous sodium sulphate, the solvent is removed in a rotary evaporator. The product is purified by suction filtration on silica gel with cyclohexane/ethyl acetate 20:1 as mobile phase. 51.52 g of product are obtained.

TLC: $R_f$: 0.47 (cyclohexane/ethyl acetate 1:1).

HPLC (method 2): $R_t$: 6.09 min.

$^1$H-NMR (300 MHz, DMSO-$d_6$, δ/ppm): 7.10 (d, 2H), 6.81 (d, 2H), 3.88 (t, 2H), 3.57 (s, 3H), 2.77 (t, 2H), 2.57 (t, 2H), 1.72-1.64 (m, 7H), 1.37-1.09 (m, 6H), 0.93-0.81 (m, 2H).

MS (DCI, NH$_3$): M/Z=321.9 (M+NH$_4^+$).

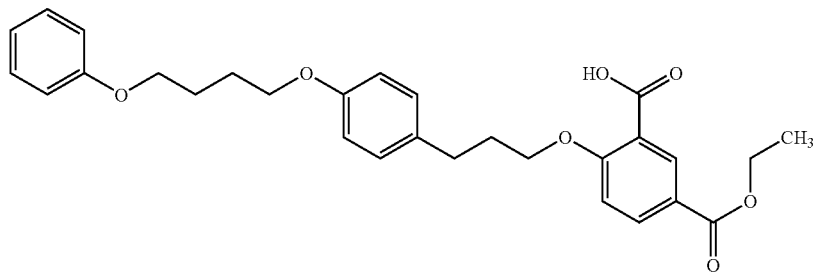

Example XVIII

3-[4-(3-Cyclohexylpropoxy)phenyl]propan-1-ol

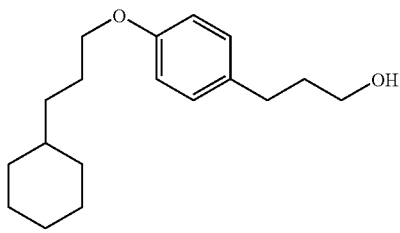

3-[4-(3-Cyclohexylpropoxy)phenyl]propan-1-ol is obtained in analogy to the process described in Example II by reduction of methyl 3-[4-(3-cyclohexylpropoxy)phenyl]-propanoate with lithium aluminium hydride.

TLC: $R_f$: 0.30 (cyclohexane/ethyl acetate 1:1).

HPLC (method 1): $R_t$: 5.60 min.

$^1$H-NMR (300 MHz, DMSO-$d_6$, δ/ppm): 7.08 (d, 2H), 6.80 (d, 2H), 4.38 (t, 1H), 3.88 (t, 2H), 3.39 (quart., 2H), 2.51 (t, 2H), 1.71-1.61 (m, 9H), 1.32-1.12 (m, 6H), 0.93-0.81 (m, 2H).

MS (DCI, NH$_3$): m/z=394.1 (M+NH$_4^+$).

Example XIX 1-(3-Bromopropyl)-4-(3-cyclohexylpropoxy)benzene

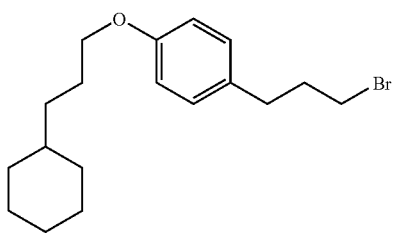

1-(3-Bromopropyl)-4-(3-cyclohexylpropoxy)benzene is obtained in analogy to the process described in Example IV from 3-[4-(3-cyclohexylpropoxy)phenyl]propan-1-ol bromination with triphenylphosphine and tetrabromomethane.

TLC: $R_f$: 0.69 (cyclohexane/ethyl acetate 1:1).

HPLC (method 4): $R_t$: 7.27 min.

$^1$H-NMR (300 MHz, DMSO-$d_6$, δ/ppm): 7.10 (d, 2H), 6.82 (d, 2H), 3.89 (t, 2H), 3.48 (t, 2H), 2.62 (t, 2H), 2.03 (quint., 2H), 1.73-1.60 (m, 7H), 1.30-1.12 (m, 6H), 0.93-0.81 (m, 2H).

MS (DCI, NH$_3$): m/z=338 and 340 (M$^+$), 356 and 358 (M+NH$_4^+$).

Example XX

3-[4-(3-Cyclohexylpropoxy)phenyl]propyl methanesulphonate

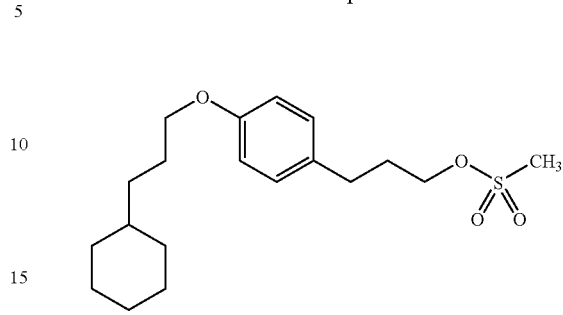

43.3 g of diisopropylethylamine and 25.6 g of methanesulphonyl chloride are added to a solution of 30.89 g of 3-[4-(3-cyclohexylpropoxy)phenyl]propan-1-ol in 250 ml of anhydrous THF at 0° C. The mixture is left to stir at room temperature for one hour. Then 50 ml each of water and ethyl acetate are added. The phases are separated and the organic phase is washed successively with water and saturated sodium chloride solution. After drying over anhydrous magnesium sulphate, the solvent is removed in a rotary evaporator. The residue is triturated with petroleum ether. Filtration with suction and drying results in 37.8 g of product.

HPLC (method 5): $R_t$: 5.57 min.

$^1$H-NMR (200 MHz, CDCl$_3$, δ/ppm): 7.08 (d, 2H), 6.83 (d, 2H), 4.22 (t, 2H), 3.90 (t, 2H), 3.01 (s, 3H), 2.70 (t, 2H), 2.04 (d quart., 2H), 1.89-0.78 (m, 15H).

MS (DCI, NH$_3$): m/z 372.2 (M+NH$_4^+$).

Example XXI

Methyl 3-{4-[4-(cyclohexyloxy)butoxy]phenyl}propanoate

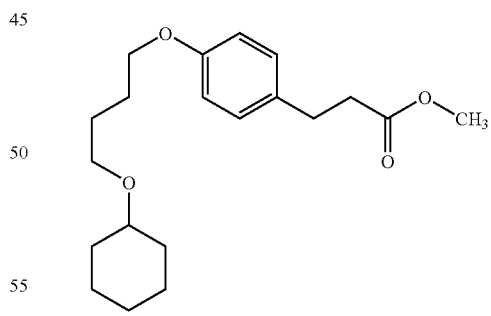

Methyl 3-{4-[4-(cyclohexyloxy)butoxy]phenyl}propanoate is obtained in analogy to the process described in Example I by alkylation of methyl 3-(4-hydroxyphenyl)-propanoate with (4-bromobutoxy)cyclohexane.

$^1$H-NMR (200 MHz, CDCl$_3$, δ/ppm): 7.09 (d, 2H), 6.82 (d, 2H), 3.94 (t, 2H), 3.67 (s, 3H), 3.49 (t, 2H), 3.30-3.15 (m, 1H), 2.88 (t, 2H), 2.59 (t., 2H), 1.94-1.17 (m, 14H).

LC-MS (method 6): $R_t$: 3.01 min, m/z=335 (M+H$^+$).

Example XXII

3-{4-[4-(Cyclohexyloxy)butoxy]phenyl}propan-1-ol

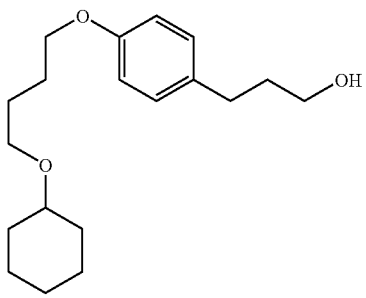

3-{4-[4-(Cyclohexyloxy)butoxy]phenyl}propan-1-ol is obtained in analogy to the process described in Example II by reduction of methyl 3-{4-[4-(cyclohexyloxy)-butoxy]phenyl}propanoate with lithium aluminium hydride.

$^1$H-NMR (400 MHz, CDCl$_3$, δ/ppm): 7.10 (d, 2M), 6.82 (d, 2H), 3.95 (t, 2H), 3.67 (t, 2H), 3-49 (t, 2H), 3.23-3.19 (m, 1H), 2.63 (t, 2H), 1.92-1.20 (16H).

LC-MS (method 6): R$_t$: 2.67 min, m/z 307 (M+H$^+$).

Example XXIII 1-(3-Bromopropyl)-4-[4-(cyclohexyloxy)butoxy]benzene

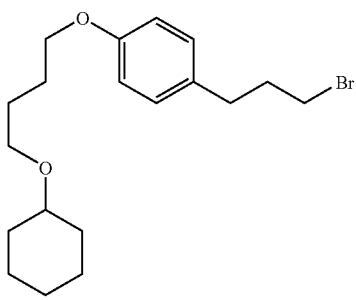

1-(3-Bromopropyl)-4-[4-(cyclohexyloxy)butoxy]benzene is obtained in analogy to the process described in Example IV by bromination of 3-{4-[4-(cyclohexyloxy)-butoxy]phenyl}propan-1-ol with triphenylphosphine and tetrabromomethane.

$^1$H-NMR (400 MHz, CDCl$_3$, δ/ppm): 7.09 (d, 2H), 6.82 (d, 2H), 3.97 (t, 2H), 3.50 (t, 2H), 3.38 (t, 2H), 3.23-3.18 (m, 1H), 2.71 (t, 2H), 2.12 (quint, 2H), 1.92-1.82 (m, 4H), 1.77-1.70 (m, 4H), 1.57-1.19 (6H).

MS (EI+): m/z=369 and 371 (M+H$^+$).

Example XXIV

Methyl 3-{4-[(4-isopropoxybenzyl)oxy]phenyl}propanoate

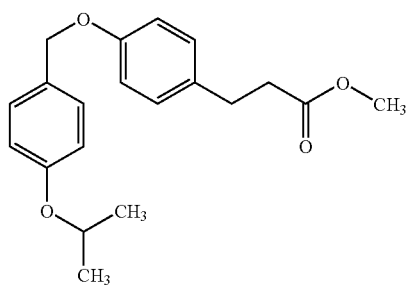

A solution of 11.0 g of 4-isopropoxybenzyl chloride and 10.7 g of methyl 3-(4-hydroxyphenyl)propanoate in 120 ml of butyronitrile is mixed with 12.4 g of potassium carbonate and heated to reflux for 15 hours. The solvent is then distilled out in a rotary evaporator. The residue is taken up in ethyl acetate and washed successively with water and saturated sodium chloride solution. After drying over sodium sulphate, the organic phase is evaporated and the product is purified by suction filtration through silica gel with cyclohexane/ethyl acetate 9:1. 9.4 g of product are obtained.

HPLC (method 1): R$_t$: 5.33 min.

$^1$H-NMR (300 MHz, DMSO-d$_6$, δ/ppm): 7.32 (d, 2H), 7.11 (d, 2H), 6.90 (d, 2H), 6.89 (d, 2H), 4.94 (s, 2H), 4.60 (sep, 1H), 3.57 (s, 3H), 2.78 (t, 2H), 2.57 (t, 2H), 1.27 (d, 6H).

MS (DCI, NH$_3$): m/z 346.2 (M+NH$_4^+$).

Example XXV

3-{4-[(4-Isopropoxybenzyl)oxy]phenyl}propan-1-ol

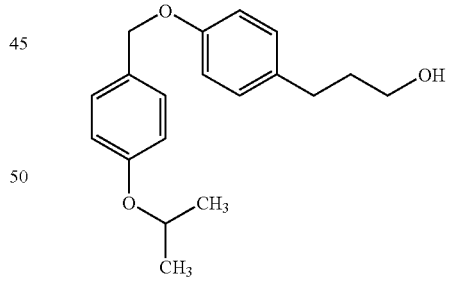

3-{4-[(4-Isopropoxybenzyl)oxy]phenyl}propan-1-ol is obtained in analogy to the process described in Example II by reduction of methyl 3-{4-[(4-isopropoxybenzyl)-oxy]phenyl}propanoate with lithium aluminium hydride.

TLC: R$_f$: 0.48 (cyclohexane/ethyl acetate 1:1).

HPLC (method 1): R$_t$: 4.87 min.

$^1$H-NMR (300 MHz, CDCl$_3$, δ/ppm): 7.32 (d, 2H), 7.11 (d, 2H), 6.90 (d, 2H), 6.89 (d, 2H), 4.93 (s, 2H), 4.54 (sep, 1H), 3.68 (t broad, 2H), 2.64 (t, 2H), 1.93-1.79 (m, 2H), 1.33 (d, 6H), 1.26 (s broad, 1H).

MS (DCI, NH$_3$): m/z=318 (M+NH$_4^+$).

Example XXVI 1-(3-Bromopropyl)-4-[(4-isopropoxybenzyl)oxy]benzene

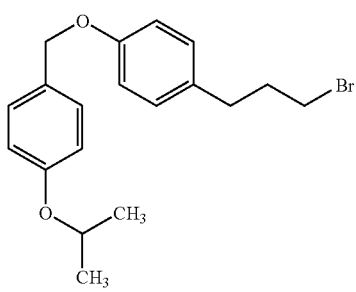

1-(3-Bromopropyl)-4-[(4-isopropoxybenzyl)oxy]benzene is obtained in analogy to the process described in Example IV from 3-{4-[(4-isopropoxybenzyl)oxy]phenyl}propan-1-ol by bromination with triphenylphosphine and tetrabromomethane.

TLC: $R_f$: 0.48 (cyclohexane/ethyl acetate 20:1).

HPLC (method 5): $R_t$: 4.87 min.

$^1$H-NMR (300 MHz, CDCl$_3$, δ/ppm): 7.32 (d, 2H), 7.10 (d, 2H), 6.90 (d, 2H), 6.89 (d, 2H), 4.94 (s, 2H), 4.53 (sep, 1H), 3.38 (t, 2H), 2.71 (t, 2H), 2.12 (pent, 2H), 1.33 (d, 6H).

MS (DCI, NH$_3$): M/Z=380 and 382 (M+NH$_4^+$).

Example XXVII

Methyl 4-(cyclopropylmethoxy)benzoate

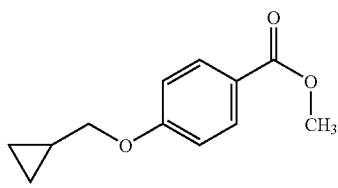

A solution of 3.0 g of methyl 4-hydroxybenzoate and 2.93 g of cyclopropylmethyl bromide in 60 ml of anhydrous acetonitrile is mixed with 3.27 g of potassium carbonate and heated to reflux for 15 hours. The solvent is then removed in a rotary evaporator. The residue is taken up in ethyl acetate and washed successively with water and saturated sodium chloride solution. Drying over solid sodium sulphate is followed by evaporation to dryness. The product is purified by suction filtration through silica gel with cyclohexane/ethyl acetate 5:1 as mobile phase. 4.0 g of a solid are obtained.

TLC: $R_f$: 0.29 (cyclohexane/ethyl acetate 5:1).

HPLC (method 1): $R_t$: 4.77 min.

$^1$H-NMR (400 MHz, DMSO-d$_6$, δ/ppm): 7.89 (d, 2H), 7.02 (d, 21), 3.90 (d, 2H), 3.81 (s, 3H), 1.28-1.19 (m, 1H), 0.61-0.57 (m, 2H), 0.36-0.32 (m, 2M).

MS (DCI, NH$_3$): m/z=207.1 (M+H$^+$), 224.1 (M+NH$_4^+$).

Example XXVIII

[4-(Cyclopropylmethoxy)phenyl]methanol

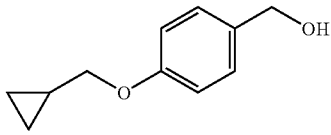

[4-(Cyclopropylmethoxy)phenyl]methanol is obtained analogously to the process described in Example II by reduction of methyl 4-(cyclopropylmethoxy)-benzoate with lithium aluminium hydride.

TLC: $R_f$: 0.38 (cyclohexane/ethyl acetate 1:1).

HPLC (method 1): $R_t$: 3.91 min.

$^1$H-NMR (300 MHz, DMSO-d$_6$, δ/ppm): 7.20 (d, 2H), 6.86 (d, 2H), 4.98 (t, 1H), 4.40 (d, 2H), 3.78 (d, 2H), 1.27-1.12 (m, 1H), 0.58-0.52 (m, 2H), 0.32-0.27 (m, 2H).

MS (DCI, NH$_3$): m/z 161 (M+H$^+$), 178 (M+NH$_4^+$), 195 (M+N$_2$H$_7$+).

Example XXIX 1-(Chloromethyl)-4-(cyclopropylmethoxy)benzene

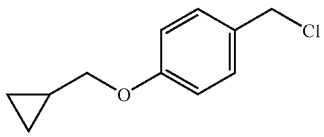

2.54 g of [4-(cyclopropylmethoxy)phenyl]methanol are dissolved in 30 ml of anhydrous dichloromethane and, at room temperature, 1.56 ml of thionyl chloride are added dropwise. After the addition is complete, the mixture is left to stir at room temperature for 30 minutes. The mixture is then evaporated to dryness in a rotary evaporator. 2.77 g of product are obtained.

TLC: $R_f$: 0.60 (cyclohexane/ethyl acetate 5:1).

$^1$H-NMR (300 MHz, DMSO-d$_6$, δ/ppm): 7.33 (d, 2H), 6.91 (d, 2H), 4.70 (s, 2H), 3.81 (d, 2H), 1.28-1.13 (m, 1H), 0.59-0.52 (m, 2H), 0.33-0.28 (m, 2H).

MS (EI+): m/z=196 (M$^+$).

Example XXX 1-(Chloromethyl)-2-isopropoxybenzene

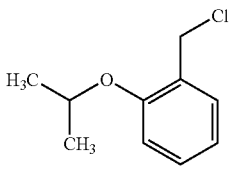

1-(Chloromethyl)-2-isopropoxybenzene is obtained in analogy to the process described in Example XXIX from (2-isopropoxyphenyl)methanol by reaction with thionyl chloride. The product is purified by vacuum distillation.

b.p. 54° C. (0.16 mbar).

$^1$H-NMR (200 MHz, DMSO-d$_6$, δ/ppm): 7.38 (d, 1H), 7.29 (d, 1H), 7.05 (d, 1H), 6.91 (t, 1H), 4.68 (s, 2H), 4.67 (hep, 1H), 1.29 (d, 6H).

Example XXXI

[(4-Bromobutoxy)methyl]cyclopropane

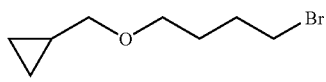

2.8 g of a 60% suspension of sodium hydride in mineral oil are added in portions to a solution of 5.0 g of hydroxymethylcyclopropane in 25 ml of toluene at room temperature. The mixture is then heated at 100° C. for 2 hours. After this, it is allowed to reach room temperature and a solution of 14.9 g of 1,4-dibromobutane in 15 ml of toluene is added. The mixture is left to stir at 100° C. for a further 15 hours. Then, at room temperature, 10 ml of water are added, the phases are separated, and the toluene is removed in a rotary evaporator. The product is isolated by vacuum distillation.

b.p. 58-63° C. (0.56 mbar).

$^1$H-NMR (300 MHz, DMSO-d$_6$, δ/ppm): 3.53 (t, 2H), 3.38 (t, 2H), 3.18 (d, 2H), 1.89-1.79 (m, 2H), 1.63-1.54 (m, 2H), 1.02-0.91 (m, 1H), 0.47-0.41 (m, 2H), 0.14-0.10 (m, 2H).

Example XXXII

Methyl cis-3-hydroxycyclohexanecarboxylate

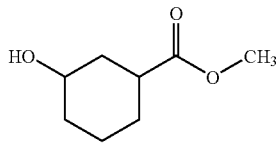

A total of 2.51 g of solid sodium borohydride is added in portions to a solution of 20.7 g of methyl 3-oxocyclohexanecarboxylate in 520 ml of methanol at a temperature of −78° C. After 2.5 hours at −78° C., 5 ml of water are added, and the reaction mixture is allowed to reach room temperature. The solvent is then removed in a rotary evaporator. Ethyl acetate/water extraction is carried out. Drying of the organic phase over anhydrous sodium sulphate, filtration and removal of ethyl acetate result in 19.0 g of an oil. According to NMR, the product consists of a mixture of two diastereomers in the ratio 94:6. In analogy to similar sodium borohydride reductions described in the literature for cyclohexanones substituted in position 3, it is concluded that the main product must be the cis isomer.

$^1$H-NMR (300 MHz, DMSO-d$_6$, δ/ppm, main isomer): 4.60 (d, 1H), 3.58 (s, 3H), 3.43-3.32 (m, 1H), 2.32 (tt, 1H), 2.03-1.97 (m, 1H), 1.82-1.67 (in, 3H), 1.31-0.96 (m, 4H).

MS (DCI, NH$_3$): m/z=159 (M+H$^+$), 176 (M+NH$_4^+$).

Example XXXIII

Methyl cis-3-{[(4-methylphenyl)sulphonyl]oxy}cyclohexanecarboxylate

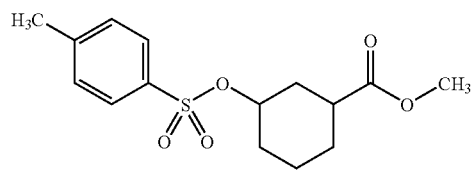

32 g of para-toluenesulphonyl chloride are added to a solution of 18.97 g of methyl cis-3-hydroxycyclohexanecarboxylate and 97 ml of pyridine in 410 ml of anhydrous dichlormethane at a temperature of 0° C. The cooling bath is removed and the reaction mixture is left to stir at room temperature overnight. The solvent and excess pyridine are then removed in a rotary evaporator. The residue resulting from this is taken up in ethyl acetate. Insolubles are removed by filtration and the filtrate is concentrated. The solid residue is stirred a total of six times with approx. 500 ml of petroleum ether each time. This results in 29.7 g of a solid.

HPLC (method 1): R$_t$: 4.67 min.

$^1$H-NMR (300 MHz, DMSO-d$_6$, δ/ppm): 7.79 (d, 2H), 7.48 (d, 2H), 4.53-4.44 (m, 1H), 3.57 (s, 3H), 2.42 (s, 3H), 2.07-1.99 (m, 1H), 1.78-1.69 (m, 3H), 1.49 (quart., 1H), 1.41-1.13 (m, 3H).

MS (DCI, NH$_3$): m/z=330 (M+NH$_4^+$).

Example XXXIV

-Methyl trans-3-azidocyclohexanecarboxylate

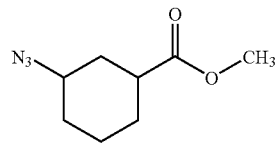

A solution of 29.6 g of methyl cis-3-{[(4-methylphenyl)sulphonyl]oxy}cyclohexanecarboxylate in 660 ml of DMF is mixed with 6.49 g of sodium azide and stirred at 80° C. for 15 hours. At room temperature, 1000 ml of water are added and the product is extracted three times with approx. 300 ml of diethyl ether each time. The organic extract is washed with saturated sodium chloride solution and dried over anhydrous sodium sulphate. Filtration and evaporation at room temperature results in 16.8 g of an oil. The assignment of the product to the trans isomer results from experience that reactions of this type take place with inversion of the stereochemistry at the reaction site.

$^1$H-NMR (200 MHz, DMSO-d$_6$, δ/ppm): 3.94 (quint., 1H), 3.60 (s, 3H), 2.68-2.56 (m, 1H), 1.82-1.72 (m, 3H), 1.62-1.43 (m, 5H).

MS (DCI, NH$_3$): m/z=201 (M+NH$_4^+$), 218 (M+N$_2$H$_7^+$).

Example XXXV

Methyl trans-3-aminocyclohexanecarboxylate hydrochloride

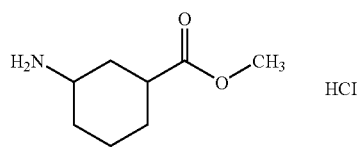

Method 1:

A solution of 16.45 g of methyl trans-3-azidocyclohexancarboxylate in 502 ml of methanol is initially mixed with 1.68 g of 10% palladium on carbon and 17.29 g of ammonium formate and then heated to reflux for 1 hour. It is then filtered through a little Tonsil and evaporated. The residue is dissolved in a little ethyl acetate, and 30 ml of a 4 molar solution of hydrogen chloride in dioxane are added. After 20 minutes, the mixture is evaporated to dryness. 16.3 g of a solid are obtained.

$^1$H-NMR (400 MHz, DMSO-$d_6$, δ/ppm): 8.23 (s broad, 3H), 3.61 (s, 3H), 3.07-3.00 (m, 1H), 2.51-2.42 (m, 1H), 2.17 (d broad, 1H), 1.93-1.74 (m, 3H), 1.42-1.11 (m, 4H).

MS (DCI, $NH_3$): m/Z=158 ($M+H^+$).

Method 2:

Methyl trans-3-aminocyclohexanecarboxylate hydrochloride can also be obtained by the method described in Example XXXV, method 1, from methyl trans-3-azido-cyclohex-4-enecarboxylate. In this case, merely the amount of ammonium formate employed is doubled.

Example XXXVI trans-3-Azidocyclohex-4-enecarboxylic acid

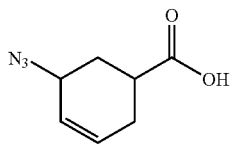

A solution of 10.6 g of sodium azide in 70 ml of water is added to a solution of 18.4 g of racemic cis-6-oxabicyclo[3.2.1]oct-3-en-7-one in 175 ml of THF. The reaction mixture is then heated to reflux for 15 hours. The THF is subsequently stripped off in a rotary evaporator at a bath temperature of 30° C. The remaining aqueous phase is mixed with 165 ml of 2 molar sodium hydroxide solution and extracted twice with 110 ml of toluene each time and once with diethyl ether. The aqueous phase is then acidified with concentrated hydrochloric acid at about 10° C. The product is extracted with dichloromethane. The organic extract is dried over anhydrous sodium sulphate, filtered and concentrated. 19.7 g of an oil, which becomes solid under storage in a refrigerator, are obtained. Assignment of the product to the trans isomer results from the experience that reactions of this type take place with inversion of the stereochemistry at the reaction site.

HPLC (method 1): $R_t$: 3.62 min.

$^1$H-NMR (300 MHz, DMSO-$d_6$, δ/ppm): 12.38 (s, broad, 1H), 6.09-6.03 (m, 1H), 5.82-5.77 (m, 1H), 4.14 (pseudo-d, 1H), 2.59-2.48 (m, 1H, partly covered by DMSO signal), 2.37-2.28 (m, 1H), 2.18-2.07 (m, 1H), 2.01-1.96 (m, 1H), 1.82-1.73 (m, 1H).

MS (ESI-): m/z=166 ($M-H^-$), 333 ($2M-H^-$).

Example XXXVII

Methyl trans-3-azidocyclohex-4-enecarboxylate

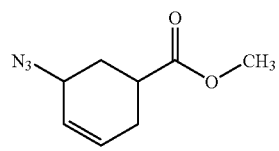

32.6 ml of trimethylsilyl chloride are added dropwise to a solution of 19.5 g of trans-3-azidocyclohex-4-enecarboxylic acid in 1.5 l of anhydrous methanol at 0° C. After one hour at 0° C., the mixture is stirred at room temperature for a further hour. It is then evaporated to dryness. 19.1 g of an oil are obtained.

TLC (cyclohexane/ethyl acetate 1:1): $R_f$: 0.75.

HPLC (method 1): $R_t$: 4.24 min.

$^1$H-NMR (300 MHz, DMSO-$d_6$, δ/ppm): 6.08-6.02 (m, 1H), 5.82-5.77 (m, 1H), 4.17 (pseudo-d, 1H), 3.62 (s, 3H), 2.69-2.59 (m, 1H), 2.38-2.29 (m, 1H), 2.20-2.08 (m, 1H), 2.02-1.94 (m, 1H), 1.85-1.76 (m, 1H).

MS (DCI, $NH_3$): m/Z=199 ($M+NH_4^+$).

Example XXXVIII

Methyl 3-{4-[(triisopropylsilyl)oxy]phenyl}propanoate

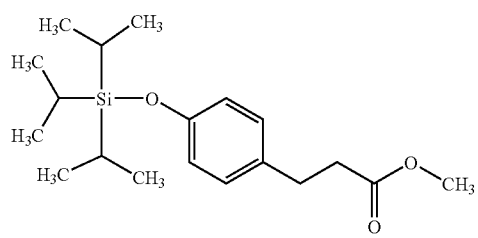

13 ml of triisopropylsilyl chloride are added to a solution of 10 g of methyl 3-(4-hydroxyphenyl)propanoate and 11.77 g of imidazole in 22 ml of DMF at room temperature. The mixture is left to stir at room temperature. After 15 hours, the mixture is poured into 200 ml of 5% strength aqueous sodium dihydrogen phosphate solution and extracted with ethyl acetate. The organic phase is washed with water and saturated sodium chloride solution. Drying over anhydrous sodium sulphate, filtration, evaporation. The crude product is purified by suction filtration on silica gel with cyclohexane/ethyl acetate 30:1. 19.38 g of an oil are obtained.

TLC (cyclohexane/ethyl acetate 9:1): $R_f$: 0.53.

HPLC (method 4): $R_t$: 6.27 min.

¹H-NMR (200 MHz, DMSO-d₆, δ/ppm): 7.09 (d, 2H), 6.77 (d, 2H), 3.56 (s, 3H), 2.78 (t, 2H), 2.58 (t, 2H), 1.28-1.13 (m, 3H), 1.05 (d, 18H).
MS (DCI, NH₃): m/z=354 (M+NH₄⁺).

Example XXXIX

3-{4-[(Triisopropylsilyl)oxy]phenyl}propan-1-ol

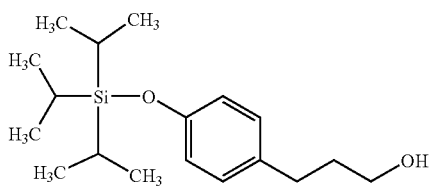

14.4 ml of a 1 molar solution of lithium aluminium hydride in THF are introduced. While stirring, a solution of 19.22 g of methyl 3-{4-[(triisopropylsilyl)-oxy]phenyl}propanoate in 58 ml of THF is added dropwise in such a way that the mixture just starts to boil. After the addition is complete, the mixture is left to stir at room temperature for 30 minutes. Then excess lithium aluminium hydride is hydrolyzed by cautious addition of 1 ml of methanol. The mixture is poured into 20% strength aqueous sodium potassium tartrate solution and extracted with ethyl acetate. The organic phase is washed successively with water and saturated sodium chloride solution. Drying over anhydrous sodium sulphate. Filtration and evaporation are followed by purification of the product by MPLC on silica gel with cyclohexane/ethyl acetate 9:1 as mobile phase. 10.7 g of an oil are obtained.

TLC (cyclohexane/ethyl acetate 9:1): R_f: 0.17.
HPLC (method 4): R_t: 5.78 min.
¹H-NMR (300 MHz, DMSO-d₆, δ/ppm): 7.05 (d, 2H), 6.77 (d, 2H), 4.39 (t, 1H), 3.38 (quart, 2H), 2.53 (t, 2H), 1.67 (m, 2H), 1.28-1.16 (m, 3H), 1.05 (d, 18H).
MS (DCI, NH₃): m/z=326 (M+NH₄⁺), 634 (2M+NH₄⁺).

Example XL

[4-(3-Bromopropyl)phenoxy](triisopropyl)silane

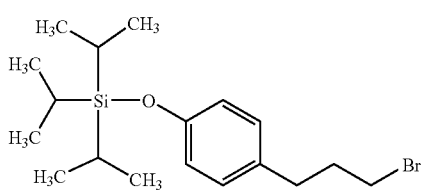

A solution of 16.85 g of 3-{4-[(triisopropylsilyl)oxy] phenyl}propan-1-ol in 15 ml of THF is mixed with 17.19 g of triphenylphosphine. As soon as it has dissolved, 21.73 g of tetrabromomethane are added, and the mixture is stirred at room temperature. The reaction mixture initially heats up somewhat during this, and after about 5 minutes a solid starts to separate out. After 2 hours, the precipitate which has separated out is filtered off and the solvent is removed in a rotary evaporator. The residue is purified by MPLC on silica gel with cyclohexane/ethyl acetate 50:1 as mobile phase. 17.53 g of an oil are obtained.

TLC (cyclohexane/ethyl acetate 4:1): R_f: 0.65.
HPLC (method 4): R_t: 8.19 min.
¹H-NMR (300 MHz, DMSO-d₆, δ/ppm): 7.09 (d, 2H), 6.79 (d, 2H), 3.48 (t, 2H), 2.63 (t, 2H), 2.07 (m, 2H), 1.28-1.17 (m, 3H), 1.07 (d, 18H).
MS (DCI, NH₃): m/z=388 and 390 (M+NH₄⁺).

Example XLI

Methyl 3-({[3-(methoxycarbonyl)cyclohexyl]amino}carbonyl)-4-(3-{4-[(triisopropyl-silyl)oxy] phenyl}propoxy)benzoate

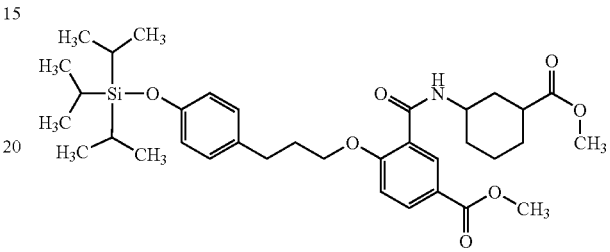

A solution of 2.66 g of [4-(3-bromopropyl)phenoxy](tri-isopropyl)silane and 2.40 g of the (+)-B-enantiomer of methyl 4-hydroxy-3-({[3-(methoxycarbonyl)cyclo-hexyl] amino}carbonyl)benzoate (see Example IX, method 2) in 100 ml of butyronitrile is admixed with 1.19 g of potassium carbonate and stirred at a bath temperature of 120° C. for 16 hours. The solvent is then removed in a rotary evaporator, and the residue is partitioned between ethyl acetate and aqueous sodium dihydrogen phosphate solution. The organic phase is washed successively with water and saturated sodium chloride solution. Drying over anhydrous sodium sulphate. Filtration and concentration are followed by purification of the product by suction filtration on silica gel with cyclohexane/ethyl acetate 2:1 as mobile phase. 3.91 g of an oil are obtained.

TLC (cyclohexane/ethyl acetate 1:1): R_f: 0.51.
HPLC (method 4): R_t: 7.14 min.
¹H-NMR (300 MHz, DMSO-d₆, δ/ppm): 8.21 (d, 1H), 8.08 (d broad, 1H), 8.01 (dd, 1H), 7.21 (d, 1H), 7.09 (d, 2H), 6.78 (d, 2H), 4.14 (pseudo-t, 3H), 3.82 (s, 3H), 3.57 (s, 3H), 2.70 (pseudo-t, 3H), 2.07 (m, 2H), 1.82 (m, 2H), 1.70-1.48 (m, 6H), 1.27-1.17 (m, 3H), 1.05 (d, 18H).
MS (DCI, NH₃): m/z=626 (M+H⁺), 643 (M+NH₄⁺).

Example XLII

Methyl 4-[3-(4-hydroxyphenyl)propoxy]-3-({[3-(methoxycarbonyl)cyclohexyl]-amino}carbonyl) benzoate

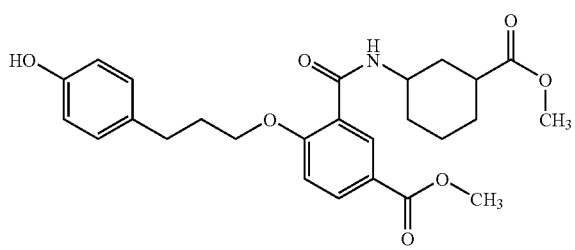

6.5 ml of a 1 molar solution of tetra-n-butylammonium fluoride in THF are added to a solution of 3.90 g of methyl 3-({[3-(methoxycarbonyl)cyclohexyl]amino}carbonyl)-4-(3-{4-[(triisopropylsilyl)oxy]phenyl}propoxy)benzoate in 40 ml of THF at 0° C. The mixture is stirred at room temperature for 10 minutes. The mixture is then evaporated to dryness, mixed with saturated ammonium chloride solution and extracted with ethyl acetate. Drying over anhydrous sodium sulphate is followed by filtration and evaporation. The resulting crude product is purified by suction filtration on silica gel with cyclohexane/ethyl acetate 1:1 as mobile phase. 2.64 g of an oil are obtained.

TLC (cyclohexane/ethyl acetate 1:1): $R_f$: 0.17.
HPLC (method 1): $R_t$: 4.48 min.
$^1$H-NMR (300 MHz, DMSO-$d_6$, δ/ppm): 9.11 (s, 1H), 8.22 (d, 1H), 8.08 (d broad, 1H), 8.01 (dd, 1H), 7.22 (d, 1H), 7.00 (d, 2H), 6.68 (d, 2H), 4.13 (pseudo-t, 3H), 3.83 (s, 3H), 3.58 (s, 3H), 2.75-2.62 (m, 3H), 2.05 (quint, 2H), 1.82 (m, 2H), 1.69-1.49 (m, 6H).
MS (DCI, NH$_3$): m/z=470 (M+H$^+$), 487 (M+NH$_4^+$).

Example XLIII

Ethyl (2E)-3-{4-[5-phenoxypent-1-en-1-yl]phenyl}acrylate (E/Z mixture)

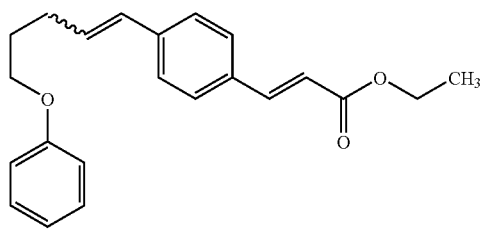

3.16 g of (4-phenoxybutyl)(triphenyl)phosphonium bromide are suspended in 25 ml of THF under argon and cooled to −40° C. 2.36 ml of n-butyllithium (1.6 molar in hexane) are added dropwise, and the mixture is warmed to 0° C. after 5 minutes and cooled again to −40° C. after 15 minutes. A solution of 0.70 g of ethyl 4-formylcinnamate in THF is added dropwise and, after 5 minutes, the reaction mixture is warmed to room temperature. The solvent is removed in a rotary evaporator. 0.75 g of product is obtained as an E/Z mixture.

HPLC (method 5): $R_t$: 5.44 min.
LC-MS (method 8): $R_t$: 4.0 min, m/z (EI+)=336.

Example XLIV (2E)-3-{4-[5-Phenoxypent-1-en-1-yl]phenyl}prop-2-en-1-ol (E/Z mixture)

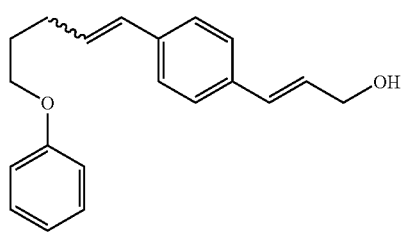

A solution of 457 mg of ethyl (2E)-3-{4-[5-phenoxypent-1-en-1-yl]phenyl}acrylate (E/Z mixture) in 4 ml of toluene is cooled to −30° C., and 0.53 ml of a solution of diisobutylaluminium hydride (about 5.5 molar in hexane) is added dropwise. After 30 minutes, the mixture is warmed to 0° C., saturated ammonium chloride solution is added, the mixture is extracted with dichloromethane, and the organic phase is dried over sodium sulphate. The solvent is removed in a rotary evaporator. 85 mg of product are obtained.

HPLC (method 5): $R_t$: 4.91 min.
$^1$H-NMR (200 MHz, CDCl$_3$, δ/ppm): 7.40-7.19 (m, 6H), 6.98-6.83 (m, 3H), 6.67-6.29 (m, 3H), 5.70 (dt, 1H), 4.33 (t 211), 3.98 (t, 2H), 2.55 (dq, 2H), 2.05-1.86/m, 2H), 1.42 (t, 1H).
MS (DCI, NH$_3$): m/z=312 (M+NH$_4^+$).

Example XLV

3-[4-(5-Phenoxypentyl)phenyl]propan-1-ol

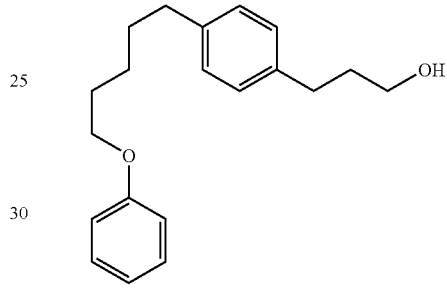

About 5 mg of palladium on carbon (10%) are added to a solution of 98 mg of (2E)-3-{4-[5-phenoxypent-1-en-1-yl]phenyl}prop-2-en-1-ol in about 5 ml of ethyl acetate, and the mixture is hydrogenated under 1 bar of hydrogen at room temperature overnight. The mixture is filtered to remove catalyst and concentrated, and the residue is purified on silica gel with cyclohexane/ethyl acetate 3:1. 53 mg of product are obtained.

HPLC (method 5): $R_t$: 5.07 min.
$^1$H-NMR (400 MHz, CDCl$_3$, δ/ppm): 7.31-7.23 (m, 5M), 7.21-7.19 (m, 1H), 6.96-6.86 (m, 3H), 3.95 (t, 2H), 3.68 (q, 2H), 2.68 (t, 2H), 2.62 (t, 2H), 1.94-1.87 (m, 4H), 1.73-1.63 (m, 2H), 1.56-1.47 (m, 2H), 1.37-1.30 (m, 1H).
LC-MS (method 9): $R_t$: 2.72 min, m/z (EI+) 298.

Example XLVI 1-(3-Iodopropyl)-4-(5-phenoxypentyl)benzene

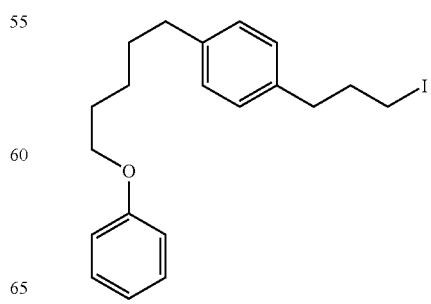

A solution of 53 mg of 3-[4-(5-phenoxypentyl)phenyl]propan-1-ol in diethyl ether/acetonitrile 3:1 is cooled to 0° C. and, under argon, 24 mg of imidazole, 70 mg of triphenylphosphine and 68 mg of iodine are added. The mixture is stirred for 30 minutes and the reaction is stopped by adding concentrated sodium thiosulphate solution. The mixture is extracted with ethyl acetate, and the organic phase is washed with saturated sodium chloride solution, dried over sodium sulphate and concentrated. The residue is purified on silica gel with cyclohexane/ethyl acetate 40:1. 34 mg of product are obtained.

MS (DCI, NH$_3$): m/z=426 (M+NH$_4^+$).

Example XLVII 4-(Biphenyl-4-ylmethoxy)phenyl acetate

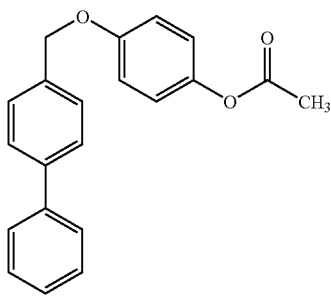

2.35 g of anhydrous potassium carbonate are added to a solution of 2.80 g of 4-biphenylmethyl bromide and 1.72 g of 4-hydroxyphenyl acetate in 75 ml of butyronitrile, and the reaction mixture is stirred at 120° C. overnight. It is filtered with suction, washed with acetonitrile, and concentrated. The residue is taken up in ethyl acetate, washed with water and saturated sodium chloride solution, dried over sodium sulphate and filtered, and the solvent is removed in a rotary evaporator. This is followed by stirring with ethyl acetate, filtration with suction and washing of the resulting crystals several times with ethyl acetate. 1.36 g of product are obtained. A further 0.36 g of product can be isolated from the mother liquor after concentration and chromatography on silica gel with dichloromethane.

HPLC (method 5): R$_t$: 5.04 min.

$^1$H-NMR (200 MHz, DMSO-d$_6$, δ/ppm): 7.73-7.62 (m, 4H), 7.58-7.32 (m, 5H), 7.05 (s, 4H), 5.15 (s, 2H), 2.24 (s, 3H).

MS (EI): m/z=318 (M$^+$).

Example XLVIII 4-(Biphenyl-4-ylmethoxy)phenol

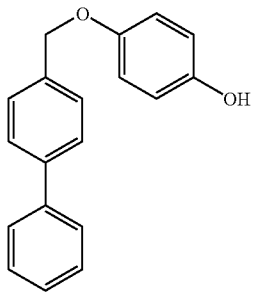

1.30 g of 4-(biphenyl-4-ylmethoxy)phenyl acetate in 25 ml of THF are slowly added dropwise to 4.5 ml of a solution of lithium aluminium hydride (1 molar in THF). The reaction is complete after 30 minutes, and hydrochloric acid (1 molar) is added dropwise until the precipitate which has initially separated out redissolves. The solution is extracted with dichloromethane, the organic phase is washed once each with water and saturated sodium chloride solution, dried over sodium sulphate and filtered, and the solvent is removed in a rotary evaporator. 1.11 g of product are obtained.

HPLC (method 5): R$_t$: 4.75 min.

$^1$H-NMR (200 MHz, CDCl$_3$, δ/ppm): 8.89 (s, 1H), 7.66 (d, 4H), 7.53-7.33 (m, 5H), 6.84 (d, 2H), 6.68 (d, 2H), 5.04 (s, 2H).

MS (DCI, NH$_3$): m/z=294 (M+NH$_4^+$).

Example XLIX

Methyl [4-(biphenyl-4-ylmethoxy)phenoxy]acetate

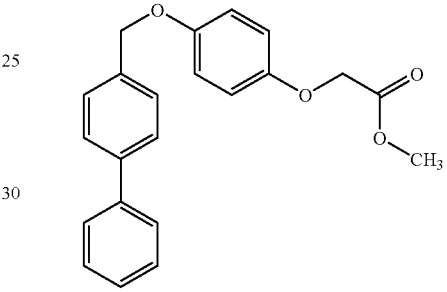

1.95 g of caesium carbonate are added to a solution of 1.10 g of 4-(biphenyl-4-ylmethoxy)phenol and 0.41 ml of methyl bromoacetate in 20 ml of DMF, and the reaction mixture is stirred at room temperature overnight and then at 80° C. for 4 hours. The solvent is removed in a rotary evaporator, the residue is triturated with water, and the crystals which have separated out are filtered off with suction and dried at 40° C. under high vacuum overnight. 1.36 g of product are obtained.

HPLC (method 5): R$_t$: 4.98 min.

$^1$H-NMR (200 MHz, CDCl$_3$, δ/ppm): 7.66-7.41 (m, 9H), 6.98-6.81 (m, 4H), 5.05 (s, 2H), 4.58 (s, 2H), 3.81 (s, 3H).

MS (DCI, NH$_3$): m/z=366 (M+NH$_4^+$).

Example L

2-[4-(Biphenyl-4-ylmethoxy)phenoxy]ethanol

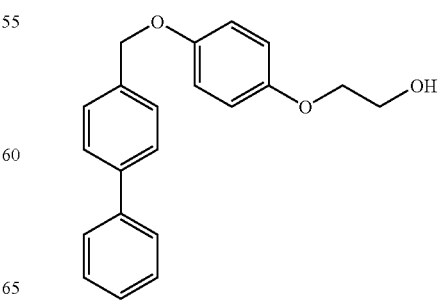

3.82 ml of lithium aluminium hydride (1 molar in THF) are slowly added dropwise to a solution of 1.21 g of methyl [4-(biphenyl-4-ylmethoxy)phenoxy]acetate in 40 ml of THF. The mixture is stirred at room temperature overnight. After addition of hydrochloric acid (1 molar), dichloromethane and water, the insoluble crystals are filtered off with suction and dried at 40° C. under high vacuum overnight (221 mg of product). A further 700 mg of product are obtained from the organic phase after washing with water and saturated sodium chloride solution, drying over sodium sulphate, filtration and removal of the solvent in vacuo.

HPLC (method 5): $R_t$: 4.73 min.

$^1$H-NMR (200 MHz, DMSO-$d_6$, δ/ppm): 7.77-7.32 (m, 9H), 6.98-6.80 (m, 4H), 5.07 (s, 2H), 4.84 (t, 1H), 3.92 (s, 2H), 3.77-3.60 (m, 2H).

MS (DCI, NH$_3$): m/z=338 (M+NH$_4^+$).

Example LI

4-{[4-(2-Bromoethoxy)phenoxy]methyl}biphenyl

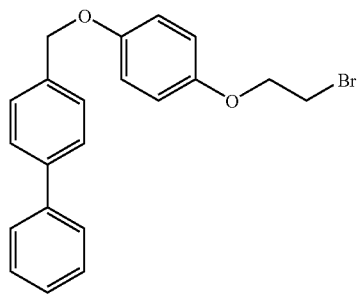

800 mg of 2-[4-(biphenyl-4-ylmethoxy)phenoxy]ethanol are introduced into 25 ml of dichloromethane under argon, 1.16 g of tetrabromomethane are added, and the mixture is stirred at room temperture for 10 minutes. The mixture is cooled to 0° C. and, after addition of 1.83 g of triphenylphosphine, stirred at 0° C. for one hour and at room temperature for 2 hours. It is concentrated, and the residue is taken up in a little dichloromethane and filtered through silica gel. 480 mg of product are obtained.

HPLC (method 5): $R_t$: 5.30 min.

$^1$H-NMR (300 MHz, DMSO-$d_6$, δ/ppm): 7.73-7.63 (m, 4H), 7.56-7.33 (m, 5H), 7.02-6.88 (m, 4H), 5.11 (s, 2H), 4.26 (t, 2H), 3.77 (t, 2H).

MS (EI): m/z=383 and 385 (M$^+$).

Example LII

Methyl {4-[5-phenoxypent-1-en-1-yl]phenoxy}acetate (E/Z mixture)

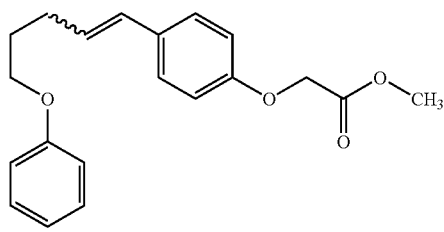

Preparation takes place in analogy to Example XLIII from methyl (4-formylphenoxy)acetate and (4-phenoxybutyl)(triphenyl)phosphonium bromide. The product is obtained as an E/Z mixture.

HPLC (method 5): $R_t$: 5.03 min.

$^1$H-NMR (300 MHz, CDCl$_3$, δ/ppm): 7.32-7.18 (m, 4H), 6.96-6.81 (m, 5H), 6.43-6.34 (m, 1H), 6.12 (dt, 0.5H), 5.63 (dt, 0.5H), 4.62 (d, 2H), 4.00 (q, 2H), 3.81 (d, 3H), 2.50 (dq, 1H), 2.38 (dq, 1H), 2.01-1.87 (m, 2H).

LC-MS (method 10): $R_t$: 3.49 min, m/z=233 (M–C$_6$H$_5$O).

Example LIII

2-{4-[(1Z)-5-Phenoxypent-1-en-1-yl]phenoxy}ethanol

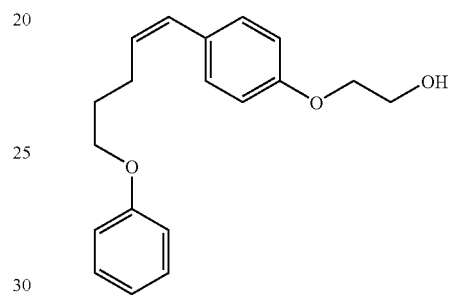

Preparation takes place in analogy to Example XLIV from methyl {4-[5-phenoxypent-1-en-1-yl]phenoxy}acetate (E/Z mixture). The double-bond isomers are separated by HPLC (stability. C-30 5 μm 250 mm×20 mm No. 20101; acetonitrile/water 3:1; flow rate: 25 ml/min; UV detection: 210 nm).

HPLC (method 5): $R_t$: 4.80 min.

$^1$H-NMR (300 MHz, CDCl$_3$, δ/ppm): 7.30-7.20 (m, 4H), 6.93 (t, 1H), 6.60-6.85 (m, 4H), 6.39 (d, 1H), 5.62 (dt, 1H), 4.11-4.07 (m, 2H), 4.01-3.95 (m, 4H), 2.51 (dq, 2H), 2.00-1.91 (m, 3H).

LC-MS (method 9): $R_t$: 2.51 min, m/z=205 (M–C$_6$H$_5$O).

Example LIV 1-(2-Iodoethoxy)-4-[(1Z)-5-phenoxypent-1-en-1-yl]benzene

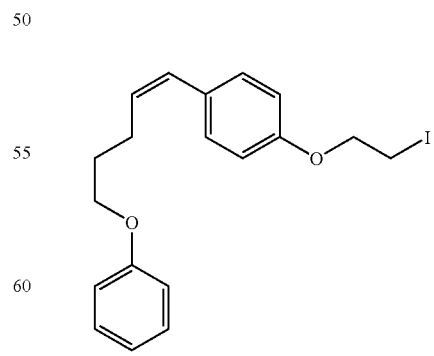

Preparation takes place in analogy to Example XLVI from 2-{4-[(1Z)-5-phenoxypent-1-en-1-yl]phenoxy}ethanol.

HPLC (method 5): $R_t$: 5.55 min.

Example LV

1-Iodo-4-(4-phenoxybutoxy)benzene

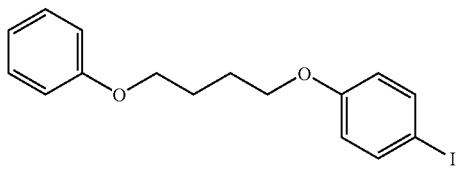

Preparation takes place in analogy to Example XVII from 4-phenoxybutyl bromide and 4-iodophenol.

HPLC (method 5): $R_t$: 5.56 min.

$^1$H-NMR (200 MHz, CDCl$_3$, δ/ppm): 7.60-7.49 (m, 2H), 7.37-7.20 (m, 2H), 7.00-6.82 (m, 3H), 6.74-6.62 (m, 2H), 4.10-3.90 (m, 4H), 2.06-1.89 (m, 4H).

MS (DCI, NH$_3$): m/z=386 (M+NH$_4^+$).

Example LVI

3-[4-(4-phenoxybutoxy)phenyl]prop-2-yn-1-ol

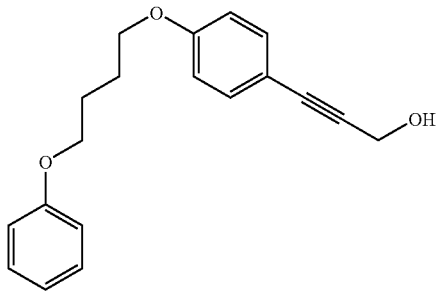

155 mg of copper(I) iodide, 57 mg of triphenylphosphine and 152 mg of bis(triphenylphosphine)palladium(II) chloride are added to a solution of 1.00 g of 1-iodo-4-(4-phenoxybutoxy)benzene in 15 ml triethylamine under argon. 457 mg of propargyl alcohol are added dropwise to the mixture, and it is stirred at 60° C. for one hour. The reaction mixture is filtered through Celite and washed several times with ethyl acetate and dichloromethane. The combined phases are washed three times with water, twice with dilute hydrochloric acid and once with saturated sodium chloride solution, dried over sodium sulphate, filtered and concentrated. The residue is purified on silica gel with cyclohexane/ethyl acetate 5:1. 737 mg of product are obtained.

$^1$H-NMR (300 MHz, CDCl$_3$, δ/ppm): 7.40-7.23 (m, 4H), 6.96-6.79 (m, 5H), 4.48 (d, 2H), 4.08-3.98 (m, 4H), 2.03-1.94 (m, 4H), 1.57 (t, 1H).

MS (DCI, NH$_3$): m/z=297 (M+NH$_4^+$).

Example LVII 1-(3-Bromoprop-1-yn-1-yl)-4-(4-phenoxybutoxy)benzene

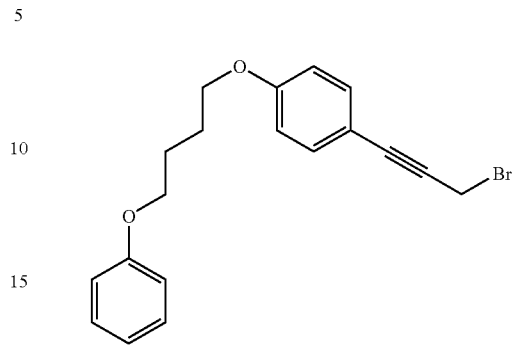

Preparation takes place in analogy to Example IV from 3-[4-(4-phenoxybutoxy)phenyl]prop-2-yn-1-ol.

HPLC (method 5): $R_t$: 5.32 min.

$^1$H-NMR (300 MHz, CDCl$_3$, δ/ppm): 7.40-7.23 (m, 4H), 6.97-6.79 (m, 5H), 4.16 (s, 2H), 4.10-3.96 (m, 4H), 2.03-1.92 (m, 4H).

MS (DCI, NH$_3$): m/z=376 and 378 (M+NH$_4^+$).

Example LVIII

2-[4-(5-phenoxypentyl)phenoxy]ethanol

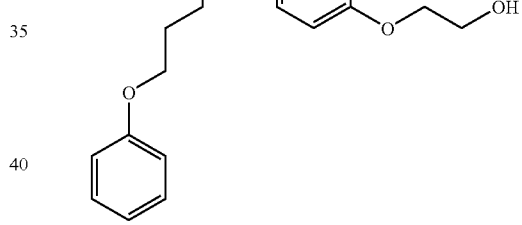

Preparation takes place in analogy to Example XLV from 2-{4-[5-phenoxypent-1-en-1-yl]phenoxy}ethanol.

HPLC (method 5): $R_t$: 4.88 min.

$^1$H-NMR (300 MHz, CDCl$_3$, δ/ppm): 7.30-7.23 (m, 2H), 7.12-7.07 (m, 2H), 6.95-6.82 (m, 5H), 4.09-4.05 (m, 2H), 3.98-3.91 (m, 4H), 2.59 (t, 2H), 1.99 (t, 1H), 1.85-1.75 (m, 2H), 1.72-1.61 (m, 2H), 1.55-1.43 (m, 2H).

LC-MS (method 10): $R_t$: 3.35 min, m/z (EI+)=300.

Example LIX 1-(2-Iodoethoxy)-4-(5-phenoxypentyl)benzene

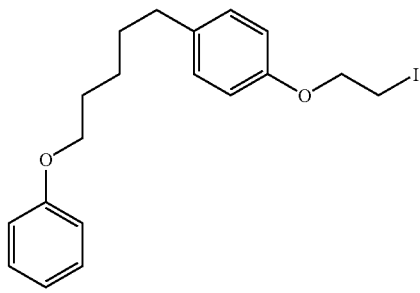

Preparation takes place in analogy to Example XLVI from 2-[4-(5-phenoxypentyl)-phenoxy]ethanol.

HPLC (method 5): $R_t$: 5.58 min.

MS (DCI, NH$_3$): m/z=428 (M+NH$_4^+$).

Example LX

Methyl 3-{4-[(4-phenoxybut-2-yn-1-yl)oxy]phenyl}propanoate

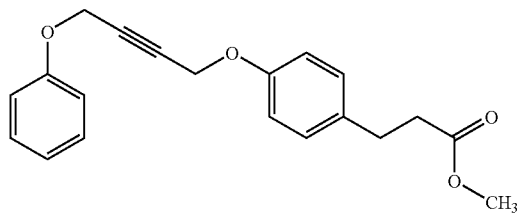

Preparation takes place in analogy to Example XVII from [(4-bromobut-2-yn-1-yl)oxy]benzene and methyl 3-(4-hydroxyphenyl)propanoate.

HPLC (method 5): $R_t$: 4.77 min.

$^1$H-NMR (300 MHz, CDCl$_3$, δ/ppm): 7.27 (dd, 2H), 7.09 (d 2H), 7.03-6.90 (m, 3H), 6.86 (d, 2H), 4.70 (dd, 4H), 3.67 (s, 3H), 2.89 (t, 2H), 2.59 (t, 2H).

MS (DCI, NH$_3$): m/z=342 (M+NH$_4^+$).

Example LXI

3-{4-[(4-phenoxybut-2-yn-1-yl)oxy]phenyl}propan-1-ol

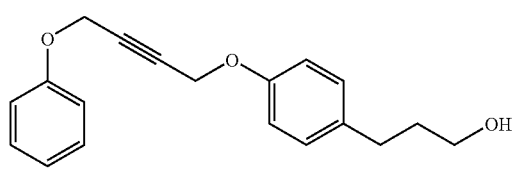

Preparation takes place in analogy to Example II from methyl 3-{4-[(4-phenoxybut-2-yn-1-yl)oxy]phenyl}propanoate.

HPLC (method 5): $R_t$: 4.42 min.

$^1$H-NMR (300 MHz, CDCl$_3$, δ/ppm): 7.31-7.24 (m, 2H), 7.10 (d, 2H), 7.00 (d, 1H), 6.94 (dd, 2H), 6.86 (d, 2H), 4.71 (dd, 4H), 3.71-3.62 (m, 2H), 2.66 (t, 2H), 1.92-1.82 (m, 2H), 1.22 (t, 1H).

MS (DCI, NH$_3$): m/z=314 (M+NH$_4^+$).

Example LXII 1-(3-Bromopropyl)-4-[(4-phenoxybut-2-yn-1-yl)oxy]benzene

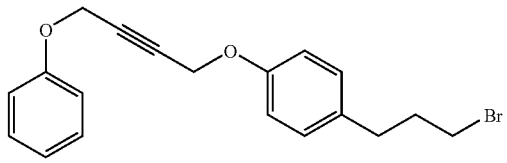

Preparation takes place in analogy to Example IV from 3-{4-[(4-phenoxybut-2-yn-1-yl)oxy]phenyl}propan-1-ol.

HPLC (method 5): $R_t$: 5.17 min.

$^1$H-NMR (300 MHz, CDCl$_3$, δ/ppm): 7.32-7.24 (m, 2H), 7.09 (d, 2H), 7.00 (d, 1H), 6.94 (dd, 2H), 6.87 (d, 2H), 4.71 (dd, 4H), 3.38 (t, 2H), 2.72 (t, 2H), 2.13 (quint, 2H).

LC-MS (method 9): $R_t$: 2.88 min, m/z (EI+)=358 and 360.

Example LXIII

Ethyl 3-{4-[5-phenoxypent-1-en-1-yl]phenyl}propanoate (E/Z mixture)

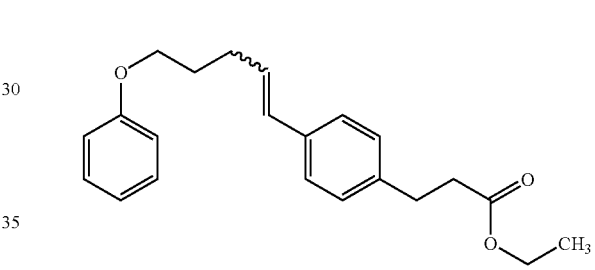

Preparation takes place in analogy to Example XLIII from (4-phenoxybutyl)-(triphenyl)phosphonium bromide and ethyl 3-(4-formylphenyl)propanoate. The product is obtained as an E/Z mixture.

HPLC (method 5): $R_t$: 5.38 min.

$^1$H-NMR (300 MHz, CDCl$_3$, δ/ppm): 7.31-7.10 (m, 6H), 6.96-6.83 (m, 3H), 6.46-6.36 (m, 1H), 6.20 (dt, 0.37H), 5.66 (dt, 0.63H), 4.12 (dq, 2H), 3.99 (q, 2H), 2.98-2.88 (m, 2H), 2.64-2.56 (m, 2H), 2.51 (dq, 1.25H), 2.39 (q, 0.75H), 2.00-1.88 (m, 2H), 1.23 (t, 3H).

LC-MS (method 9): $R_t$: 3.01 min, m/z (EI+)=338.

Example LXIV

3-{4-[(1Z)-5-phenoxypent-1-en-1-yl]phenyl}propan-1-ol

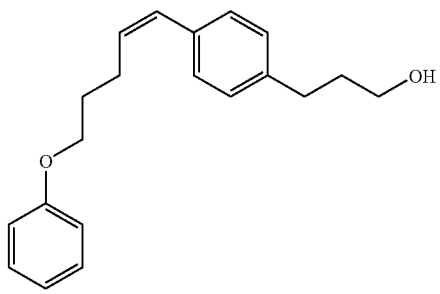

Preparation takes place in analogy to Example XLIV from ethyl 3-{4-[5-phenoxypent-1-en-1-yl]phenyl}propanoate (E/Z mixture). The double-bond isomers are separated by HPLC (Kromasil 100 C-18 5 μm 250 mm×20 mm; methanol/water 3:1; flow rate: 25 ml/min; UV detection: 210 nm).

$^1$H-NMR (400 MHz, CDCl$_3$, δ/ppm): 7.30-7.24 (m, 2H), 7.22 (d, 2H), 7.15 (d, 2H), 6.93 (t, 1H), 6.87 (d, 2H), 6.43 (d, 1H), 5.66 (dt, 1H), 3.98 (t, 2H), 3.68 (t, 2H), 2.70 (t, 2H), 2.53 (dq, 2H), 1.98-1.86 (m, 4H), 1.23 (s, broad, 1H).

LC-MS (method 9): R$_t$: 2.61 min, m/z=203 (M−OC$_6$H$_5$).

Example LXV (4Z)-5-[4-(3-Bromopropyl)phenyl]pent-4-en-1-yl phenyl ether

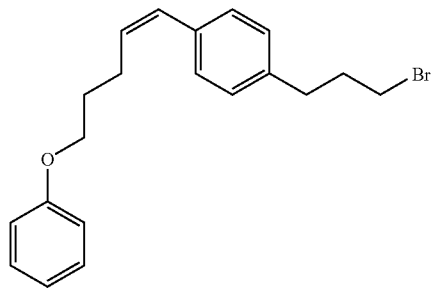

Preparation takes place in analogy to Example IV from 3-{4[(1Z)-5-phenoxypent-1-en-1-yl]phenyl}propan-1-ol.
HPLC (method 5): R$_t$: 5.69 min.

Example LXVI

3-{4-[(1E)-5-Phenoxypent-1-en-1-yl]phenyl}propan-1-ol

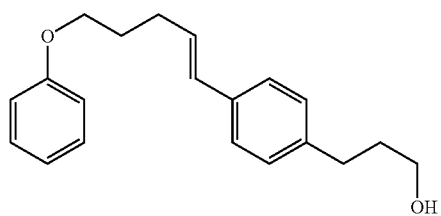

Preparation takes place in analogy to Example XLIV from ethyl 3-{4-[5-phenoxypent-1-en-1-yl]phenyl}propanoate (E/Z mixture). The double-bond isomers are separated by HPLC (Kromasil 100 C-18 5 μm 250 mm×20 mm; methanol/water 3:1; flow rate: 25 ml/min; UV detection: 210 nm].

$^1$H-NMR (400 MHz, CDCl$_3$, δ/ppm): 7.30-7.24 (m, 4H), 7.13 (d, 2H), 6.96-6.88 (m, 3H), 6.41 (d, 1H), 6.21 (dt, 1H), 4.01 (t, 2H), 3.68 (t, 2H), 2.69 (t, 2H), 2.39 (q, 2H), 2.00-1.84 (m, 4H), 1.23 (s, broad, 1H).

LC-MS (method 9): R$_t$: 2.63 min, m/z=203 (M−OC$_6$H$_5$).

Example LXVII (4E)-5-[4-(3-Bromopropyl)phenyl]pent-4-en-1-yl phenyl ether

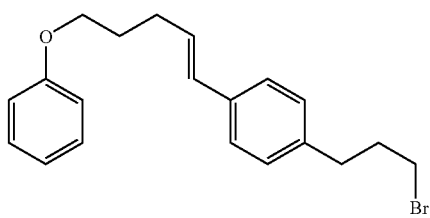

Preparation takes place in analogy to Example IV from 3-{4-[(1E)-5-phenoxypent-1-en-1-yl]phenyl}propan-1-ol.
HPLC (method 5): R$_t$: 5.68 min.

Example LXVIII

Methyl (2E)-3-[4-(4-phenoxybutoxy)phenyl]acrylate

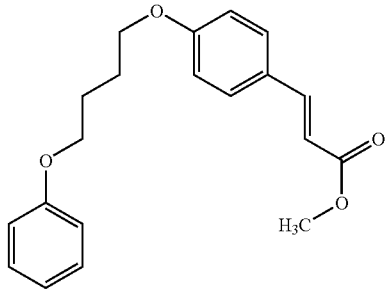

Preparation takes place in analogy to Example I from methyl (2E)-3-(4-hydroxy-phenyl)acrylate and (4-bromobutoxy)benzene.
HPLC (method 2): R$_t$: 5.4 min.

$^1$H-NMR (200 MHz, DMSO-d$_6$, δ/ppm): 7.73-7.61 (m, 3H), 7.34-7.22 (m, 2H), 7.04-6.86 (m, 5H), 6.48 (d, 1H), 4.15-3.95 (m, 4H); 3.70 (s, 3H), 1.93.1.81 (m, 4H).

MS (DCI, NH$_3$): m/z=327 (M+H$^+$), 344 (M+NH$_4^+$).

Example LXIX (2E)-3-[4-(4-Phenoxybutoxy)phenyl]prop-2-en-1-ol

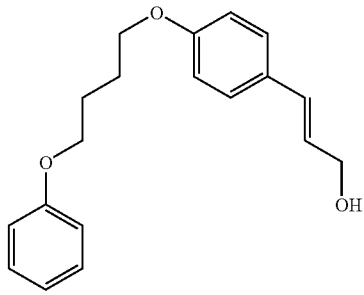

Preparation takes place in analogy to Example II from methyl (2E)-3-[4-(4-phenoxybutoxy)phenyl]acrylate.

$^1$H-NMR (300 MHz, CDCl$_3$, δ/ppm): 7.34-7.24 (m, 4H), 6.97-6.82 (m, 5H), 6.56 (d, 1H), 6.23 (dt, 1H), 4.30 (d,2H), 4.07-4.01 (m, 4H), 2.01-1.95 (m, 4H), 1.36 (s, broad, 1H).

Example LXX

1-[(1E)-3-Bromoprop-1-en-1-yl]-4-(4-phenoxybutoxy)benzene

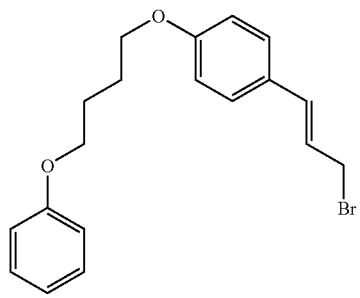

A solution of 250 mg of (2E)-3-[4-(4-phenoxybutoxy)phenyl]prop-2-en-1-ol in 10 ml of dichloromethane is cooled to −10° C., and 82 mg of phosphorus tribromide in 0.5 ml of dichloromethane are added dropwise. The mixture is stirred for one hour, during which it warms to room temperature. Saturated sodium bicarbonate solution is added to the mixture, which is extracted several times with diethyl ether, and the organic phase is dried over sodium sulphate, filtered and concentrated. 164 mg of product are obtained.

HPLC (method 5): R$_t$: 5.20 min.

$^1$H-NMR (300 MHz, CDCl$_3$, δ/ppm): 7.35-7.21 (m, 4H), 6.98-6.80 (m, 5H), 6.58 (d, 1H), 6.25 (dt, 1H), 4.17 (d,2H), 4.08-3.96 (m, 4H), 2.06-1.92 (m, 4H).

MS (DCI, NH$_3$): m/z=378 and 380 (M+NH$_4$$^+$), 281 (M−Br$^-$).

Example LXXI

[2-(Methoxycarbonyl)cyclohexyl]-methaneammonium bromide

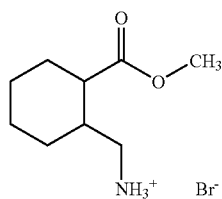

2.90 g of octahydro-1H-isoindol-1-one are stirred in 80 ml of concentrated hydrobromic acid at 100° C. overnight. Addition of about 5 ml of methanol is followed by heating for a further 5 hours and, after cooling, the reaction mixture is concentrated. Seed crystals are added to the residue, or it is scratched, it is then stirred with ethyl acetate and filtered with suction to remove solvent. For complete conversion, it is taken up in about 5 ml of methanol and, after addition of a few drops of concentrated sulphuric acid, stirred under reflux for about two hours. After cooling, the reaction mixture is concentrated, stirred with ethyl acetate, filtered with suction and dried in vacuo.

HPLC (method 5): R$_t$: 3.15 min.

$^1$H-NMR (400 MHz, DMSO-d$_6$, δ/ppm): 7.75 (s, broad, 3H), 3.61 (s, 3H), 2.95-2.73 (m, 3H), 2.05-1.92 (m, 1H), 1.86-1.73 (m, 1H), 1.66-1.22 (7H).

MS (DCI, NH$_3$): m/z=172 (M+H$^+$).

Example LXXII

Methyl 1-[5-(methoxycarbonyl)-2-(3-{4-[(triisopropylsilyl)oxy]phenyl}propoxy)-benzoyl]piperidine-4-carboxylate

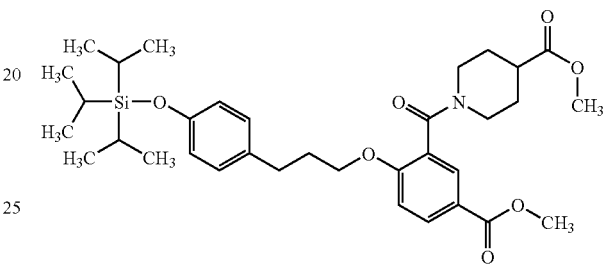

Methyl 1-[5-(methoxycarbonyl)-2-(3-{4-[(triisopropylsilyl)oxy]phenyl}propoxy)-benzoyl]piperidine-4-carboxylate is prepared by the process described in Example XLI from [4-(3-bromopropyl)phenoxy](triisopropyl)silane and methyl 1-[2-hydroxy-5-(methoxycarbonyl)benzoyl]-4-piperidinecarboxylate.

HPLC (method 4): R$_t$: 6.63 min.

MS (ESI): m/z 612 (M+H$^+$).

Example LXXIII

Methyl 1-[2-[3-(4-hydroxyphenyl)propoxy]-5-(methoxycarbonyl)benzoyl]piperidine-4-carboxylate

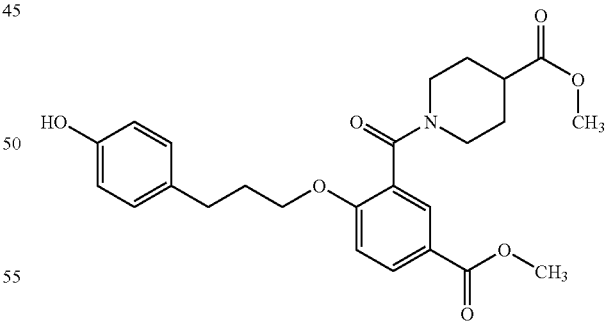

Methyl 1-[2-[3-(4-hydroxyphenyl)propoxy]-5-(methoxycarbonyl)benzoyl]piperidine-4-carboxylate is prepared in analogy to the process described in Example XLII from methyl 1-[5-(methoxycarbonyl)-2-(3-{4-[(triisopropylsilyl)oxy]phenyl}propoxy)-benzoyl]piperidine-4-carboxylate.

HPLC (method 1): R$_t$: 4.30 min.

$^1$H-NMR (200 MHz, CDCl$_3$, δ/ppm): 8.02 (dd, 1H), 7.93 and 7.90 (2 d, together 1H), 7.00 (d, 2H), 6.88 (d, 1H), 6.75 (d, 2H), 5.67 (d, 1H), 4.62 (m, 1H), 4.02 (m, 2H), 3.87 (s, 3H), 3.70 and 3.63 (2 s, together 3H), 3.49 (m, 1H), 3.27 (m, 1H), 3.12-2.95 (m, 2H), 2.72-2.52 (m, 3H), 2.11-1.97 (m, 3H), 1.84-1.63 (m, 2H).

MS (DCI, NH$_3$): m/z=456 (M+H$^+$).

Exemplary Embodiments

Example 1

Methyl 1-[5-(methoxycarbonyl)-2-({3-[4-(4-phenoxybutoxy)phenyl]propanoyl}-amino)benzoyl]-4-piperidinecarboxylate

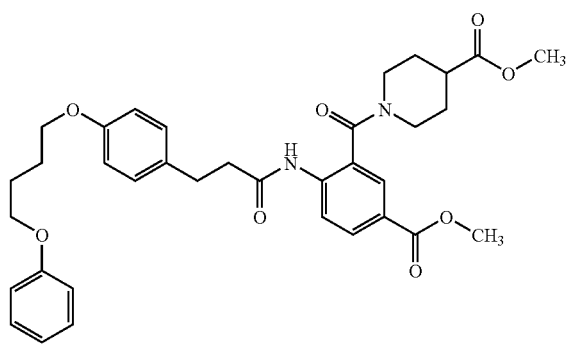

2 ml of pyridine and a solution of 470 mg of 3-[4-(4-phenoxybutoxy)phenyl]propanoyl chloride in 7.5 ml of dichloromethane are added to a solution of 450 mg of methyl 1-[2-amino-5-(methoxycarbonyl)benzoyl]-4-piperidinecarboxylate in 7.5 ml of dichloromethane. The reaction mixture is left to stir at room temperature for 15 hours. It is then acidified with 2 molar hydrochloric acid and extracted with ethyl acetate. The organic extract is washed with saturated brine and dried over anhydrous sodium sulphate. Filtration and evaporation result in a crude product which is purified by flash chromatography (silica gel, cyclohexane/ethyl acetate 2:1). 617 mg of product are obtained.

TLC: R$_f$: 0.55 (cyclohexane/ethyl acetate 1:9).

HPLC (method 1): R$_t$: 5.08 min.

$^1$H-NMR (300 MHz, DMSO-d$_6$, δ/ppm): 9.76 (s, 1H), 7.97 (dd, 1H), 7.82-7.77 (m, 2H), 7.30-7.23 (m, 2H), 7.13 (d, 2H), 6.93-6.89 (m, 3H), 6.84 (d, 2H), 4.32 (m 1H), 4.00 (m, 4H), 3.83 (s, 3H), 3.60 (s, 3H), 2.92-2.77 (m, 4H), 2.64-2.56 (m, 3H), 1.93-1.42 (m, 9H).

MS (ESI+): m/z 617 (M+H$^+$).

Example 2

Methyl 3-({[3-(methoxycarbonyl)cyclohexyl]amino}carbonyl)-4-{3-[4-(4-phenoxybutoxy)phenyl]propoxy}benzoate (racemate B)

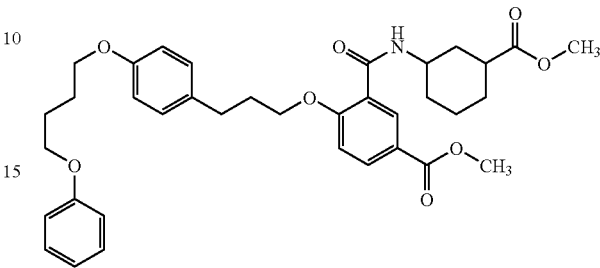

A solution von 542 mg of 1-(3-bromopropyl)-4-(4-phenoxybutoxy)benzene and 500 mg of methyl 4-hydroxy-3-({[3-(methoxycarbonyl)cyclohexyl]amino}carbonyl)-benzoate (racemate B) in 50 ml of butyronitrile is mixed with 248 mg of potassium carbonate and heated to reflux for 15 hours. 5% strength sodium dihydrogen phosphate solution is then added to the reaction mixture, and it is extracted with ethyl acetate. The organic extract is washed with saturated brine and dried over anhydrous sodium sulphate. Filtration and evaporation result in a crude product which is purified by suction filtration through silica gel with cyclohexane/ethyl acetate 2:1 as mobile phase. 672 mg of product are obtained.

TLC: R$_f$: 0.33 (cyclohexane/ethyl acetate 1:1).

HPLC (method 1): R$_t$: 5.68 min.

$^1$H-NMR (300 MHz, DMSO-d$_6$, δ/ppm): 8.21 (d, 1M, 8.08 (d broad, 1H), 8.00 (dd, 1H), 7.30-7.20 (m, 3H), 7.12 (d, 2H), 6.94-6.88 (m, 3H), 6.84 (d, 2H), 4.17-4.12 (m, 3H), 4.01 (m, 4H), 3.83 (s, 3H), 3.57 (s, 3H), 2.73-2.68 (m, 3H), 2.08 (m, 1H), 1.88-1.81 (m, 6H), 1.69-1.49 (m, 6H).

MS (ESI+): m/z=618 (M+H$^+$), 640 (M+Na$^+$).

Example 3

Methyl 3-({[3-(methoxycarbonyl)cyclohexyl]amino}carbonyl)-4-{3-[4-(4-phenoxy-butoxy)phenyl]propoxy}benzoate (racemate A)

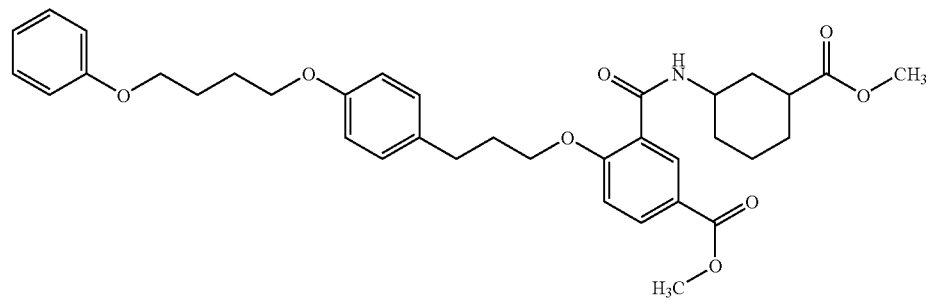

Methyl 3-({[3-(methoxycarbonyl)cyclohexyl]amino}carbonyl)-4-{3-[4-(4-phenoxy-butoxy)phenyl]propoxy}benzoate (racemate A) is prepared in analogy to the process described in Example 2 from 1-(3-bromopropyl)-4-(4-phenoxybutoxy)benzene and methyl 4-hydroxy-3-({[3-(methoxycarbonyl)cyclohexyl]amino}carbonyl)benzoate (racemate A).

TLC: $R_f$: 0.38 (cyclohexane/ethyl acetate 1:1).

HPLC (method 1): $R_t$: 5.67 min.

$^1$H-NMR (300 MHz, DMSO-$d_6$, δ/ppm): 8.20 (d, 1H), 8.07 (d broad, 1H), 8.00 (dd, 1H), 7.30-7.18 (m, 3H), 7.12 (d, 2H), 6.94-6.88 (m, 3H), 6.84 (d, 2H), 4.13 (t, 2H), 4.01 (m, 4H), 3.84 (m, 1H), 3.83 (s, 3H), 3.57 (s, 3H), 2.70 (t, 2H), 2.48 (m, 1H), 2.17 (m, 1H), 2.03 (m, 2H), 1.92-1.73 (m, 7H), 1.43-1.12 (m, 4H).

MS (ESI): m/z=618 (M+H$^+$), 640 (M+Na$^+$).

Example 4

Methyl 1-(5-(methoxycarbonyl)-2-{3-[4-(4-phenoxybutoxy)phenyl]propoxy}-benzoyl)-4-piperidinecarboxylate Example 5

Methyl 1-[2-{3-[4-(1,1'-biphenyl-4-ylmethoxy)phenyl]propoxy}-5-(ethoxycarbonyl)-benzoyl]-4-piperidinecarboxylate

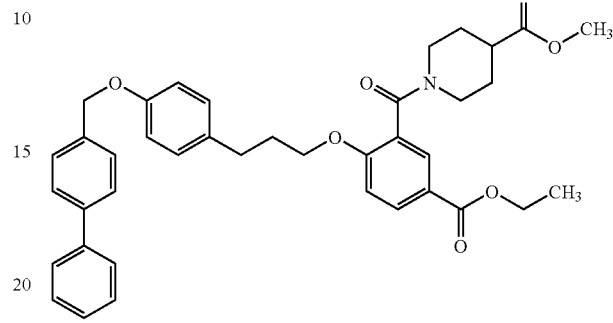

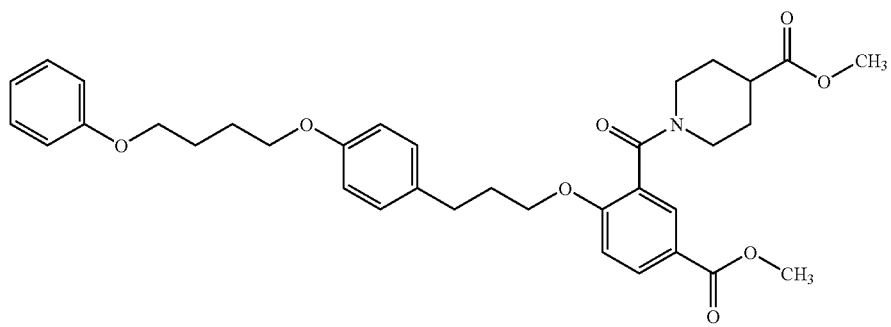

Methyl 1-(5-(methoxycarbonyl)-2-{3-[4-(4-phenoxybutoxy)phenyl]propoxy}-benzoyl)-4-piperidinecarboxylate is prepared in analogy to the process described in Example 2 from 1-(3-bromopropyl)-4-(4-phenoxybutoxy)benzene and methyl 1-[2-hydroxy-5-(methoxycarbonyl)benzoyl]-4-piperidinecarboxylate.

HPLC (method 1): $R_t$: 5.42 min.

$^1$H-NMR (400 MHz, DMSO-$d_6$, δ/ppm): 7.97 (d, 1H), 7.73 (dd, 1H), 7.29-7.25 (m, 2H), 7.17 (d, 1H), 7.12-7.09 (m, 2H), 6.93-6.90 (m, 3H), 6.86-6.83 (m, 2H), 4.43 (m, 1H), 4.16-3.97 (m, 6H), 3.82 (s, 3H), 3.60 and 3.54 (2 s, 3H), 3.29 (m, 1H), 3.11-2.98 (m, 1H), 2.92 (m, 1H), 2.71-2.60 (m, 3H), 2.03-1.72 (m, 8), 1.64-1.50 (m, 2H).

MS (DCI, NH$_3$+): m/z=604.3 (M+H$^+$), 621.3 (M+NH$_4^+$).

75 mg of N-[(3-dimethylamino)propyl]-N'-ethylcarbodiimide hydrochloride (EDC), 27 mg of 1-hydroxy-1H-benzotriazole hydrate (HOBT) and 40 mg of triethylamine, are successively added to a suspension of 100 mg of 2-{3-[4-(1,1'-biphenyl-4-ylmethoxy)phenyl]propoxy}-5-(ethoxycarbonyl)benzoic acid and 39 mg of methyl piperidine-4-carboxylate hydrochloride in 30 ml of dichloromethane. Water is added to the reaction mixture after 15 hours at room temperature. After phase separation, the aqueous phase is extracted with ethyl acetate. The combined dichloromethane and ethyl acetate phases are washed with saturated brine and dried over anhydrous sodium sulphate. Filtration and concentration result in a crude product which is purified by suction filtration through silica gel with cyclohexane/ethyl acetate 1:1 as mobile phase. 120 mg of product are obtained.

HPLC (method 1): $R_t$: 5.75 min.

$^1$H-NMR (200 MHz, DMSO-$d_6$, δ/ppm): 7.97 (dd, 1H), 7.75-7.66 (m, 5H), 7.53-7.37 (m, 5H), 7.19-7.11 (m, 3H); 6.96-6.92 (m, 2H), 5.12 (s, 2H), 4.48-4.37 (m, 1H), 4.28 (quart; 2H), 4.13-3.98 (m, 2H), 3.60 and 3.53 (2 s, 3H), 3.28 (m, 1H), 3.14-2.86 (m, 2H), 2.71-2.59 (m, 3H), 2.02-1.88 (m, 3H), 1.79-1.54 (m, 3H), 1.31 (t, 3H).

MS (ESI+): m/z=636.1 (M+H$^+$).

Example 6

Ethyl 3-({cis-[2-(ethoxycarbonyl)cyclohexyl]amino}carbonyl)-4-{3-[4-(4-phenoxy-butoxy)phenyl]propoxy}benzoate

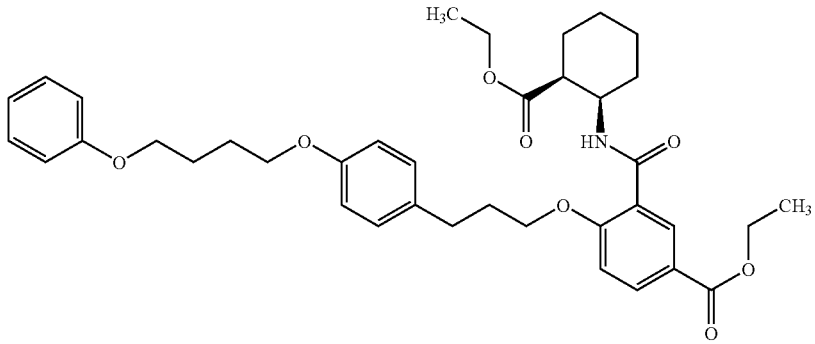

39 mg (0.20 mmol) of N-[(3-dimethylamino)propyl]-N'-ethylcarbodiimide hydrochloride (EDC) and 27.4 mg (0.20 mmol) of 1-hydroxy-1H-benzotriazole hydrate (HOBT) are successively added to a suspension of 100 mg (0.20 mmol) of 5-(ethoxycarbonyl)-2-{3-[4-(4-phenoxybutoxy)phenyl]propoxy}benzoic acid in 30 ml of dichloromethane at RT. After 30 min, 41 mg (0.41 mmol) of triethylamine and 38 mg (0.18 mmol) of ethyl cis-2-amino-1-cyclohexanecarboxylate hydrochloride are added, and the mixture is stirred overnight. 10 ml of water are then added, the phases are separated, and the aqueous phase is extracted with dichloromethane (three times 25 ml). The combined organic phases are washed with saturated sodium chloride solution, dried, (sodium sulphate) and concentrated in a rotary evaporator. The crude product is purified by column chromatography (silica gel 60, mobile phase gradient cyclohexane-->cyclohexane-ethyl acetate 5:1). 102 mg of product are obtained.

HPLC (method 2): $R_t$: 6.22 min $^1$H-NMR (300 MHz, CDCl$_3$, δ/ppm): 8.33 (d, 1H), 8.43 (d, 1H), 8.07 (dd, 1H), 7.31-7.23 (m, 2H), 7.11 (d, 2H), 6.96-6.86 (m, 4H), 6.83 (d, 2H), 4.47 (m, 1H), 4.35 (m, 2H), 4.23-3.96 (m, 8H); 2.93-2.70 (m, 3H), 2.38-2.15 (m, 2H), 2.12-1.90 (m, 6H), 1.81-1.61 (m, 3H), 1.37 (t, 3H), 1.19 (t, 3H).

MS (ESIpos): m/z=646 (M+H)$^+$

Example 7

Ethyl 3-{[4-(2-ethoxy-2-oxoethyl)-1-piperidinyl]carbonyl}-4-{3-[(4-phenoxybutoxy)phenyl]propoxy}benzoate

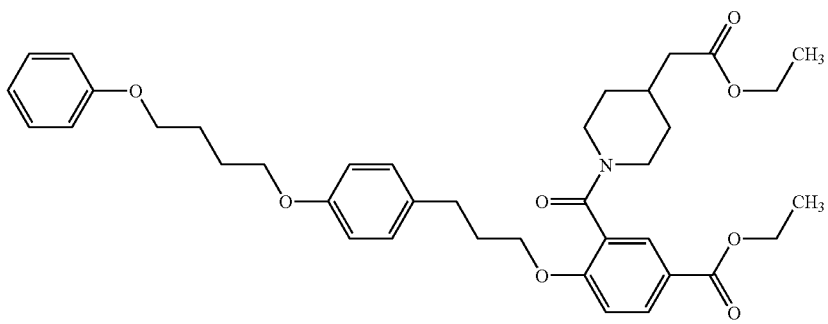

The compound is prepared in analogy to the process described in Example 6 from 5-(ethoxycarbonyl)-2-{3-[4-(4-phenoxybutoxy)-phenyl]propoxy}benzoic acid and ethyl 4-piperidineacetate [CAS No. 59184-90-6]. The crude product is purified by HPLC [YMC GEL ODS-AQ-S 5/15 µm, gradient: acetonitrile/(water+0.2% TFA) 10:90 ... 95:5].

LC-MS (method 3): $R_t$: 5.12 min.

MS (ESI+): m/z=646 (M+H$^+$).

Example 8

Methyl 1-(5-(ethoxycarbonyl)-2-{3-[4-(4-phenoxy-butoxy)phenyl]propoxy}benzoyl)-3-azetidinecarboxylate

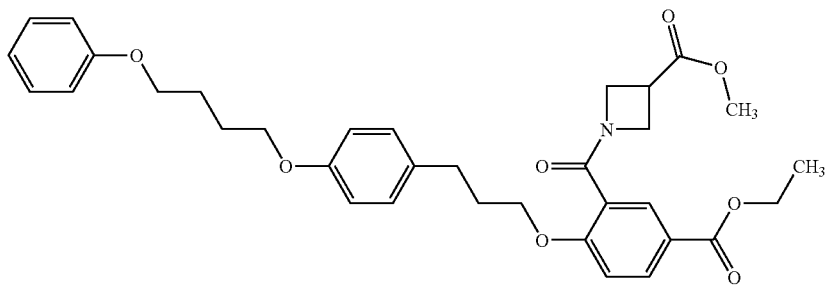

The compound is prepared in analogy to the process described in Example 6 from 5-(ethoxycarbonyl)-2-{3-[4-(4-phenoxybutoxy)phenyl]propoxy}benzoic acid and methyl 3-azetidinecarboxylate [CAS No. 343238-58-4]. The crude product is immediately reacted further without purification.

LC-MS (method 3): $R_t$: 4.84 min.

MS (ESI+): m/z=590 (M+H$^+$).

Example 9

Ethyl 4-{3-[4-(1,1'-biphenyl-4-ylmethoxy)phenyl] propoxy}-3-({cis-[2-(ethoxy-carbonyl)cyclohexyl] amino}carbonyl)benzoate

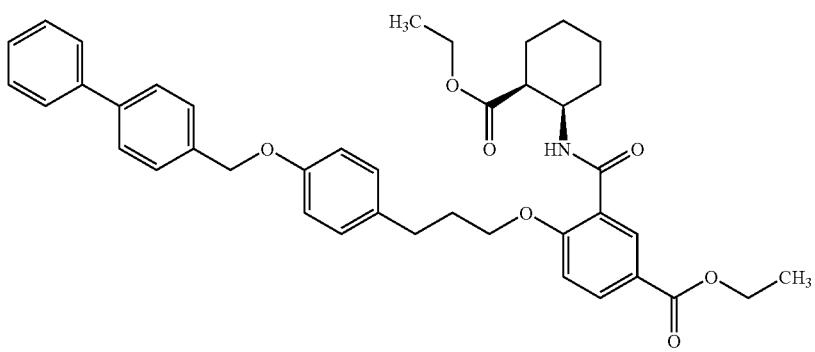

The compound is prepared in analogy to the process described in Example 6 from 2-{3-[4-(1,1'-biphenyl-4-yl-methoxy)phenyl]propoxy}-5-(ethoxycarbonyl)benzoic acid and ethyl cis-2-amino-1-cyclohexanecarboxylate hydrochloride.

HPLC (method 4): $R_t$: 6.42 min.

$^1$H-NMR (200 MHz, DMSO-d$_6$, δ/ppm): 8.43-8.33 (m, 2H), 8.03 (dd, 1H), 7.71-7.63 (m, 4H), 7.56-7.11 (m, 8H), 6.95 (d, 2H), 5.12 (s, 2H), 4.48-4.14 (m, 5H), 3.99 (m, 2H), 2.86-2.65 (m, 3H), 2.22-2.03 (m, 2H), 1.92-1.24 (m, 8H), 1.31 (t, 3H), 1.08 (t, 3H).

MS (ESI+): m/z=664 (M+H$^+$).

Example 10

Ethyl 4-{3-[4-(1,1'-biphenyl-4-ylmethoxy)phenyl]
propoxy}-3-({cis-[4-(methoxy-carbonyl)cyclohexyl]
amino}carbonyl)benzoate

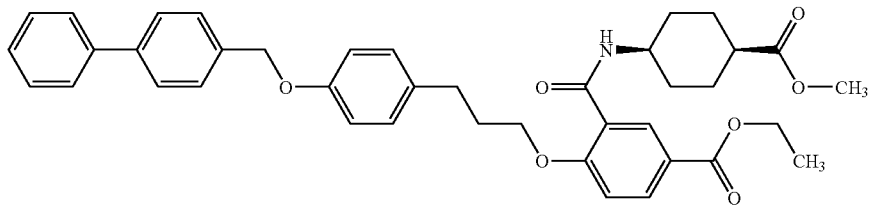

The compound is prepared in analogy to the process described in Example 6 from 2-{3-[4-(1,1'-biphenyl-4-yl-methoxy)phenyl]propoxy}-5-(ethoxycarbonyl)benzoic acid and ethyl cis-4-amino-1-cyclohexanecarboxylate.

HPLC (method 2): $R_t$: 5.93 min.

$^1$H-NMR (300 MHz, DMSO-$d_6$, δ/ppm): 8.21 (d, 1H), 8.08 (d, 1H), 7.99 (dd, 1H), 7.70-7.64 (m, 4H), 7.54-7.43 (m, 4H), 7.40-7.33 (m, 1H), 7.20 (d, 1H), 7.14 (d, 2H), 6.94 (d, 2H), 5.11 (s, 2H), 4.30 (q, 2H), 4.14 (t, 2H), 3.97 (m, broad, 1H), 3.53 (s, 3H), 2.69 (t, 2H), 2.50 (m, concealed, 1H), 2.06 (m, 2H), 2.90-1.76 (m, 2H), 1.75-1.54 (m, 6H), 1.31 (t, 3H).

MS (ESI+): m/z=650 (M+H$^+$).

Example 11

3-{[(3-Carboxycyclohexyl)amino]carbonyl}-4-{3-
[4-(4-phenoxybutoxy)phenyl]-propoxy}benzoic acid
(racemate B)

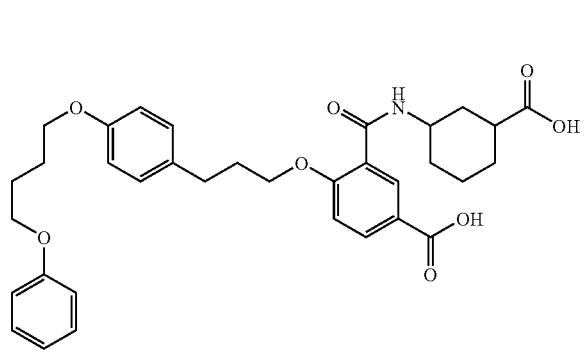

A solution of 638 mg of methyl 3-({[3-(methoxycarbonyl)cyclohexyl]-amino}carbonyl)-4-{3-[4-(4-phenoxybutoxy)phenyl]propoxy}benzoate (racemate B) in 4 ml of tetrahydrofuran (THF) and 4 ml of methanol is mixed with 4 ml of 2 molar sodium hydroxide solution and heated at 60° C. for one hour. The pH is then adjusted to a value of 3-4 with 2 molar hydrochloric acid, and the mixture is extracted with ethyl acetate. The organic extract is washed with saturated sodium chloride solution and dried over anhydrous sodium sulphate. Filtration and evaporation result in a crude product which is purified by recrystallization from diethyl ether. 589 mg of product are isolated.

Melting point: 182-183° C.

HPLC (method 1): $R_t$: 4.95 min.

$^1$H-NMR (300 MHz, DMSO-$d_6$, δ/ppm): 12.38 (s broad, 2H), 8.21 (d, 1H), 8.05 (d, 1H), 7.98 (dd, 1H), 7.29-7.23 (m, 2H), 7.19-7.11 (m, 3H), 6.93-6.88 (m, 3H), 6.85 (d, 2H), 4.15-4.10 (m, 3H), 4.01 (m, 4H), 2.71 (t, 2H), 2.62 (m, 1H), 2.07 (m, 2H), 1.91-1.70 (m, 6H), 1.62-1.16 (m, 6H).

MS (ESI+): m/z=590 (M+H$^+$), 612 (M+Na$^+$).

Example 12

3-{[(3-Carboxycyclohexyl)amino]carbonyl}-4-{3-
[4-(4-phenoxybutoxy)phenyl]-propoxy}benzoic acid
(racemate A)

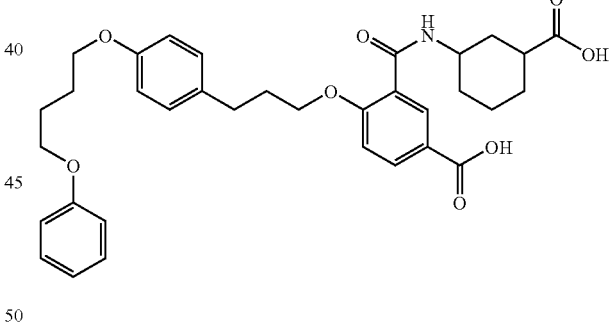

3-{[(3-Carboxycyclohexyl)amino]carbonyl}-4-{3-[4-(4-phenoxybutoxy)phenyl]-propoxy}benzoic acid (racemate A) is prepared in analogy to the process described in Example 11 from methyl 3-({[3-(methoxycarbonyl)cyclohexyl]amino}carbonyl)-4-{3-[4-(4-phenoxybutoxy)phenyl]propoxy}benzoate (racemate A).

Melting point: >210° C.

HPLC (method 1): $R_t$: 4.91 min.

$^1$H-NMR (200 MHz, DMSO-$d_6$, δ/ppm): 12.48 (s broad, 2H), 8.18 (d, 1H), 8.09 (d, 1H), 7.98 (dd, 1H), 7.32-7.11 (m, 5H), 6.96-6.83 (m, 5H), 4.12 (t, 2H), 4.01 (m, 4H), 3.82 (m, 1H), 2.70 (t, 2H), 2.38 (m, 1H), 2.19-1.73 (m, 10H), 1.41-1.10 (m, 4H).

MS (ESI+): m/z=590 (M+H$^+$), 612 (M+Na$^+$).

Example 13

1-(2-{3-[4-(1,1'-Biphenyl-4-ylmethoxy)phenyl]propoxy}-5-carboxybenzoyl)-4-piperidinecarboxylic acid

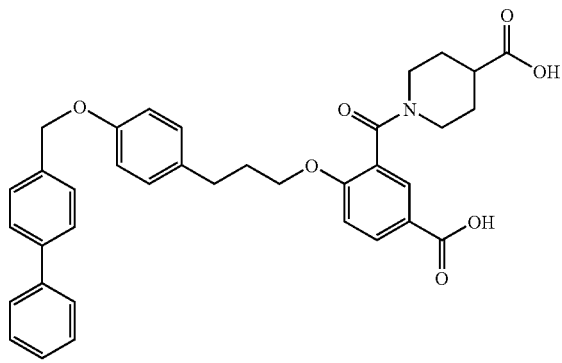

1-(2-{3-[4-(1,1'-Biphenyl-4-ylmethoxy)phenyl]propoxy}-5-carboxybenzoyl)-4-piperidinecarboxylic acid is prepared in analogy to the process described in Example 11 from methyl 1-[2-{3-[4-(1,1'-biphenyl-4-ylmethoxy)phenyl]propoxy}-5-(ethoxycarbonyl)-benzoyl]-4-piperidinecarboxylate.

Melting point: 193-194° C.
HPLC (method 1): $R_t$: 4.93 min.
$^1$H-NMR (200 MHz, DMSO-$d_6$, δ/ppm): 12.31 (s broad, 2H), 7.93 (dd, 1H), 7.72-7.64 (m, 5H), 7.55-7.32 (m, 5H), 7.17-7.12 (m, 3H), 6.98-6.92 (m, 2H), 5.12 (s, 2H), 4.48-4.37 (m, 1H), 4.15-3.97 (m, 2H), 3.29 (m, 1H), 3.13-2.83 (m, 2H), 2.70-2.59 (m, 3H), 2.02-1.89 (m, 3H), 1.80-1.70 (m, 1H), 1.62-1.47 (m, 2H).
MS (ESI+): 594 (M+H$^+$), 616 (M+Na$^+$).

Example 14

1-[5-Carboxy-2-({3-[4-(4-phenoxybutoxy)phenyl]propanoyl}amino)benzoyl]-4-piperidinecarboxylic acid

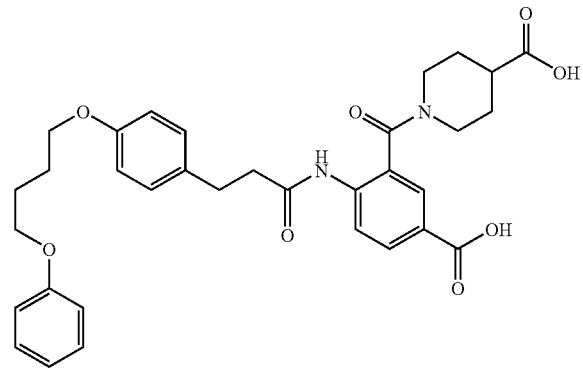

1-[5-Carboxy-2-({3-[4-(4-phenoxybutoxy)phenyl]propanoyl}amino)benzoyl]-4-piperidinecarboxylic acid is prepared in analogy to the process described in Example 11 from methyl 1-[5-(methoxycarbonyl)-2-({3-[4-(4-phenoxybutoxy)phenyl]-propanoyl}amino)benzoyl]-4-piperidinecarboxylate.

HPLC (method 1): $R_t$: 4.61 min.
$^1$H-NMR (300 MHz, DMSO-$d_6$, δ/ppm): 12.63 (s broad, 2H), 9.73 (s, 1H), 7.93 (dd, 1H), 7.77-7.73 (m, 2H), 7.29-7.25 (m, 2H), 7.14 (d, 2H), 6.93-6.90 (m, 3H), 6.84 (d, 2H), 4.32 (m 1H), 4.00 (m, 4H), 3.30 (1H), 2.90-2.78 (m, 4H), 2.62 (m, 2H), 2.48 (m, 1H), 1.93-1.82 (m, 5H), 1.69 (m, 1H), 1.59-1.39 (m, 2H).
MS (ESI-): m/z=587.2 (M-H$^-$).

Example 15

1-(5-Carboxy-2-{3-[4-(4-phenoxybutoxy)phenyl]propoxy}benzoyl)-4-piperidine-carboxylic acid

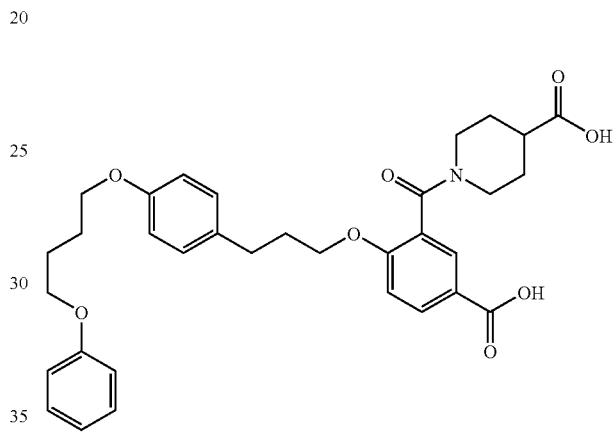

1-(5-Carboxy-2-{3-[4-(4-phenoxybutoxy)phenyl]propoxy}benzoyl)-4-piperidine-carboxylic acid is prepared in analogy to the process described in Example 11 from methyl 1-(5-(methoxycarbonyl)-2-{3-[4-(4-phenoxybutoxy)phenyl]propoxy}-benzoyl)-4-piperidinecarboxylate.

Melting point: 142-143° C.
HPLC (method 1): $R_t$: 4.70 min.
$^1$H-NMR (300 MHz, DMSO-$d_6$, δ/ppm): 7.93 (dd, 1H), 7.70 (dd, 1H), 7.29-7.24 (m, 2H), 7.17-7.11 (m, 3H), 6.93-6.82 (m, 5H), 4.41 (m, 1H), 4.13-3.96 (m, 6H), 3.31 (m, 1H), 3.11-2.89 (m, 2H), 2.63 (t, 2H), 2.53 (m, 1H), 1.99-1.83 (m, 7), 1.76 (m, 1H), 1.67-1.48 (m, 2H).
MS (DCI, NH$_3^+$): m/z 576.3 (M+H$^+$), 593.2 (M+NH$_4^+$).

Example 16

3-{[(4-Carboxycyclohexyl)amino]carbonyl}-4-{3-[4-(4-phenoxybutoxy)phenyl]-propoxy}benzoic acid

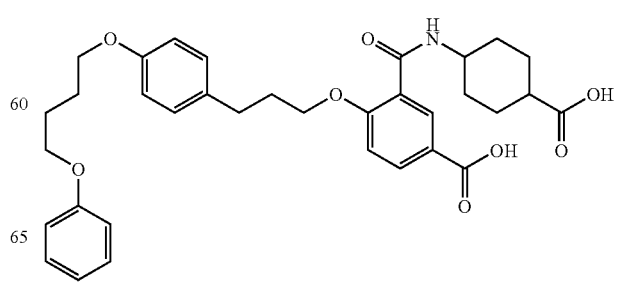

3-{[(4-Carboxycyclohexyl)amino]carbonyl}-4-{3-[4-(4-phenoxybutoxy)phenyl]-propoxy}benzoic acid is prepared in analogy to the process described in Example 11 from methyl 3-({[4-(methoxycarbonyl)cyclohexyl]amino}carbonyl)-4-{3-[4-(4-phenoxybutoxy)phenyl]propoxy}benzoate.

Melting point: 163-165° C.

$^1$H NMR (500 MHz, DMSO-$d_6$, δ/ppm): 8.21 (d, 1H), 8.09 (d, 1H), 7.97 (dd, 2H), 7.30-7.22 (m, 2H), 7.16 (d, 1H), 7.11 (d, 2H), 6.99-6.82 (m, 5H), 4.12 (t, 2H), 4.02-3.95 (m, 5H), 2.68 (t, 2H), 2.28 (t, 1H), 2.10-2.00 (m, 2H), 1.90-1.76 (m, 6H), 1.72-1.60 (m, 6H).

MS: m/z=590 (M+H$^+$).

Example 17

4-{3-[4-(1,1'-Biphenyl-4-ylmethoxy)phenyl]propoxy}-3-{[cis-(4-carboxycyclohexyl)amino]carbonyl}benzoic acid

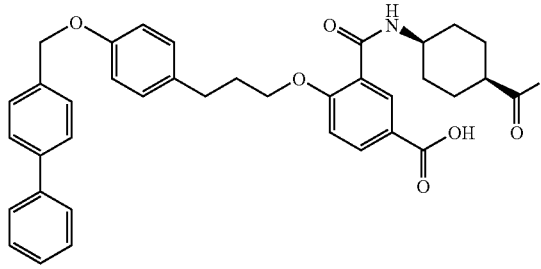

The compound is prepared in analogy to the process described in Example 11 from ethyl 4-{3-[4-(1,1'-biphenyl-4-ylmethoxy)phenyl]propoxy}-3-({cis-[4-(methoxycarbonyl)cyclohexyl]amino}carbonyl)benzoate.

HPLC (method 2): R$_t$: 5.04 min.

$^1$H-NMR (300 MHz, DMSO-$d_6$, δ/ppm): 12.41 (s, broad, 2H), 8.21 (d, 1H), 8.09 (d, 1H), 7.96 (dd, 1H), 7.70-7.63 (m, 4H), 7.54-7.43 (m, 4H), 7.40-7.33 (m, 1H), 7.18-7.12 (m, 3H), 6.95 (d, 2H), 5.11 (s, 2H), 4.12 (t, 2H), 3.97 (m, broad, 1H), 2.69 (t, 2H), 2.41 (m, broad, 1H), 2.08 (m, 2H), 1.90-1.78 (m, 2H), 1.75-1.55 (m, 6H).

MS (ESI+): m/z=608 (M+H$^+$).

Example 18

3-{[4-(Carboxymethyl)-1-piperidinyl]carbonyl}-4-{3-[4-(4-phenoxybutoxy)phenyl]-propoxy}benzoic acid

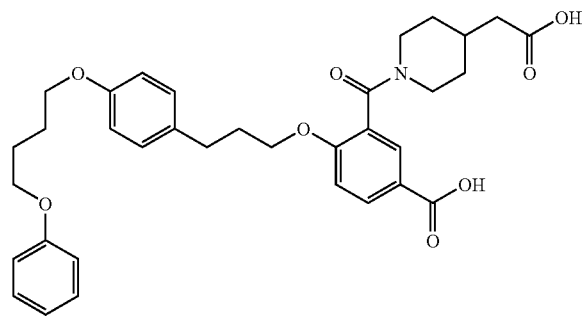

The compound is prepared in analogy to the process described in Example 11 from ethyl 3-{[4-(2-ethoxy-2-oxoethyl)-1-piperidinyl]carbonyl}-4-{3-[(4-phenoxybutoxy)phenyl]propoxy}benzoate. The crude product obtained is purified by HPLC [YMC GEL ODS-AQ-S 5/15 μm, gradient: acetonitrile/(water+0.2% TFA) 10:90 ... 95:5].

Melting point: 192° C.

LC-MS (method 3): R$_t$: 3.76 min.

$^1$H-NMR (300 MHz, DMSO-$d_6$ δ/ppm): 12.40 (s, broad, 2H), 7.94-7.91 (m, 1), 7.68 (dd, 1H), 7.30-7.22 (m, 2H), 7.15-7.07 (m, 3H), 6.95-6.80 (m, 5H), 4.50 (m, 1H), 4.18-3.90 (m, 6H), 3.09-2.90 (m, 1H), 2.83-2.58 (m, 3H), 2.22-2.08 (m, 2H), 2.02-1.71 (m, 9H), 1.59 (m, 1H), 1.27-0.92 (m, 2H).

MS (ESI+): m/z=590 (M+H$^+$).

Example 19

3-({cis-[2-Carboxycyclohexyl]amino}carbonyl)-4-{3-[4-(4-phenoxybutoxy)phenyl]-propoxy}benzoic acid

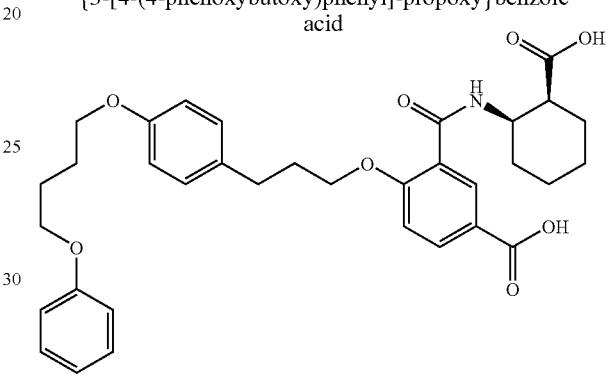

The compound is prepared in analogy to the process described in Example 11 from ethyl 3-({cis-[2-(ethoxycarbonyl)cyclohexyl]amino}carbonyl)-4-{3-[4-(4-phenoxy-butoxy)phenyl]propoxy}benzoate.

HPLC (method 2): R$_t$: 5.16 min.

$^1$H-NMR (300 MHz, DMSO-$d_6$, δ/ppm): 12.59 (s, broad, 2H), 8.50-8.42 (m, 2), 8.00 (dd, 1H), 7.30-7.18 (m, 3H), 7.13 (d, 2H), 6.95-6.82 (m, 5H), 4.35 (m, 1H), 4.20 (m, 2H), 2.79-2.63 (m, 3H), 2.14 (m, 2H), 1.93-1.77 (m, 6H), 1.70-1.53 (m, 3H), 1.46-1.33 (m, 3H).

MS (ESI+): m/z=590 (M+H$^+$).

Example 20

1-(5-Carboxy-2-{3-[4-(4-phenoxybutoxy)phenyl]propoxy}benzoyl)-3-azetidine-carboxylic acid

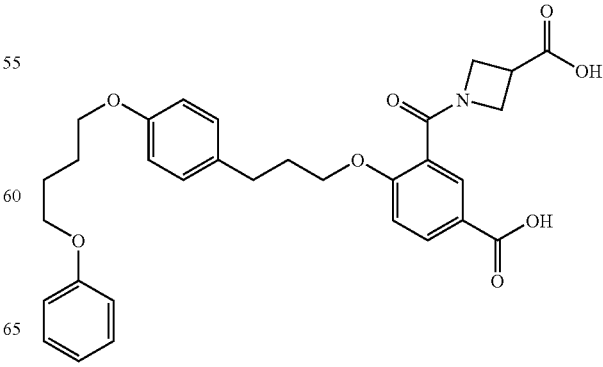

The compound is prepared in analogy to the process described in Example 11 from methyl 1-(5-(ethoxycarbonyl)-2-{3-[4-(4-phenoxybutoxy)phenyl]propoxy}benzoyl)-3-azetidinecarboxylate.

$^1$H-NMR (300 MHz, DMSO-d$_6$, δ/ppm): 12.73 (s, broad, 2H), 7.95 (dd, 1H), 7.82 (d, 1H), 7.27 (m, 2H), 7.16-7.11 (m, 3H), 6.93-6.83 (m, 5H), 4.21 (t, 1H), 4.13-3.95 (m, 9H), 3.49-3.37 (m, 1H), 2.68 (t, 2H), 2.01 (quint, 2H), 1.85 (m, 4H).

LC-MS (method 3): R$_t$: 3.67 min.
MS (ESI+): m/z=548 (M+H$^+$).

Example 21

4-{3-[4-(1,1'-Biphenyl-4-ylmethoxy)phenyl]propoxy}-3-({cis-[2-carboxycyclohexyl]amino}carbonyl)benzoic acid

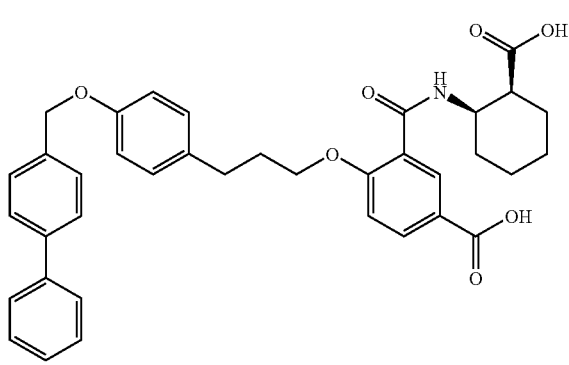

The compound is prepared in analogy to the process described in Example 11 from ethyl 4-{3-[4-(1,1'-Biphenyl-4-ylmethoxy)phenyl]propoxy}-3-({cis-[2-(ethoxycarbonyl)cyclohexyl]amino}carbonyl)benzoate.

HPLC (method 2): R$_t$: 5.28 min.
$^1$H-NMR (200 MHz, DMSO-d$_6$, δ/ppm): 12.66 (s, broad, 2H), 8.56-8.43 (m, 2H), 8.00 (dd, 1H), 7.72-7.62 (m, 4H), 7.56-7.31 (m, 5H), 7.27-7.12 (m, 3H), 6.95 (d, 2H), 5.11 (s, 2H), 4.42-4.09 (m, 3H), 3.57 (m, 3H), 2.72 (m, 3H), 2.25-2.03 (m, 2H), 1.97-1.29 (m, 5H).
MS (ESI+): m/z=608 (M+H$^+$).

Example 22

Methyl 4-{3-[4-(3-cyclohexylpropoxy)phenyl]propoxy}-3-({[3-(methoxycarbonyl)-cyclohexyl]amino}carbonyl)benzoate

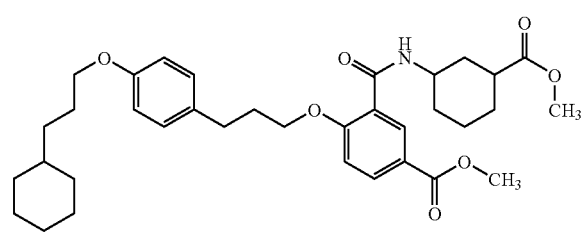

A solution of 17.88 g of (+)-B-enantiomer of methyl 4-hydroxy-3-({[3-(methoxycarbonyl)cyclohexyl]amino}carbonyl)benzoate (see. Example IX, method 2) and 19.9 g of 1-(3-bromopropyl)-4-(3-cyclohexylpropoxy)benzene in 160 ml of anhydrous DMF is mixed with 20.85 g of cesium carbonate and heated at about 50 to 60° C. for 3 hours. After cooling to room temperature, the mixture is poured into 180 ml of 0.001 molar hydrochloric acid and extracted with ethyl acetate. The organic phase is washed successively with water and saturated brine, drying over h anhydrous sodium sulphate, filtration, evaporation. An oil is obtained and is mixed with a little ethyl acetate and cyclohexane. A solid precipitates out. The suspension is cooled in an ice bath for 1 hour. The solid is then filtered off with suction and washed with a little cyclohexane. 26.0 g of a solid are obtained.

TLC: R$_f$: 0.43 (cyclohexane/ethyl acetate 1:1).
HPLC (method 2): R$_t$: 6.75 min.
$^1$H-NMR (300 MHz, DMSO-d$_6$, δ/ppm): 8.21 (d, 1H), 8.07 (d, 1H), 8.00 (dd, 1H), 7.21 (d, 1H), 7.11 (d, 2H), 6.82 (d, 2H), 4.13 (pseudo-t, 3H), 3.89 (t, 2H), 3.83 (s, 3H), 3.56 (s, 3H), 2.68 (pseudo-t, 3H), 2.07 (quint., 2H), 1.88-1.78 (m, 2H), 1.71-1.49 (m, 13H), 1.32-1.09 (m, 6H), 0.92-0.80 (m, 2H).
MS (DCI, NH$_3$): m/z=594.3 (M+H$^+$), 611.4 (M+NH$_4^+$)

Example 23

3-{[(3-Carboxycyclohexyl)amino]carbonyl}-4-{3-[4-(3-cyclohexylpropoxy)phenyl]-propoxy}benzoic acid

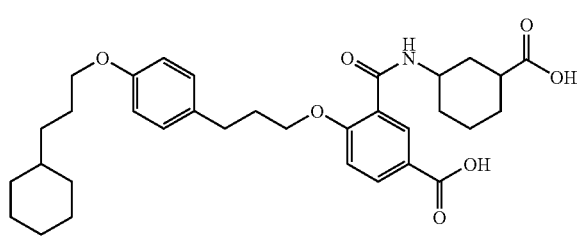

A solution of 90.73 g of methyl 4-{3-[4-(3-cyclohexylpropoxy)phenyl]propoxy}-3-({[3-(methoxycarbonyl)cyclohexyl]amino}carbonyl)benzoate in 500 ml of THF and 500 ml of methanol is mixed with 300 ml of 2 molar sodium hydroxide solution and heated to 60° C. After one hour, the organic solvents are removed as far as possible in a rotary evaporator. 325 ml of 2 molar hydrochloric acid are added to the residue with stirring. A precipitate separates out during this and is filtered off with suction and washed with water. The product is purified by recrystallization from a mixture of 500 ml of acetone and 1000 ml of water. 77.5 g of product are obtained. m.p.: 160° C.

HPLC (method 1): R$_t$: 5.61 min.
$^1$H-NMR (400 MHz, DMSO-d$_6$, δ/ppm): 12.48 (s broad, 2H), 8.21 (d, 1H), 8.07 (d, 1H), 7.98 (dd, 1H), 7.18 (d, 1H), 7.12 (d, 2H), 6.82 (d, 2H), 4.12 (pseudo-t, 3H), 3.88 (t, 2H), 2.70 (pseudo-t, 2H), 2.62 (m, 1H), 2.07 (quint., 2H), 1.89-1.47 (m, 15H), 1.31-1.07 (m, 6H), 0.91-0.82 (m, 2H).
MS (ESI+): m/z=566.5 (M+H$^+$).

Example 24

Methyl 4-(3-{4-[4-(cyclohexyloxy)butoxy]phenyl}propoxy)-3-({[3-(methoxycarbonyl)cyclohexyl]amino}carbonyl)benzoate

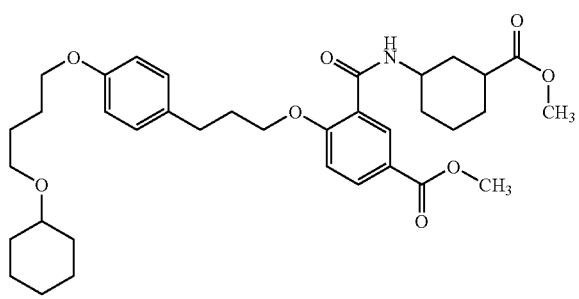

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-bromopropyl)-4-[4-(cyclohexyloxy)butoxy]benzene.

TLC: $R_f$: 0.46 (cyclohexane/ethyl acetate 1:1).

HPLC (method 2): $R_t$: 6.08 min.

$^1$H-NMR (300 MHz, DMSO-$d_6$, δ/ppm): 8.22 (d, 1H), 8.08 (d, 1H), 8.00 (dd, 1H), 7.21 (d, 1H), 7.11 (d, 2H), 6.82 (d, 2H), 4.13 (pseudo-t, 3H), 3.92 (t, 2H), 3.82 (s, 3H), 3.57 (s, 3H), 3.42 (t, 2H), 3.21 (m, 1H), 2.69 (pseudo-t, 3H), 2.07 (quint., 2H), 1.83-1.42 (m, 16H), 1.19 (m, 6H).

MS (DCI, NH$_3$): m/z=624 (M+H$^+$), 641 (M+NH$_4^+$).

Example 25

3-{[(3-Carboxycyclohexyl)amino]carbonyl}-4-(3-{4-[4-(cyclohexyloxy)butoxy]-phenyl}propoxy)benzoic acid

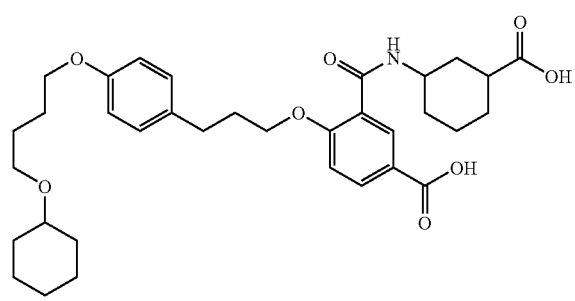

Preparation takes place in analogy to Example 23 from methyl 4-(3-{4-[4-(cyclohexyloxy)butoxy]phenyl}propoxy)-3-({[3-(methoxycarbonyl)cyclohexyl]amino}carbonyl)benzoate.

m.p.: 161-162° C.

HPLC (method 2): $R_t$: 5.27 min.

$^1$H-NMR (300 MHz, DMSO-$d_6$, δ/ppm): 12.43 (s broad, 2H), 8.22 (d, 1H), 8.05 (d, 1H), 7.98 (dd, 1H), 7.18 (d, 1H), 7.11 (d, 2H), 6.82 (d, 2H), 4.13 (pseudo-t, 3H), 3.93 (t, 2H), 3.42 (t, 2H), 3.21 (m, 1H), 2.70 (pseudo-t, 2H), 2.62 (m, 1H), 2.07 (quint., 2H), 1.91-1.42 (m, 17H), 1.21 (m, 5H).

MS (ESI-): m/z=594 (M-H$^+$)$^-$.

Example 26

Methyl 3-({[3-(methoxycarbonyl)cyclohexyl]amino}carbonyl)-4-{3-[4-(4-phenoxy-butoxy)phenyl]propoxy}benzoate

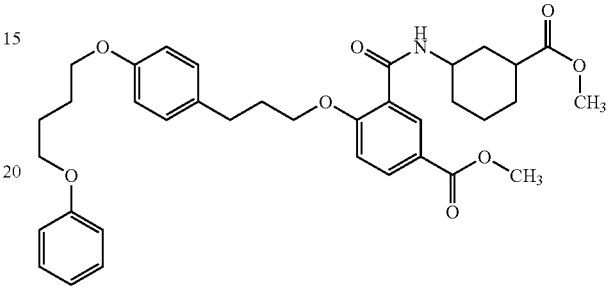

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-bromopropyl)-4-[4-(phenoxy)butoxy]benzene.

TLC: $R_f$: 0.35 (cyclohexane/ethyl acetate 1:1).

HPLC (method 2): $R_t$: 5.80 min.

$^1$H-NMR (200 MHz, DMSO-$d_6$, δ/ppm): 8.20 (d, 1H), 8.12 (d, 1H), 8.01 (dd, 1H), 7.31-7.19 (m, 3H), 7.12 (d, 2H), 6.90-6.83 (m, 5H), 4.13 (pseudo-t, 3H), 3.99 (m, 4H), 3.83 (s, 3H), 3.57 (s, 3H), 2.70 (pseudo-t, 3H), 2.08 (quint., 2H), 1.85 (m, 6H), 1.68-1.49 (m, 6H).

MS (ESI+): m/z=618 (M+H$^+$), 640 (M+Na$^+$).

Example 27

3-{[(3-Carboxycyclohexyl)amino]carbonyl}-4-{3-[4-(4-phenoxybutoxy)phenyl]-propoxy}benzoic acid

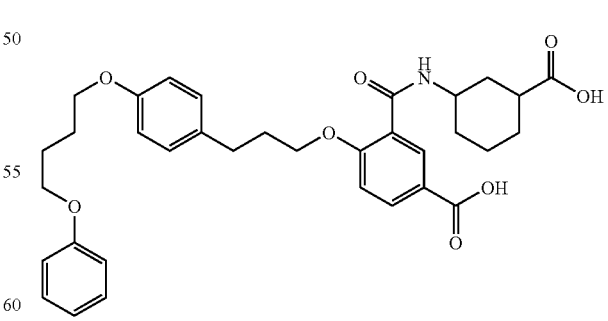

Preparation takes place in analogy to Example 23 from methyl 3-({[3-(methoxycarbonyl)cyclohexyl]amino}carbonyl)-4-{3-[4-(4-phenoxybutoxy)phenyl]-propoxy}-benzoate. Since the product does not precipitate on acidification, it is extracted with ethyl acetate, and the organic extract is dried over anhydrous sodium sulphate. Filtration and evaporation result in the product.

HPLC (method 2): $R_t$: 5.03 min.

$^1$H-NMR (300 MHz, DMSO-d$_6$, δ/ppm): 12.39 (s broad, 2H), 8.21 (d, 1H), 8.05 (d, 1H), 7.98 (dd, 1H), 7.30-7.23 (dd, 2H), 7.18 (d, 1H), 7.12 (d, 2H), 6.94-6.82 (m, 5H), 4.13 (pseudo-t, 3H), 4.00 (m, 4H), 2.70 (pseudo-t, 2H), 2.62 (m, 1H), 2.07 (quint., 2H), 1.90-1.48 (m, 12H).

LC-MS (method 11): $R_t$: 3.80 min, m/z (ESI+)=590 (M+H$^+$).

Example 28

Ethyl 4-{3-[4-(biphenyl-4-ylmethoxy)phenyl]propoxy}-3-({[(1S,3R)-3-(methoxycarbonyl)cyclopentyl]amino}carbonyl)benzoate

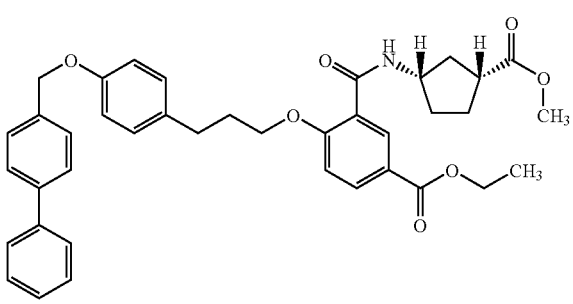

Preparation takes place in analogy to Example 5 from 2-{3-[4-(1,1'-biphenyl-4-yl-methoxy)phenyl]propoxy}-5-(ethoxycarbonyl)benzoic acid and methyl (1R,3S)-3-aminocyclopentanecarboxylate hydrochloride.

HPLC (method 2): $R_t$: 5.95 min.

$^1$H-NMR (300 MHz, DMSO-d$_6$, δ/ppm): 8.22 (d, 1H), 8.18 (d, 1H), 8.00 (dd, 1H), 7.69-7.65 (m, 4H), 7.53-7.43 (m, 4H), 7.39-7.33 (m, 1H), 7.22 (d, 1H), 7.14 (d, 2H), 6.94 (d, 2H), 5.11 (s, 2H), 4.30 (quart., 2H), 4.14 (t, 2H), 3.55 (s, 3H), 2.88 (quint., 1H), 2.71 (pseudo-t, 2H), 2.32-2.22 (m, 1H), 2.08 (quint., 2H), 1.99-1.82 (m, 3H), 1.78-1.57 (m, 2H), 1.31 (t, 3H).

MS (ESI+): m/z=636 (M+H$^+$).

Example 29

4-{3-[4-(Biphenyl-4-ylmethoxy)phenyl]propoxy}-3-({[(1S,3R)-3-carboxycyclopentyl]amino}carbonyl)benzoic acid

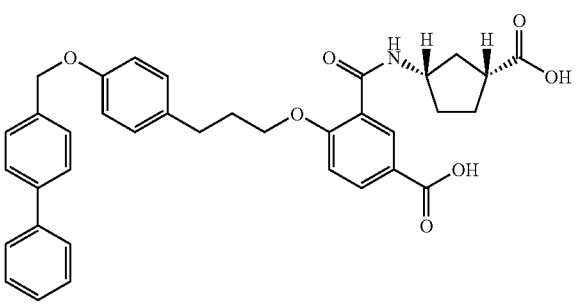

Preparation takes place in analogy to Example 23 from ethyl 4-{3-[4-(biphenyl-4-ylmethoxy)phenyl]propoxy}-3-({[(1S,3R)-3-(methoxycarbonyl)cyclopentyl]amino}carbonyl)benzoate.

HPLC (method 12): $R_t$: 8.05 min.

$^1$H-NMR (300 MHz, DMSO-d$_6$, δ/ppm): 12.28 (s broad), 8.23 (d, 1H), 8.18 (d, 1H), 7.98 (dd, 1H), 7.69-7.64 (m, 4H), 7.53-7.43 (m, 4H), 7.39-7.35 (m, 1H), 7.18-7.13 (m, 3H), 6.94 (d, 2H), 5.11 (s, 2H), 4.31 (m, 1H), 4.14 (t, 2H), 2.78 (quint., 1H), 2.70 (pseudo-t, 2H), 2.29-2.20 (m, 1H), 2.08 (quint., 2H), 1.99-1.82 (m, 3H), 1.78-1.53 (m, 2H).

LC-MS (method 8): $R_t$: 3.55 min, m/z (ESI+)=594 (M+H$^+$).

Example 30

Methyl 1-[2-{3-[4-(3-cyclohexylpropoxy)phenyl]propoxy}-5-(methoxycarbonyl)-benzoyl]piperidine-4-carboxylate

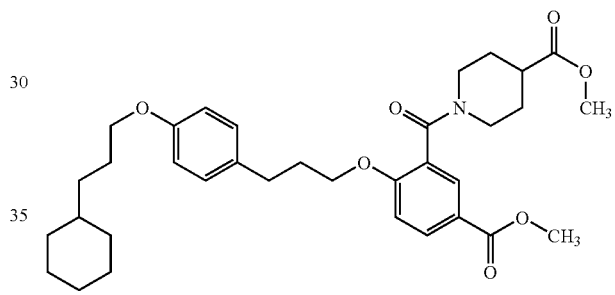

A solution of 6.47 g of methyl 1-[2-hydroxy-5-(methoxycarbonyl)benzoyl]-4-piperidinecarboxylate and 8.2 g of 1-(3-bromopropyl)-4-(3-cyclohexylpropoxy)-benzene in 82 ml of butyronitrile is mixed with 4.18 g of potassium carbonate and heated to reflux for 15 hours. The reaction solution is then evaporated to dryness, and the residue is taken up in water and extracted with ethyl acetate. The organic phase is dried over sodium sulphate, filtered and concentrated. The crude product is purified by suction filtration through silica gel with cyclohexane/ethyl acetate 5:1 to cyclohexane/ethyl acetate 1:1 as mobile phase. 10.8 g of an oil are obtained.

TLC: $R_f$: 0.36 (cyclohexane/ethyl acetate 1:1).

HPLC (method 2): $R_t$: 6.07 min.

$^1$H-NMR (300 MHz, DMSO-d$_6$, δ/ppm): 7.97 (dd, 1H), 7.76 and 7.69 (each d, together 1H), 7.17 (d, 1H), 7.08 (d, 2H), 6.82 (d, 2H), 4.43 and 4.39 (together 1H), 4.17-3.96 (m, 2H), 3.89 (t, 2H), 3.82 (s, 3H), 3.61 and 3.57 (each s, together 3H), 3.11-2.88 (m, 2H), 2.63 (m, 3H), 1.96 (m, 3H), 1.77-1.50 (m, 10H), 1.32-1.09 (m, 7H), 0.92-0.80 (m, 2H).

MS (ESI): m/z=580 (M+H$^+$).

Example 31

1-(5-Carboxy-2-{3-[4-(3-cyclohexylpropoxy)phenyl]propoxy}benzoyl)piperidine-4-carboxylic acid

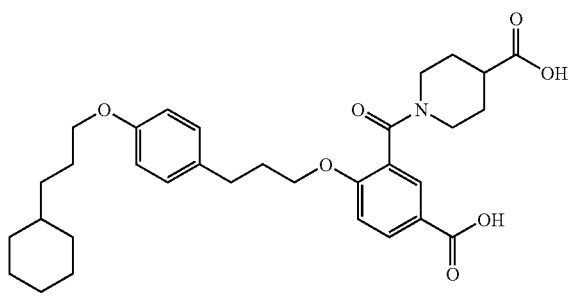

Absolution of 10.4 g of methyl 1-[2-{3-[4-(3-cyclohexylpropoxy)phenyl]propoxy}-5-(methoxycarbonyl)benzoyl]piperidine-4-carboxylate in a mixture of 160 ml of THF and 160 ml of methanol is mixed with 160 ml of 2 molar sodium hydroxide solution and stirred at a temperature of 60° C. for 1 hour. The organic solvents are then removed as far as possible in a rotary evaporator. 165 ml of 2 molar hydrochloric acid are added to the remaining aqueous solution with stirring. A precipitate separates out. Precipitation is completed by stirring at 0° C. The precipitate is filtered off with suction and washed with water. The crude product is purified by recrystallization from a solvent mixture composed of 250 ml of acetone and 200 ml of water. 8.7 g of a solid are obtained and are again heated to reflux in a mixture of 300 ml of water and 100 ml of acetone for 6 hours. Cooling to 0° C., filtration, washing with water and drying result in 8.6 g of a solid.

m.p.: 183.4-184.5° C.

HPLC (method 2): $R_t$: 5.32 min.

$^1$H-NMR (300 MHz, DMSO-$d_6$, δ/ppm): 12.51 (s broad, 2H), 7.93 (dd, 1H), 7.72 and 7.67 (each d, together 1H), 7.13 (d, 1H), 7.09 (d, 2H), 6.83 and 6.90 (each d, together 2H), 4.43 and 4.38 (together 1H), 4.15-3.94 (m, 2H), 3.88 (t, 2H), 3.11-2.88 (m, 2H), 2.62 (m, 2H), 2.54 (m, 1H), 1.96 (m, 3H), 1.78-1.47 (m, 10H), 1.37-1.09 (m, 7H), 0.93-0.81 (m, 2H).

MS (ESI): m/z=552 (M+H$^+$).

Example 32

Methyl 4-(3-{4-[(4-isopropoxybenzyl)oxy]phenyl}propoxy)-3-({[3-(methoxycarbonyl)cyclohexyl]amino}carbonyl)benzoate

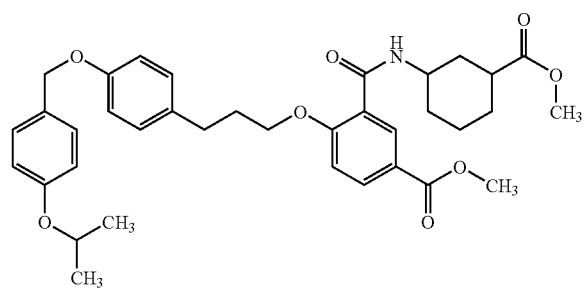

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-bromopropyl)-4-[(4-isopropoxybenzyl)oxy]benzene.

TLC: $R_f$: 0.43 (cyclohexane/ethyl acetate 1:1).

HPLC (method 2): $R_t$: 5.69 min.

$^1$H-NMR (400 MHz, DMSO-$d_6$, δ/ppm): 8.21 (d, 1H), 8.10 (d broad, 1H), 8.01 (dd, 1H), 7.32 (d, 2H), 7.22 (d, 1H), 7.13 (d, 2H), 6.91 (2 d, 4H), 4.95 (s, 2H), 4.60 (sep, 1H), 4.13 (pseudo-t, 3H), 3.83 (s, 3H), 3.57 (s, 3H), 2.69 (pseudo-t, 3H), 2.07 (pseudo-quint., 3H), 1.82 (m, 2H), 1.68-1.47 (m, 6H), 1.24 (d, 6H).

MS (DCI, NH$_3$): m/z=618 (M+H$^+$), 635 (M+NH$_4^+$).

Example 33

3-{[(3-Carboxycyclohexyl)amino]carbonyl}-4-(3-{4-[(4-isopropoxybenzyl)oxy]-phenyl}propoxy)benzoic acid

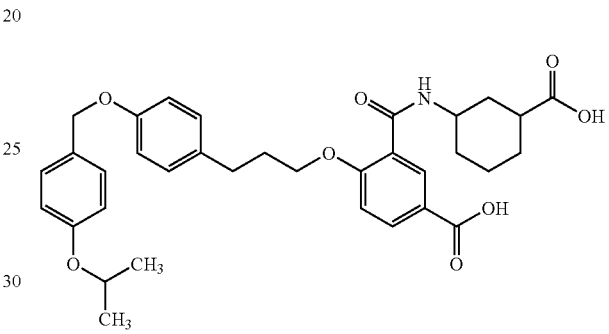

Preparation takes place in analogy to Example 23 from methyl 4-(3-{4-[(4-isopropoxybenzyl)oxy]phenyl}propoxy)-3-({[3-(methoxycarbonyl)cyclohexyl]amino}carbonyl)benzoate.

HPLC (method 2): $R_t$: 4.97 min.

$^1$H-NMR (300 MHz, DMSO-$d_6$, δ/ppm): 12.47 (5 broad, 2H), 8.22 (d, 1H), 8.07 (d broad, 1H), 7.98 (dd, 1H), 7.32 (d, 2H), 7.18 (d, 1H), 7.13 (d, 2H), 6.91 (2 d, 4H), 4.96 (s, 2H), 4.59 (sep, 1H), 4.13 (pseudo-t, 3H), 2.71 (pseudo-t, 2H), 2.63 (m, 1H), 2.08 (pseudo-quint., 2H), 1.91-1.47 (m, 8H), 1.25 (d, 6H).

MS (ESI): m/z=590 (M+H$^+$).

Example 34

Methyl 4-(3-{4-[3-(5,5-dimethyl-1,3-dioxan-2-yl)propoxy]phenyl}propoxy)-3-({[3-(methoxycarbonyl)cyclohexyl]amino}carbonyl)benzoate

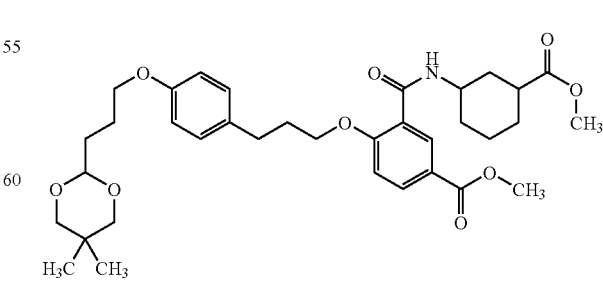

A solution of 130 mg of methyl 4-[3-(4-hydroxyphenyl)propoxy]-3-({[3-(methoxycarbonyl)cyclohexyl]

amino}carbonyl)benzoate and 85.9 mg of 2-(3-bromopropyl)-5,5-dimethyl-1,3-dioxane in 1 ml of anhydrous DMF is mixed with 128.8 mg of caesium carbonate and stirred at 100° C. for 15 hours. The reaction mixture is then loaded completely onto an RP-HPLC system and chromatographed with a water/acetonitrile gradient. Evaporation of the product fractions results in 87.5 mg of a solid.

TLC (cyclohexane/ethyl acetate 1:1): $R_f$: 0.37.

HPLC (method 2): $R_t$: 5.54 min.

$^1$H-NMR (300 MHz, DMSO-$d_6$, δ/ppm): 8.22 (d, 1H), 8.08 (d broad, 1H), 8.01 (dd, 1H), 7.22 (d, 1H), 7.11 (d, 2H), 6.83 (d, 2H), 4.48 (t, 1H), 4.14 (pseudo-t, 3H), 3.93 (t, 2H), 3.83 (s, 3H), 3.58 (s, 3H), 3.52 (d, 2H), 3.39 (d, 2H), 2.70 (m, 3H), 2.07 (quint, 2H), 1.84-1.72 (m, 4H), 1.68-1.50 (m, 8H), 1.09 (s, 3H), 0.68 (s, 3H).

LC-MS (method 13): $R_t$: 4.3 min. m/z (ESI+)=626 (M+H$^+$).

Example 35

Methyl 3-{[(3-carboxycyclohexyl)amino]carbonyl}-4-(3-{4-[3-(5,5-dimethyl-1,3-dioxan-2-yl)propoxy]phenyl}propoxy)benzoate

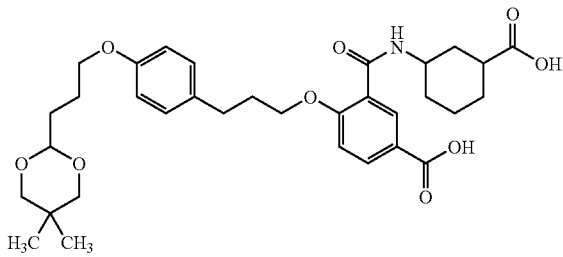

A solution of 70.0 mg of methyl 4-(3-{4-[3-(5,5-dimethyl-1,3-dioxan-2-yl)propoxy]-phenyl}propoxy)-3-({[3-(methoxycarbonyl)cyclohexyl]amino}carbonyl)benzoate in 1 ml each of methanol, THF and 2 molar sodium hydroxide solution is stirred at a temperature of 60° C. for 2 hours. Then 1.1 ml of 2 molar hydrochloric acid are added, and the reaction mixture is left to stand open at room temperature for 15 hours. A precipitate separates out and is filtered off with suction and washed with water. If the precipitation is incomplete, extraction with ethyl acetate is possible. The organic extract is dried over anhydrous sodium sulphate and evaporated. 53.3 mg of a solid are obtained.

HPLC (method 2): $R_t$: 4.86 min.

$^1$H-NMR (200 MHz, DMSO-$d_6$, δ/ppm): 12.52 (s broad, 2H), 8.21 (d, 1H), 8.09 (d broad, 1H), 7.98 (dd, 1H), 7.19 (d, 1H), 7.13 (d, 2H), 6.83 (d, 2H), 4.48 (t, 1H), 4.13 (pseudo-t, 3H), 3.92 (t, 2H), 3.52 (d, 2H), 3.39 (d, 2H), 2.73-2.60 (m, 3H), 2.07 (quint, 2H), 1.87-1.47 (m, 12H), 1.09 (s, 3H), 0.68 (s, 3H).

LC-MS (method 14): $R_t$: 3.13 min, m/z (ESI+)=598 (M+H$^+$).

Example 36

Methyl 3-({[3-(methoxycarbonyl)cyclohexyl]amino}carbonyl)-4-(3-{4-[(4-propoxybenzyl)oxy]phenyl}propoxy)benzoate

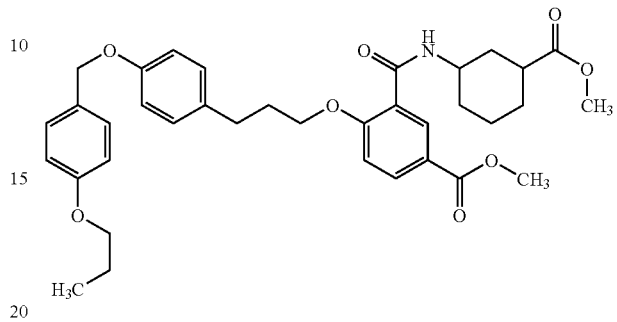

Methyl 3-({[3-(methoxycarbonyl)cyclohexyl]amino}carbonyl)-4-(3-{4-[(4-propoxybenzyl)oxy]phenyl}propoxy)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-propoxybenzene.

TLC (cyclohexane/ethyl acetate 1:1): $R_f$: 0.39.

HPLC (method 2): $R_t$: 5.67 min.

MS (ESI): m/z=618 (M+H$^+$), 640 (M+Na$^+$).

Example 37

3-{[(3-Carboxycyclohexyl)amino]carbonyl}-4-(3-{4-[(4-propoxybenzyl)oxy]-phenyl}propoxy)benzoic acid

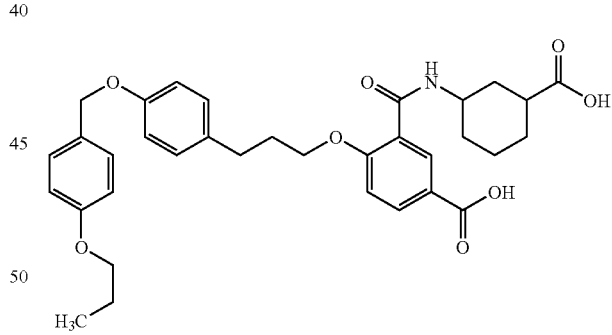

3-{[(3-Carboxycyclohexyl)amino]carbonyl}-4-(3-{4-[(4-propoxybenzyl)oxy]-phenyl}propoxy)benzoic acid is prepared in analogy to the process described in Example 35 from methyl 3-({[3-(methoxycarbonyl)cyclohexyl]amino}carbonyl)-4-(3-{4-[(4-propoxybenzyl)oxy]phenyl}propoxy)benzoate.

HPLC (method 2): $R_t$: 5.05 min.

$^1$H-NMR (200 MHz, DMSO-$d_6$, δ/ppm): 12.52 (s broad, 2H), 8.20 (d, 1H), 8.09 (d broad, 1H), 7.98 (dd, 1H), 7.33 (d, 2H), 7.19 (d, 1H), 7.13 (d, 2H), 6.92 (d, 2H), 6.91 (d, 2H), 4.96 (s, 2H), 4.12 (pseudo-t, 3H), 3.91 (t, 2H), 2.73-2.58 (m, 3H), 2.06 (m, 2H), 1.87-1.48 (m, 10H), 0.97 (t, 3H).

MS (ESI): m/z=588 (M−H$^+$).

Example 38

Methyl 4-[3-(4-{[4-(cyclopropylmethoxy)benzyl]oxy}phenyl)propoxy]-3-({[3-(methoxycarbonyl)cyclohexyl]amino}carbonyl)benzoate

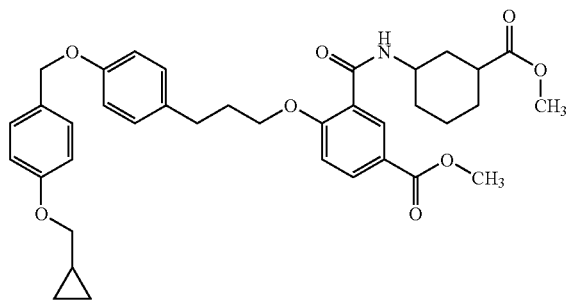

Methyl 4-[3-(4-{[4-(cyclopropylmethoxy)benzyl]oxy}phenyl)propoxy]-3-({[3-(methoxycarbonyl)cyclohexyl]amino}carbonyl)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-(cyclopropylmethoxy)benzene.

TLC (cyclohexane/ethyl acetate 1:1): $R_f$: 0.35.
HPLC (method 2): $R_t$: 5.58 min.
MS (ESI): m/z=630 (M+H$^+$), 652 (M+Na$^+$).

Example 39

3-{[(3-Carboxycyclohexyl)amino]carbonyl}-4-[3-(4-{[4-(cyclopropylmethoxy)-benzyl]oxy}phenyl)propoxy]benzoic acid

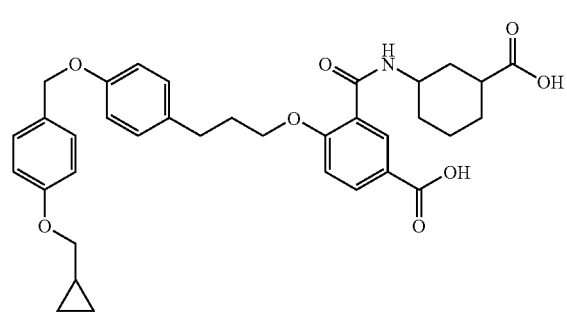

3-{[(3-Carboxycyclohexyl)amino]carbonyl}-4-[3-(4-{[4-(cyclopropylmethoxy)-benzyl]oxy}phenyl)propoxy]benzoic acid is prepared in analogy to the process described in Example 35 from methyl 4-[3-(4-{[4-(cyclopropylmethoxy)benzyl]-oxy}phenyl)propoxy]-3-({[3-(methoxycarbonyl)cyclohexyl]amino}carbonyl)-benzoate.

HPLC (method 2): $R_t$: 4.99 min.
$^1$H-NMR (200 MHz, DMSO-d$_6$, δ/ppm): 12.52 (s broad, 2H), 8.20 (d, 1H), 8.08 (d broad, 1H), 7.98 (dd, 1H), 7.33 (d, 2H), 7.18 (d, 1H), 7.13 (d, 2H), 6.91 (2 d, 4H), 4.95 (s, 2H), 4.12 (pseudo-t, 3H), 3.80 (d, 2H), 2.73-2.57 (m, 3H), 2.07 (m, 2H), 1.87-1.46 (m, 8H), 1.30-1.13 (m, 2H), 0.57 (m, 2H), 0.32 (m, 2H).
MS (ESI): m/z=600 (M−H$^+$).

Example 40

Methyl 3-({[3-(methoxycarbonyl)cyclohexyl]amino}carbonyl)-4-(3-{4-[(4-phenoxy-benzyl)oxy]phenyl}propoxy)benzoate

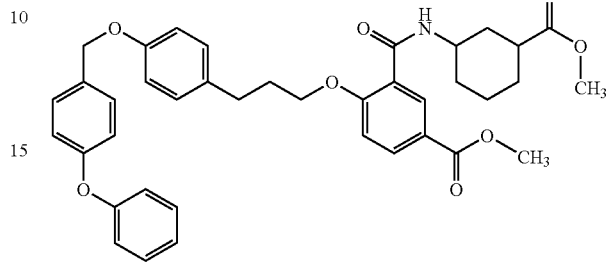

Methyl 3-({[3-(methoxycarbonyl)cyclohexyl]amino}carbonyl)-4-(3-{4-[(4-phenoxybenzyl)oxy]phenyl}propoxy)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-phenoxybenzene.

TLC (cyclohexane/ethyl acetate 1:1): $R_f$: 0.36.
HPLC (method 2): $R_t$: 5.86 min.
MS (ESI): m/z=652 (M+H$^+$), 674 (M+Na$^+$).

Example 41

3-{[(3-Carboxycyclohexyl)amino]carbonyl}-4-(3-{4-[(4-phenoxybenzyl)oxy]-phenyl}propoxy)benzoic acid

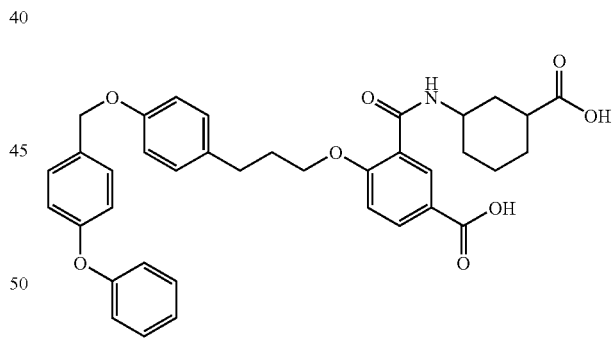

3-{[(3-Carboxycyclohexyl)amino]carbonyl}-4-(3-{4-[(4-phenoxybenzyl)oxy]-phenyl}propoxy)benzoic acid is prepared in analogy to the process described in Example 35 from methyl 3-({[3-(methoxycarbonyl)cyclohexyl]amino}carbonyl)-4-(3-{4-[(4-phenoxybenzyl)oxy]phenyl}propoxy)benzoate.

HPLC (method 2): $R_t$: 5.19 min.
$^1$H-NMR (300 MHz, DMSO-d$_6$, δ/ppm): 12.45 (s broad, 2H), 8.21 (d, 1H), 8.04 (d broad, 1H), 7.98 (dd, 1H), 7.40 (d, 1H), 7.38 (d, 2H), 7.21-6.88 (m, 11H), 5.05 (s, 2H), 4.13 (pseudo-t, 3H), 2.07 (t, 2H), 2.61 (m, 1H), 2.07 (m, 2H), 1.90-1.47 (m, 8H).
LC-MS (method 8): $R_t$: 3.62 min, m/z (ESI+) 624 (M+H$^+$).

Example 42

Methyl 4-(3-{4-[(4-isobutoxybenzyl)oxy]phenyl}propoxy)-3-({[3-(methoxycarbonyl)cyclohexyl]amino}carbonyl)benzoate

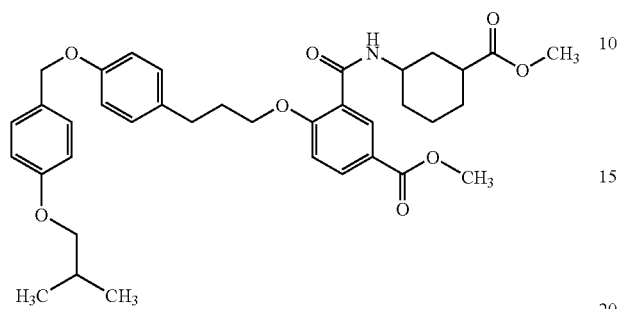

Methyl 4-(3-{4-[(4-isobutoxybenzyl)oxy]phenyl}propoxy)-3-({[3-(methoxycarbonyl)cyclohexyl]amino}carbonyl)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-isobutoxybenzene.

TLC (cyclohexane/ethyl acetate 1:1): $R_f$: 0.37.
HPLC (method 2): $R_t$: 5.91 min.
MS (ESI): m/z=632 (M+H$^+$), 654 (M+Na$^+$).

Example 43

3-{[(3-Carboxycyclohexyl)amino]carbonyl}-4-(3-{4-[(4-isobutoxybenzyl)-oxy]phenyl}propoxy)benzoic acid

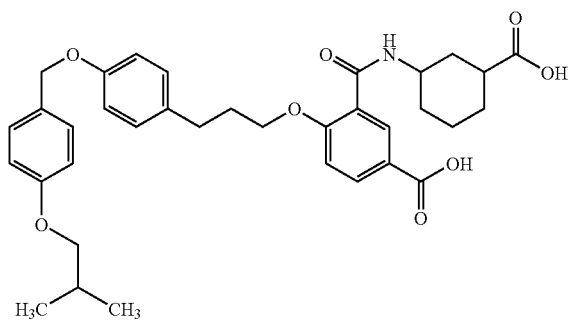

3-{[(3-Carboxycyclohexyl)amino]carbonyl}-4-(3-{4-[(4-isobutoxybenzyl)-oxy]phenyl}propoxy)benzoic acid is prepared in analogy to the process described in Example 35 from methyl 4-(3-{4-[(4-isobutoxybenzyl)oxy]phenyl}propoxy)-3-({[3-(methoxycarbonyl)cyclohexyl]amino}carbonyl)benzoate.

HPLC (method 2): $R_t$: 5.26 min.
$^1$H-NMR (200 MHz, DMSO-d$_6$, δ/ppm): 12.51 (s broad, 2H), 8.20 (d, 1H), 8.08 (d broad, 1H), 7.98 (dd, 1H), 7.33 (d, 2H), 7.18 (d, 1H), 7.13 (d, 2H), 6.91 (d, 2H), 6.90 (d, 2H), 4.97 (s, 2H), 4.12 (pseudo-t, 3H), 3.73 (d, 2H), 2.73-2.58 (m, 3H), 2.10-1.90 (m, 3H), 1.86-1.68 (m, 3H), 1.63-1.47 (m, 5H), 0.97 (d, 6H).
LC-MS (method 8): $R_t$: 3.66 min m/z (ESI+)=604 (M+H$^+$).

Example 44

Methyl 3-({[3-(methoxycarbonyl)cyclohexyl]amino}carbonyl)-4-{3-[4-(5,6,7,8-tetrahydronaphthalen-2-ylmethoxy)phenyl]propoxy}benzoate

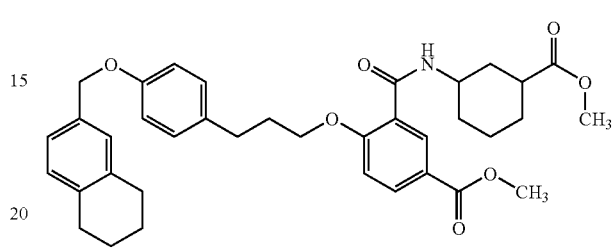

Methyl 3-({[3-(methoxycarbonyl)cyclohexyl]amino}carbonyl)-4-{3-[4-(5,6,7,8-tetrahydronaphthalen-2-ylmethoxy)phenyl]propoxy}benzoate is prepared in analogy to the process described in Example 34 from methyl 4-[3-(4-hydroxyphenyl)-propoxy]-3-({[3-(methoxycarbonyl)cyclohexyl]amino}carbonyl)benzoate and 6-(chloromethyl)-1,2,3,4-tetrahydronaphthalene.

TLC (cyclohexane/ethyl acetate 1:1): $R_f$: 0.47.
HPLC (method 2): $R_t$: 5.97 min.
MS (ESI): m/z=614 (M+H$^+$), 636 (M+Na$^+$).

Example 45

3-{[(3-Carboxycyclohexyl)amino]carbonyl}-4-{3-[4-(5,6,7,8-tetrahydronaphthalen-2-ylmethoxy)phenyl]propoxy}benzoic acid

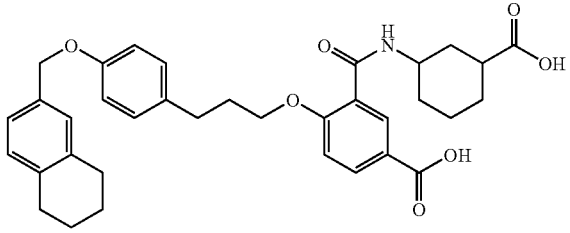

3-{[(3-Carboxycyclohexyl)amino]carbonyl}-4-{3-[4-(5,6,7,8-tetrahydronaphthalen-2-ylmethoxy)phenyl]propoxy}benzoic acid is prepared in analogy to the process described in, Example 35 from methyl 3-({[3-(methoxycarbonyl)cyclohexyl]amino}-carbonyl)-4-{3-[4-(5,6,7,8-tetrahydronaphthalen-2-ylmethoxy)phenyl]-propoxy}benzoate.

HPLC (method 2): $R_t$: 5.26 min.
$^1$H-NMR (200 MHz, DMSO-d$_6$, δ/ppm): 12.51 (s broad, 2H), 8.19 (d, 1H), 8.08 (d broad, 1H), 7.98 (dd, 1H), 7.22-6.88 (m, 8H), 4.97 (pseudo-d, 2H), 4.12 (pseudo-t, 3H), 2.72 (m, 7H), 2.08 (m, 2H), 1.87-1.48 (m, 12H).
LC-MS (method 8): $R_t$: 3.65 min, m/z (ESI+)=584 (M+H$^+$).

Example 46

Methyl 4-(3-{4-[(4-Cyclohexylbenzyl)oxy]phenyl}propoxy)-3-({[3-(methoxycarbonyl)cyclohexyl]amino}carbonyl)benzoate

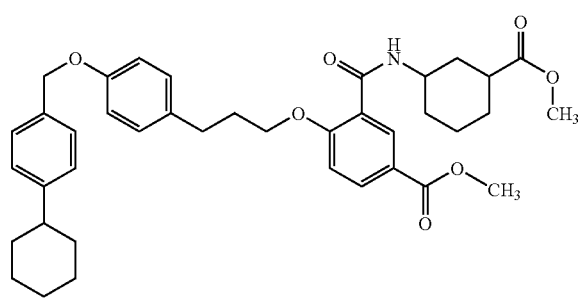

Methyl 4-(3-{4-[(4-cyclohexylbenzyl)oxy]phenyl}propoxy)-3-({[3-(methoxycarbonyl)cyclohexyl]amino}carbonyl)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-cyclohexylbenzene.

TLC (cyclohexane/ethyl acetate 1:1): $R_f$: 0.47.
HPLC (method 2): $R_t$: 6.49 min.
LC-MS (method 13): $R_t$: 4.9 min, m/z (ESI+)=642 (M+H$^+$).

Example 47

3-{[(3-Carboxycyclohexyl)amino]carbonyl}-4-(3-{4-[(4-cyclohexylbenzyl)oxy]-phenyl}propoxy)benzoic acid

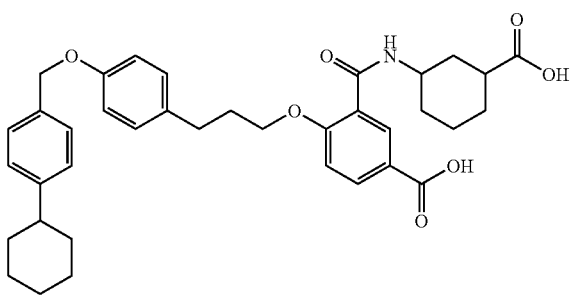

3-{[(3-Carboxycyclohexyl)amino]carbonyl}-4-(3-{4-[(4-cyclohexylbenzyl)oxy]-phenyl}propoxy)benzoic acid is prepared in analogy to the process described in Example 35 from methyl 4-(3-{4-[(4-cyclohexylbenzyl)oxy]phenyl}propoxy)-3-({[3-(methoxycarbonyl)cyclohexyl]amino}carbonyl)benzoate.

HPLC (method 2): $R_t$: 5.66 min.
$^1$H-NMR (200 MHz, DMSO-d$_6$, δ/ppm): 12.51 (s broad, 2H), 8.19 (d, 1H), 8.08 (d broad, 1H), 7.97 (dd, 1H), 7.33 (d, 2H), 7.23-7.11 (m, 5H), 6.91 (d, 2H), 5.01 (s, 2H), 4.12 (pseudo-t, 3H), 2.73-2.56 (m, 3H), 2.07 (m, 2H), 1.87-1.14 (m, 19H).
LC-MS (method 14): $R_t$: 3.57 min, m/z (ESI+)=614 (M+H$^+$).

Example 48

Ethyl 4-{3-[4-(biphenyl-4-ylmethoxy)phenyl]propoxy}-3-({[(1R,3S)-3-(methoxycarbonyl)cyclopentyl]amino}carbonyl)benzoate

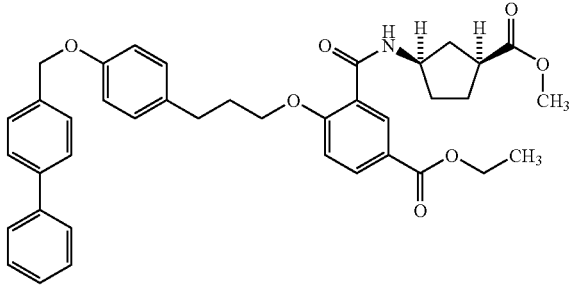

Preparation takes place in analogy to Example 5 from 2-{3-[4-(1,1'-biphenyl-4-yl-methoxy)phenyl]propoxy}-5-(ethoxycarbonyl)benzoic acid and methyl (1S,3R)-3-aminocyclopentanecarboxylate hydrochloride.

HPLC (method 2): $R_t$: 6.02 min.
$^1$H-NMR (200 MHz, DMSO-d$_6$, δ/ppm): 8.23 (d broad, 1H), 8.21 (d, 1H), 8.00 (dd, 1H), 7.69-7.65 (m, 4H), 7.53-7.43 (m, 4H), 7.39-7.33 (m, 1H), 7.22 (d, 1H), 7.14 (d, 2H), 6.94 (d, 2H), 5.11 (s, 2H), 4.30 (quart., 2H), 4.14 (t, 2H), 3.55 (s, 3H), 2.88 (quint., 1H), 2.71 (pseudo-t, 2H), 2.32-2.22 (m, 1H), 2.08 (quint., 2H), 1.99-1.82 (m, 3H), 1.78-1.57 (m, 2H), 1.31 (t, 3H).
MS (ESI+): m/z=636 (M+H$^+$).

Example 49

4-{3-[4-(Biphenyl-4-ylmethoxy)phenyl]propoxy}-3-({[(1R,3S)-3-carboxycyclopentyl]amino}carbonyl)benzoic acid

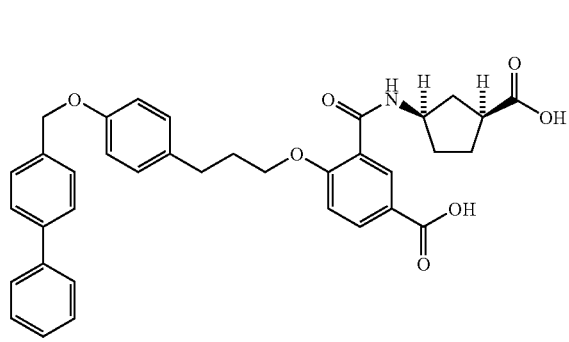

Preparation takes place in analogy to Example 23 from ethyl 4-{3-[4-(biphenyl-4-ylmethoxy)phenyl]propoxy}-3-({[(1R,3S)-3-(methoxycarbonyl)cyclopentyl]amino}-carbonyl)benzoate.

$^1$H-NMR (300 MHz, DMSO-d$_6$, δ/ppm): 11 (s broad), 8.23 (d, 1H), 8.19 (d, 1H), 7.98 (dd, 1H), 7.70-7.65 (m, 4H), 7.53-7.33 (m, 5H), 7.18-7.13 (m, 3H), 6.94 (d, 2H), 5.11 (s, 2H), 4.30 (m, 1H), 4.22 (t, 2H), 2.78 (quint., 1H), 2.70 (t, 2H), 2.23 (m, 1H), 2.08 (quint., 2H), 1.99-1.82 (m, 3H), 1.73 (m, 1H), 1.59 (m, 1H).
LC-MS (method 8): $R_t$: 3.56 min, m/z (ESI+)=594 (M+H$^+$).

Example 50

Methyl 3-({[3-(methoxycarbonyl)cyclohexyl]amino}carbonyl)-4-[3-(4-{[4-(trifluoromethoxy)benzyl]oxy}phenyl)propoxy]benzoate

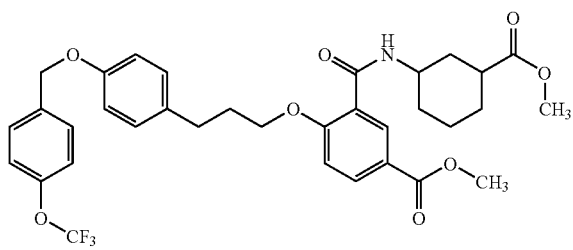

Methyl 3-({[3-(methoxycarbonyl)cyclohexyl]amino}carbonyl)-4-[3-(4-{[4-(trifluoromethoxy)benzyl]oxy}phenyl)propoxy]benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(chloromethyl)-4-trifluoromethoxybenzene.

TLC (cyclohexane/ethyl acetate 1:1): $R_f$: 0.36.
HPLC (method 2): $R_t$: 6.62 min.
MS (ESI): m/z=644 (M+H$^+$).

Example 51

3-{[(3-Carboxycyclohexyl)amino]carbonyl}-4-[3-(4-{[4-(trifluoromethoxy)benzyl]-oxy}phenyl)propoxy]benzoic acid

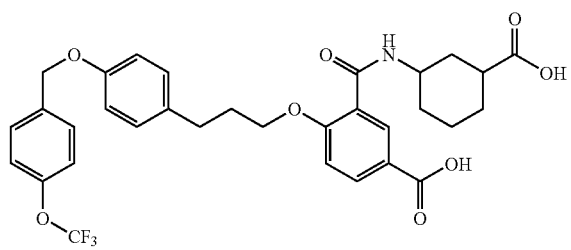

3-{[(3-Carboxycyclohexyl)amino]carbonyl}-4-[3-(4-{[4-(trifluoromethoxy)-benzyl]oxy}phenyl)propoxy]benzoic acid is prepared in analogy to the process described in Example 35 from methyl 3-({[3-(methoxycarbonyl)cyclohexyl]amino}carbonyl)-4-[3-(4-{[4-(trifluoromethoxy)benzyl]oxy}-phenyl)propoxy]benzoate.

HPLC (method 2): $R_t$: 5.04 min.
$^1$H-NMR (200 MHz, DMSO-d$_6$, δ/ppm): 12.37 (s broad, 2H), 8.19 (d, 1H), 8.08 (d broad, 1H), 7.98 (dd, 1H), 7.57 (d, 2H), 7.38 (d, 2H), 7.18 (d, 2H), 7.17 (d, 2H), 6.93 (d, 2H), 5.01 (s, 2H), 4.12 (pseudo-t, 3H), 2.74-2.56 (m, 3H), 2.08 (m, 2H), 1.87-1.43 (m, 8H).
MS (ESI): m/z 614 (M−H$^+$).

Example 52

Methyl 4-(3-{4-[3-(4-chlorophenyl)propoxy]phenyl}propoxy)-3-({[3-(methoxycarbonyl)cyclohexyl]amino}carbonyl)benzoate

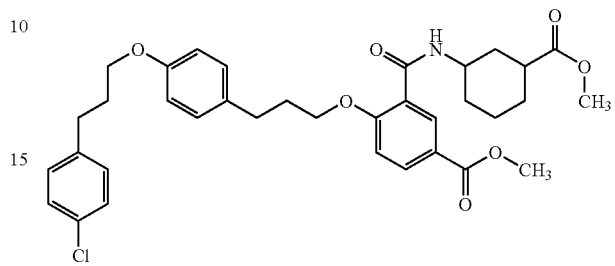

Methyl 4-(3-{4-[3-(4-chlorophenyl)propoxy]phenyl}propoxy)-3-({[3-(methoxycarbonyl)cyclohexyl]amino}carbonyl)benzoate is prepared in analogy to the process described in Example 34 from methyl 4-[3-(4-hydroxyphenyl)propoxy]-3-({[3-(methoxycarbonyl)cyclohexyl]amino}carbonyl)benzoate and 1-(3-bromopropyl)-4-chlorobenzene.

TLC (cyclohexane/ethyl acetate 1:1): $R_f$: 0.44.
HPLC (method 2): $R_t$: 5.90 min.
LC-MS (method 13): $R_t$: 4.5 min, m/z (ESI+)=622 and 623 (M+H$^+$).

Example 53

3-{[(3-Carboxycyclohexyl)amino]carbonyl}-4-(3-{4-[3-(4-chlorophenyl)propoxy]-phenyl}propoxy)benzoic acid

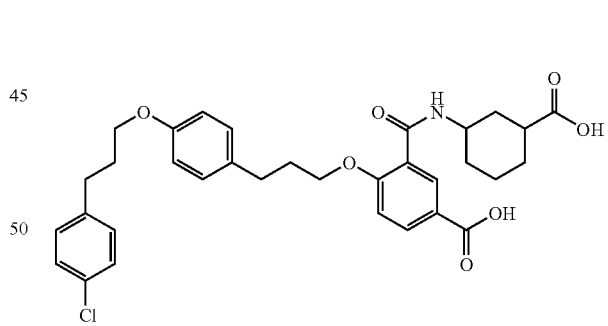

3-{[(3-Carboxycyclohexyl)amino]carbonyl}-4-(3-{4-[3-(4-chlorophenyl)propoxy]-phenyl}propoxy)benzoic acid is prepared in analogy to the process described in Example 35 from methyl 4-(3-{4-[3-(4-chlorophenyl)propoxy]phenyl}propoxy)-3-({[3-(methoxycarbonyl)cyclohexyl]amino}carbonyl)benzoate.

HPLC (method 2): $R_t$: 5.21 min.
LC-MS (method 14): $R_t$: 3.37 min, m/z (ESI+)=594 and 596 (M+H$^+$).

Example 54

Methyl 4-{3-[4-(3-Cyclohexylpropoxy)phenyl]propoxy}-3-{[3-(2-ethoxy-2-oxo-ethyl)azetidin-1-yl]carbonyl}benzoate

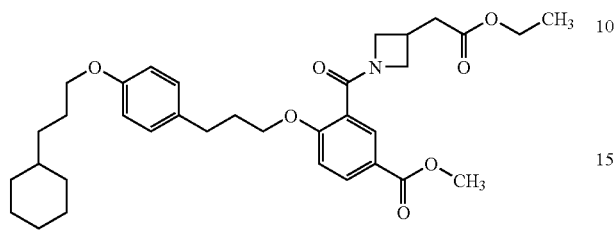

Preparation takes place in analogy to the process described in Example 22 from methyl 3-{[3-(2-ethoxy-2-oxoethyl)azetidin-1-yl]carbonyl}-4-hydroxybenzoate and 1-(3-bromopropyl)-4-(3-cyclohexylpropoxy)benzene.

HPLC (method 5): $R_t$: 5.83 min.

$^1$H-NMR (300 MHz, DMSO-$d_6$, δ/ppm): 7.97 (dd, 1H), 7.83 (d, 1H), 7.20-7.09 (m, 3H), 6.83 (d, 2H), 4.19-3.94 (m, 6H), 3.94-3.86 (m, 2H), 3.82 (s, 3H), 3.75-3.67 (m, 1H), 3.63-3.54 (m, 1H), 2.95-2.82 (m, 1H), 2.74-2.62 (m, 4H), 2.05-1.96 (m, 2H), 1.75-1.55 (m, 7H), 1.33-1.08 (m, 9H), 0.96-0.78 (m, 2H).

MS (ESI+): m/z=580 (M+H$^+$).

Example 55

3-{[3-(Carboxymethyl)azetidin-1-yl]carbonyl}-4-{3-[4-(3-cyclohexylpropoxy)-phenyl]propoxy}benzoic acid

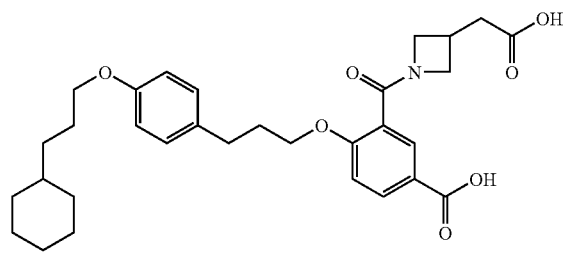

Preparation takes place in analogy to Example 11 from methyl 4-{3-[4-(3-cyclohexylpropoxy)phenyl]-propoxy}-3-{[3-(2-ethoxy-2-oxoethyl)azetidin-1-yl]carbonyl}benzoate.

HPLC (method 5): $R_t$: 5.05 min.

$^1$H-NMR (300 MHz, DMSO-$d_6$, δ/ppm): 12.48 (s, broad, 2H), 7.94 (dd, 1H), 7.81 (d, 1H), 7.13 (pseudo-d, 3H), 6.82 (d, 2H), 4.19-4.04 (m, 3H), 3.98 (t, 1H), 3.89 (t, 2H), 3.70 (q, 1H), 3.57 (q, 1H), 2.93-2.77 (m, 1H), 2.75-2.54 (m, 4H), 2.09-1.95 (m, 2H), 1.76-1.55 (m, 7H), 1.35-1.04 (m, 6H), 0.97-0.79 (m, 2H).

MS (ESI+): m/z=538 (M+H$^+$).

Example 56

Methyl 3-({[3-(methoxycarbonyl)cyclohexyl]amino}carbonyl)-4-{3-[4-(5-phenoxy-pentyl)phenyl]propoxy}benzoate Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-iodopropyl)-4-(5-phenoxypentyl)benzene.

HPLC (method 5): $R_t$: 5.57 min.

$^1$H-NMR (300 MHz, CDCl$_3$, δ/ppm): 8.87 (d, 1H), 8.09 (dd, 1H), 7.86 (d, 1H), 7.30-7.22 (m, 2H), 7.14-7.06 (m, 4H), 6.98-6.84 (m, 4H), 4.43-4.34 (m, 1H), 4.19 (t, 2H), 3.95 (t, 2H), 3.89 (s, 3H), 3.65 (s, 3H), 2.81 (t, 2H), 2.65-2.54 (m, 3H), 2.30-2.19 (m, 2H), 2.01-1.94 (m, 2H), 1.87-1.62 (m, 9H), 1.56-1.47 (m, 3H).

LC-MS (method 9): $R_t$: 3.19 min. m/z (EI+)=615.

Example 57

3-{[(3-Carboxycyclohexyl)amino]carbonyl}-4-{3-[4-(5-phenoxypentyl)phenyl]-propoxy}benzoic acid Preparation takes place in analogy to Example 11 from methyl 3-({[3-(methoxycarbonyl)cyclohexyl]amino}carbonyl)-4-{3-[4-(5-phenoxypentyl)phenyl]-propoxy}benzoate.

HPLC (method 5): $R_t$: 4.94 min.

$^1$H-NMR (300 MHz, CDCl$_3$, δ/ppm): 8.92 (d, 1H), 8.12 (dd, 1H), 7.86 (d, 1H), 7.29-7.22 (m, 2H), 7.12-7.08 (m, 4H), 6.98-6.85 (m, 4H), 4.48-4.34 (m, 1H), 4.18 (t, 2H), 3.94 (t, 2H), 2.82 (t, 2H); 2.72-2.56 (m, 3H), 2.30-1.23 (m, 18H).

LC-MS (method 9): $R_t$: 2.75 min, m/z (EI+)=587.

Example 58

Ethyl 3-{[3-(2-ethoxy-2-oxoethyl)azetidin-1-yl]carbonyl}-4-{3-[4-(4-phenoxybutoxy)phenyl]-propoxy}benzoate

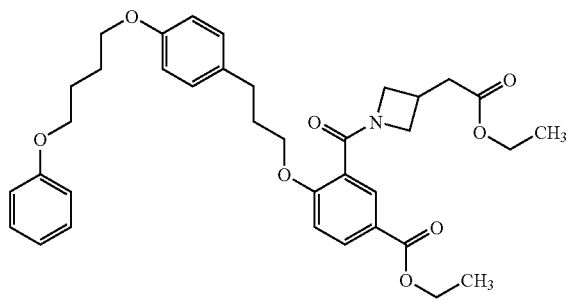

Preparation takes place in analogy to Example IX, method 3, from 3-(2-ethoxy-2-oxoethyl)azetidinium chloride and 5-(ethoxycarbonyl)-2-{3-[4-(4-phenoxybutoxy)-phenyl]propoxy}benzoic acid.

HPLC (method 5): $R_t$: 5.19 min.

$^1$H-NMR (300 MHz, CDCl$_3$, δ/ppm): 8.07-8.00 (m, 2H), 7.31-7.23 (m, 2H), 7.10 (d, 2H), 6.96-6.81 (m, 6H), 4.40-4.30 (m, 4H), 4.17-3.98 (m, 8H), 3.90-3.83 (m, 1H), 3.70-3.62 (m, 1H), 3.05-2.93 (m, 1H), 2.79-2.70 (m, 2H), 2.70-2.55 (m, 2H), 2.17-2.07 (m, 2H), 2.00-1.93 (m, 4H), 1.37 (t, 3H), 1.22 (t, 3H).

MS (ESI+): m/z=618 (M+H$^+$).

Example 59

3-{[3-(Carboxymethyl)azetidin-1-yl]carbonyl}-4-{3-[4-(4-phenoxybutoxy)phenyl]-propoxy}benzoic acid

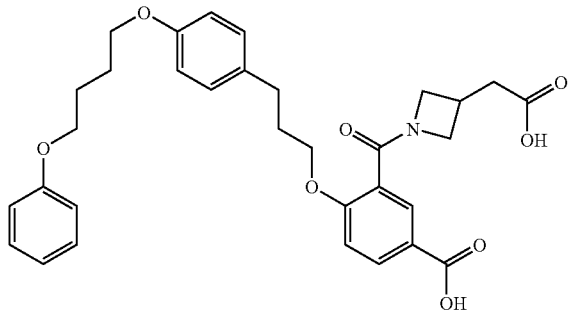

Preparation takes place in analogy to Example 11 from ethyl 3-{[3-(2-ethoxy-2-oxoethyl)azetidin-1-yl]carbonyl}-4-{3-[4-(4-phenoxybutoxy)phenyl]propoxy}-benzoate.

HPLC (method 5): $R_t$: 4.39 min.

$^1$H-NMR (300 MHz, DMSO-d$_6$, δ/ppm): 12.48 (s, broad, 2H), 7.94 (dd, 1H), 7.81 (d, 1H), 7.31-7.24 (m, 2H), 7.14 (pseudo-d, 3H), 6.95-6.82 (m, 5H), 4.18-3.95 (m, 8H), 3.69 (dd, 1H), 3.62-3.56 (m, 1H), 2.92-2.80 (m, 1H), 2.69 (t, 2H), 2.61-2.55 (m, 2H), 2.08-1.96 (m, 2H), 1.89-1.81 (m, 4H).

LC-MS (method 6): $R_t$: 2.32 min, m/z (EI+)=561.

Example 60

Methyl 4-{2-[4-(biphenyl-4-ylmethoxy)phenoxy]ethoxy}-3-({[3-(methoxycarbonyl)-cyclohexyl]amino}carbonyl)benzoate

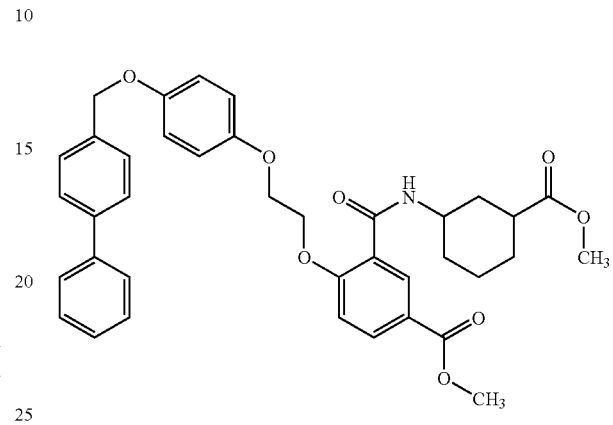

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 4-{[4-(2-bromoethoxy)phenoxy]methyl}biphenyl.

HPLC (method 5): $R_t$: 5.22 min.

$^1$H-NMR (200 MHz, CDCl$_3$, δ/ppm): 8.90 (d, 1H), 8.15 (dd, 1H), 7.91 (d, 1H), 7.65-7.34 (m, 8H), 7.08-6.82 (m, 6H), 5.06 (s, 2H), 4.53-4.45 (m, 2H), 4.42-4.32 (m, 3H), 3.91 (s, 3H), 3.61 (s, 3H), 2.52-2.38 (m, 1H), 1.84 (t, 2H), 1.76-1.24 (m, 6H).

MS (ESI+): m/z=638 (M+H$^+$).

Example 61

4-{2-[4-(Biphenyl-4-ylmethoxy)phenoxy]ethoxy}-3-{[(3-carboxycyclohexyl) amino]-carbonyl}benzoic acid

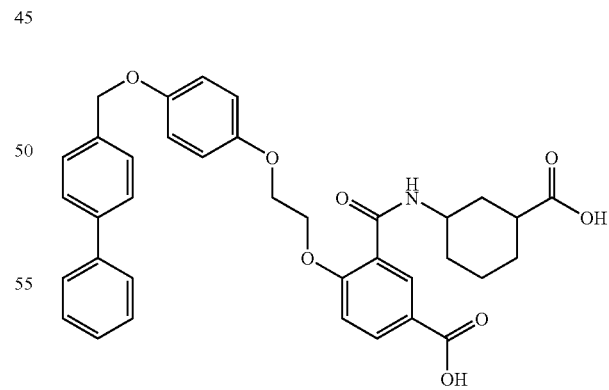

Preparation takes place in analogy to Example 11 from methyl 4-{2-[4-(biphenyl-4-ylmethoxy)phenoxy]ethoxy}-3-({[3-(methoxycarbonyl)cyclohexyl]amino}carbonyl)-benzoate.

HPLC (method 5): $R_t$: 4.66 min.

$^1$H-NMR (300 MHz, DMSO-d$_6$, δ/ppm): 8.39 (d, 1H), 8.06-7.99 (m, 2H), 7.69-7.65 (m, 4H), 7.54-7.44 (m, 4H), 7.39-7.27 (m, 2H), 7.00-6.90 (m, 4H), 5.10 (s, 2H), 4.55-4.49 (m, 2H), 4.37-4.33 (m, 2H), 4.14-4.04 (m, 1H), 2.47-2.38 (m, 1H), 1.80-1.22 (m, 8H).

LC-MS (method 9): $R_t$: 2.53 min, m/z (EI+)=609.

Example 62

Methyl 4-{3-[4-(2-biphenyl-4-ylethyl)phenyl]propoxy}-3-({[3-(methoxycarbonyl)-cyclohexyl]amino}carbonyl)benzoate

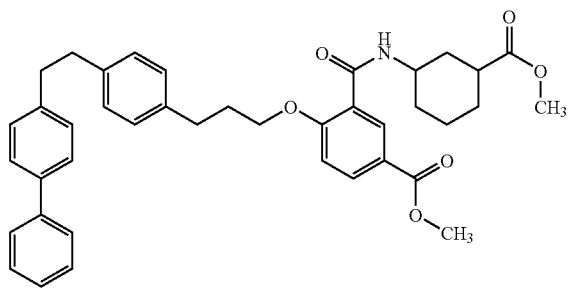

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 4-{2-[4-(3-iodopropyl)phenyl]ethyl}biphenyl.

HPLC (method 5): $R_t$: 5.64 min.

$^1$H-NMR (300 MHz, CDCl$_3$, δ/ppm): 8.87 (d, 1H), 8.09 (dd, 1H), 7.85 (d, 1H), 7.61-7.55 (m, 2H), 7.54-7.48 (m, 2H), 7.46-7.39 (m, 3H), 7.36-7.22 (m, 2H), 7.18-7.08 (m, 4H), 6.96 (d, 1H), 4.44-4.30 (m, 1H), 4.19 (t, 2H), 3.89 (s, 3H), 3.65 (s, 3H), 2.83 (t, 2H), 2.69-2.55 (m, 1H), 2.31-2.19 (m, 2H), 2.02-1.95 (m, 2H), 1.81-1.62 (m, 5H), 1.40-1.22 (m, 5H).

LC-MS (method 9): $R_t$: 3.24 min, m/z (EI+)=633.

Example 63

4-{3-[4-(2-Biphenyl-4-ylethyl)phenyl]propoxy}-3-{[(3-carboxycyclohexyl)amino]-carbonyl}benzoic acid

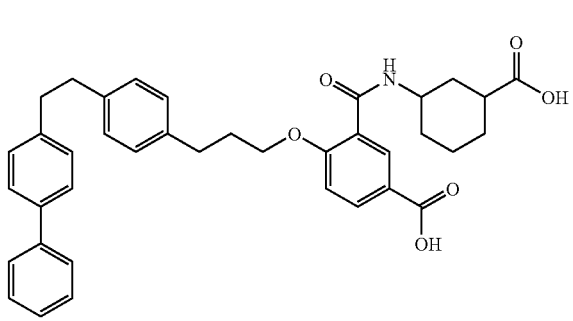

Preparation takes place in analogy to Example 11 from methyl 4-{3-[4-(2-biphenyl-4-ylethyl)phenyl]propoxy}-3-({[3-(methoxycarbonyl)cyclohexyl]amino}carbonyl)-benzoate.

HPLC (method 5): $R_t$: 5.03 min.

LC-MS (method 9): $R_t$: 2.82 min, m/z (EI+)=605.

Example 64

Methyl 3-({[3-(methoxycarbonyl)cyclohexyl]amino}carbonyl)-4-{2-[4-(4-phenoxy-butoxy)phenoxy]ethoxy}benzoate

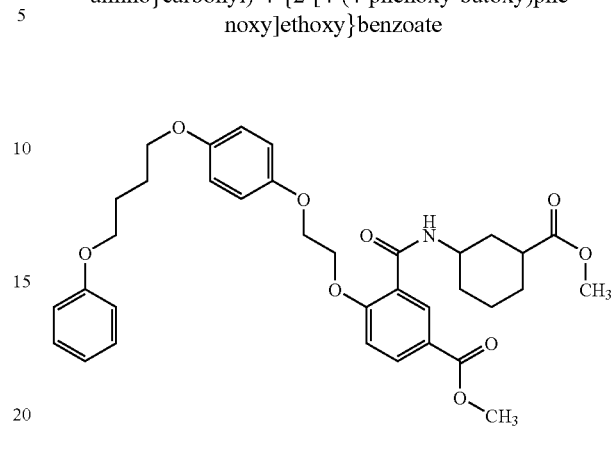

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(2-bromoethoxy)-4-(4-phenoxybutoxy)benzene.

HPLC (method 5): $R_t$: 5.11 min.

$^1$H-NMR (200 MHz, CDCl$_3$, δ/ppm): 8.90 (d, 1H), 8.15 (dd, 1H), 7.92 (d, 1H), 7.33-7.22 (m, 2H), 7.07-6.81 (m, 8H), 4.55-4.46 (m, 2H), 4.42-4.32 (m, 2H), 4.07-3.95 (m, 4H), 3.90 (s, 3H), 3.62 (s, 3H), 2.53-2.36 (m, 1H), 2.04-1.78 (m, 6H), 1.70-1.25 (m, 7H).

MS (ESI+): m/z=620 (M+H$^+$).

Example 65

3-{[(3-Carboxycyclohexyl)amino]carbonyl}-4-{2-[4-(4-phenoxybutoxy)phenoxy]-ethoxy}benzoic acid

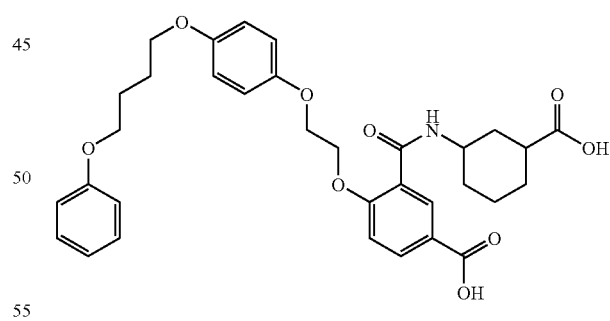

Preparation takes place in analogy to Example 11 from methyl 3-({[3-(methoxycarbonyl)cyclohexyl]amino}carbonyl)-4-{2-[4-(4-phenoxybutoxy)-phenoxy]ethoxy}benzoate.

HPLC (method 5): $R_t$: 4.52 min.

$^1$H-NMR (300 MHz, DMSO-d$_6$, δ/ppm): 12.45 (s, broad, 2H); 7.39 (d, 1H), 8.07-7.98 (m, 2H), 7.34-7.22 (m, 3H), 6.95-6.83 (m, 7H), 4.56-4.49 (m, 2H), 4.37-4.32 (m, 2H), 4.15-3.93 (m, 5H), 2.48-2.39 (m, 1H), 1.89-1.22 (m, 12H).

LC-MS (method 9): $R_t$: 2.42 min, m/z (EI+)=591.

Example 66

Methyl 3-({[3-(methoxycarbonyl)cyclohexyl]amino}carbonyl)-4-(2-{4-[(1Z)-5-phenoxypent-1-en-1-yl]phenoxy}ethoxy)benzoate

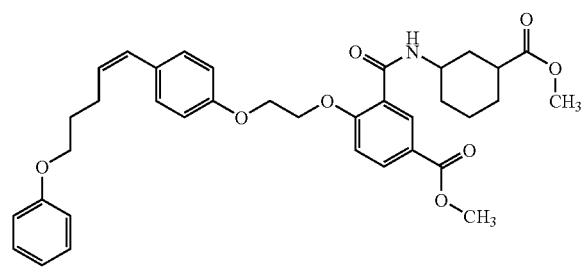

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(2-iodoethoxy)-4-[(1Z)-5-phenoxypent-1-en-1-yl]benzene.

HPLC (method 5): $R_t$: 5.33 min.

$^1$H-NMR (300 MHz, CDCl$_3$, δ/ppm): 8.90 (d, 1H), 8.14 (dd, 1H), 7.85 (d, 1H), 7.29-7.21 (m, 4H), 7.04 (d, 1H), 6.94-6.83 (m, 5H), 6.39 (d, 1H), 5.64 (dt, 1H), 4.56-4.50 (m, 2H), 4.44-4.30 (m, 2H), 4.39-4.30 (m, 1H), 3.99 (t, 2H), 3.91 (s, 3H), 3.61 (s, 3H), 2.54-2.32 (m, 3H), 2.10-1.7 (m, 5H), 1.48-1.23 (m, 5H).

LC-MS (method 14): $R_t$: 3.63 min, m/z (EI+)=615.

Example 67

3-{[(3-Carboxycyclohexyl)amino]carbonyl}-4-(2-{4-[(1Z)-5-phenoxypent-1-en-1-yl]phenoxy}ethoxy)benzoic acid

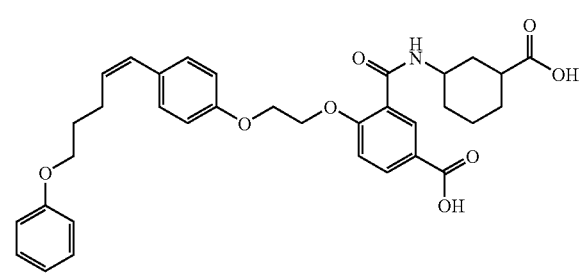

Preparation takes place in analogy to Example 11 from methyl 3-({[3-(methoxycarbonyl)cyclohexyl]amino}carbonyl)-4-(2-{4-[(1Z)-5-phenoxypent-1-en-1-yl]phenoxy}ethoxy)benzoate.

HPLC (method 5): $R_t$: 4.67 min.

$^1$H-NMR (300 MHz, CDCl$_3$, δ/ppm): 8.88 (s, 1H), 8.10 (d, 1H), 7.88 (d, 1H), 7.30-7.16 (m, 3H), 7.01-6.81 (m, 7H), 6.36 (d, 1H), 5.65-5.54 (m, 1H), 4.52-4.28 (m, 5H), 4.01-3.91 (m, 2H), 2.54-2.42 (m, 2H), 2.03-1.18 (m, 11H).

LC-MS (method 9): $R_t$: 2.54 min, m/z (EI+)=587.

Example 68

Methyl 1-[2-{2-[4-(Biphenyl-4-ylmethoxy)phenoxy]ethoxy}-5-(methoxycarbonyl)-benzoyl]piperidine-4-carboxylate

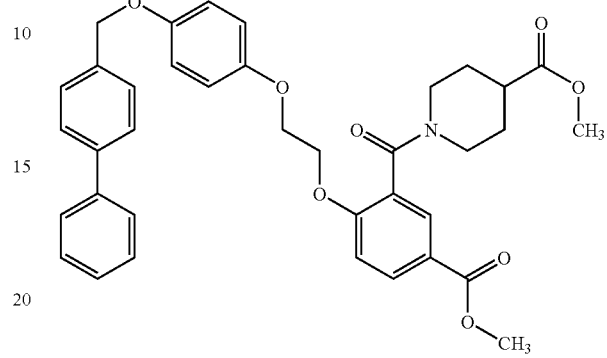

Preparation takes place in analogy to Example 22 from methyl 1-[2-hydroxy-5-(methoxycarbonyl)benzoyl]piperidine-4-carboxylate and 4-{[4-(2-bromoethoxy)-phenoxy]methyl}biphenyl.

HPLC (method 5): $R_t$: 5.02 min.

$^1$H-NMR (300 MHz, CDCl$_3$, δ/ppm): 8.05 (d, 1H), 7.95 (dd, 1H), 7.64-7.55 (m, 4H), 7.52-7.40 (m, 4H), 7.38-7.33 (m, 1H), 7.03-6.90 (m, 3H), 6.88-6.81 (m, 2H), 5.06 (s, 2H), 4.54-4.18 (m, 5H), 3.89 (s, 3H), 3.68 and 3.57 (s, together 3H), 3.53-3.37 (m, 1H), 3.15-2.88 (m, 2H), 2.56-2.39 (m, 1H), 2.01-1.88 (m, 1H), 1.87-1.60 (m, 3H).

LC-MS (method 9): $R_t$: 2.79 min, m/z (EI+)=623.

Example 69

1-(2-{2-[4-(Biphenyl-4-ylmethoxy)phenoxy]ethoxy}-5-carboxybenzoyl)piperidine-4-carboxylic acid

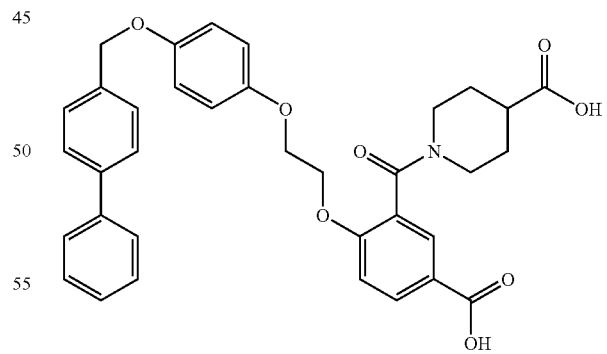

Preparation takes place in analogy to Example 11 from methyl 1-[2-{2-[4-(biphenyl-4-ylmethoxy)phenoxy]ethoxy}-5-(methoxycarbonyl)benzoyl]piperidine-4-carboxylate.

HPLC (method 5): $R_t$: 4.42 min.

$^1$H-NMR (300 MHz, DMSO-d$_6$, δ/ppm): 12.52 (s, broad, 2H), 7.96 (dd, 1H); 7.75-7.64 (m, 5H), 7.56-7.43 (m, 4H), 7.40-7.33 (m, 1H), 7.25 (d, 1H), 7.01-6.86 (m, 4H), 5.08 (d, 2H), 4.48-4.38 (m, 2H), 4.34-4.21 (m, 3H), 3.15-2.75 (m, 2H), 2.48-2.37 (m, 1H), 1.91-1.26 (m, 4H).

Example 70

Methyl 3-({[3-(methoxycarbonyl)cyclohexyl]amino}carbonyl)-4-({3-[4-(4-phenoxy-butoxy)phenyl]prop-2-yn-1-yl}oxy)benzoate

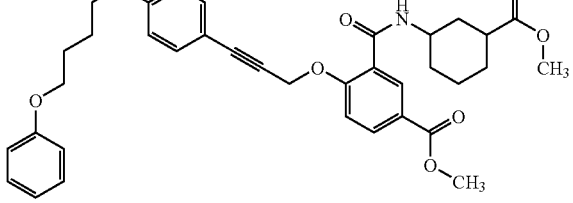

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-bromoprop-1-yn-1-yl)-4-(4-phenoxy-butoxy)benzene.

HPLC (method 5): $R_t$: 5.23 min.

$^1$H-NMR (400 MHz, CDCl$_3$, δ/ppm): 8.9 (d, 1H), 8.15 (dd, 1H), 7.98 (d, 1H), 7.38 (d, 2H), 7.31-7.25 (m, 2H), 7.10 (d, 1H), 6.94 (t, 1H), 6.89 (d, 2H), 6.84 (d, 2H), 5.09 (s, 2H), 4.47-4.40 (m, 1H), 4.08-4.01 (m, 4H), 3.91 (s, 3H), 3.62 (s, 3H), 2.64-2.57 (m, 1H), 2.11-1.95 (m, 5H), 1.88-1.80 (m, 1H), 1.72-1.49 (m, 6H).

MS (CI+): m/z=614 (M+H$^+$).

Example 71

3-{[(3-Carboxycyclohexyl)amino]carbonyl}-4-({3-[4-(4-phenoxybutoxy)phenyl]-prop-2-yn-1-yl}oxy)benzoic acid

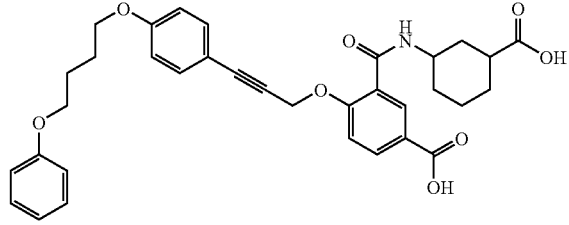

Preparation takes place in analogy to Example 11 from methyl 3-({[3-(methoxycarbonyl)cyclohexyl]amino}carbonyl)-4-({3-[4-(4-phenoxybutoxy)-phenyl]prop-2-yn-1-yl}oxy)benzoate.

$^1$H-NMR (400 MHz, DMSO-d$_6$, δ/ppm): 12.55 (s, broad, 2H), 8.23 (d, 1H), 8.13 (d, 1H), 8.04 (dd, 1H), 7.40 (d, 2H), 7.34 (d, 1H), 7.26 (dd, 2H), 6.98-6.88 (m, 5H), 5.22 (s, 2H), 4.18-3.97 (m, 5H), 2.62-2.55 (m, 1H), 1.92-1.43 (m, 12H).

LC-MS (method 6): $R_t$: 2.59 min, m/z (EI+)=585.

Example 72

Methyl 3-({[3-(methoxycarbonyl)cyclohexyl]amino}carbonyl)-4-(3-{4-[(4-phenoxy-but-2-yn-1-yl)oxy]phenyl}propoxy)benzoate

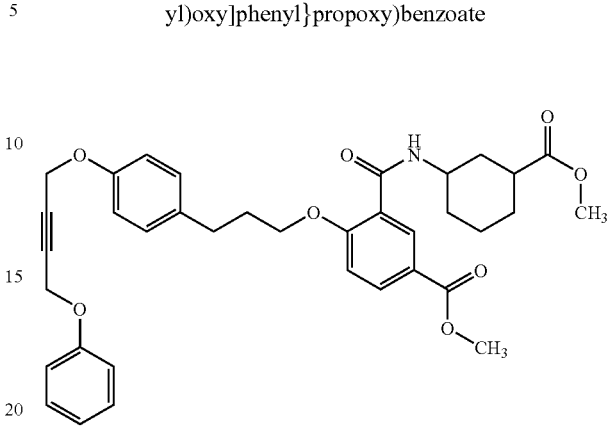

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-(3-bromopropyl)-4-[(4-phenoxybut-2-yn-1-yl)oxy]benzene.

HPLC (method 5): $R_t$: 5.00 min.

$^1$H-NMR (200 MHz, CDCl$_3$, δ/ppm): 8.87 (d, 1H), 8.09 (dd, 1H), 7.86 (d, 1H), 7.35-7.21 (m, 1H), 7.10 (d, 2H), 7.04-6.81 (m, 7H), 4.71 (s, 4H), 4.46-4.32 (m, 1H), 4.18 (t, 2H), 3.89 (s, 3H), 3.65 (s, 3H), 2.70 (t, 2H), 2.72-2.52 (m, 2H), 2.32-2.14 (m, 2H), 1.98 (t, 2H), 1.88-1.45 (m, 5H).

LC-MS (method 6): $R_t$: 3.14 min, m/z (EI+)=613.

Example 73

3-{[(3-Carboxycyclohexyl)amino]carbonyl}-4-(3-{4-[(4-phenoxybut-2-yn-1-yl)oxy]-phenyl}propoxy)benzoic acid

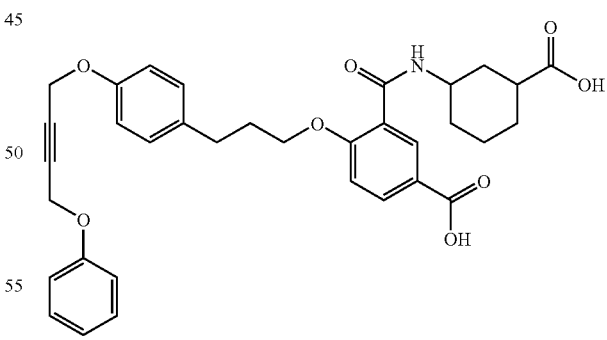

Preparation takes place in analogy to Example 11 from methyl 3-({[3-(methoxycarbonyl)cyclohexyl]amino}carbonyl)-4-(3-{4-[(4-phenoxybut-2-yn-1-yl)oxy]phenyl}propoxy)benzoate.

HPLC (method 5): $R_t$: 4.39 min.

$^1$H-NMR (400 MHz, CDCl$_3$, δ/ppm): 8.68 (d, 1H), 8.06 (dd, 1H), 7.94 (d, 1H), 7.27 (t, 2H), 7.10 (d, 2H), 7.03 (d, 1H), 6.98-6.82 (m, 5H), 4.74 (d, 4H), 4.38-4.29 (m, 1H), 4.23-4.15

(m, 2H), 2.79 (t, 2H), 2.27-2.18 (m, 2H), 2.03-1.85 (m, 2H), 1.84-1.52 (m, 7H).

LC-MS (method 7): $R_t$: 2.39 min, m/z (EI+)=585.

Example 74

Methyl 3-({[3-(methoxycarbonyl)cyclohexyl]amino}carbonyl)-4-(3-{4-[(1Z)-5-phenoxypent-1-en-1-yl]phenyl}propoxy)benzoate

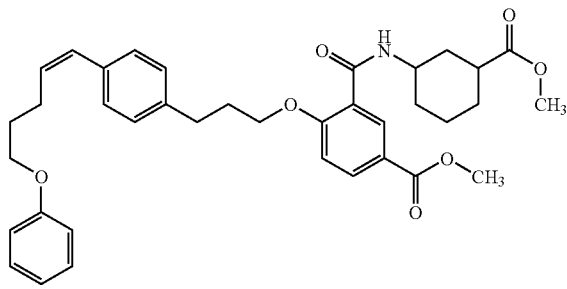

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and (4Z)-5-[4-(3-bromopropyl)phenyl]pent-4-en-1-yl phenyl ether.

HPLC (method 5): $R_t$: 5.42 min.

$^1$H-NMR (300 MHz, CDCl$_3$, δ/ppm): 8.87 (d, 1H), 8.08 (dd, 1H), 7.84 (d, 1H), 7.30-7.20 (m, 4H), 7.13 (d, 2H), 6.97-6.84 (m, 4H), 6.43 (d, 1H), 5.68 (dq, 1H), 4.43-4.34 (m, 1H), 4.19 (t, 2H), 4.02-3.94 (m, 2H), 3.89 (s, 3H), 3.65 (s, 3H), 3.42 (t, 2H), 2.84 (t, 2H), 2.64-2.54 (m, 1H), 2.53 (dq, 2H), 2.33-2.20 (m, 2H), 2.04-1.60 (m, 8H).

LC-MS (method 7): $R_t$: 3.40 min, m/z (EI+)=613.

Example 75

3-{[(3-Carboxycyclohexyl)amino]carbonyl}-4-(3-{4-[(1Z)-5-phenoxypent-1-en-1-yl]phenyl}propoxy)benzoic acid

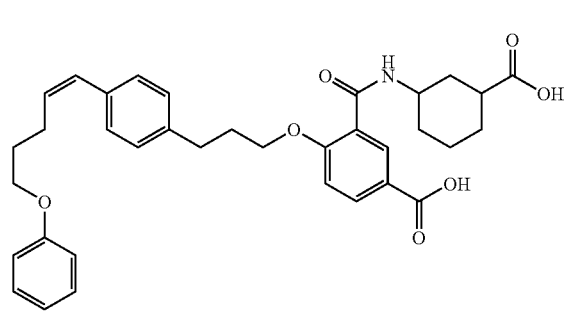

Preparation takes place in analogy to Example 11 from methyl 3-({[3-(methoxycarbonyl)cyclohexyl]amino}carbonyl)-4-(3-{4-[(1Z)-5-phenoxypent-1-en-1-yl]phenyl}propoxy)benzoate.

$^1$H-NMR (300 MHz, CDCl$_3$, δ/ppm): 8.91 (d, 1H), 8.11 (dd, 1H), 7.84 (d, 1H), 7.30-7.18 (m, 4H), 7.13 (d, 2H), 6.97-6.83 (m, 4H), 6.43 (d, 1H), 5.67 (dq, 1H), 4.48-4.35 (m, 1H), 4.19 (t, 2H), 3.98 (t, 2H), 2.84 (t, 2H), 2.73-2.61 (m, 1H), 2.51 (dq, 2H), 2.33-2.18 (m, 2H), 2.15-2.04 (m, 1H), 2.02-1.52 (m, 9H).

LC-MS (method 7): $R_t$: 2.68 min, m/z (EI+)=585.

Example 76

Methyl 3-({[3-(methoxycarbonyl)cyclohexyl]amino}carbonyl)-4-(3-{4-[(1E)-5-phenoxypent-1-en-1-yl]phenyl}propoxy)benzoate

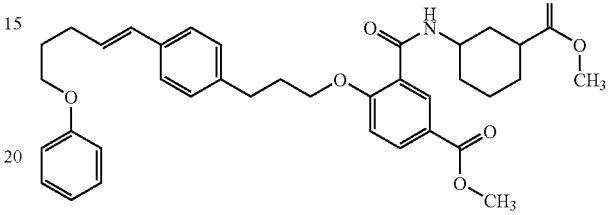

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and (4E)-5-[4-(3-bromopropyl)phenyl]pent-4-en-1-yl phenyl ether.

HPLC (method 5): $R_t$: 5.44 min.

$^1$H-NMR (300 MHz, CDCl$_3$, δ/ppm): 8.86 (d, 1H), 8.09 (d, 1H), 7.84 (d, 1H), 7.32-7.23 (m, 4H), 7.11 (d, 2H), 6.97-6.86 (m, 4H), 6.40 (d, 1H), 6.28-6.16 (m, 1H), 4.42-4.35 (m, 1H), 4.18 (t, 2H), 4.02 (t, 2H), 3.89 (s, 3H), 3.65 (s, 3H), 2.83 (t, 2H), 2.73-2.54 (m, 2H), 2.44-2.35 (m, 2H) 2.30-2.17 (m, 2H), 2.03-1.96 (m, 4H), 1.85-1.22 (m, 5H).

LC-MS (method 7): $R_t$: 3.22 min, m/z (EI+)=613.

Example 77

3-{[(3-Carboxycyclohexyl)amino]carbonyl}-4-(3-{4-[(1E)-5-phenoxypent-1-en-1-yl]-phenyl}propoxy)benzoic acid

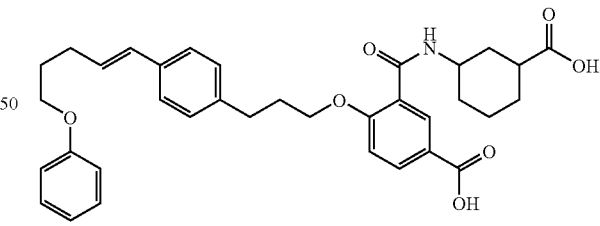

Preparation takes place in analogy to Example 11 from methyl 3-({[3-(methoxycarbonyl)cyclohexyl]amino}carbonyl)-4-(3-{4-[(1E)-5-phenoxypent-1-en-1-yl]phenyl}propoxy)benzoate.

$^1$H-NMR (300 MHz, CDCl$_3$, δ/ppm): 8.91 (d, 1H), 8.12 (dd, 1H), 7.84 (d, 1H), 7.32-7.20 (m, 5H), 7.11 (d, 1H), 6.98-6.86 (m, 4H), 6.40 (d, 1H), 6.22 (dt, 1H), 4.48-4.36 (m, 1H), 4.17 (t, 2H), 4.00 (t, 2H), 2.86 (t, 2H), 2.74-2.63 (m, 1H), 2.44-2.33 (m, 2H) 2.30-2.18 (m, 2H), 2.17-2.03 (m, 1H), 2.02-1.22 (m, 9H).

LC-MS (method 7): $R_t$: 2.72 min, m/z (EI+)=585.

Example 78

Methyl 3-({[3-(methoxycarbonyl)cyclohexyl]amino}carbonyl)-4-({(2E)-3-[4-(4-phenoxybutoxy)phenyl]prop-2-en-1-yl}oxy)benzoate

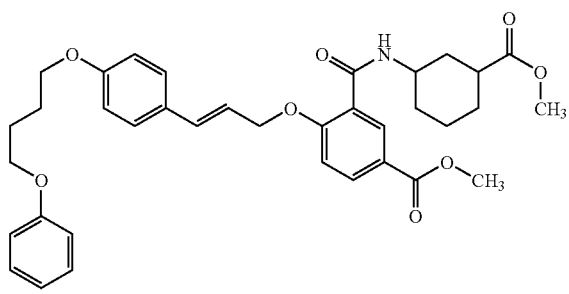

Preparation takes place in analogy to Example 22 from the (+)-B-enantiomer of methyl 4-hydroxy-3-({[3-(methoxycarbonyl)cyclohexyl]amino}carbonyl)benzoate (see Example IX, method 2) and 1-[(1E)-3-bromoprop-1-en-1-yl]-4-(4-phenoxybutoxy)benzene.

$^1$H-NMR (300 MHz, CDCl$_3$, δ/ppm): 8.94 (d, 1H), 8.17 (dd, 1H), 8.08 (d, 1H), 7.37 (d, 2H), 7.33-7.24 (m, 2H), 7.07 (d, 1H), 6.96-6.84 (m, 5H), 6.78 (d, 1H), 6.35 (dt, 1H), 4.83 (d, 2H), 4.48-4.39 (m, 1H), 4.08-4.00 (m, 4H), 3.90 (s, 3H), 3.60 (s, 3H), 2.53-2.40 (m, 1H), 2.10-1.93 (m, 5H), 1.83-1.37 (m, 7H).

MS (ESI+): m/z=638 (M+Na$^+$)

Example 79

3-{[(3-Carboxycyclohexyl)amino]carbonyl}-4-({(2E)-3-[4-(4-phenoxybutoxy)-phenyl]prop-2-en-1-yl}oxy)benzoic acid

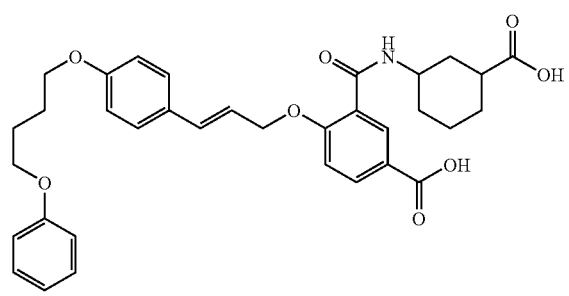

Preparation takes place in analogy to Example 11 from methyl 3-({[3-(methoxycarbonyl)cyclohexyl]amino}carbonyl)-4-({(2E)-3-[4-(4-phenoxybutoxy)-phenyl]prop-2-en-1-yl}oxy)benzoate.

HPLC (method 5): R$_t$: 4.66 min.

$^1$H-NMR (300 MHz, CDCl$_3$, δ/ppm): 8.95 (d, 1H), 8.17 (dd, 1H), 8.08 (d, 1H), 7.36 (d, 2H), 7.32-7.22 (m, 2H), 7.07 (d, 1H), 6.96-6.74 (m, 6H), 6.34 (dt, 1H), 4.83 (d, 2H), 4.50-4.40 (m, 1H), 4.08-3.96 (m, 4H), 2.58-2.46 (m, 1H), 2.08-1.46 (m, 12H).

LC-MS (method 7): R$_t$: 2.76 min, m/z (EI+)=587.

Example 80

Ethyl 3-[({[2-(methoxycarbonyl)cyclohexyl]methyl}amino)carbonyl]-4-{3-[4-(4-phenoxybutoxy)phenyl]propoxy}benzoate

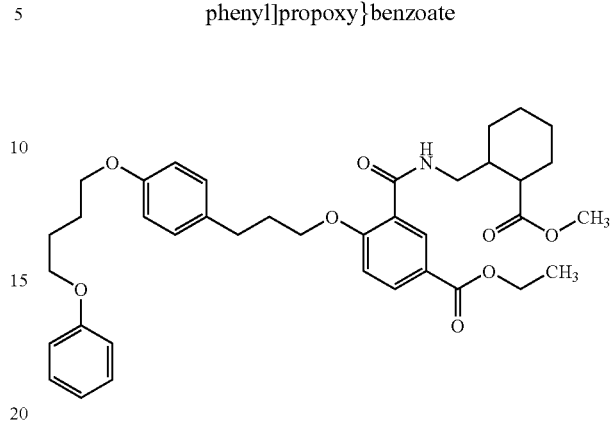

Preparation takes place in analogy to Example IX, method 3, from [2-(methoxycarbonyl)cyclohexyl]methanammonium bromide and 5-(ethoxy-carbonyl)-2-{3-[4-(4-phenoxybutoxy)phenyl]propoxy}benzoic acid.

HPLC (method 5): R$_t$: 5.62 min.

$^1$H-NMR (300 MHz, CDCl$_3$, δ/ppm): 8.86 (d, 1H), 8.09 (dd, 1H), 7.93 (t, 1H), 7.31-7.25 (m, 2H), 7.10 (d, 2H), 6.97-6.82 (m, 6H), 4.35 (q, 2H), 4.16 (t, 2H), 4.07-3.98 (m, 4H), 3.70-3.59 (m, 1H), 3.58 (s, 3H), 3.41-3.30 (m, 1H), 2.80-2.68 (m, 3H), 2.27-2.11 (m, 3H), 2.01-1.83 (m, 5H), 1:74-1.55 (m, 5H), 1.44-1.33 (m, 2H), 1.37 (t, 3H).

MS (ESI+): m/z=646 (M+H$^+$).

Example 81

3-({[(2-Carboxycyclohexyl)methyl]amino}carbonyl)-4-{3-[4-(4-phenoxybutoxy)-phenyl]propoxy}benzoic acid

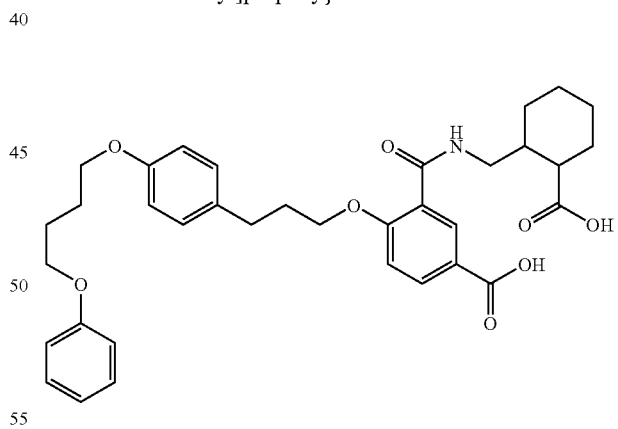

Preparation takes place in analogy to Example 11 from ethyl 3-[({[2-(methoxycarbonyl)cyclohexyl]methyl}amino)carbonyl]-4-{3-[4-(4-phenoxybutoxy)phenyl]propoxy}benzoate.

HPLC (method 5): R$_t$: 4.64 min.

$^1$H-NMR (300 MHz, DMSO-d$_6$, δ/ppm): 8.23 (d, 1H), 8.12 (t, 1H), 7.98 (dd, 1H), 7.31-7.25 (m, 2H), 7.21-7.10 (m, 3H), 6.95-9.82 (m, 5H), 4.14 (t, 2H), 4.05-3.96 (m 4H), 3.6-3.2 (m, 2H, underneath water signal), 2.68 (t, 2H), 2.62-2.56 (m, 1H), 2.12-1.93 (m, 3H), 1.88-1.82 (n, 4H), 1.82-1.12 (m, 8H).

MS (ESI−): m/z=602 (M−H$^+$)

The following compounds are additionally prepared in analogy to processes described in the above examples. (Unless indicated otherwise, all derivatives containing the
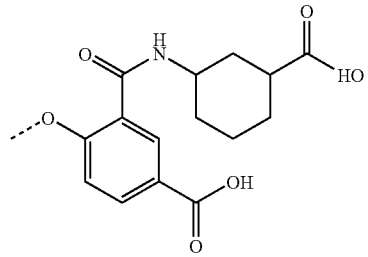
or
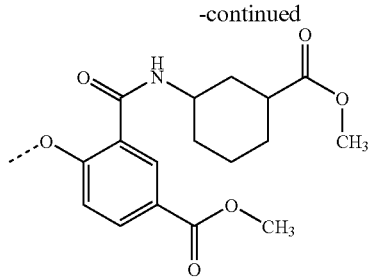
-continued
fragment are prepared from the (+) Benantiomer of the compound of Example IX, method 2.)
| Ex. No. | Structure | Molecular mass [g/mol] | HPLC method | HPLC R_t [min] | MS or LC-MS (method) |
|---|---|---|---|---|---|
| 82 | 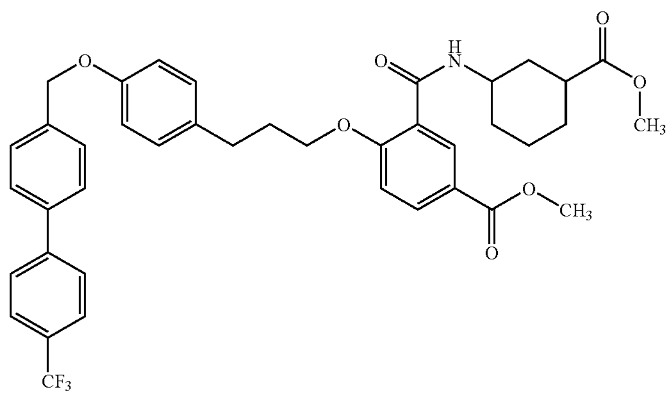 | 703 | 2 | 6.04 | 4.7 min, 704 (13) |
| 83 | 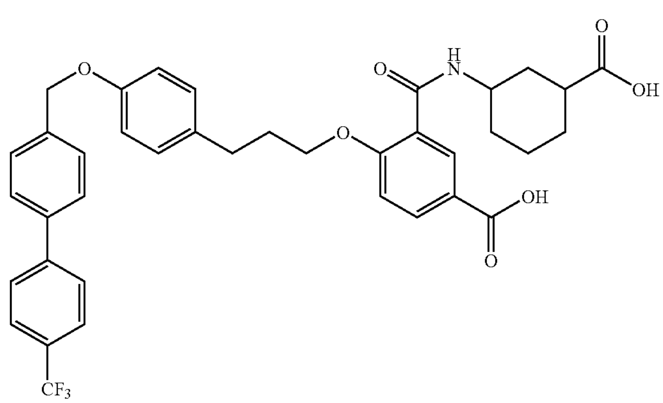 | 675 | 2 | 5.40 | 3.47 min, 675 (14) |

-continued

| Ex. No. | Structure | Molecular mass [g/mol] | HPLC method | HPLC R$_t$ [min] | MS or LC-MS (method) |
|---|---|---|---|---|---|
| 84 | 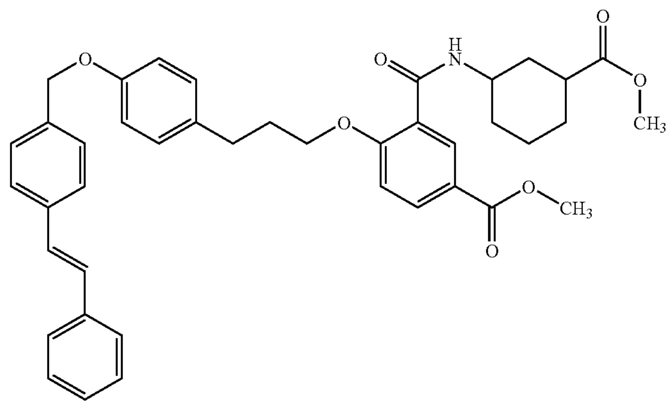 | 661 | 2 | 6.06 | 662 (ESI) |
| 85 | 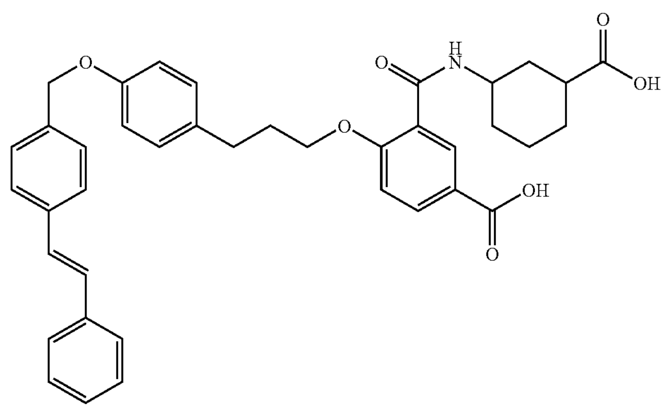 | 633 | 2 | 5.39 | 3.71 min, 633 (8) |
| 86 | 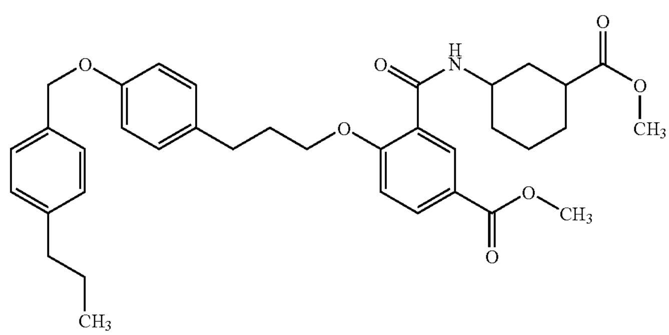 | 601 | 2 | 5.87 | 602 (ESI) |
| 87 | 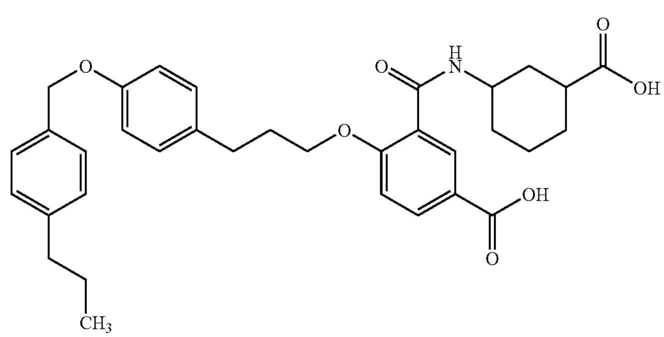 | 573 | 2 | 5.24 | 572 (ESI) |

-continued

| Ex. No. | Structure | Molecular mass [g/mol] | HPLC method | HPLC R$_t$ [min] | MS or LC-MS (method) |
|---|---|---|---|---|---|
| 88 | 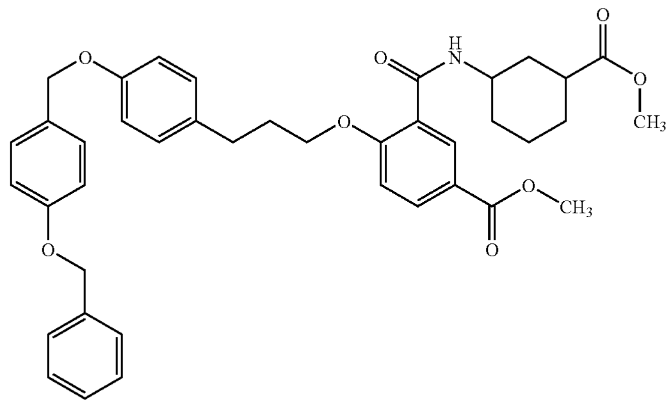 | 665 | 2 | 5.82 | 666 (ESI) |
| 89 | 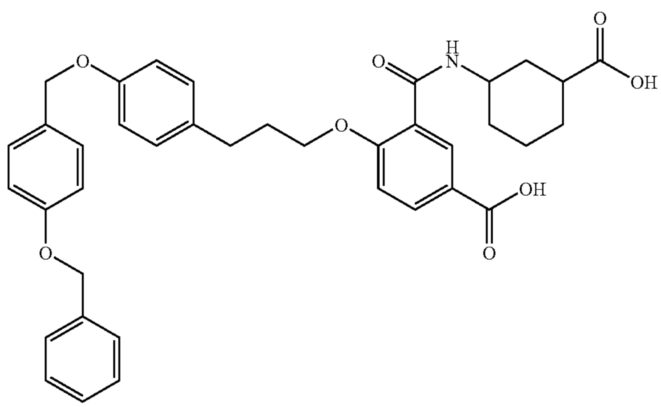 | 637 | 2 | 5.17 | 3.62 min, 637 (8) |
| 90 | 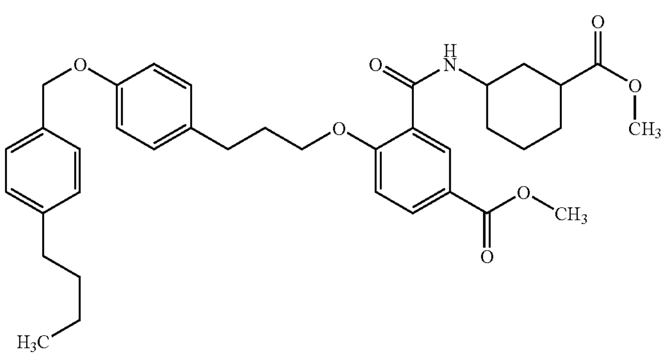 | 615 | 2 | 6.17 | 616 (ESI) |
| 91 | 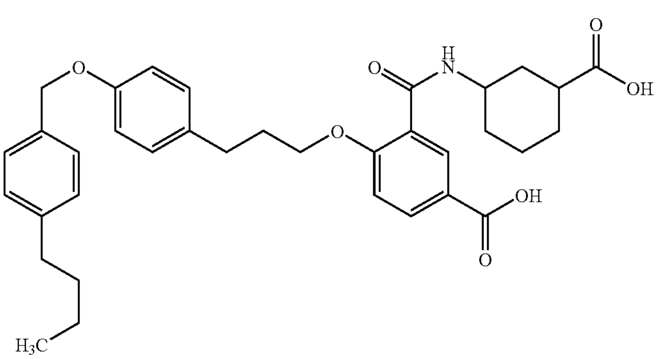 | 587 | 1 | 5.46 | 586 (ESI) |

-continued

| Ex. No. | Structure | Molecular mass [g/mol] | HPLC method | HPLC R_t [min] | MS or LC-MS (method) |
|---|---|---|---|---|---|
| 92 | 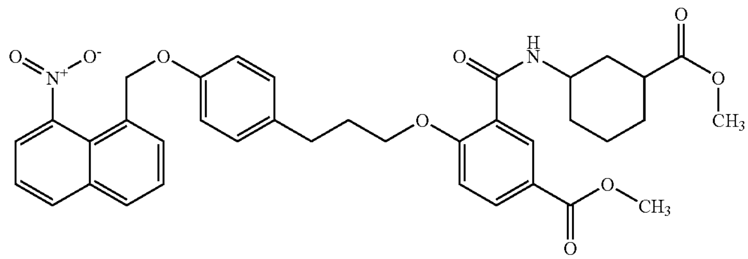 | 654 | 2 | 5.56 | 655 (ESI) |
| 93 | 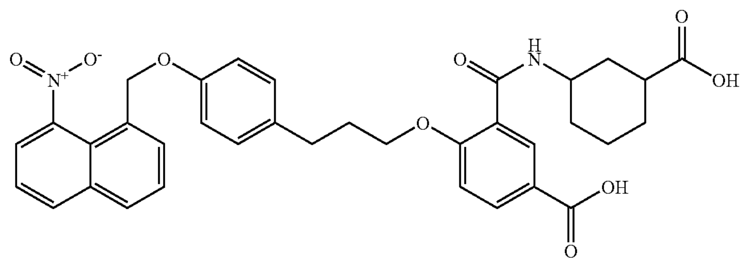 | 626 | 2 | 4.91 | 3.46 min, 626 (8) |
| 94 | 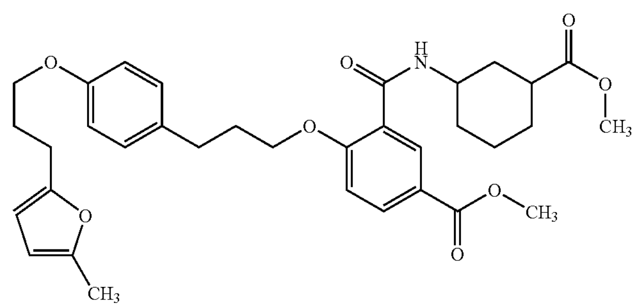 | 591 | 2 | 5.65 | 4.34 min, 592/614 (8) |
| 95 | 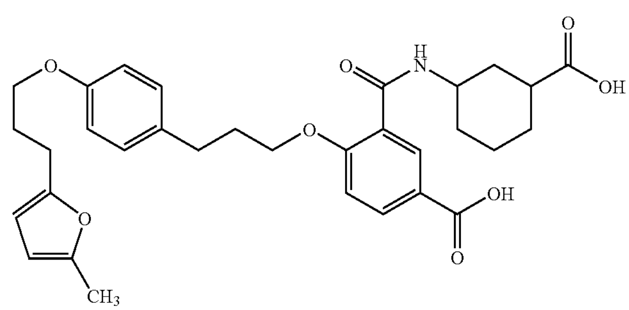 | 563 | 2 | 5.0 | 3.24 min, 563 (14) |
| 96 | 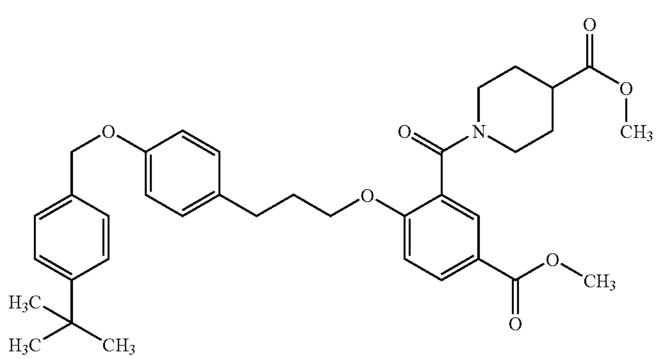 | 601 | 2 | 5.76 | 602 (DCI) |

-continued
| Ex. No. | Structure | Molecular mass [g/mol] | HPLC method | HPLC R$_t$ [min] | MS or LC-MS (method) |
|---|---|---|---|---|---|
| 97 | 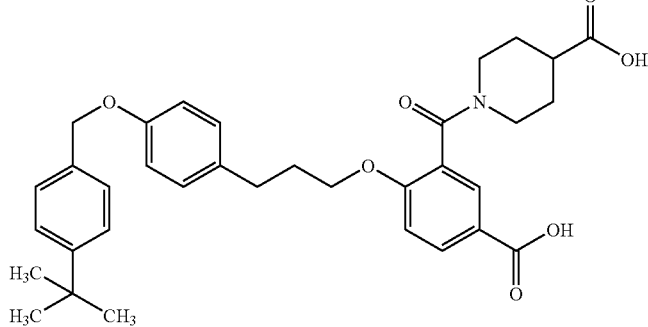 | 573 | 2 | 5.03 | 572 (ESI) |
| 98 | 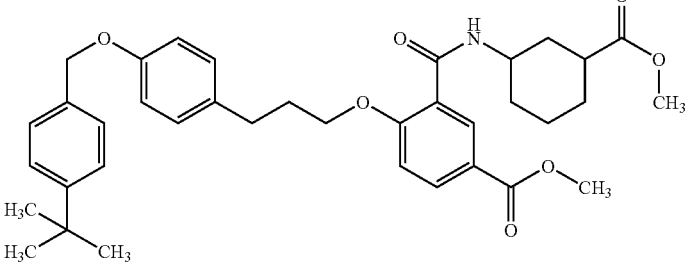 | 615 | 2 | 6.01 | 616 (ESI) |
| 99 | 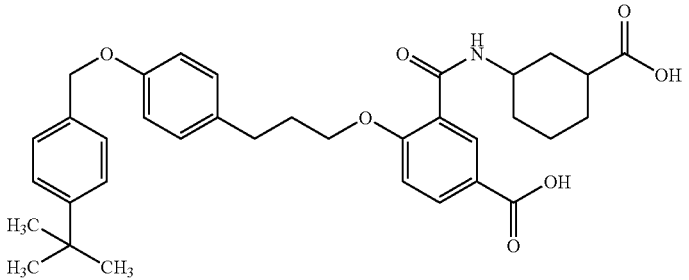 | 587 | 1 | 5.29 | 586 (ESI) |
| 100 | 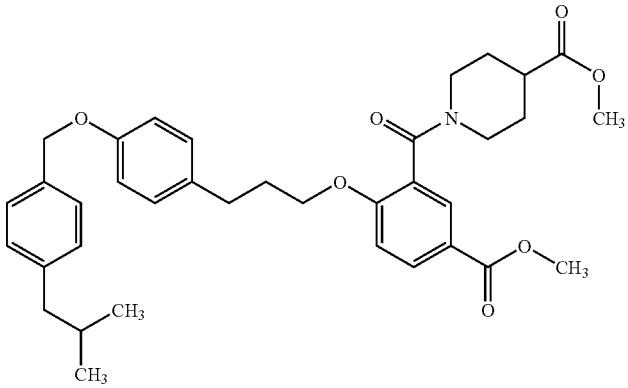 | 601 | 2 | 5.86 | 602 (DCI) |

-continued

| Ex. No. | Structure | Molecular mass [g/mol] | HPLC method | HPLC R$_t$ [min] | MS or LC-MS (method) |
|---|---|---|---|---|---|
| 101 | 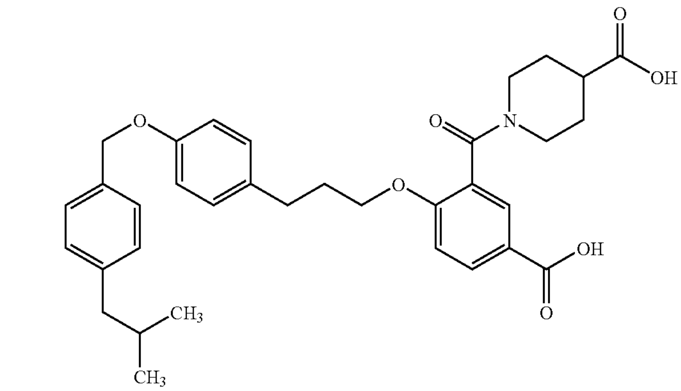 | 573 | 2 | 5.12 | 572 (ESI) |
| 102 | 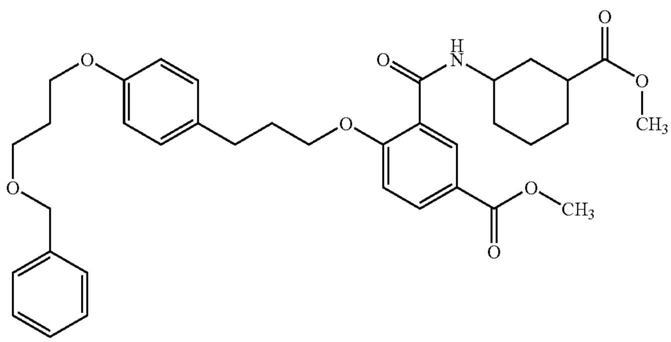 | 617 | 2 | 5.58 | 4.3 min, 617 (13) |
| 103 | 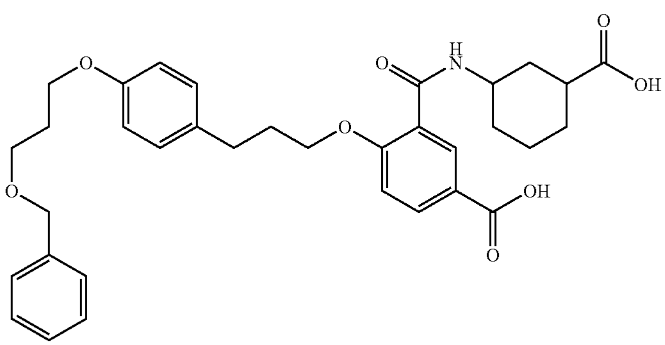 | 589 | 2 | 4.93 | 3.18 min, 589 (14) |
| 104 | 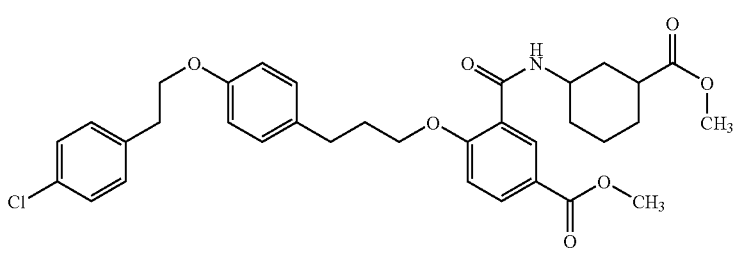 | 608 | 2 | 5.72 | 608 (ESI) |

-continued

| Ex. No. | Structure | Molecular mass [g/mol] | HPLC method | HPLC R$_t$ [min] | MS or LC-MS (method) |
|---|---|---|---|---|---|
| 105 | 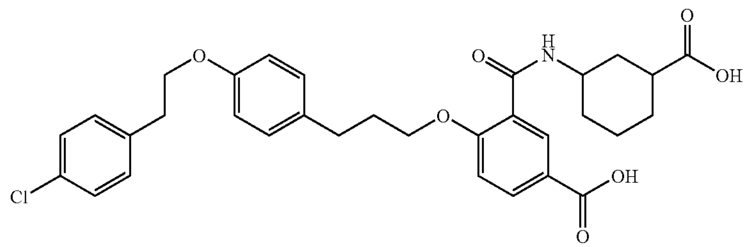 | 580 | 2 | 5.03 | 3.25 min, 579 (14) |
| 106 | 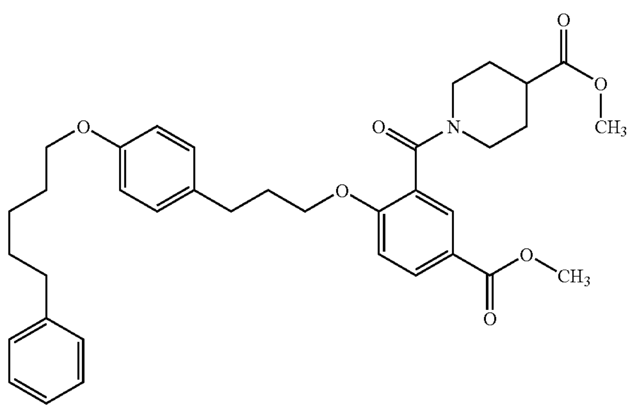 | 601 | 2 | 5.7 | 602 (ESI) |
| 107 | 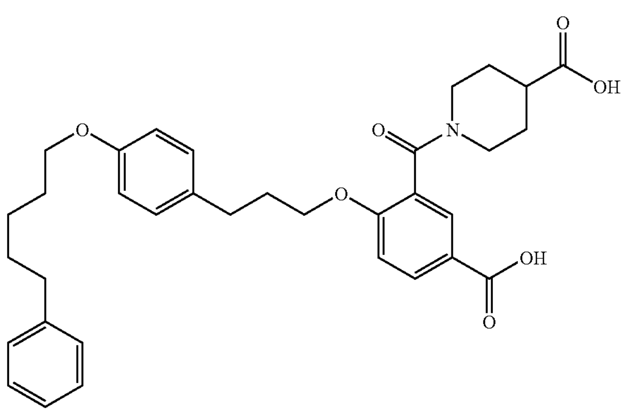 | 573 | 2 | 5.04 | 572 (ESI) |
| 108 | 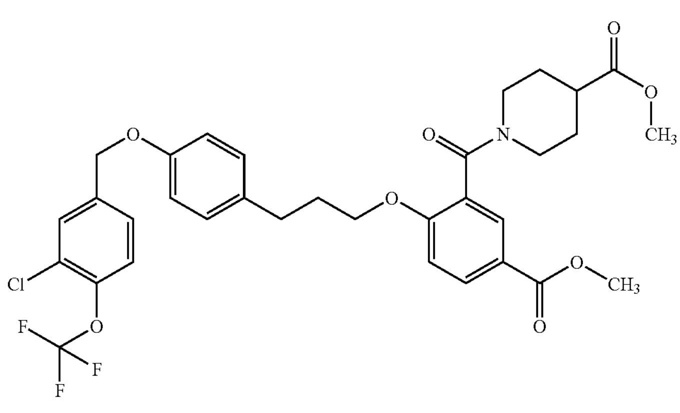 | 664 | 2 | 5.67 | 664 (ESI) |

-continued

| Ex. No. | Structure | | Molecular mass [g/mol] | HPLC method | HPLC R$_t$ [min] | MS or LC-MS (method) |
|---|---|---|---|---|---|---|
| 109 | 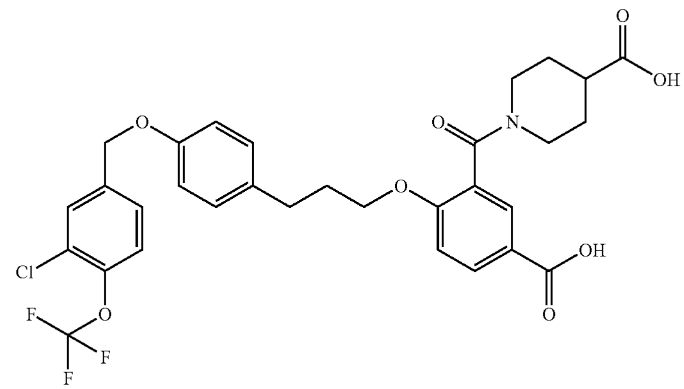 | | 636 | 2 | 5.01 | 3.49 min, 635 (8) |
| 110 | 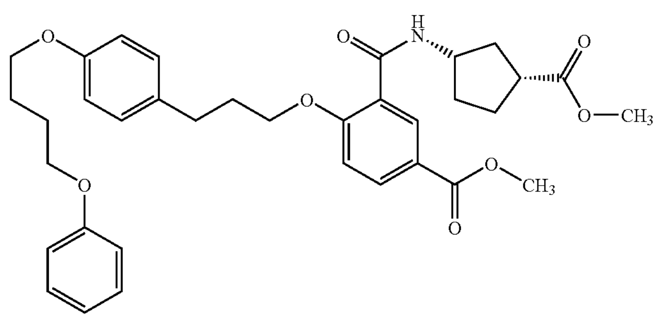 | Chiral | 617 | 2 | 5.81 | 618 (ESI) |
| 111 | 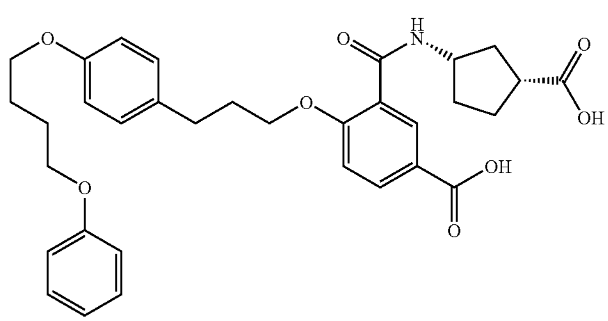 | Chiral | 575 | 12 | 7.7 | 3.44 min, 575 (8) |
| 112 | 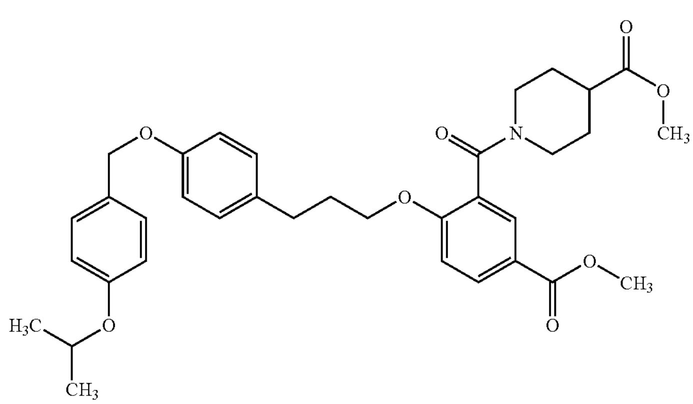 | | 603 | 2 | 5.41 | 604 (DCI) |

-continued

| Ex. No. | Structure | Molecular mass [g/mol] | HPLC method | HPLC R$_t$ [min] | MS or LC-MS (method) |
|---|---|---|---|---|---|
| 113 | 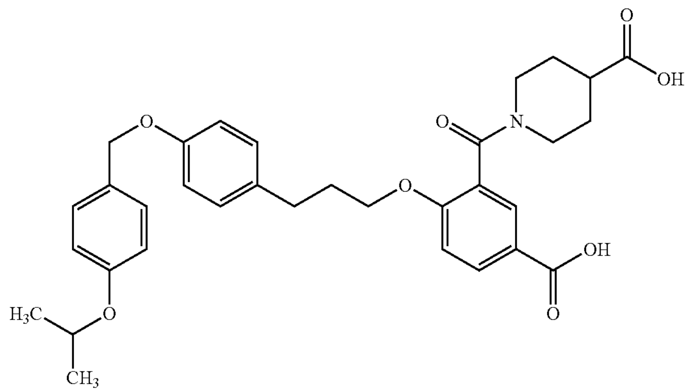 | 575 | 2 | 4.7 | 574 (ESI) |
| 114 | 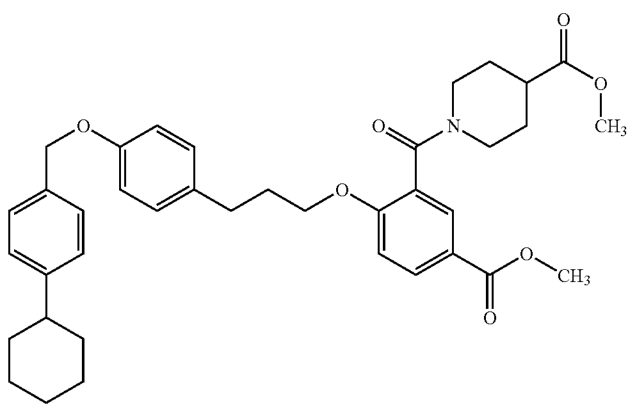 | 627 | 2 | 6.15 | 628 (DCI) |
| 115 | 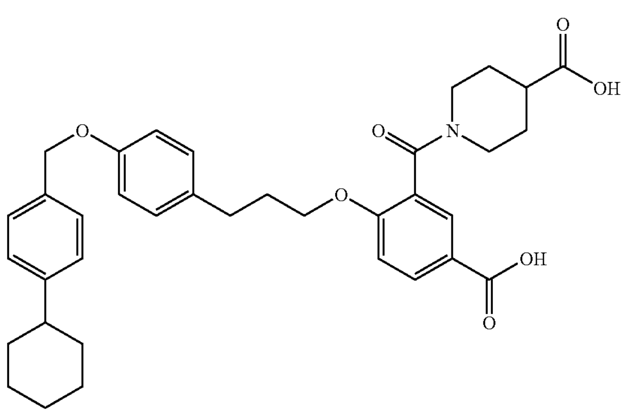 | 599 | 2 | 5.35 | 598 (ESI) |

-continued

| Ex. No. | Structure | Molecular mass [g/mol] | HPLC method | HPLC R$_t$ [min] | MS or LC-MS (method) |
|---|---|---|---|---|---|
| 116 | 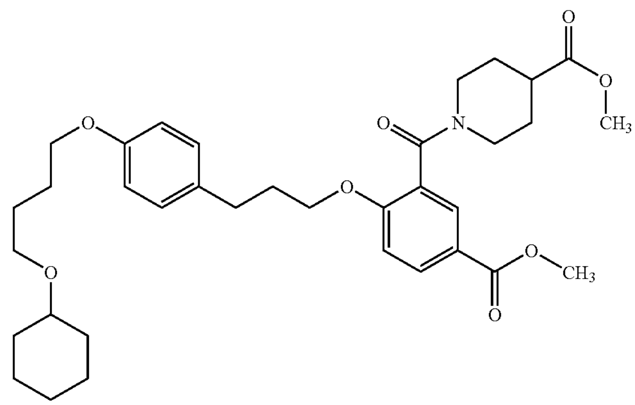 | 609 | 2 | 5.73 | 610 (DCI) |
| 117 | 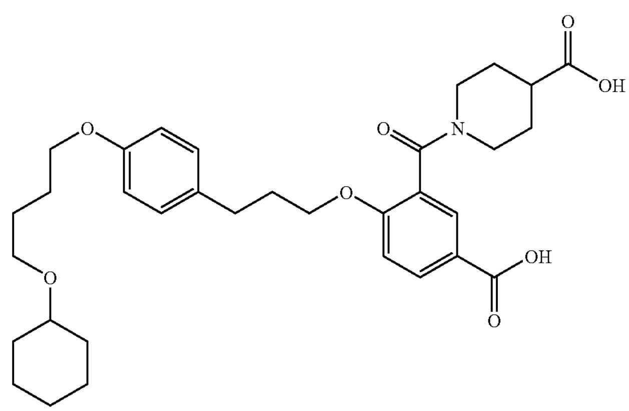 | 581 | 2 | 4.9 | 580 (ESI) |
| 118 | 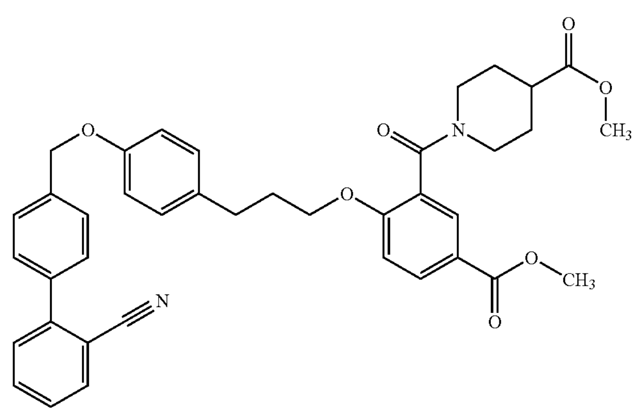 | 646 | 2 | 5.36 | 647 (DCI) |

-continued

| Ex. No. | Structure | Molecular mass [g/mol] | HPLC method | HPLC R$_t$ [min] | MS or LC-MS (method) |
|---|---|---|---|---|---|
| 119 | 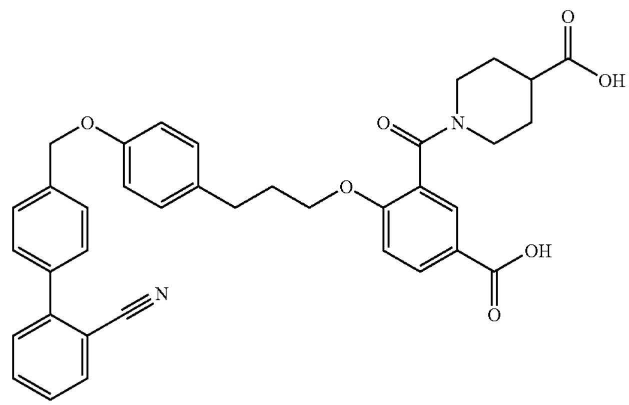 | 618 | 2 | 5.15 | 3.29 min, 619 (8) |
| 120 | 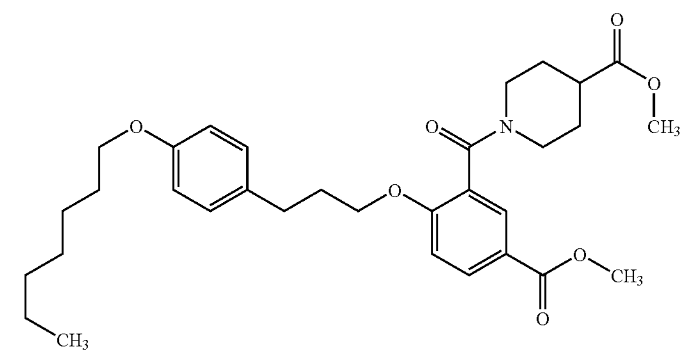 | 553 | 2 | 5.85 | 554 (ESI) |
| 121 | 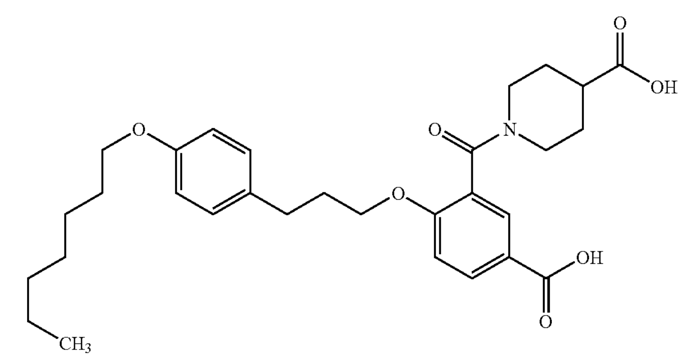 | 525 | 2 | 5.11 | 524 (ESI) |
| 122 | 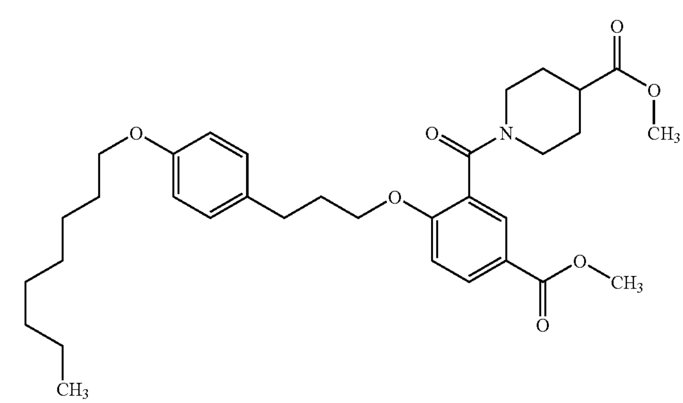 | 567 | 2 | 6.08 | 568 (ESI) |

-continued
| Ex. No. | Structure | Molecular mass [g/mol] | HPLC method | HPLC R$_t$ [min] | MS or LC-MS (method) |
|---|---|---|---|---|---|
| 123 | 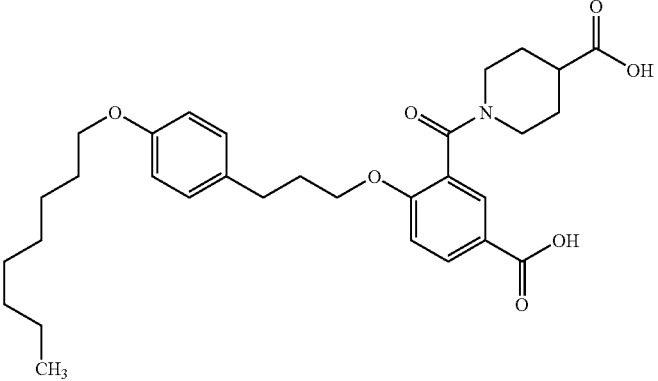 | 539 | 2 | 5.31 | 538 (ESI) |
| 124 | 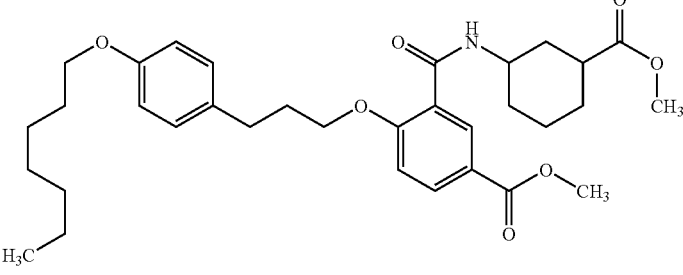 | 567 | 2 | 6.18 | 568 (ESI) |
| 125 | 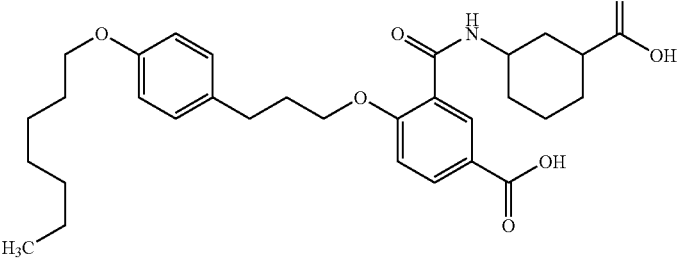 | 539 | 2 | 5.45 | 538 (ESI) |
| 126 | 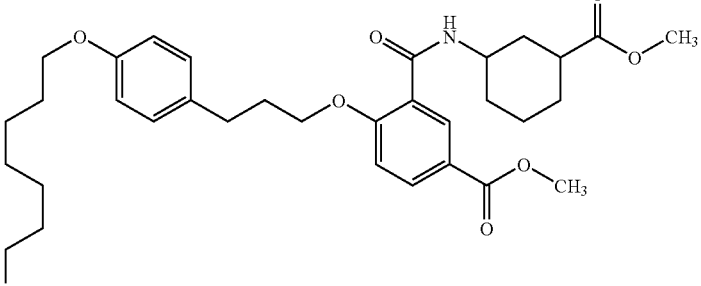 | 581 | 2 | 6.50 | 582 (ESI) |

-continued

| Ex. No. | Structure | Molecular mass [g/mol] | HPLC method | HPLC R$_t$ [min] | MS or LC-MS (method) |
|---|---|---|---|---|---|
| 127 | 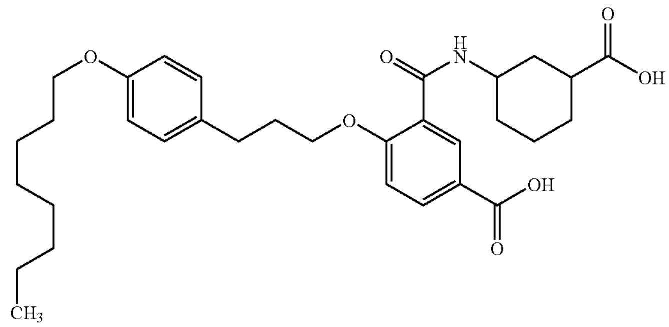 | 553 | 2 | 5.66 | 552 (ESI) |
| 128 | 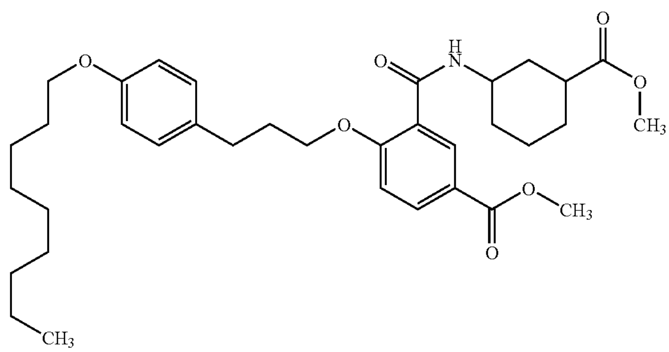 | 595 | 2 | 7.08 | 5.1 min, 595 (13) |
| 129 | 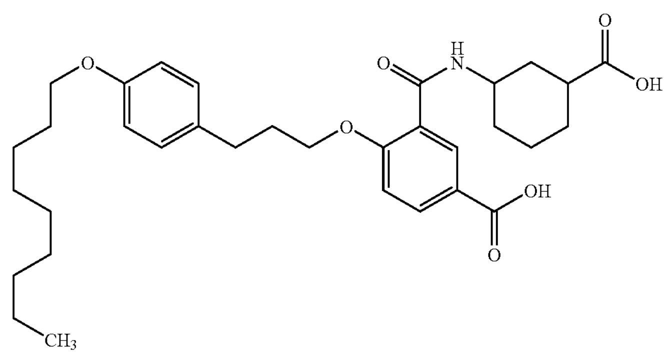 | 567 | 2 | 5.86 | 3.64 min, 567 (14) |
| 130 | 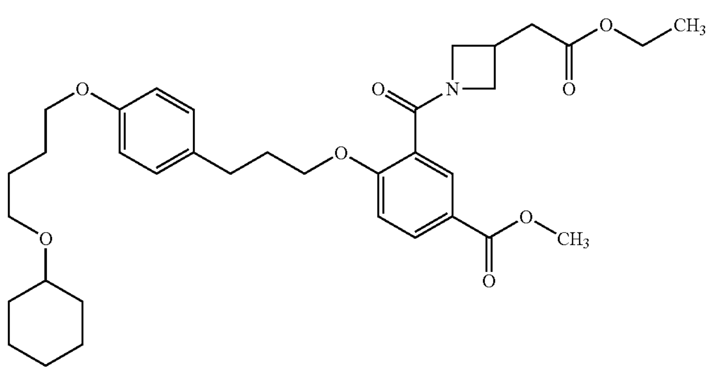 | 609 | — | — | 3.08 min, 610 (6) |

-continued

| Ex. No. | Structure | Molecular mass [g/mol] | HPLC method | HPLC R$_t$ [min] | MS or LC-MS (method) |
|---|---|---|---|---|---|
| 131 | 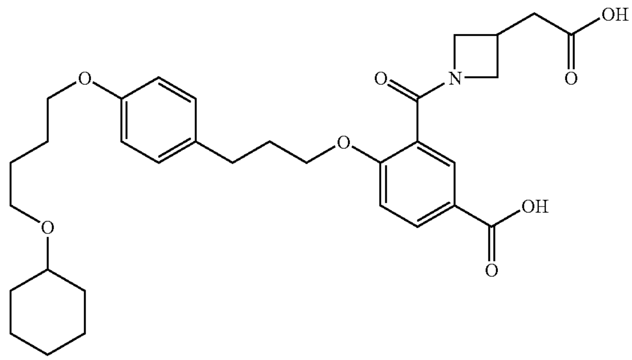 | 567 | — | — | 2.60 min, 568 (7) |
| 132 | 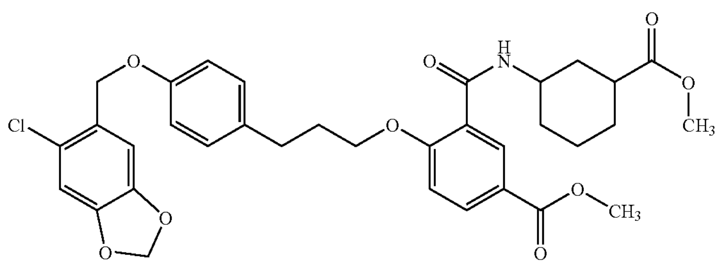 | 538 | 2 | 5.63 | 638 (ESI) |
| 133 | 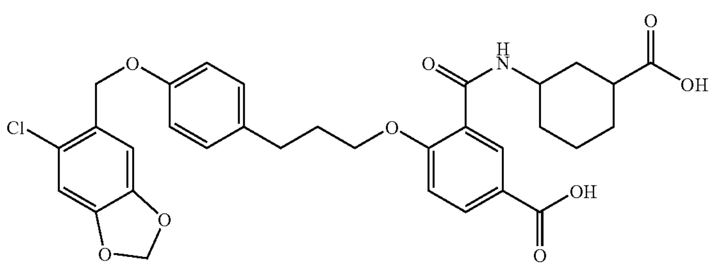 | 610 | 2 | 4.94 | 3.46 min, 609 (8) |
| 134 | 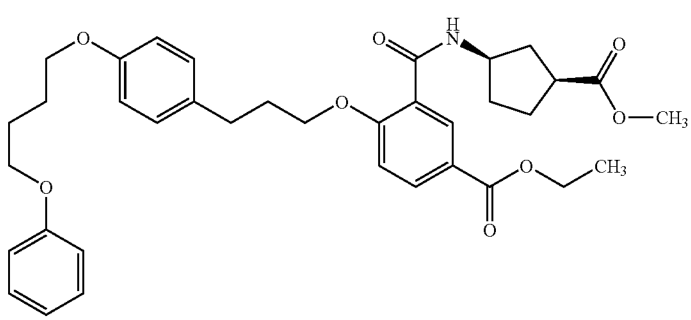 | 617 | 2 | 5.8 | 618 (ESI) |
| 135 | 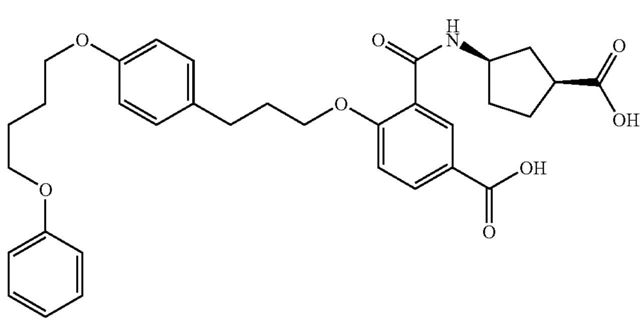 | 575 | — | — | 3.45 min, 575 (8) |

-continued
| Ex. No. | Structure | Molecular mass [g/mol] | HPLC method | HPLC R_t [min] | MS or LC-MS (method) |
|---|---|---|---|---|---|
| 136 | 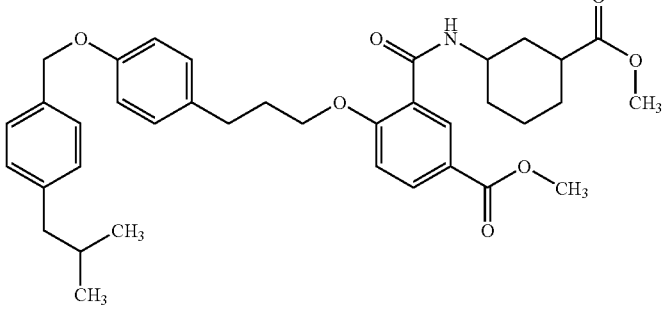 | 615 | 2 | 6.13 | 616 (ESI) |
| 137 | 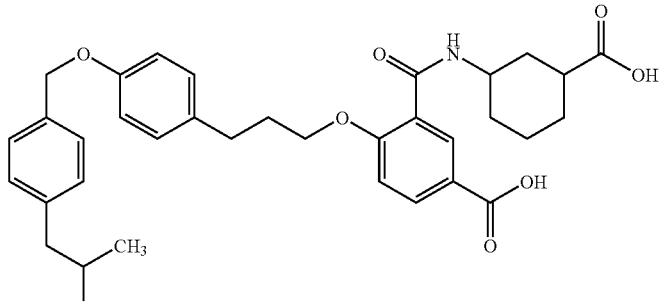 | 587 | 1 | 5.43 | 586 (ESI) |
| 138 | 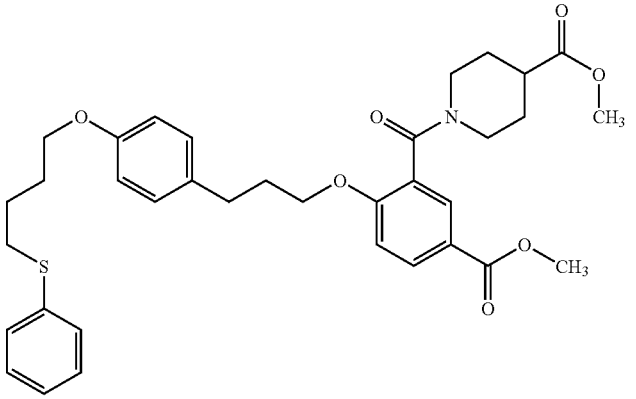 | 619 | 2 | 5.59 | 620 (DCI) |
| 139 | 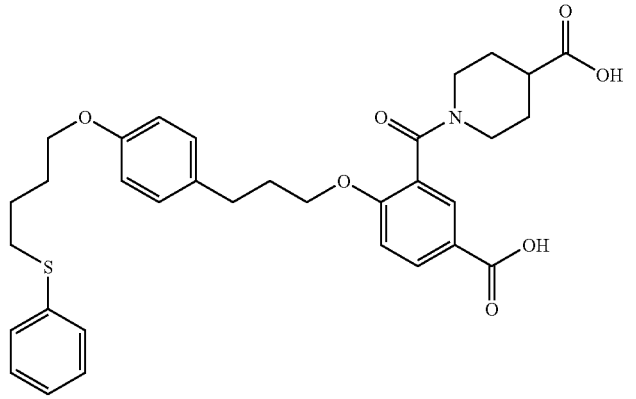 | 591 | 2 | 4.89 | 590 (ESI) |

-continued

| Ex. No. | Structure | Molecular mass [g/mol] | HPLC method | HPLC R$_t$ [min] | MS or LC-MS (method) |
|---|---|---|---|---|---|
| 140 | 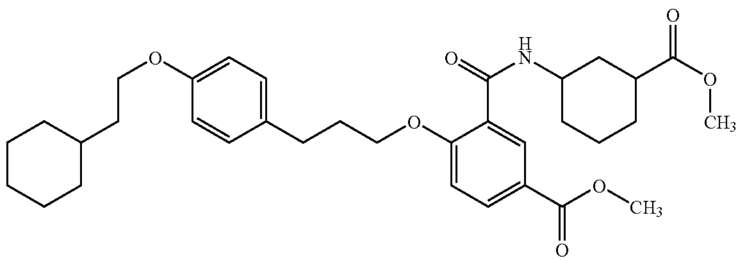 | 579 | 2 | 6.30 | 580 (ESI) |
| 141 | 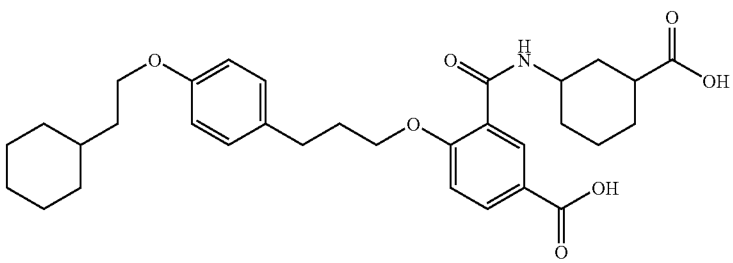 | 551 | 1 | 5.35 | 550 (ESI) |
| 142 | 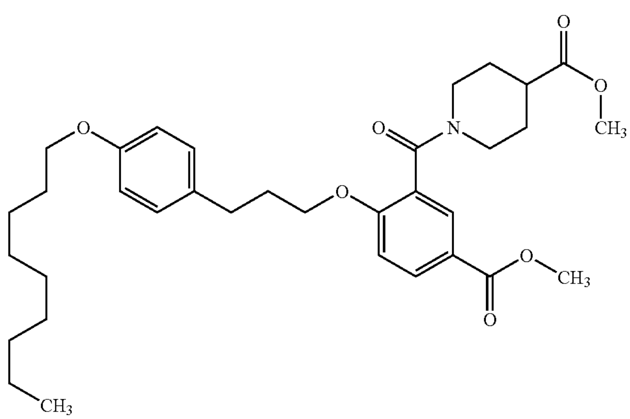 | 581 | 2 | 6.49 | 582 (DCI) |
| 143 | 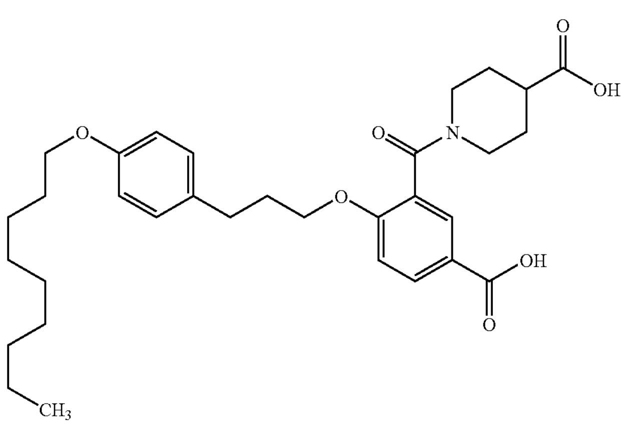 | 553 | 2 | 5.51 | 552 (ESI) |

-continued

| Ex. No. | Structure | Molecular mass [g/mol] | HPLC method | HPLC R$_t$ [min] | MS or LC-MS (method) |
|---|---|---|---|---|---|
| 144 | 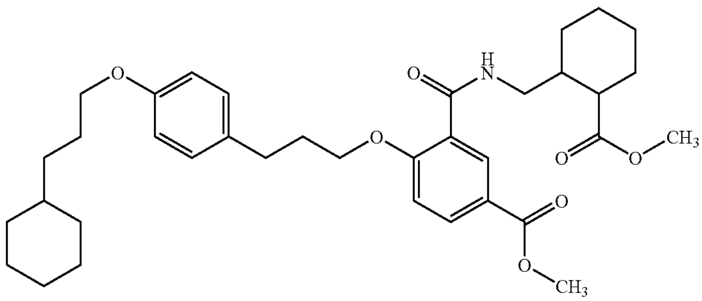 | 607 | — | — | 608 (ESI) |
| 145 | 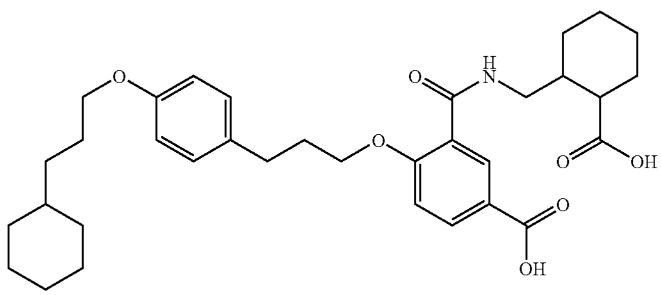 | 579 | — | — | 3.24 min, 579 (7) |
| 146 | 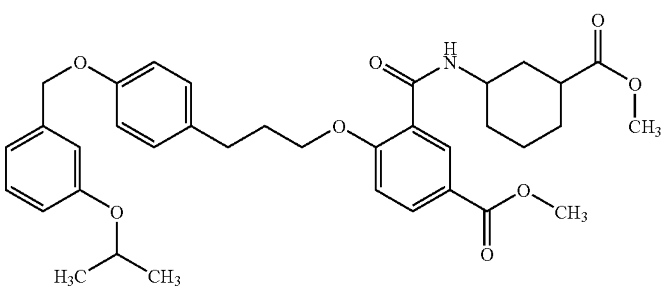 | 617 | 2 | 5.60 | 618 (ESI) |
| 147 | 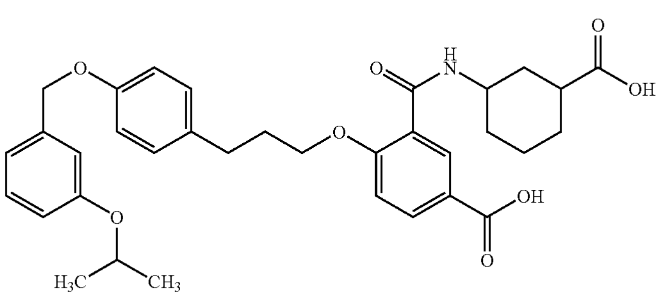 | 589 | 2 | 4.9 | 2.52 min, 589 (9) |

-continued

| Ex. No. | Structure | Molecular mass [g/mol] | HPLC method | HPLC R$_t$ [min] | MS or LC-MS (method) |
|---|---|---|---|---|---|
| 148 | 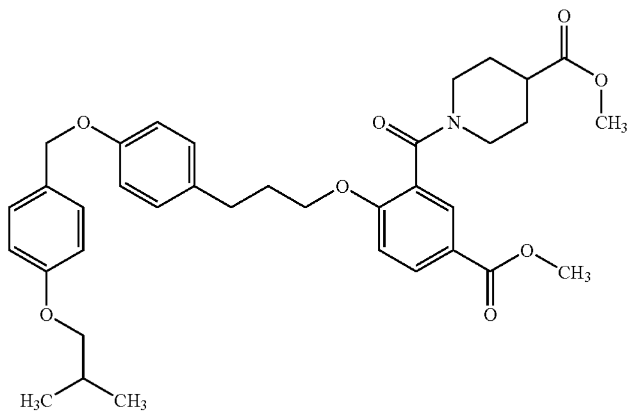 | 617 | 2 | 5.69 | 618 (DCI) |
| 149 | 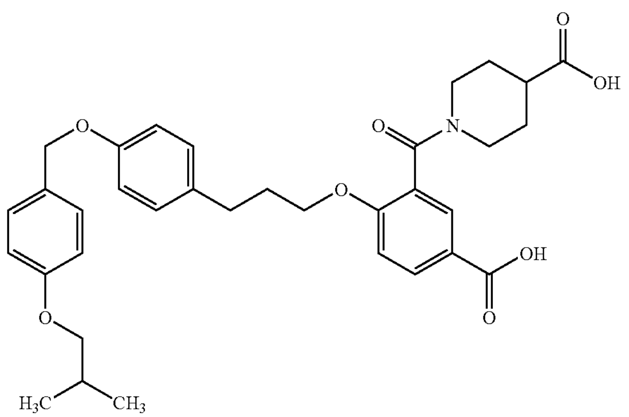 | 589 | 2 | 4.99 | 588 (ESI) |
| 150 | 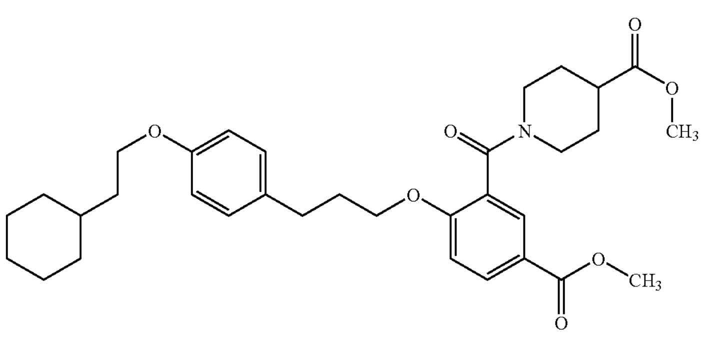 | 565 | 2 | 5.83 | 566 (DCI) |
| 151 | 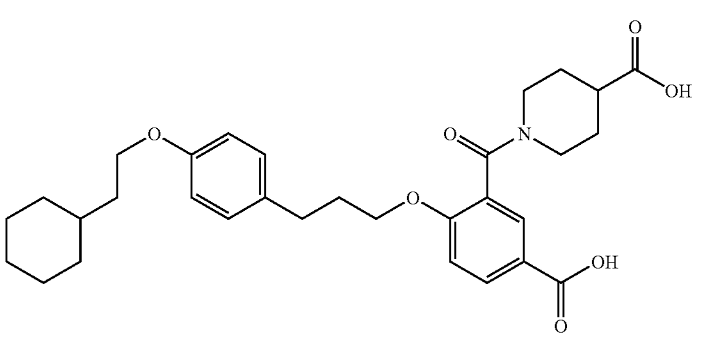 | 537 | 2 | 5.06 | 538 (ESI) |

-continued

| Ex. No. | Structure | Molecular mass [g/mol] | HPLC method | HPLC R$_t$ [min] | MS or LC-MS (method) |
|---|---|---|---|---|---|
| 152 | 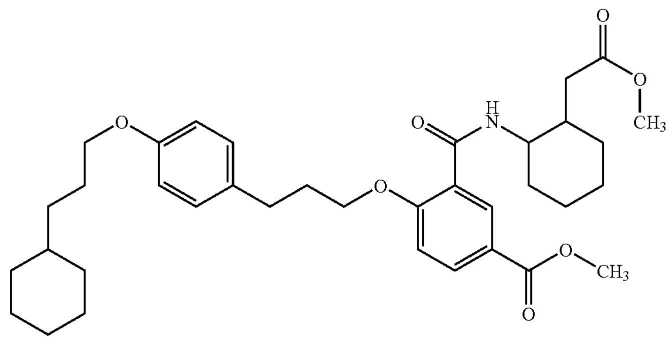 | 607 | 2 | 6.60 | 608 (ESI) |
| 153 | 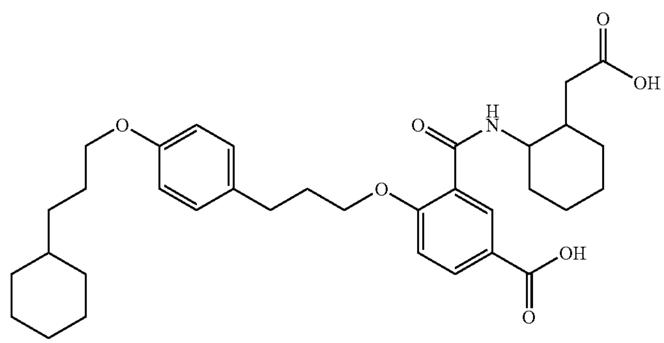 | 579 | 2 | 5.69 | 578 (ESI) |
| 154 | 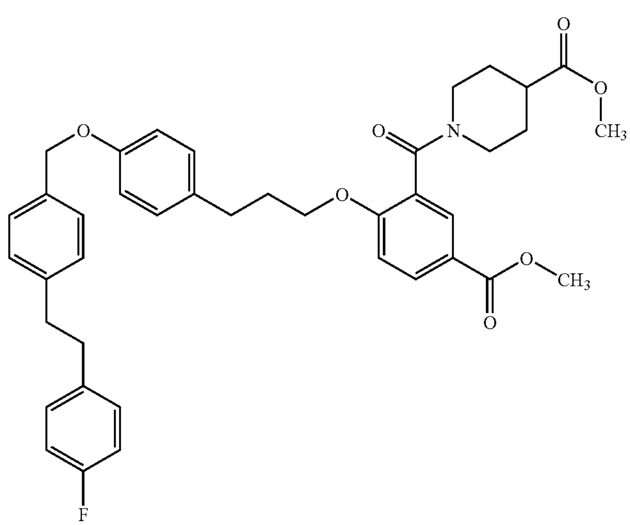 | 667 | 2 | 4.32 | 456 (ESI) |

-continued

| Ex. No. | Structure | Molecular mass [g/mol] | HPLC method | HPLC R$_t$ [min] | MS or LC-MS (method) |
|---|---|---|---|---|---|
| 155 | 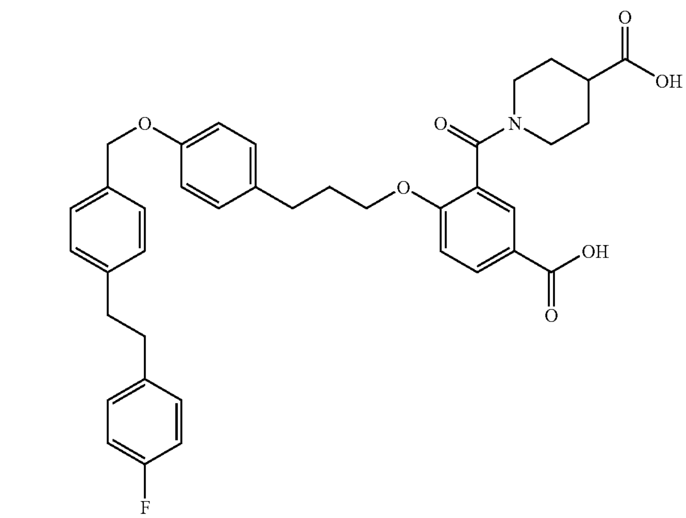 | 639 | 2 | 4.74 | 3.6 min, 639 (8) |
| 156 | 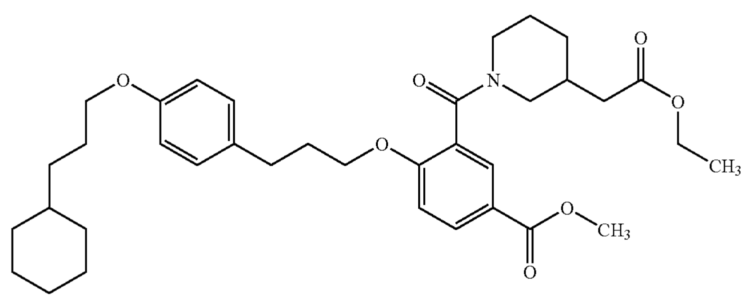 | 607 | 1 | 6.47 | 608 (ESI) |
| 157 | 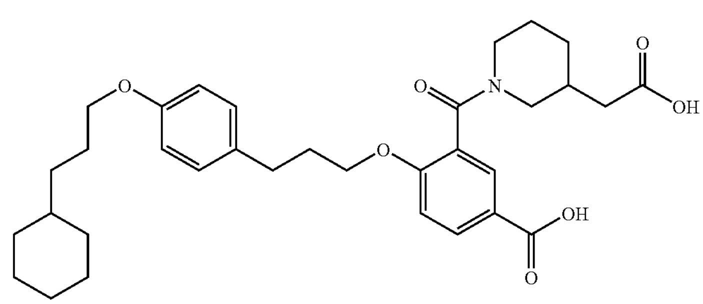 | 565 | 2 | 5.45 | 564 (ESI) |
| 158 | 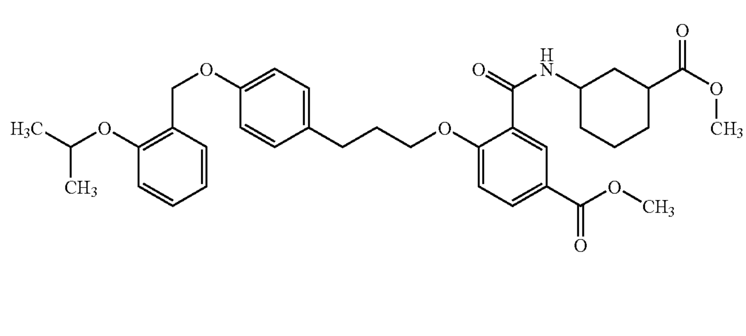 | 617 | 2 | 5.69 | 618 (ESI) |

-continued

| Ex. No. | Structure | Molecular mass [g/mol] | HPLC method | HPLC R$_t$ [min] | MS or LC-MS (method) |
|---|---|---|---|---|---|
| 159 | 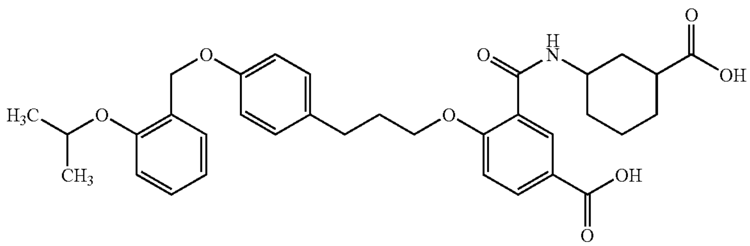 | 589 | 2 | 5.06 | 588 (ESI) |
| 160 | 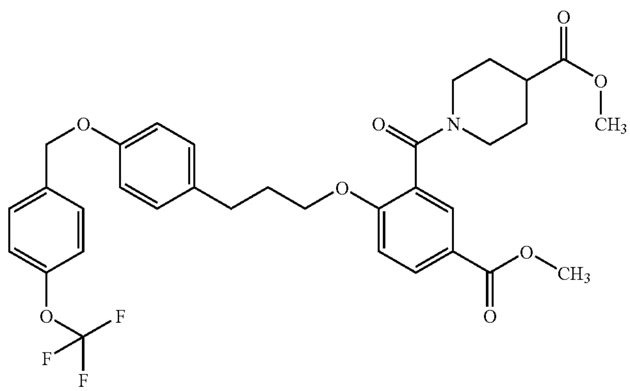 | 629 | 2 | 5.49 | 630 (ESI) |
| 161 | 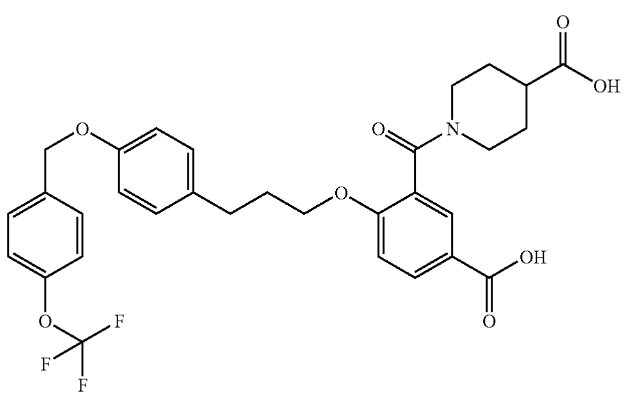 | 601 | 2 | 4.80 | 602 (ESI) |
| 162 | 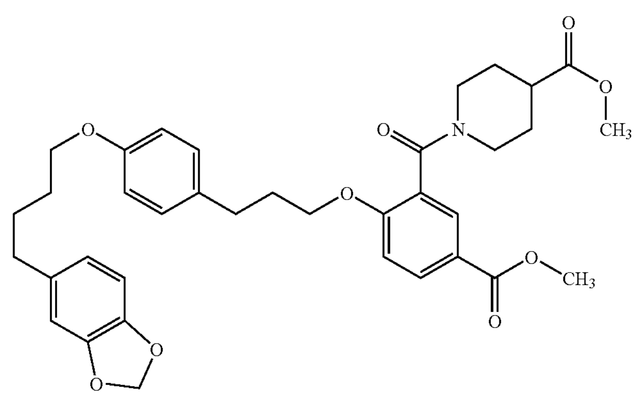 | 631 | — | — | — |

-continued

| Ex. No. | Structure | Molecular mass [g/mol] | HPLC method | HPLC R$_t$ [min] | MS or LC-MS (method) |
|---|---|---|---|---|---|
| 163 | 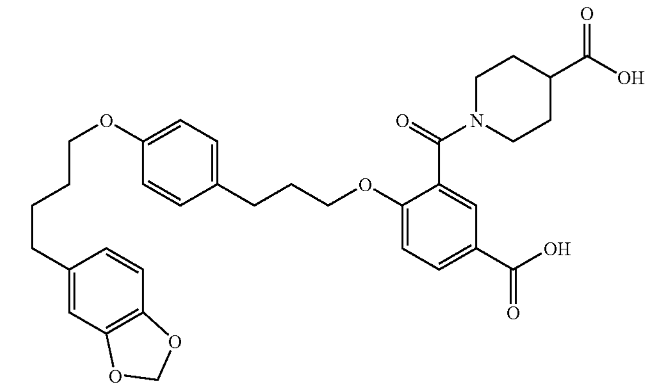 | 603 | — | — | — |
| 164 | 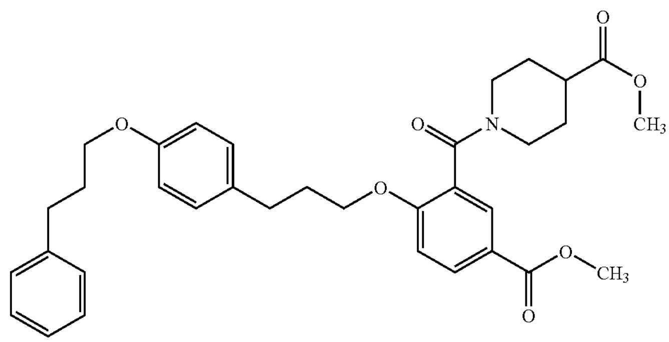 | 573 | 2 | 5.45 | 574 (ESI) |
| 165 | 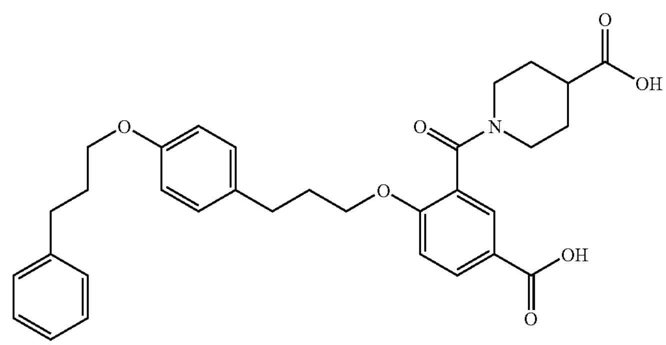 | 545 | 2 | 4.77 | 3.27 min, 545 (8) |
| 166 | 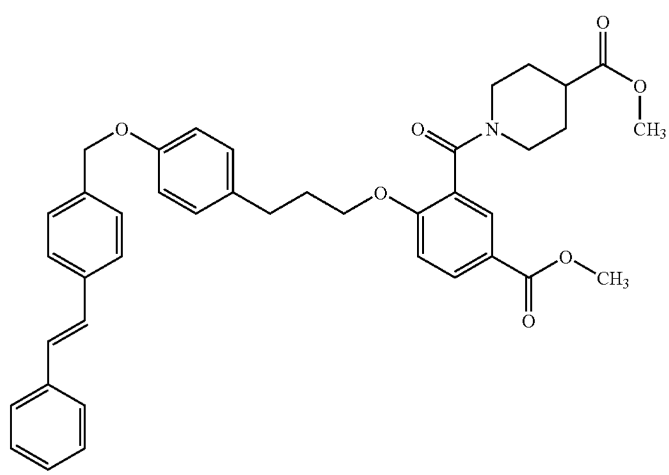 | 647 | 2 | 5.82 | 648 (DCI) |

| Ex. No. | Structure | Molecular mass [g/mol] | HPLC method | HPLC R_t [min] | MS or LC-MS (method) |
|---|---|---|---|---|---|
| 167 | 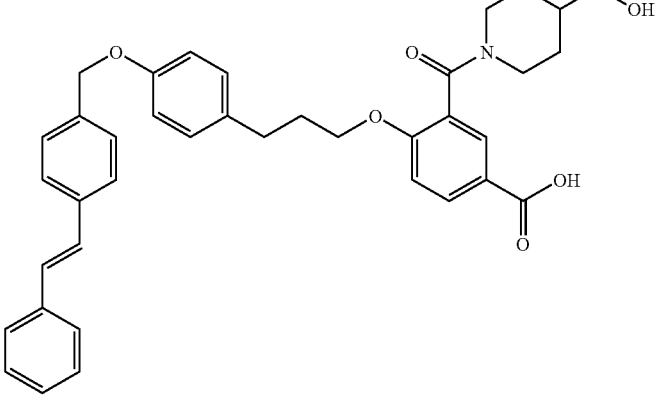 | 619 | 2 | 5.1 | 618 (ESI) |
| 168 | 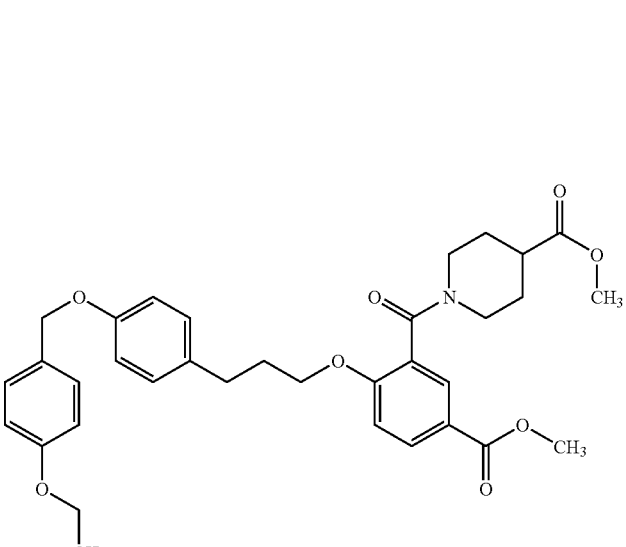 | 589 | 2 | 5.3 | 590 (DCI) |
| 169 | 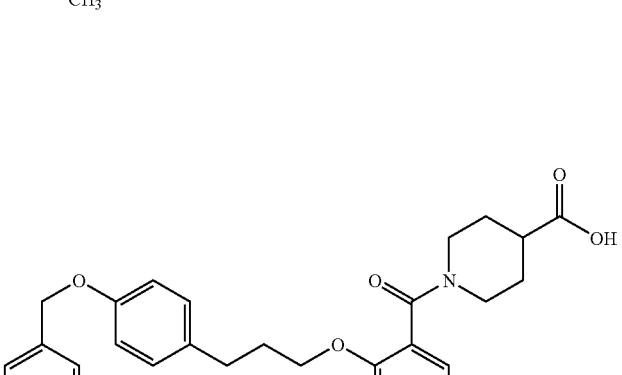 | 561 | 2 | 4.62 | 560 (ESI) |

-continued

| Ex. No. | Structure | Molecular mass [g/mol] | HPLC method | HPLC R$_t$ [min] | MS or LC-MS (method) |
|---|---|---|---|---|---|
| 170 | 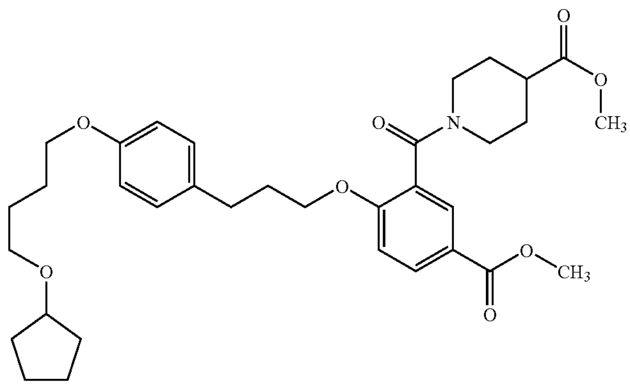 | 595 | 2 | 5.57 | 596 (DCI) |
| 171 | 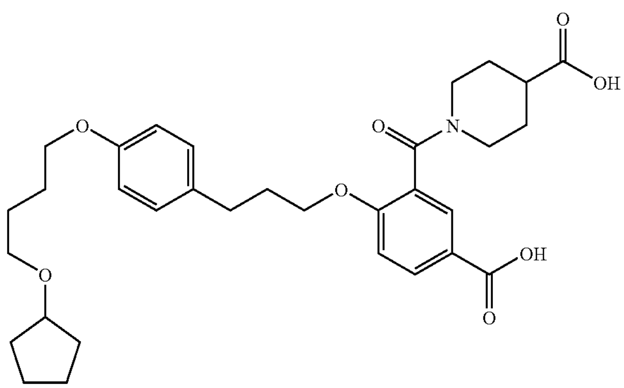 | 567 | 2 | 4.8 | 566 (ESI) |
| 172 | 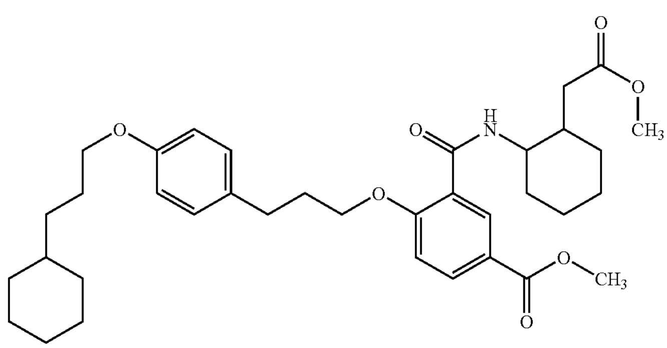 | 607 | 2 | 6.63 | 608 (ESI) |
| 173 | 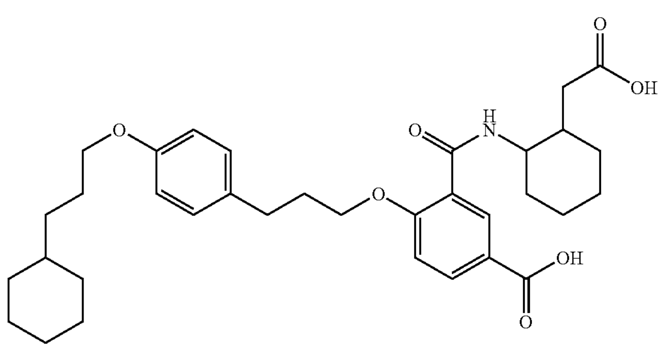 | 579 | 2 | 5.74 | 578 (ESI) |

-continued

| Ex. No. | Structure | Molecular mass [g/mol] | HPLC method | HPLC R$_t$ [min] | MS or LC-MS (method) |
|---|---|---|---|---|---|
| 174 | 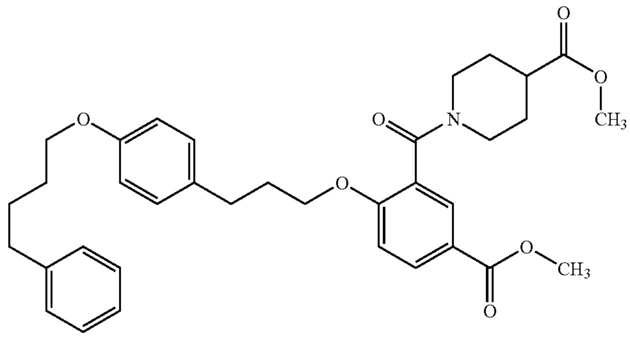 | 587 | 2 | 5.56 | 588 (ESI) |
| 175 | 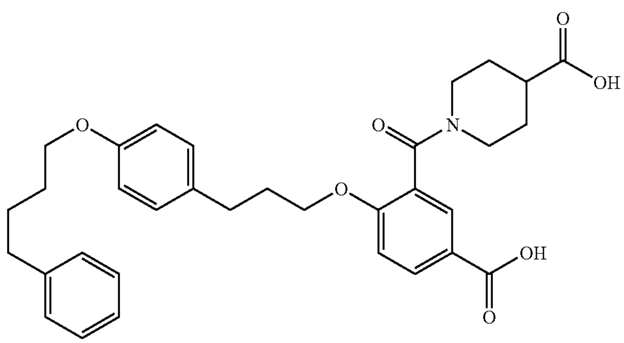 | 559 | 2 | 4.89 | 560 (ESI) |
| 176 | 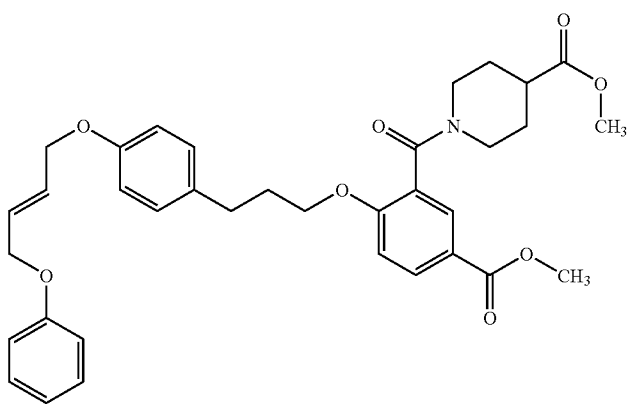 | 601 | 2 | 5.27 | 602 (ESI) |
| 177 | 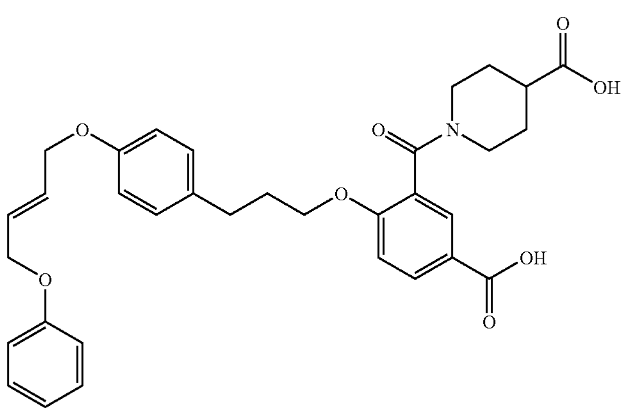 | 573 | 2 | 4.67 | 574 (ESI) |

-continued

| Ex. No. | Structure | Molecular mass [g/mol] | HPLC method | HPLC R_t [min] | MS or LC-MS (method) |
|---|---|---|---|---|---|
| 178 | 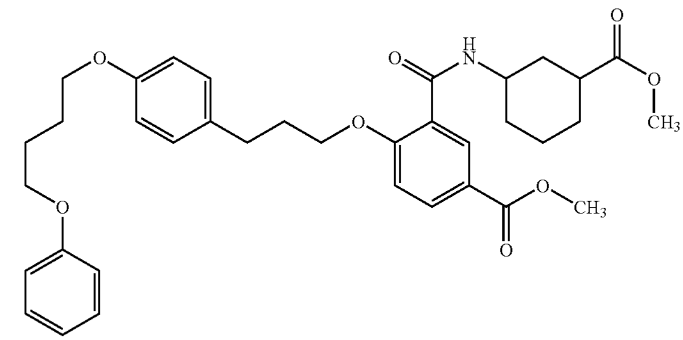 | 617 | 1 | 5.69 | 618 (ESI) |
| 179 | prepared from (−)-B-enantiomer (Example IX, method 2) | 589 | 1 | 4.99 | 3.96 min, 589 (8) |
| 180 | 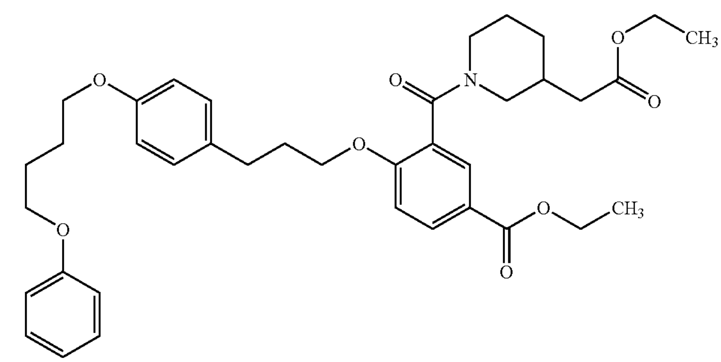 | 645 | 4 | 5.78 | 646 (ESI) |
| 181 | 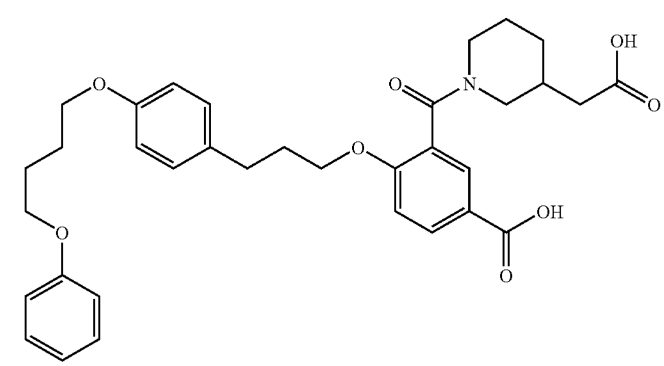 | 589 | 2 | 4.89 | 588 (ESI) |

-continued

| Ex. No. | Structure | Molecular mass [g/mol] | HPLC method | HPLC R_t [min] | MS or LC-MS (method) |
|---|---|---|---|---|---|
| 182 | 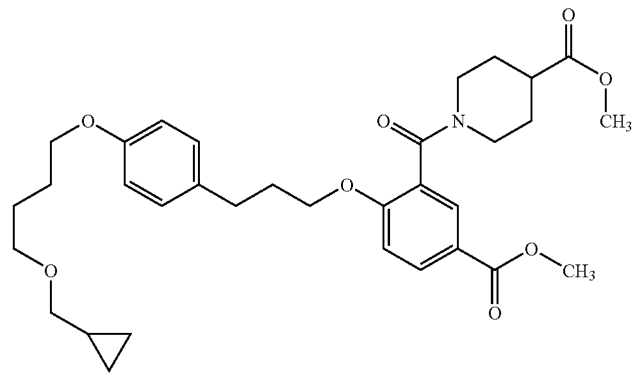 | 581 | 2 | 5.26 | 582 (DCI) |
| 183 | 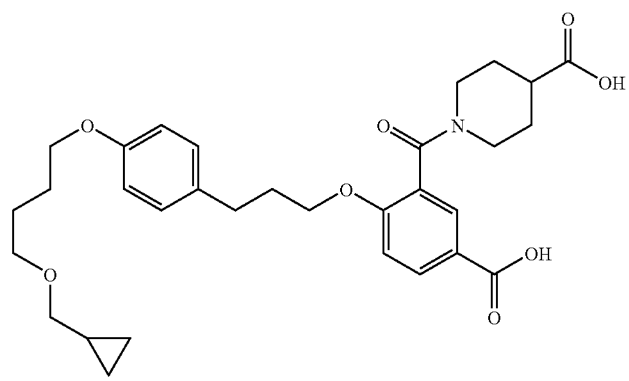 | 553 | 1 | 4.52 | 554 (ESI) |
| 184 | 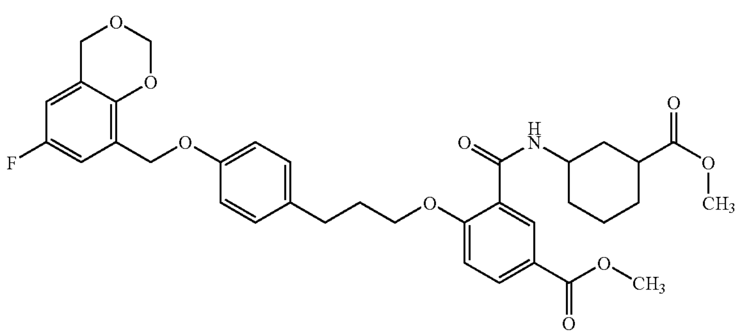 | 635 | 2 | 5.37 | 636 (ESI) |
| 185 | 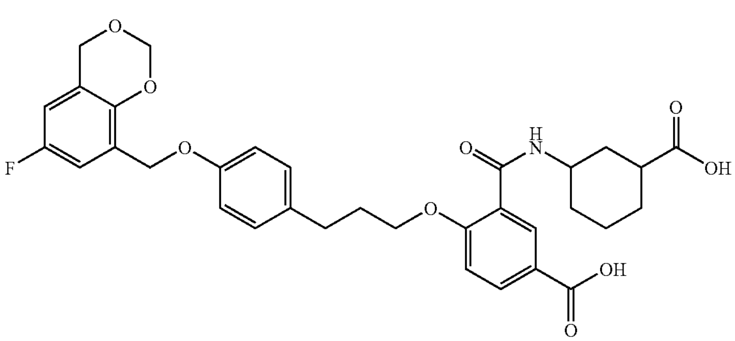 | 607 | 2 | 4.66 | 3.22 min, 607 (8) |

-continued

| Ex. No. | Structure | Molecular mass [g/mol] | HPLC method | HPLC R$_t$ [min] | MS or LC-MS (method) |
|---|---|---|---|---|---|
| 186 | 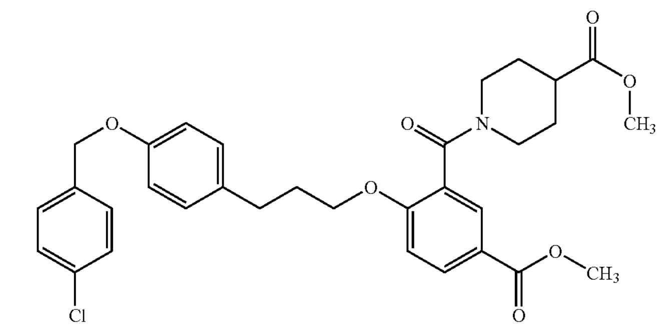 | 580 | 2 | 5.39 | 580 (DCI) |
| 187 | 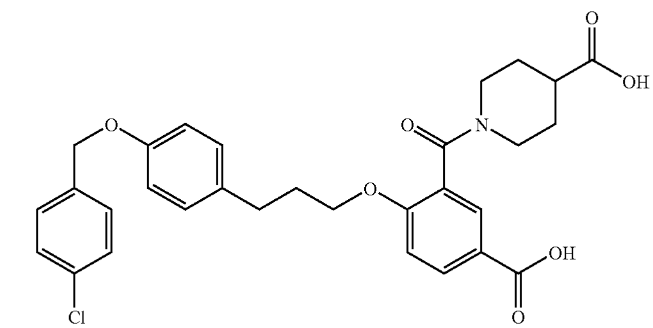 | 552 | 2 | 4.71 | 550 (ESI) |
| 188 | 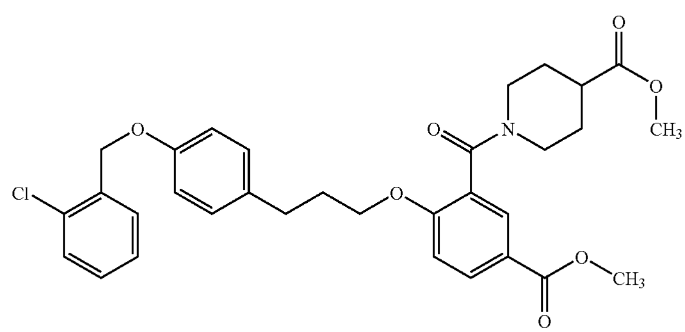 | 580 | 2 | 5.41 | 580 (ESI) |
| 189 | 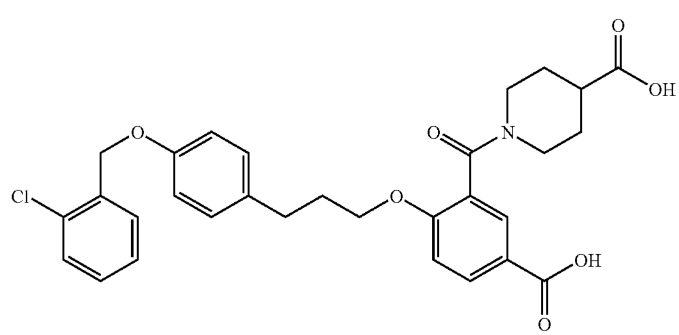 | 552 | 2 | 4.6 | 550 (ESI) |

-continued

| Ex. No. | Structure | Molecular mass [g/mol] | HPLC method | HPLC R$_t$ [min] | MS or LC-MS (method) |
|---|---|---|---|---|---|
| 190 | 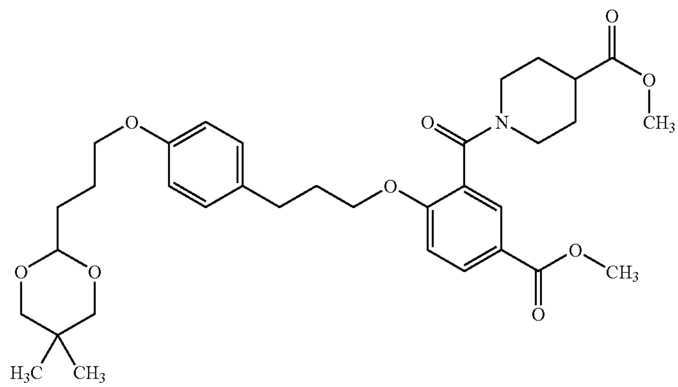 | 611 | 2 | 5.27 | 612 (DCI) |
| 191 | 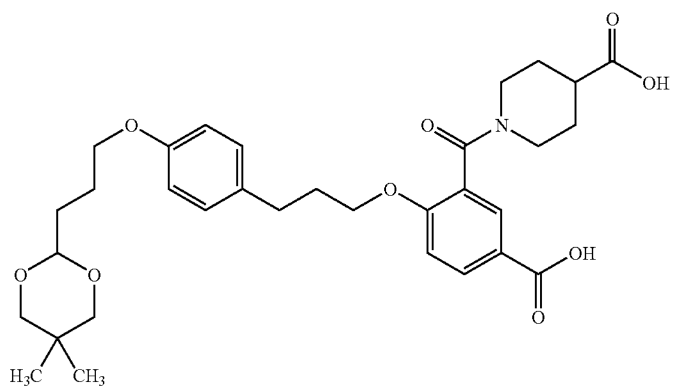 | 583 | 2 | 4.56 | 582 (ESI) |
| 192 | cis/trans mixture | 725 | 4 | 6.13 | 726 (ESI) |
| 193 | cis/trans mixture | 607 | 2 | 5.02 | 608 (EI+) |

-continued

| Ex. No. | Structure | Molecular mass [g/mol] | HPLC method | HPLC R_t [min] | MS or LC-MS (method) |
|---|---|---|---|---|---|
| 194 | 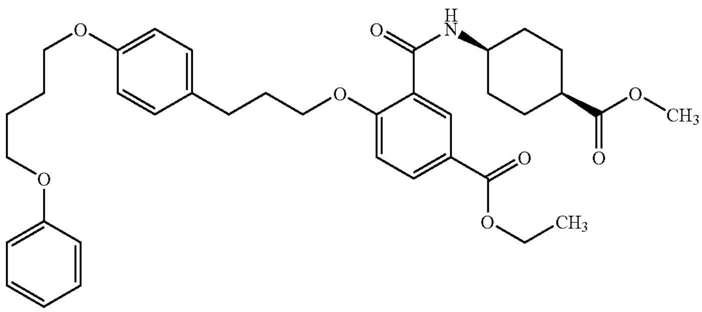 | 631 | 2 | 5.78 | 632 (ESI) |
| 195 | 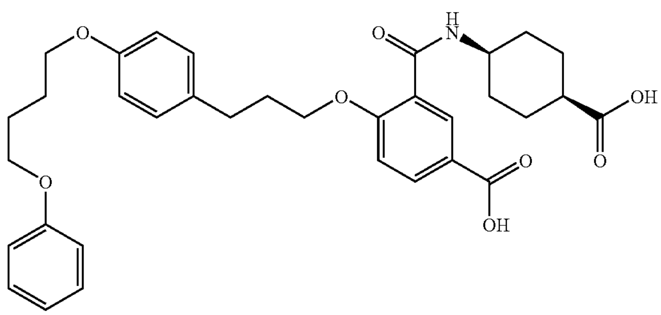 | 589 | 2 | 4.83 | 590 (ESI) |
| 196 | (+) enantiomer | 649 | 2 | 5.88 | 650 (ESI) |
| 197 | (+) enantiomer | 593 | 2 | 5.05 | 3.92 min, 594 (8, EI+) |

| Ex. No. | Structure | Molecular mass [g/mol] | HPLC method | HPLC R$_t$ [min] | MS or LC-MS (method) |
|---|---|---|---|---|---|
| 198 | 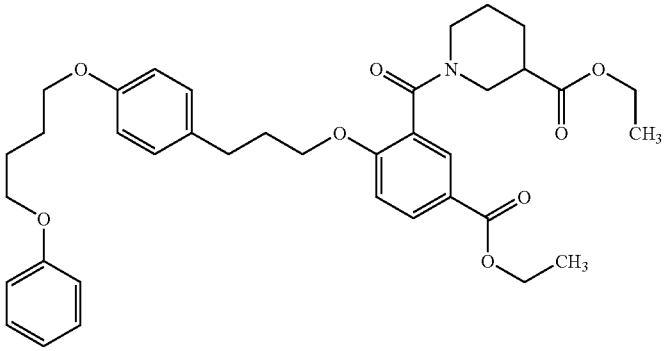 (+) enantiomer | 631 | 2 | 5.73 | 632 (ESI) |
| 199 | 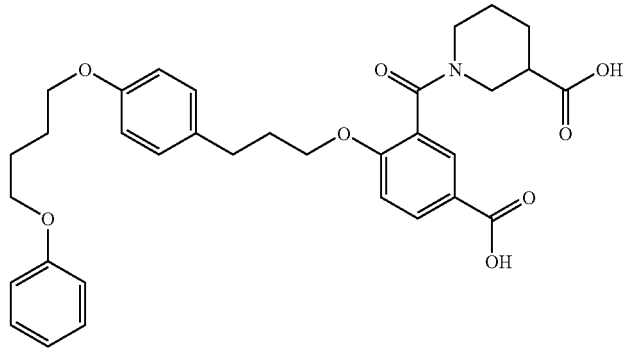 (+) enantiomer | 575 | 2 | 4.90 | 3.82 min, 576 (8, EI+) |
| 200 | 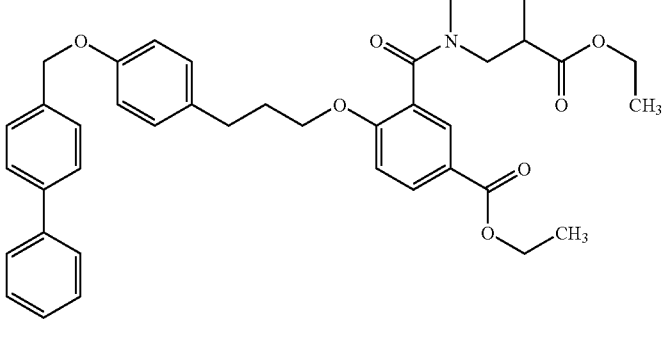 | 649 | 1 | 5.92 | 650 (ESI) |
| 201 | 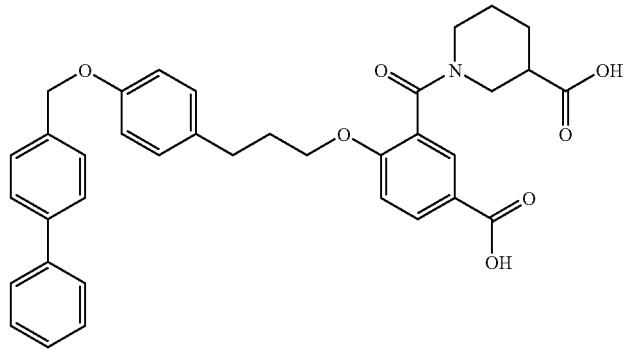 | 593 | 1 | 5.01 | 594 (DCI, NH$_3$) |

| Ex. No. | Structure | Molecular mass [g/mol] | HPLC method | HPLC R$_t$ [min] | MS or LC-MS (method) |
|---|---|---|---|---|---|
| 202 | 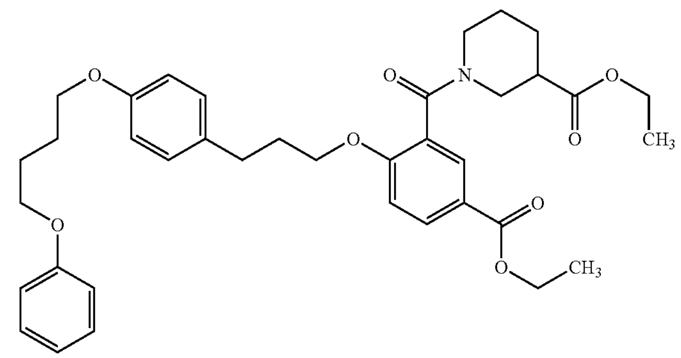 | 631 | 1 | 5.77 | 632 (ESI) |
| 203 | 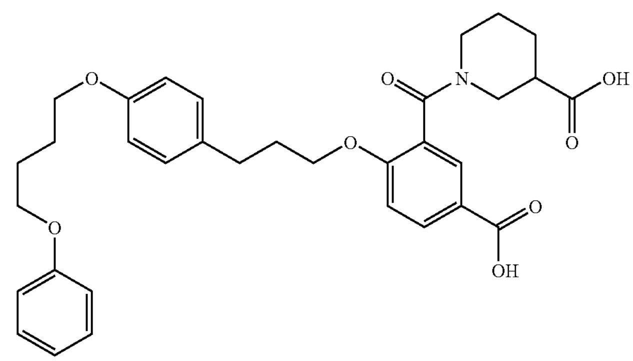 | 575 | 1 | 4.88 | 576 (DCI, NH$_3$) |

B. Assessment of the Physiological Activity

Abbreviations:

DMEM Dulbecco's modified Eagle medium

FCS Fetal calf serum

HEPES 4-(2-hydroxyethyl)-1-piperazineethanesulphonic acid

1. Cellular In Vitro Test to Determine the CysLT2 Activity

A recombinant cell line is used to identify antagonists of the human cysteinyl-leukotriene 2 receptor (CysLT2R) and to quantify the activity of the substances described herein. The cell is originally derived from a hamster ovary epithelial cell (Chinese Hamster Ovary, CHO K1, ATCC: American Type Culture Collection, Manassas, Va. 20108, USA). The test cell line constitutively expresses the calcium-sensitive photoprotein aequorin which, after reconstitution with the cofactor coelenterazine, emits light when the cytoplasmic calcium concentration is increased (Rizzuto R, Simpson A W, Brini M, Pozzan T.; Nature 358 (1992) 325-327). The cell is additionally stably transfected with the human CysLT2 receptor (Heise et.al., JBC 275 (2000) 30531-30536). The resulting CysLT2R test cell responds to stimulation of the recombinant CysLT2 receptor (agonists: leukotriene D4 (LTD4) and leukotriene C4 (LTC4)) with an intracellular release of calcium ions, which can be quantified through the resulting aequorin luminescence with a suitable luminometer (Milligan G, Marshall F, Rees S, Trends in Pharmacological Sciences 17 (1996) 235-237). Preincubation with antagonists of the CysLT2 receptor reduces the calcium release induced by the agonists LTD4 and LTC4 and thus the measured amount of light.

Test procedure: The cells are plated out two days before the test in culture medium (DMEM/F12 with Glutamax, Gibco Cat.# 61965-026; 10% FCS, Gibco Cat.# 10270-106; 1.4 mM sodium pyruvate, Gibco Cat.# 11360-039; 1.8 mM sodium bicarbonate, Gibco Cat.# 25080-060; 10 mM HEPES, Gibco Cat.# 15290-026; now belongs to Invitrogen GmbH, 76131 Karlsruhe) in 384- (or 1536-)well microtitre plates and kept in a cell incubator (96% humidity, 5% V/V CO$_2$, 37° C.). On the day of the test, the culture medium is replaced by Tyrode solution (in mM: 140 NaCl, 5 KCl, 1 MgCl$_2$, 2 CaCl$_2$; 20 glucose, 20 HEPES) which additionally contains the cofactor coelenterazine (50 µM), and the microtitre plate is then incubated for a further 3-4 hours. 15 minutes after the test substances have been transferred into the wells of the microtitre plate, the resulting light signal is measured after addition of the LTD4 ($3 \times 10^{-8}$ M) in the luminometer. The results are shown in Table 1.

2. Cellular In Vitro Test to Determine the CysLT1 Activity

A recombinant cell line is used to identify antagonists of the human cysteinyl-leukotriene 1 receptor (CysLT1R) and to quantify the activity of the substances described herein. The cell is originally derived from a hamster ovary epithelial cell (Chinese Hamster Ovary, CHO K1, ATCC: American Type Culture Collection, Manassas, Va. 20108, USA). The test cell line constitutively expresses the calcium-sensitive photoprotein aequorin which, after reconstitution with the cofactor coelenterazine, emits light when the cytoplasmic calcium concentration is increased (Rizzuto R, Simpson A W, Brini M, Pozzan T.; Nature 358 (1992) 325-327). The cell is additionally stably transfected with the human CysLT1 receptor (Lynch et al., Nature 399 (1999) 789-793). The resulting CysLT1R test cell responds to stimulation of the recombinant CysLT1 receptor (agonist: leukotriene D4 (LTD4)) with an intracellular release of calcium ions, which can be quantified through the resulting aequorin luminescence with a suitable luminometer (Milligan G, Marshall F, Rees S. *Trends in Pharmacological Sciences* 17 (1996) 235-237). Preincubation with antagonists of the CysLT1 receptor reduces the calcium release induced by the agonist LTD4 and thus the measured amount of light.

Test procedure: The cells are plated out two days before the test in culture medium (DMEM/F12 with Glutamax, Gibco Cat.# 61965-026; 10% FCS, Gibco Cat.# 10270-106; 1.4 mM sodium pyruvate, Gibco Cat.# 11360-039; 1.8 mM sodium bicarbonate, Gibco Cat.# 25080-060; 10 mM HEPES, Gibco Cat.# 15290-026; now belongs to Invitrogen GmbH, 76131 Karlsruhe) in 384- (or 1536-)well microtitre plates and kept in a cell incubator (96% humidity, 5% V/V $CO_2$, 37° C.). On the day of the test, the culture medium is replaced by Tyrode solution (in mM: 140 NaCl, 5 KCl, 1 $MgCl_2$, 2 $CaCl_2$, 20 glucose, 20 HEPES) which additionally contains the cofactor coelenterazine (50 µM), and the microtitre plate is then incubated for a further 3-4 hours. 15 minutes after the test substances have been transferred into the wells of the microtitre plate, the resulting light signal is measured after addition of the LTD4 ($3\times10^{-9}$M) in the luminometer. The results are shown in Table 1.

TABLE 1

CysLT1 activity/CysLT2 activity comparison

| Example No. | CysLT1: $IC_{50}$ (nM) | CysLT2: $IC_{50}$ (nM) |
|---|---|---|
| 11 | >10000 | 35 |
| 23 | 2000 | 5 |
| 25 | >10000 | 6 |
| 31 | 2500 | 14 |
| 33 | >10000 | 15 |

3. In Vivo Test to Detect the Cardiovascular Effect: Langendorff Guinea Pig Heart The heart is removed after opening the chest cavity of anaesthetized guinea pigs and is introduced into a conventional Langendorff apparatus. The coronary arteries are subjected to a constant volume (10 ml/min) perfusion, and the perfusion pressure arising thereby is recorded via an appropriate pressure transducer. A decrease in the perfusion pressure in this arrangement corresponds to a relaxation of the coronary arteries. At the same time, the pressure developed by the heart during each contraction (the left ventricular pressure) is measured by a balloon introduced into the left ventricle, and a further pressure transducer. The rate at which the isolated heart beats is found by calculation from the number of contractions per unit time.

To detect the effect of CysLT2 receptor antagonists, the perfusion with the agonist LTC4 ($10^{-8}$ M) is started 15 minutes before addition of increasing concentrations of the test substance ($10^{-8}$ to $10^{-6}$ M).

TABLE 2

Change in the perfusion pressure in isolated guinea pig hearts after addition of LTC4 in absence and presence of various concentratons of test substances

| | Perfusion pressure relative to control without LTC4 [%] | | | |
|---|---|---|---|---|
| Ex. No. | LTC4 ($10^{-8}$M) no test sub. | LTC4 ($10^{-8}$M) + test sub. ($10^{-8}$M) | LTC4 ($10^{-8}$M) + test sub. ($10^{-7}$M) | LTC4 ($10^{-8}$M) + test sub. ($10^{-6}$M) |
| 11 | 127 | 125 | 112 | 108 |
| 23 | 134 | 133 | 127 | 111 |
| 25 | 131 | 128 | 123 | 111 |
| 31 | 130 | 128 | 123 | 112 |
| 33 | 127 | 122 | 121 | 108 |

TABLE 3

Change in the left ventricular pressure in isolated guinea pig hearts after addition of LTC4 in absence and presence of various concentratons of test substances

| | Left ventricular pressure relative to control without LTC4 [%] | | | |
|---|---|---|---|---|
| Ex. No. | LTC4 ($10^{-8}$M) no test sub. | LTC4 ($10^{-8}$M) + test sub. ($10^{-8}$M) | LTC4 ($10^{-8}$M) + test sub. ($10^{-7}$M) | LTC4 ($10^{-8}$M) + test sub. ($10^{-6}$M) |
| 11 | 47 | 44 | 60 | 79 |
| 23 | 59 | 72 | 84 | 97 |
| 25 | 46 | 55 | 71 | 89 |
| 31 | 54 | 67 | 81 | 87 |
| 33 | 44 | 44 | 57 | 84 |

C. Exemplary Embodiments of Pharmaceutical Compositions

The compounds of the invention can be converted into pharmaceutical preparations in the following way:

Tablets:

Composition:

100 mg of the compound of Example 11, 50 mg of lactose (monohydrate), 50 mg of microcrystalline cellulose, 10 mg of polyvinylpyrrolidone (PVP) (from BASF, Ludwigshafen, Germany), 10 mg of crosslinked Na carboxymethylcellulose and 2 mg of magnesium stearate.

Tablet weight 222 mg. Diameter 8 mm, radius of curvature 12 mm.

Production:

The mixture of active ingredient, lactose and cellulose is granulated with a 5% strength solution (m/m) of the PVP in water. The granules are dried and then mixed with the crosslinked Na carboxymethylcellulose and the magnesium stearate for 5 minutes. This mixture is compressed in a conventional tablet press (see above for tablet format). As a guideline, a compressive force of 15 kN is used for the compression.

Suspension which can be Administered Orally:

Composition:

1000 mg of the compound of Example 11, 1000 mg of ethanol (96%), 400 mg of xanthan gum (from FMC, Pennsylvania, USA) and 97.6 g of water. 10 g of oral suspension correspond to a single dose of 100 mg of the compound of the invention.

Production:

The xanthan gum is suspended in ethanol, and the active ingredient is added to the suspension. The water is added while stirring. The mixture is stirred for about 6 h until the xanthan gum has finished swelling.

Solution which can be Administered Orally:

Composition 500 mg of the compound of Example 11, 2.5 g of polysorbate and 97 g of poly-ethylene glycol 400. 20 g of oral solution correspond to a single dose of 100 mg of the compound of the invention.

Production

The active ingredient is suspended by stirring in the mixture of polyethylene glycol and polysorbate. The stirring process is continued until the active ingredient has completely dissolved.

Solution which can be Administered Intravenously:

The active ingredient is dissolved in a concentration below the saturation solubility in a physiologically tolerated solvent (see Examples). The solution is sterilized by filtration and dispensed into sterile and pyrogen-free injection/infusion containers.

Composition I:

100 mg of the compound of Example 11, 15 g of polyethylene glycol 400 and 250 g of a 2% strength aqueous sodium bicarbonate solution for injections.

Production:

The compound of Example 11 is dissolved together with polyethylene glycol 400 by stirring in the 2% strength aqueous sodium bicarbonate solution. The solution is sterilized by filtration (pore diameter 0.22 µm) and dispensed under aseptic conditions into heat-sterilized infusion bottles. The latter are closed with infusion stoppers and crimped caps.

Composition II:

100 mg of the compound of Example 11 and 250 ml of an aqueous solution of 0.31 g of anhydrous citric acid and 5.66 g of sodium monohydrogen phosphate dihydrate.

Production:

The compound of Example 11 is dissolved by stirring in the aqueous solution. The solution is sterilized by filtration and dispensed under aseptic conditions into sterile and pyrogen-free injection/infusion containers.

Composition III:

100 mg of the compound of Example 11 and 250 ml of an aqueous solution of 0.044 g of anhydrous citric acid, 0.81 g of sodium monohydrogen phosphate dihydrate and 1.87 g of sodium chloride.

Production:

The compound of Example 11 is dissolved by stirring in the aqueous solution. The solution is sterilized by filtration and dispensed under aseptic conditions into sterile and pyrogen-free injection/infusion containers.

The invention claimed is:

1. A compound of the formula

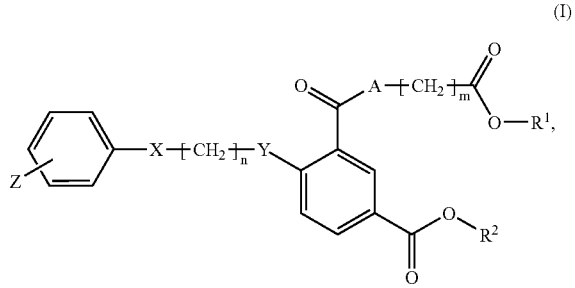

(I)

in which

A is a 6-membered nitrogen-containing saturated heterocycle which is bonded via the nitrogen atom to the keto group and which optionally has a carbonyl group adjacent to a nitrogen atom, m 0, 1 or 2, n is 1, 2, 3 or 4, $R^1$ is hydrogen or $(C_1-C_6)$-alkyl, $R^2$ is hydrogen or $(C_1-C_6)$-alkyl, X is a bond, —CH═CH—, —C≡C— or O, Y is O, *—NH—C(═O)— or NH, in which

* is the point of linkage to the phenyl ring, and

Z is located in the position meta or para to the substituent X and is either $(C_6-C_{10})$-alkoxy which may comprise 1 or 2 further oxygen atoms in the chain, or a radical

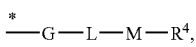

in which

G is a bond, O or S,

L is $(C_1-C_6)$-alkanediyl, $(C_3-C_6)$-alkenediyl or $(C_3-C_6)$-alkynediyl,

M is a bond, O or S, $R^4$ is $(C_6-C_{10})$-aryl, biphenylyl, phenoxyphenyl, benzyloxyphenyl, (E)-phenylvinylphenyl, 2-phenylethyiphenyl, tetrahydronaphthyl, benzyl, heteroaryl, 5- to 10-membered heterocyclyl, $(C_3-C_7)$-cycloalkyl or $(C_3-C_7)$-cycloalkylmethyl, where aryl, biphenylyl, phenoxyphenyl, benzyloxyphenyl, (E)-phenylvinylphenyl, 2-phenylethyiphenyl, tetrahydronaphthyl, benzyl, heteroaryl, heterocyclyl, cycloalkyl and cycloalkylmethyl in turn may be substituted up to three times independently of one another by halogen, cyano, nitro, trifluoromethyl, trifluoromethoxy, $(C_1$-

$C_6$)-alkyl, ($C_1$-$C_6$)-alkoxy, ($C_2$-$C_6$)-alkenyl, ($C_3$-$C_7$)-cycloalkyl, ($C_3$-$C_7$)-cycloalkylmethoxy, ($C_5$-$C_7$)-cyclo-alkenyl, ($C_3$-$C_7$)-cycloalkoxy or ($C_5$-$C_7$)-cycloalkenyloxy, and

* is the point of linkage to the phenyl ring, or a salt thereof.

2. The compound of claim 1, in which

A is a 6-membered nitrogen-containing saturated heterocycle which is bonded via the nitrogen atom to the keto group, m is 0 or 1, n is 1, 2 or 3, $R^1$ is hydrogen, $R^2$ is hydrogen, X is a bond or O, Y is O or *—NH—C(=O)—, in which

* is the point of linkage to the phenyl ring, and

Z is located in the position meta or para to the substituent X and is either ($C_7$-$C_9$)-alkoxy, which may comprise 1 further oxygen atom in the chain, or a radical

—G—L—M—$R^4$, in which

G is a bond or O,

L is ($C_1$-$C_6$)-alkanediyl or ($C_3$-$C_6$)-alkenediyl,

M is a bond, O or S, $R^4$ is phenyl, naphthyl, biphenylyl, phenoxyphenyl, benzyloxyphenyl, (E)-phenylvinylphenyl, 2-phenylethylphenyl, tetrahydronaphthyl, benzyl, 1,3-dioxanyl, 1,4-dioxanyl, dimethyl-1,3-dioxanyl, tetrahydro-2H-pyranyl, ($C_3$-$C_7$)-cycloalkyl or ($C_3$-$C_7$)-cycloalkylmethyl, where phenyl, naphthyl, biphenylyl, phenoxyphenyl, benzyloxyphenyl, (E)-phenylvinylphenyl, 2-phenylethylphenyl, tetrahydronaphthyl, benzyl, cycloalkyl and cycloalkylmethyl in turn may be substituted up to three times independently of one another by halogen, cyano, nitro, trifluoromethyl, trifluoromethoxy, ($C_1$-$C_6$)-alkyl, ($C_1$-$C_6$)-alkoxy, ($C_3$-$C_7$)-cycloalkyl, ($C_3$-$C_7$)-cycloalkylmethoxy or ($C_3$-$C_7$)-cycloalkoxy, and

* is the point of linkage to the phenyl ring, or a salt thereof.

3. The compound of claim 1, in which

A—[$CH_2$]$_m$—$CO_2R^1$ is a radical

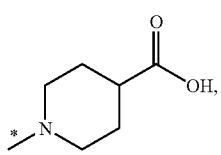

4. The compound of claim 1, in which

* is the point of linkage to the keto group, n is 3, $R^2$ is hydrogen,

X is a bond,

Y is O, and

Z is located in the position pam to the substituent X and is either n-octyloxy, n-heptyloxy, or a radical

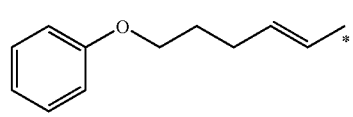

in which

* is the point of linkage to the phenyl ring, or a radical

—G—L—M—$R^4$, in which

G is O,

L is methanediyl, n-propanediyl or n-butanediyl,

M is a bond or O, $R^4$ is phenyl, 4-biphenylyl, 4-phenoxyphenyl, 4-benzyloxyphenyl, 1,2,3,4-tetrahydronaphth-6-yl, 5,5-dimethyl-1,3-dioxan-2-yl or cyclohexyl, where phenyl in turn may be substituted once by halogen, trifluoromethoxy, ($C_3$-$C_4$)-alkyl, ($C_3$-$C_4$)-alkoxy, cyclopentyl, cyclohexyl or ($C_3$-$C_6$)-cycloalkylmethoxy, and

* is the point of linkage to the phenyl ring, or a salt thereof.

4. The compound of claim 1, in which

A—[$CH_2$]$_m$—$CO_2R^1$ is a radical

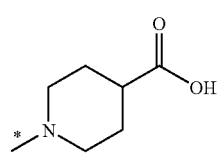

in which

* is the point of linkage to the keto group, n is 3, $R^2$ is hydrogen,

X is a bond,

Y is O, and

Z is located in the position para to the substituent X, and is either n-octyloxy, n-heptyloxy, or a radical

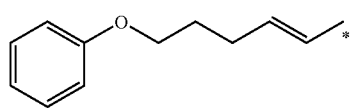

in which

* is the point of linkage to the phenyl ring, or a radical *—O—CH$_2$R$^4$, in which R$^4$ is phenyl, 4-biphenylyl, 4-phenoxyphenyl, 4-benzyloxyphenyl or 1,2,3,4-tetrahydronaphth-6-yl, where phenyl in turn may be substituted once by trifluoromethoxy, n-propyl, n-butyl, tert-butyl, n-propyloxy, isopropyloxy, isobutyloxy, cyclohexyl or cyclopropylmethoxy, and

* is the point of linkage to the phenyl ring, or a radical *—O—CH$_2$—CH$_2$—CH$_2$—R$^4$, in which R$^4$ is 4-chlorophenyl, 5,5-dimethyl-1,3-dioxan-2-yl or cyclohexyl, and

* is the point of linkage to the phenyl ring, or a radical *—O—CH$_2$—CH$_2$—CH$_2$—CH$_2$—O—R$^4$, in which R$^4$ is phenyl or cyclohexyl, and

* is the point of linkage to the phenyl ring, or a salt thereof.

5. The compound of claim 1, in which

A—[CH$_2$]$_m$—CO$_2$R$^1$ is a radical

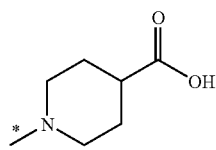

in which

* is the point of linkage to the keto group, n is 3, $R^2$ is hydrogen,

X is a bond,

Y is O, and

Z is located in the position para to the substituent X and is a radical

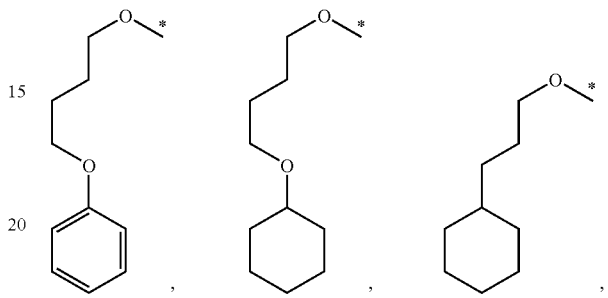

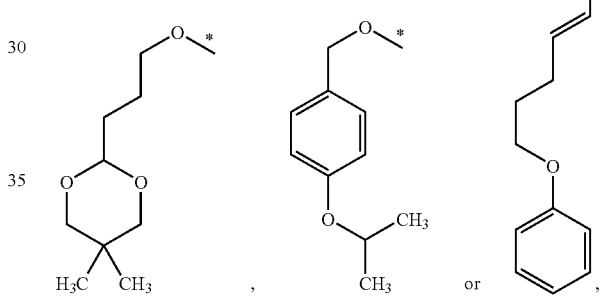

in which

* is the point of linkage to the phenyl ring, or a salt thereof.

6. The compound of claim 1, wherein the compound is 1-(5-carboxy-2-{3-[4-(3-cyclohexylpropoxy)phenyl]propoxy}benzoyl)piperidine-4-carboxylic acid, or a salt thereof.

7. A process for preparing a compound of claim 1, comprising either

[A] reacting a compound of the formula (II)

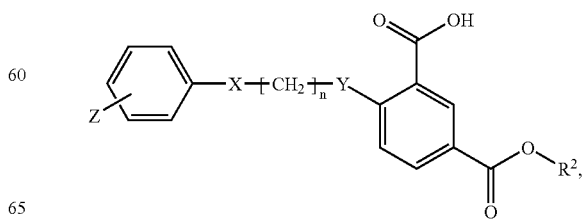

(II)

in which
R² is (C₁-C₆)-alkyl and
n, X, Y and Z have the meaning indicated in claim 1,
with a compound of the formula (III)

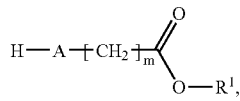
(III)

in which
R¹ is (C₁-C₆)-alkyl, and
m and A have the meaning indicated in claim 1,
or
[B1] reacting a compound of the formula (IVa)

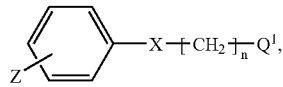
(IVa)

in which
Q¹ is a leaving group and
n, X and Z have the meaning indicated in claim 1,
with a compound of the formula (Va)

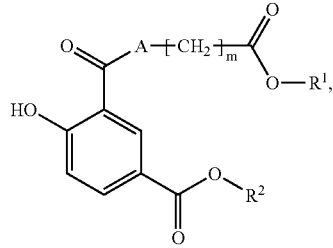
(Va)

in which
R¹ and R² are (C₁-C₆)-alkyl, and
A and m have the meaning indicated in claim 1,
or
[B2] reacting a compound of the formula (IVb)

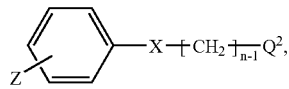
(IVb)

in which
Q² is an acid chloride group, and
n, X and Z have the meaning indicated in claim 1,
with a compound of the formula (Vb)

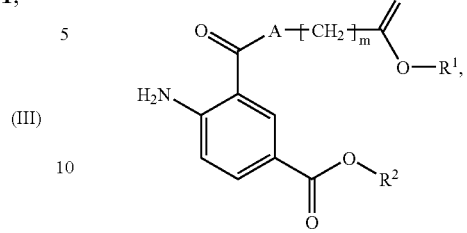
(Vb)

in which
R¹ and R² are (C₁-C₆)-alkyl, and
A and m have the meaning indicated in claim 1,
or
[B3] reacting a compound of the formula (IVa)

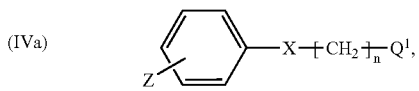
(IVa)

in which
Q¹ is a leaving group and
n, X and Z have the meaning indicated in claim 1,
with a compound of the formula (Vb)

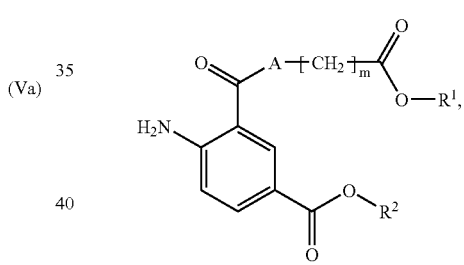
(Vb)

in which
R¹ and R² are (C₁-C₆)-alkyl, and
A and m have the meaning indicated in claim 1,
or
[C] reacting a compound of the formula (XII)

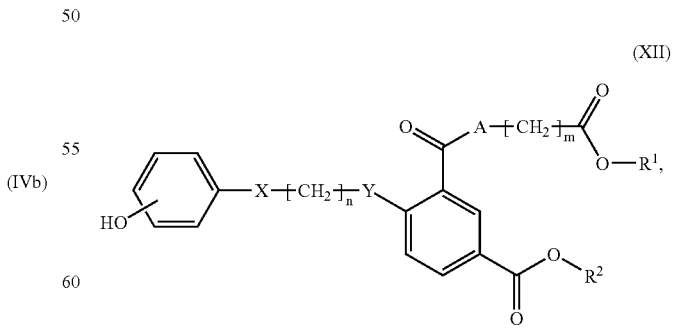
(XII)

in which
R¹ and R² are (C₁-C₆)-alkyl, and
n, m, X, Y and A have the meaning indicated in claim 1,
with a compound of the formula (XIII)

$R^4$-M-L-$Q^3$ (XIII),
in which
  $Q^3$ is a leaving group and
  $R^4$, M and L have the meaning indicated in claim 1,
or
[D] hydrolysing the two ester groups in the compound prepared by process step [A], [B1], [B2], [B3] or [C].

8. A pharmaceutical composition comprising at least one compound of claim 1 and at least one excipient.

9. A pharmaceutical composition comprising at least one compound of claim 1 and at least one further active ingredient.

* * * * *